US008691971B2

(12) United States Patent
Petersen

(10) Patent No.: US 8,691,971 B2
(45) Date of Patent: Apr. 8, 2014

(54) SELF DELIVERING BIO-LABILE PHOSPHATE PROTECTED PRO-OLIGOS FOR OLIGONUCLEOTIDE BASED THERAPEUTICS AND MEDIATING RNA INTERFERENCE

(76) Inventor: Scott G. Petersen, San Diego, CA (US)

( * ) Notice: Subject to any disclaimer, the term of this patent is extended or adjusted under 35 U.S.C. 154(b) by 170 days.

(21) Appl. No.: 13/120,409

(22) PCT Filed: Sep. 23, 2009

(86) PCT No.: PCT/US2009/058064
§ 371 (c)(1),
(2), (4) Date: Mar. 22, 2011

(87) PCT Pub. No.: WO2010/039543
PCT Pub. Date: Apr. 8, 2010

(65) Prior Publication Data
US 2011/0294869 A1   Dec. 1, 2011

Related U.S. Application Data

(60) Provisional application No. 61/099,501, filed on Sep. 23, 2008.

(51) Int. Cl.
| | |
|---|---|
| C07H 19/04 | (2006.01) |
| C07H 21/02 | (2006.01) |
| C12N 15/11 | (2006.01) |
| C12N 5/071 | (2010.01) |
| A61K 31/70 | (2006.01) |
| A61K 31/7088 | (2006.01) |

(52) U.S. Cl.
USPC ....... 536/26.1; 536/18.7; 536/22.1; 536/26.7; 536/26.8; 514/44 A; 514/44 R; 514/42

(58) Field of Classification Search
USPC .................... 536/26.1, 18.7, 22.1, 26.7, 26.8; 514/44 A, 44 R, 42
See application file for complete search history.

(56) References Cited

U.S. PATENT DOCUMENTS

| | | | |
|---|---|---|---|
| 4,667,025 A | 5/1987 | Miyoshi et al. | |
| 4,806,463 A | 2/1989 | Goodchild et al. | |
| 5,552,535 A | 9/1996 | McLean et al. | |
| 5,733,523 A | 3/1998 | Kuijpers et al. | |
| 6,124,445 A | 9/2000 | Imbach et al. | |
| 6,262,251 B1 | 7/2001 | Pieken et al. | |
| 2002/0198370 A1 | 12/2002 | Kempe | |
| 2003/0143732 A1 | 7/2003 | Fosnaugh et al. | |
| 2004/0175726 A1 | 9/2004 | Kwiatkowski | |
| 2008/0227968 A1 | 9/2008 | Komatsu et al. | |
| 2009/0093425 A1 | 4/2009 | Dowdy et al. | |

FOREIGN PATENT DOCUMENTS

| | | |
|---|---|---|
| WO | WO 9747637 A1 * | 12/1997 |
| WO | WO 02/14558 | 2/2002 |
| WO | WO 2008/008476 | 1/2008 |

OTHER PUBLICATIONS

Alvarez et al., "Photocleavable Protecting Groups as Nucleobase Protections Allowed the Solid-Phase Synthesis of Base-sensitive SATE-Prooligonucleotides," J. Org. Chem., 1999, 64(17): 6319-6328.
Astriab-Fisher et al., "Conjugates of Antisense Oligonucleotides with the Tat and Antennapedia Cell-Penetrating Peptides: Effects on Cellular Uptake, Binding to Target Sequences, and Biologic Action," Pharm. Res., 2002, 19(6): 744-754.
Breslow et al., "Recognition and catalysis in nucleic acid chemistry," Proc. Natl. Acad. Sci. USA, 1993, 90: 1201-1207.
Kosonen et al., "Hydrolysis and intramolecular transesterification of ribonucleoside 3'-phosphotriesters: the effect of alkyl groups on general and specific acid-base-catalyzed reactions of 5'-O-pivaloyluridin-3'-yl dialkyl phosphates," J. Chem. Soc., Perkins Trans. 2, 1998, 663-670.
Nielsen et al., "Selective Extraction of G-Quadruplex Ligands from a Rationally Designed Scaffold-Based Dynamic Combinatorial Library," Chem. Eur. J., 2008, 14(31): 9487-9490.
International Search Report and Written Opinion mailed Aug. 20, 2010 in International Application No. PCT/US2009/058064, filed Sep. 23, 2009.
International Preliminary Report on Patentability mailed Jan. 13, 2009 in International Application No. PCT/US2007/015966, filed Jul. 11, 2007.

* cited by examiner

*Primary Examiner* — Shaojia Anna Jiang
*Assistant Examiner* — Michael C Henry
(74) *Attorney, Agent, or Firm* — Timothy M. Brown, Esq.

(57) ABSTRACT

Disclosed herein are compositions and methods for generating ribo-nucleic neutral (RNN) or deoxyribo-nucleic-neutral (DNN) polynucleotides with reduced anionic charge, for improved intracellular delivery. Also disclosed herein are methods of using RNN and DNN compositions.

30 Claims, 10 Drawing Sheets

SELF DELIVERING BIO-LABILE PHOSPHATE PROTECTED PRO-OLIGOS FOR OLIGONUCLEOTIDE BASED THERAPEUTICS AND MEDIATING RNA INTERFERENCE

RELATED APPLICATIONS

This application claims the benefit of U.S. Provisional Application No. 61/099,501, filed Sep. 23, 2008; which is incorporated herein by reference in its entirety.

REFERENCE TO SEQUENCE LISTING

The present application is being filed with a Sequence Listing in electronic format. The Sequence Listing is provided as a file entitled TRVRS.001VPC.TXT, created Sep. 22, 2009, which is 13 KB in size. The information in the electronic format of the Sequence Listing is incorporated herein by reference in its entirety.

BACKGROUND OF THE INVENTION

1. Field of the Invention

This invention relates to compositions and methods for delivery of biomolecules into cells.

2. Description of the Related Art

Recently, as the fields of gene therapy and molecular biology have developed rapidly, an urgent need has emerged to effectively deliver biomolecules, such as proteins, nucleic acids, protein analogs, nucleic acid analogs, including oligonucleotides such RNA, DNA and analogs thereof, peptides, polypeptides, proteins, antibodies, hormones, small molecules, antiviral agents and the like into cells or tissues. Many therapeutic, research, and diagnostic applications rely upon the efficient transfer of biologically active molecules into cells, tissues, and organs.

Particularly problematic in the delivery of biomolecules is the delivery of negatively charged molecules, such as polyribonucleic acids, and polydeoxyribonucleic acids and analogs thereof, due to their size and charge. To be useful in therapeutic or research, however, an effective amount of the biomolecule, e.g., polynucleotides, oligonucleotides or the like, must be delivered into the target cells or tissue. At the same time, when used in a therapeutic setting, nucleic acid delivery methods should minimize immune responses or cytotoxicity to the host. Finally, availability of large-scale production of delivered materials, or vehicles, is desirable.

Current methods for delivery of negatively charged biomolecules include viral-based delivery systems and non-viral based delivery systems.

Virus-mediated delivery of nucleic acids is known in the art. Viral based gene nucleic acid delivery systems utilize retrovirus, adenovirus, and adeno-associated viruses. Virus-mediated nucleic acid delivery has drawbacks, however, including narrow range of cell infectivity, the elicitation of immune responses, and difficulty of large-scale production of viral vectors. (Yibin Wang et al., DDT. 5(1), 2000; Joanne T. Douglas. et al., Science & medicine 44-52 (March/April), 1997).

Non-viral delivery systems include systems such as liposomes, polymers, calcium phosphate, electroporation, and micro-injection techniques (Saghir Akhtar et al., Adv. Drug Deliv. Rev. 44:3-21; Irina Lebedeva et al., Eur. J. Pharm. Biopharm. 50:101-119, 2000; Ch. Garcia-Chaumont et al., Pharmacol. Ther. 76:151-161, 2000). Ease of preparation and large-scale production have made the use of non-viral vectors a popular option for gene therapy. (Colin W. Pouton et al., Adv. Drug Deliv. Rev. 46:187-20, 2001).

Among the non-viral vectors developed to date, liposomes are the most frequently used gene transfer vehicle and are available commercially. Many liposomes are cationic. Cationic liposomes, complexed with nucleic acids or analogs thereof, electrostatically interact with the cell surface, and the complexes are then endocytosed into the cell cytoplasm. The cationic nature of the liposomes facilitates passage of negatively charged biomolecules such as polynucleotides across the cell wall. However, while cationic liposomes mediate gene delivery effectively into cells in vitro, gene delivery in an in vivo system is quite limited as compared to viral vectors. Furthermore, the efficiency of gene delivery using cationic liposomes is generally dependent on the size of nucleic acids, and the cell line, even in an in vitro system. The major drawback of cationic liposomes, however, is their known cytotoxicity to cells (Saghir Akhtar et al., Adv. Drug Deliv. Rev. 44:3-21, 2000: Irina Lebedeva et al., Eur. J. Pharm. Biopharm. 50:101-119, 2000).

Other cationic systems, such as cationic polymers, have been used to increase the efficiency of biomolecule delivery into cells. Polymers with numerous, positively-charged amine groups are able to bind strongly with nucleic acids, and also interact with the cell, so that the required amount of the polymers as compared to that of cationic liposomes can be reduced. However, cytotoxicity and insolubility of cationic polymers in aqueous solutions are drawbacks that limit the usefulness of cationic polymers as an effective gene delivery vehicle (Dan Luo et al., Nat. biotech. 18:33-37; Saghir Akhtar et al., Adv. Drug Deliv. Rev. 44:3-21, 2000).

Another non-viral system for the delivery of biomolecules relates to the addition of a covalently linked antibody to the oligonucleotide. The antibody mediated approach to delivery of biomolecules falters due to the therapeutic being shuttled down the endosomal pathway leading to ultimate degradation of the biomolecule.

Accordingly, there exists a need for improved biomolecule delivery systems.

SUMMARY OF THE INVENTION

Disclosed herein are compounds suitable as protecting groups to mask the charge of anionic biomolecular analogs of oligonucleotides, and methods of making the same. For example, the methods and compositions disclosed herein provide polynucleotides, oligonucleotide, having reduced anionic charge, neutral charge, or cationic charge.

Figure 4A:
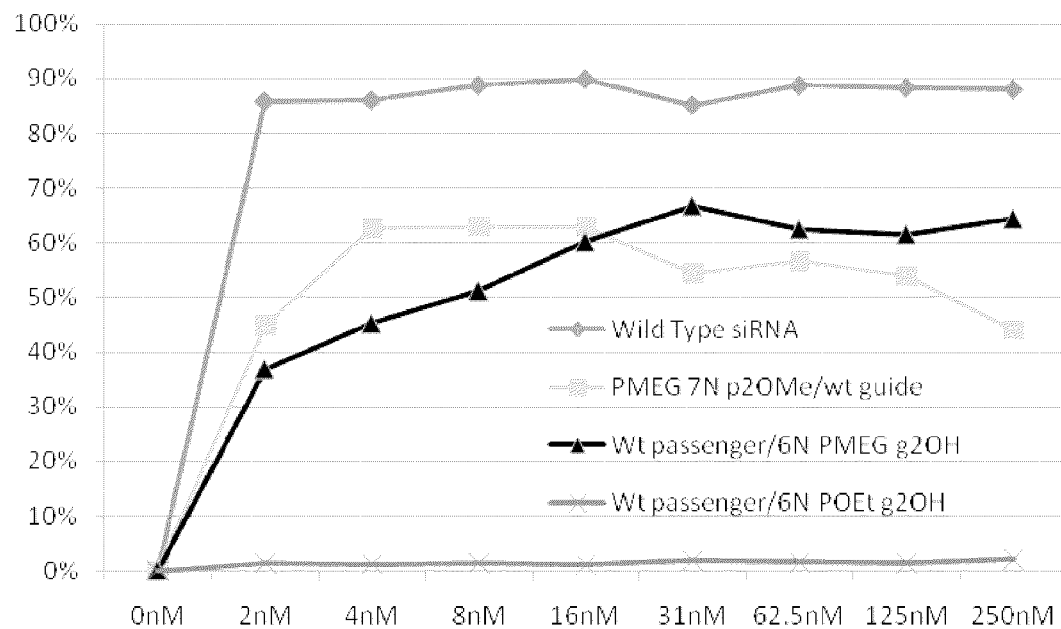
FIG. 4A shows iv-vitro Green Fluorescence Protein (GFP) knockdown in H1299 cells as measured at 72 h with double stranded siRNN constructs containing 6 neutralization sites. Also, the response over time is shown for a selected siRNN showing a time dependant increase in knockdown.
Figure 4B:
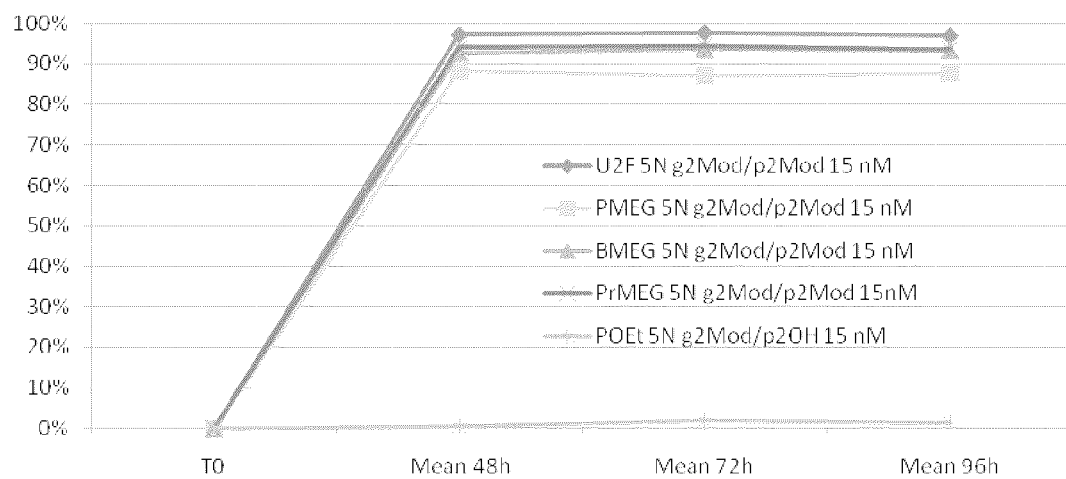
FIG. 4B shows Green Fluorescence Protein (dGFP) knockdown as response over time is shown for selected siRNN at 48 h, 72 h, and 96 h. Within the timeframes collected a reduction in gene expression was observed in all cells at levels of 87% to 94%.
Figure 4C:
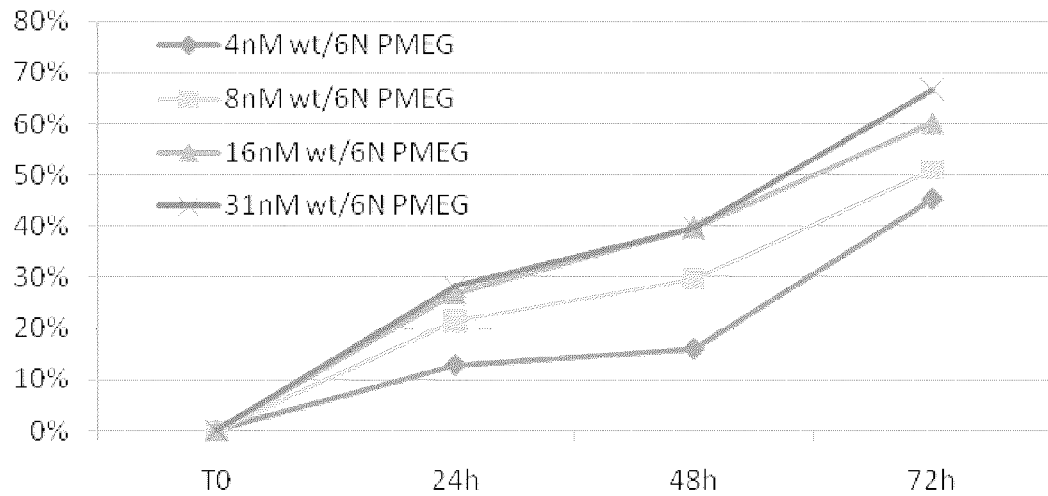
Figure 5:
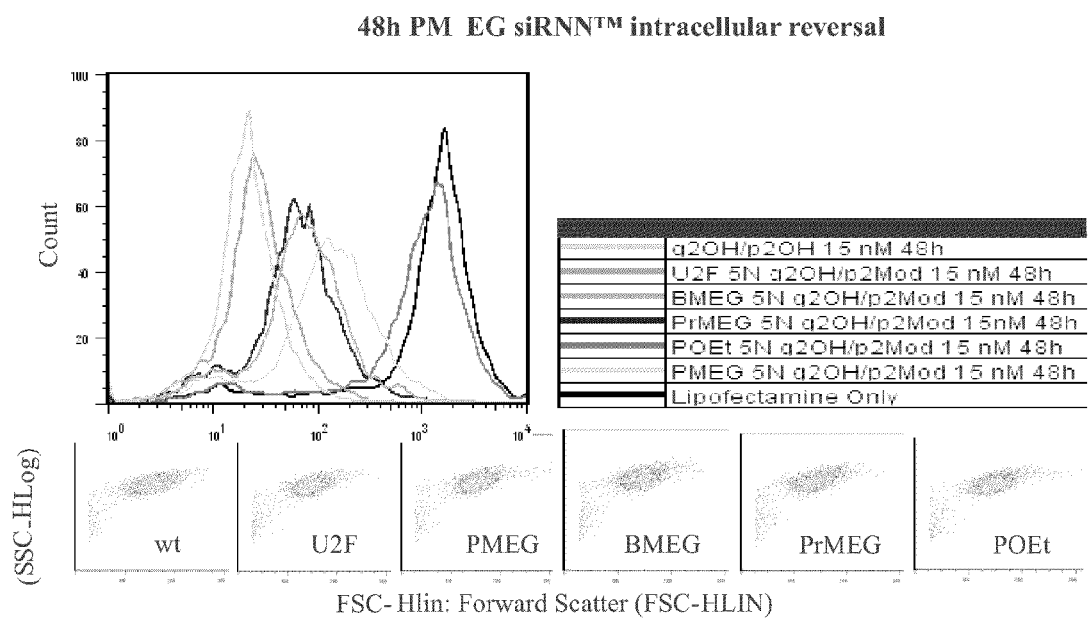

FIG. 4C shows Green Fluorescence Protein (dGFP) knockdown with a siRNN construct comprising a wild type passenger strand and a guide strand containing 6 phosphotriesters linkages at 4 nM, 8 nM, 16 nM and 31 nM vs. 3 time points 24, 48 and 72 h. Knockdown was first observed at 24 h and appeared to reach a maximum at 72 h with the 31 nM dose giving a 68% reduction in dGFP expression FIG. 5 shows a comparison of siRNA knockdown observed in H1299 cells with reversible double stranded siRNN constructs each with 5 reversible protecting groups in the guide strand. PMEG, BMEG and PrMEG, with the appropriate positive control siRNA, and the irreversible POEt siRNA negative control constructs were measured after 48 h. The observed high level of dGFP knock down proceeded for all time points taken out to 96 h.

Figure 6:
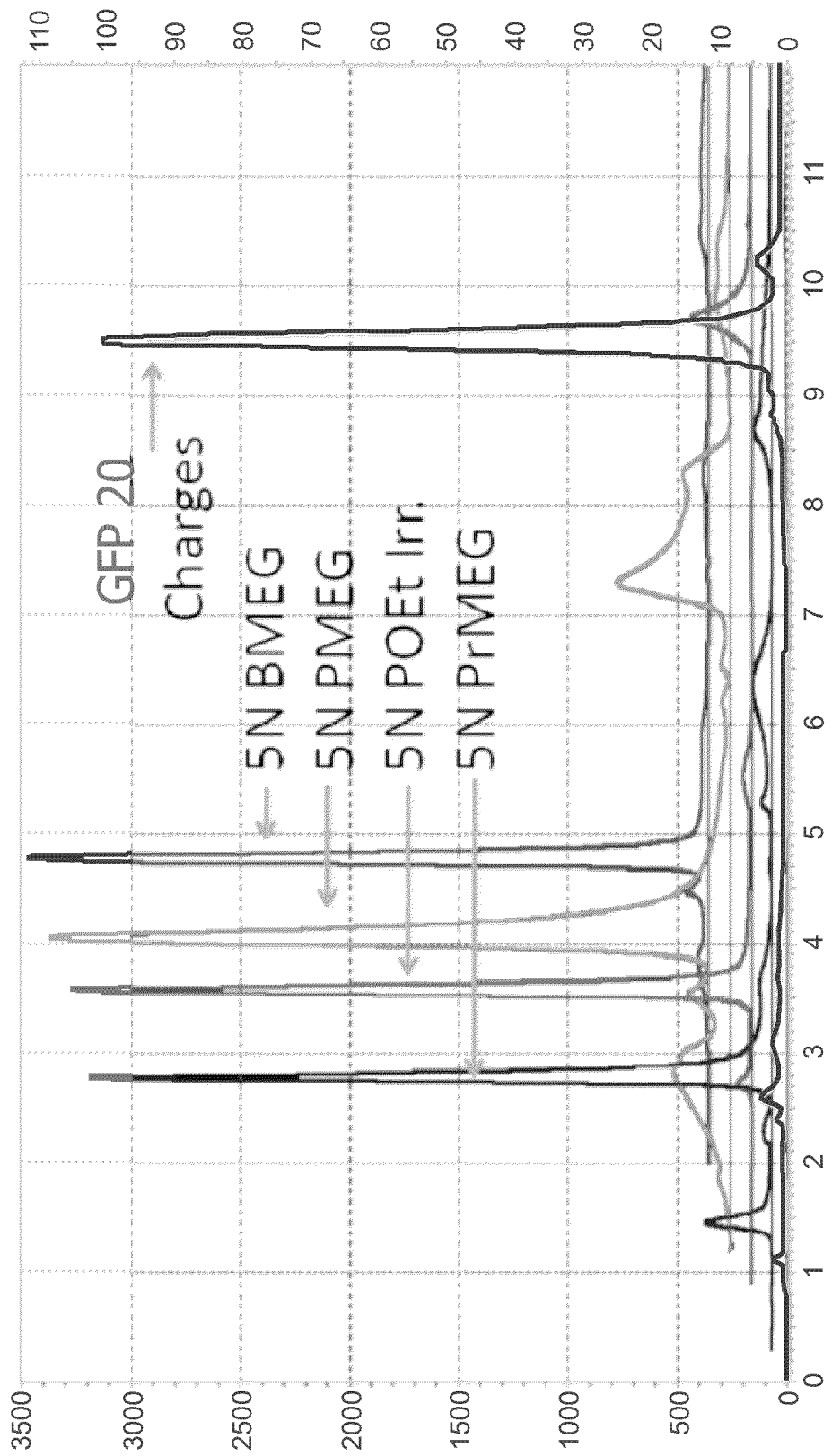

FIG. 6 is an ion exchange HPLC chromatogram overlay showing that the protecting groups in the guide strand of the dGFP sequence do not prematurely reverse. This result demonstrates that full length siRNN constructs of 21 nucleosides with at least 5 siRNN nucleotide insertions are able to be synthesized, isolated and purified.

Figure 7:
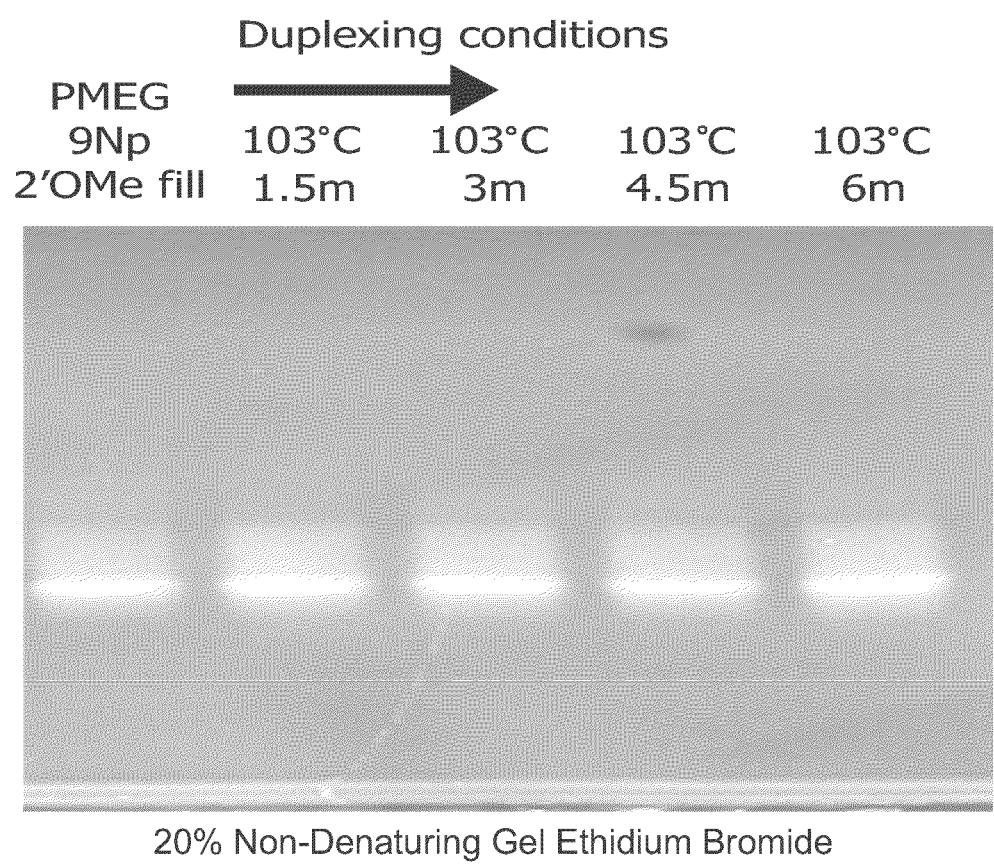

FIG. 7 is a photograph of a polyacrylamide gel stained with ethidium bromide. A 21mer RNN oligonucleotide containing 9 PMEG substitutions was heated at 103° C. for 0 min, 1.5 min, 3 min, 4.5 min and 6 min, as indicated and run on the gel.

Figure 8:
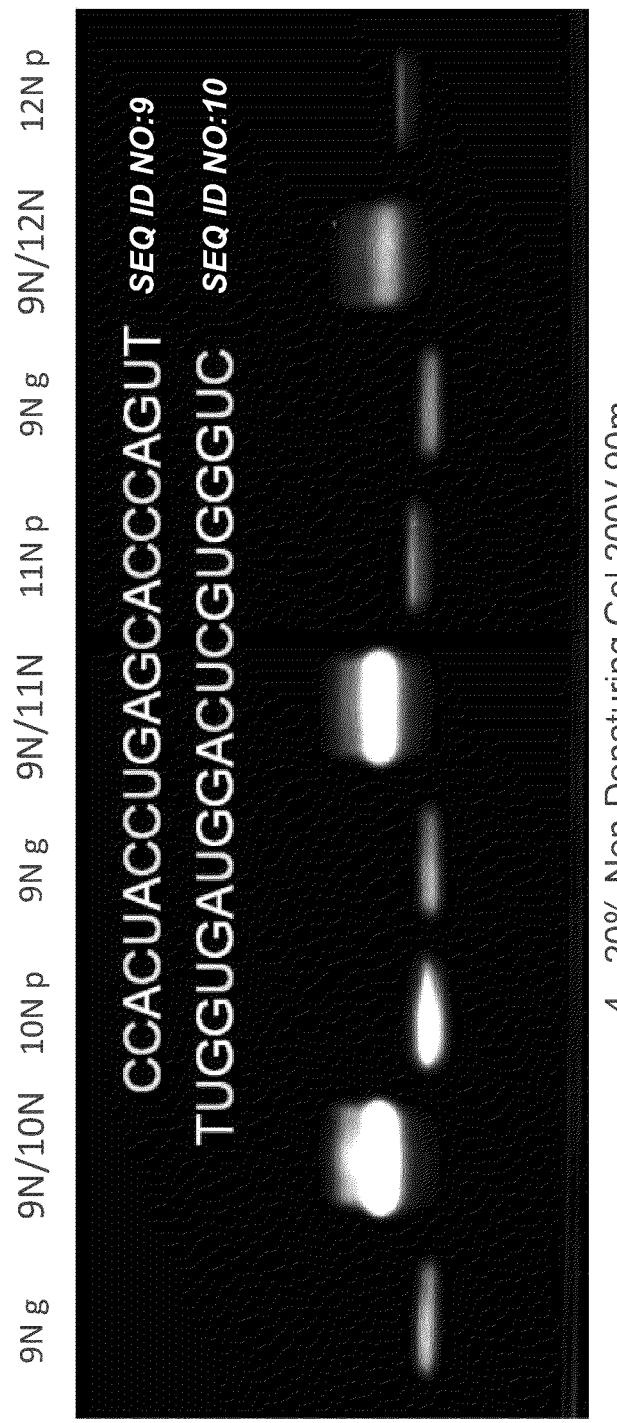

FIG. 8 is a photograph of a polyacrylamide gel demonstrating that the neutralizing groups do not interfere with hybridization of the indicated guide and passenger strands, containing the indicated number of PMEG derivatizations. "N" represents the number of PMEG derivatizations per oligo, "p" represents the passenger strand, and "g" represents the guide strand.

Figure 9:
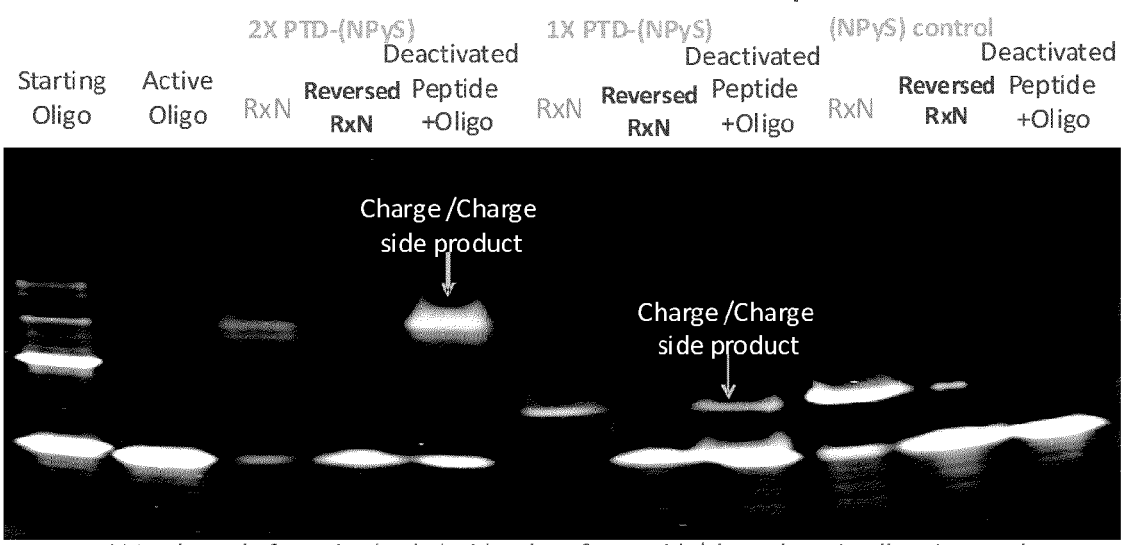

FIG. 9 is a photograph of a polyacrylamide gel stained with ethidium bromide demonstrating efficient coupling of NPyS activated 2×PTD, 1×TAT and Antennapedia to a 5' thiolated normal oligo through a disulfide bond.

Figure 10:
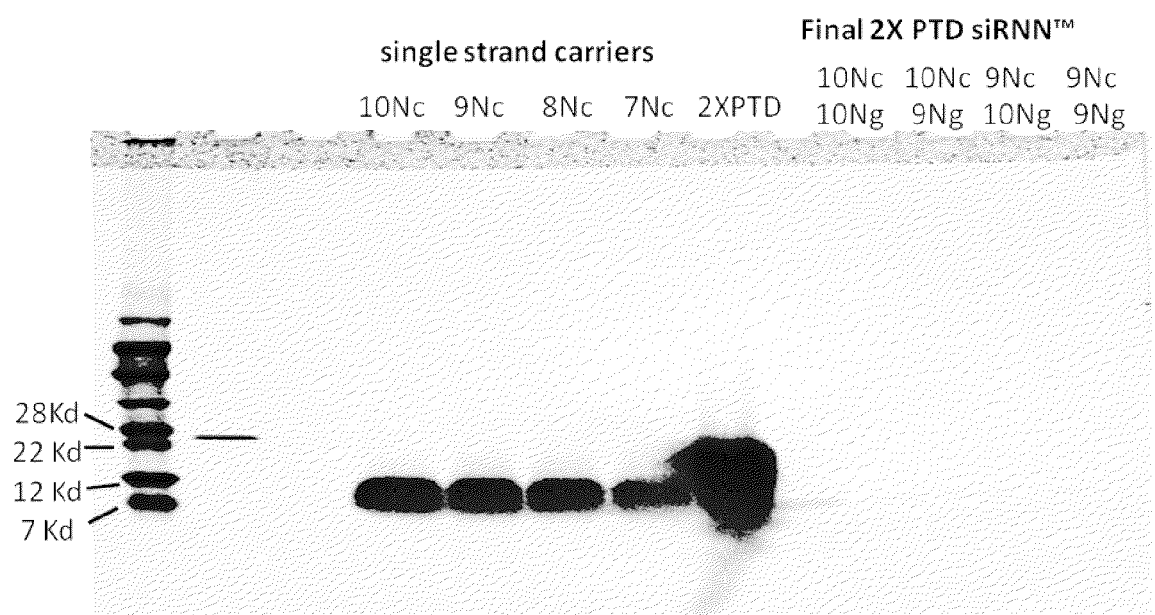

FIG. 10 is a photograph of an SDS-PAGE gel showing the hybridization of a siRNN oligonucleotide covalently liked with a PTD to a complementary siRNN oligonucleotide. The label N refers to the number of PMEG derivatizations in the oligo. The label "c" refers to the "carrier" strand oligonucleotide. The label "g" refers to the "guide" strand oligonucleotide. The lanes labeled "single strand carriers" were loaded with only the indicated single stranded RNN oligonucleotides. The lanes labeled "Final 2×PTD siRNN™" were loaded with the reaction product of the indicated carrier strand covalently linked to a 2×PTD and the complementary guide strand, following incubation under hybridization conditions.

DETAILED DESCRIPTION OF THE INVENTION

Embodiments disclosed herein relate systems and methods relating to the delivery of biomolecules, in particular anionic or negatively-charged biomolecules, into cells. The systems and methods relate to compounds useful as protecting groups that reversibly mask the negative charge of biomolecules, thereby increasing their lipophilicity and providing for enhanced delivery across cell membranes in vitro and in vivo.

Accordingly, in a first aspect, the embodiments disclosed herein relate to compounds useful as protecting groups that can be operably linked or incorporated (e.g., by a biolabile covalent bond such as a biolabile ester bond, a biolabile disulfide bone, or the like, or a non-covalent linkage), into a biomolecule such as a nucleotide, polynucleotide, oligonucleotide, or an analog thereof. The compounds described herein can be directly or indirectly linked or to an anionic biomolecule, such as phosphate groups or phosphorothioate groups on polynucleotides, and are engineered to be biolabile, such that the protecting groups are cleaved from the biomolecule upon intracellular delivery. As such, the compounds, compositions and methods disclosed herein are well-suited for use with polynucleotides, oligonucleotides and analogs thereof. The skilled artisan will appreciate, however, that the compounds or protecting groups can be operably coupled to biomolecules other than nucleotides and polynucleotides, and their derivatives. For example, the compounds or protecting groups disclosed herein can be operably linked to a protein, a small molecule, or other suitable compound.

In a second aspect, the embodiments disclosed herein relate to modified biomolecules, such as modified nucleosides, polynucleotides or oligonucleotides, comprising the compounds or protecting groups disclosed herein, as well as methods of making and using the same.

"Optional" or "optionally" means that the subsequently described event or circumstance may or may not occur, and that the description includes instances where said event or circumstance occurs and instances where it does not.

As used herein and in the appended claims, the singular forms "a," "and," and "the" include plural referents unless the context clearly dictates otherwise. Thus, for example, reference to "a cell" includes a plurality of cells.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Compounds/Protecting Groups

Provided herein are compounds that can be linked or coupled to an anionic group present on a biomolecule such as a polynucleotide, oligonucleotide, or analogs thereof. In some embodiments, the compounds can be represented by formula I:

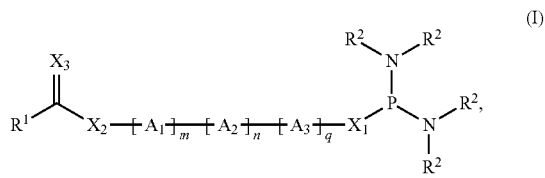

wherein:

$R^1$ is an optionally substituted substituent selected from the group consisting of $C_{1-6}$alkyl, $C_{1-6}$alkyl substituted with one or more hydroxyl groups, $C_{1-6}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, $C_{1-6}$alkylC(O)O—, arylC(O)O—, heteroarylC(O)O—, and heterocyclylC(O)O—;

each $R^2$ is individually $C_{1-6}$alkyl;

$X_1$ is O (oxygen) or S (sulfur);

$X_2$ is O (oxygen), NR$^3$, or S (sulfur);

$R^3$ is selected from the group consisting of H (hydrogen), $C_{1-6}$alkyl, $C_{1-6}$alkylC(O)—, $C_{1-6}$alkylOC(O)—, $C_{1-6}$alkyl-NHC(O)—, $C_{1-6}$alkylS(O)$_2$—, optionally substituted arylC (O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

$X_3$ is O (oxygen), NH, or S (sulfur);

each $A_1$ is —C(R$^4$)$_2$—;

each $A_2$ is individually selected from the group consisting of —NR$^6$—, —C(R$^5$)$_2$NR$^6$—, —C(R$^5$)$_2$O—, —C(R$^5$)$_2$S—, —C(R$^5$)$_2$Se—, —C(R$^5$)$_2$C(R$^5$)$_2$NR$^6$—, —C(R$^5$)$_2$C(R$^5$)$_2$O—, —C(R$^5$)$_2$C(R$^5$)$_2$S—, —C(R$^5$)$_2$C(R$^5$)$_2$Se—, and —C(R$^5$)$_2$—;

each $A_3$ is —C(R$^7$)$_2$—;

m is an integer selected from 1, 2, or 3;

n is an integer selected from 1, 2, or 3;

q is an integer selected from 1, 2, or 3;

each C(R$^4$)$_2$ is independently selected, wherein each R$^4$ is individually selected from the group consisting of H (hydrogen), halo, C$_{1-6}$alkyl, and C$_{1-6}$alkyl substituted with up to 5 fluorine, or optionally two R$^4$ groups are taken together with the carbon to which they are attached to form an optionally substituted C$_{3-7}$cycloalkyl group;

each C(R$^5$)$_2$ is independently selected, wherein each R$^5$ is individually selected from the group consisting of H (hydrogen), halo, C$_{1-6}$alkyl, and C$_{1-6}$alkyl substituted with up to 5 fluorine; or two R$^5$ are optionally taken together to form an oxo group;

each R$^6$ is individually selected from the group consisting of H (hydrogen), C$_{1-6}$alkyl, C$_{1-6}$alkylC(O)—, C$_{1-6}$alkylOC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—; and each C(R$^7$)$_2$ is independently selected, wherein each R$^7$ is individually selected from the group consisting of H (hydrogen), halo, C$_{1-6}$alkyl, and C$_{1-6}$alkyl substituted with up to 5 fluorine, or optionally two R$^7$ groups are taken together with the carbon to which they are attached to form an optionally substituted C$_{3-7}$cycloalkyl group.

In some embodiments, the compounds can be represented by formula II:

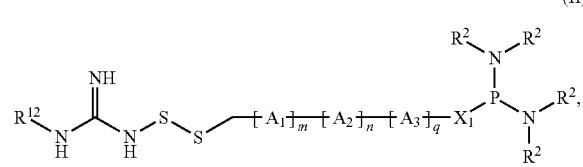

(II)

wherein:

each R$^2$ is individually C$_{1-6}$alkyl; or guanidine protecting group;

$X_1$ is O (oxygen) or S (sulfur);

each $A_1$ is —C(R$^4$)$_2$—;

each $A_2$ is individually selected from the group consisting of —NR$^6$—, —C(R$^5$)$_2$NR$^6$—, —C(R$^5$)$_2$O—, —C(R$^5$)$_2$S—, —C(R$^5$)$_2$Se—, —C(R$^5$)$_2$C(R$^5$)$_2$NR$^6$—, —C(R$^5$)$_2$C(R$^5$)$_2$O—, —C(R$^5$)$_2$C(R$^5$)$_2$S—, —C(R$^5$)$_2$C(R$^5$)$_2$Se—, and —C(R$^5$)$_2$—;

each $A_3$ is —C(R$^7$)$_2$—;

m is an integer selected from 1, 2, or 3;

n is an integer selected from 1, 2, or 3;

q is an integer selected from 1, 2, or 3;

each C(R$^4$)$_2$ is independently selected, wherein each R$^4$ is individually selected from the group consisting of H (hydrogen), halo, C$_{1-6}$alkyl, and C$_{1-6}$alkyl substituted with up to 5 fluorine, or optionally two R$^4$ groups are taken together with the carbon to which they are attached to form an optionally substituted C$_{3-7}$cycloalkyl group;

each C(R$^5$)$_2$ is independently selected, wherein each R$^5$ is individually selected from the group consisting of H (hydrogen), halo, C$_{1-6}$alkyl, and C$_{1-6}$alkyl substituted with up to 5 fluorine; or two R$^5$ are optionally taken together to form an oxo group;

each R$^6$ is individually selected from the group consisting of H (hydrogen), C$_{1-6}$alkyl, C$_{1-6}$alkylC(O)—, C$_{1-6}$alkylOC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each C(R$^7$)$_2$ is independently selected, wherein each R$^7$ is individually selected from the group consisting of H (hydrogen), halo, C$_{1-6}$alkyl, and C$_{1-6}$alkyl substituted with up to 5 fluorine, or optionally two R$^7$ groups are taken together with the carbon to which they are attached to form an optionally substituted C$_{3-7}$cycloalkyl group; and R$^{12}$ is H (hydrogen), alkylOC(O)—, or an optionally substituted arylOC(O)—.

In some embodiments, the compounds can be represented by formula VI:

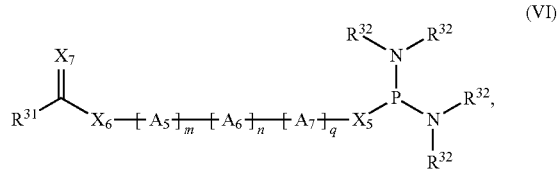

(VI)

wherein:

R$^{31}$ is an optionally substituted substituent selected from the group consisting of C$_{1-8}$alkyl, C$_{1-8}$alkenyl, C$_{1-6}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, C$_{1-6}$alkylC(O)O—, arylC(O)O—, heteroarylC(O)O—, heterocyclylC(O)O—, and C$_{1-8}$alkyl substituted with one or more hydroxyl groups; or R$^{31}$ is selected from the group consisting of (R$^{38}$)$_4$N(CH$_2$)$_r$—, (R$^{38}$)$_3$C(CH$_2$)$_r$—, (R$^{38}$)$_3$CNH(CH$_2$)$_r$—, HS(CH$_2$)$_r$—, C$_{1-8}$heteroalkyl, and guanidiny (CH$_2$)$_r$—;

each R$^{32}$ is individually C$_{1-6}$alkyl;

$X_5$ is O (oxygen) or S (sulfur);

$X_6$ is O (oxygen), NR$^{33}$, Se (selenium), or S (sulfur);

R$^{33}$ is selected from the group consisting of H (hydrogen), C$_{1-6}$alkyl, C$_{1-6}$alkylC(O)—, C$_{1-6}$alkylOC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

$X_7$ is O (oxygen), NH, or S (sulfur);

each $A_5$ is —C(R$^{34}$)$_2$—;

each $A_6$ is individually selected from the group consisting of —NR$^{36}$—, —C(R$^{35}$)$_2$NR$^{36}$—, —C(R$^{35}$)$_2$O—, —C(R$^{35}$)$_2$S—, —C(R$^{35}$)$_2$Se—, —OC(R$^{35}$)$_2$O—, —SC(R$^{35}$)$_2$S—, —SeC(R$^{35}$)$_2$Se—, —C(R$^{35}$)$_2$C(R$^{35}$)$_2$NR$^{36}$—, —C(R$^{35}$)$_2$C(R$^{35}$)$_2$O—, —C(R$^{35}$)$_2$C(R$^{35}$)$_2$S—, —C(R$^{35}$)$_2$C(R$^{35}$)$_2$Se—, and —C(R$^{35}$)$_2$—;

each A$_7$ is —C(R$^{37}$)$_2$—;

m is an integer selected from 1, 2, or 3;

n is an integer selected from 1, 2, or 3;

q is an integer selected from 1, 2, or 3;

each r is independently an integer selected from 0, 1, 2, 3, 4, 5, or 6;

each C(R$^{34}$)$_2$ is independently selected, wherein each R$^{34}$ is individually selected from the group consisting of H (hydrogen), halo, C$_{1-6}$alkyl, C$_{1-6}$alkoxy, and C$_{1-6}$alkyl substituted with up to 5 fluorine, or optionally two R$^{34}$ groups are taken together with the carbon to which they are attached to form an optionally substituted C$_{3-7}$cycloalkyl group;

each C(R$^{35}$)$_2$ is independently selected, wherein each R$^{35}$ is individually selected from the group consisting of H (hydrogen), halo, C$_{1-6}$alkyl, C$_{1-6}$alkoxy, and C$_{1-6}$alkyl substituted with up to 5 fluorine; or two R$^{35}$ are optionally taken together to form an oxo group;

each R$^{36}$ is individually selected from the group consisting of H (hydrogen), C$_{1-6}$alkyl, C$_{1-6}$alkylC(O)—, C$_{1-6}$alkyl OC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each C(R$^{37}$)$_2$ is independently selected, wherein each R$^{37}$ is individually selected from the group consisting of H (hydrogen), halo, C$_{1-6}$alkyl, C$_{1-6}$alkoxy, and C$_{1-6}$alkyl substituted with up to 5 fluorine, or optionally two R$^{37}$ groups are taken together with the carbon to which they are attached to form an optionally substituted C$_{3-7}$cycloalkyl group;

R$^{38}$ is selected from the group consisting of H (hydrogen), R$^{39}$(CH$_2$)$_r$—, optionally substituted C$_{1-6}$alkyl, optionally substituted C$_{3-7}$alkyl, optionally substituted arylalkyl, and optionally substituted aryl;

R$^{39}$ is selected from the group consisting of H (hydrogen), halo, R$^{40}$O—, and optionally substituted C$_{1-6}$alkoxyl; and R$^{40}$ is selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—.

In some embodiments, the compounds of Formula VI can be selected from the group consisting of:

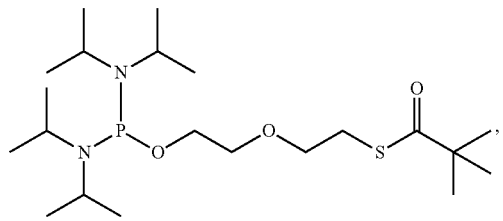

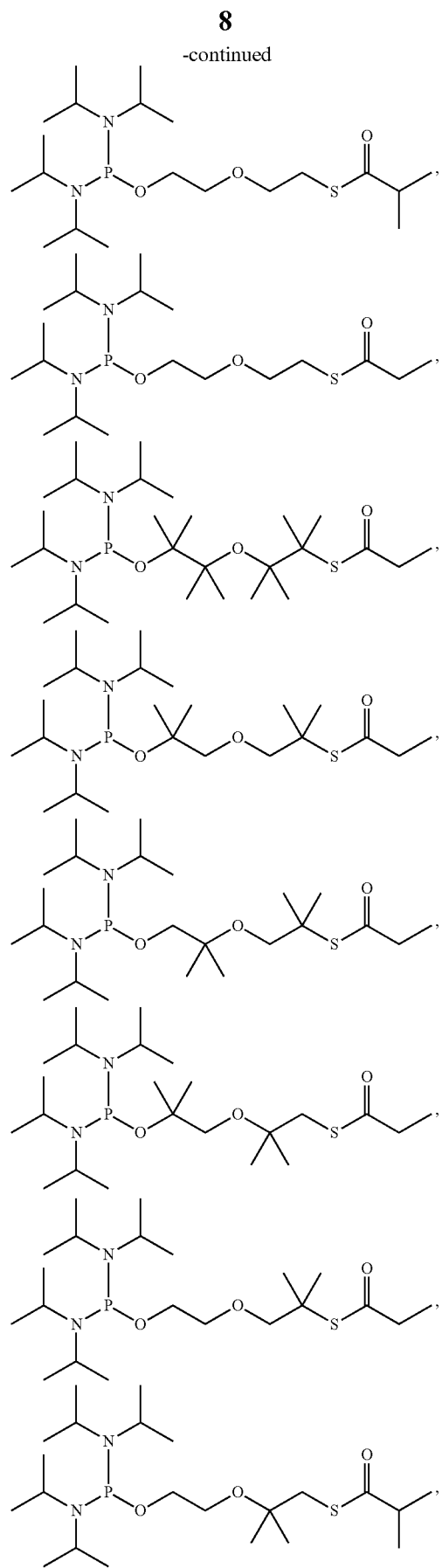

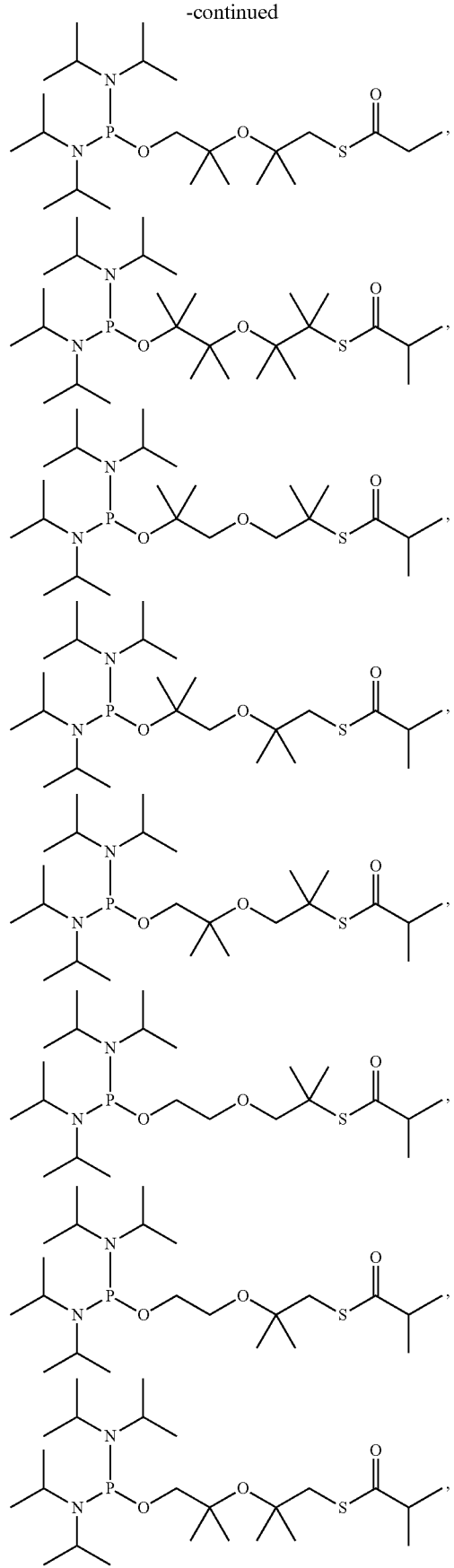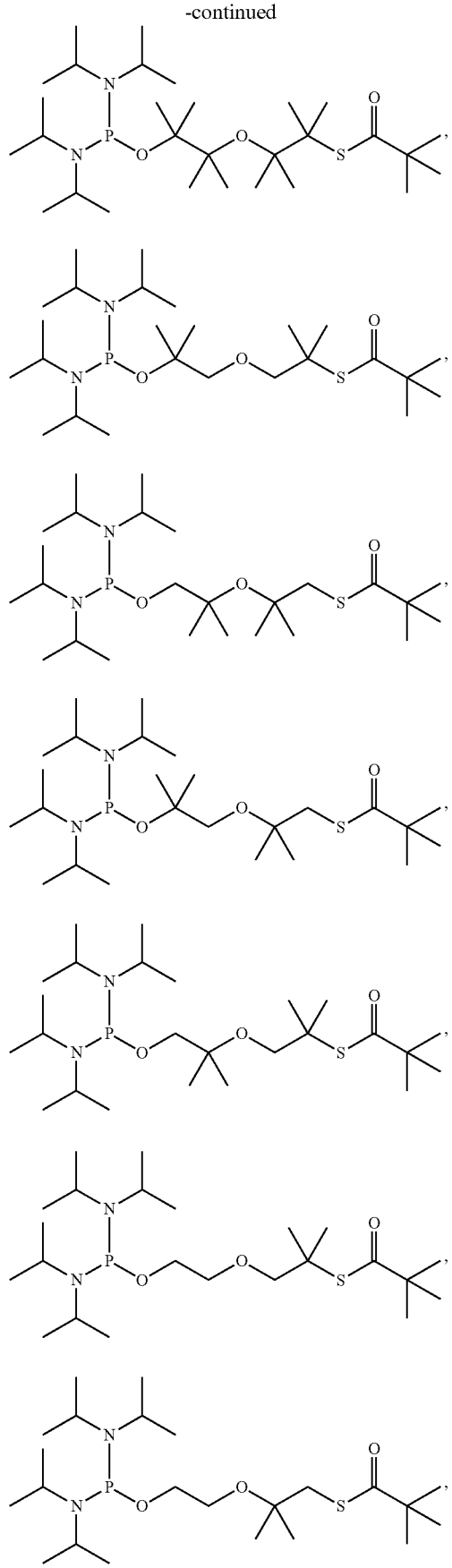

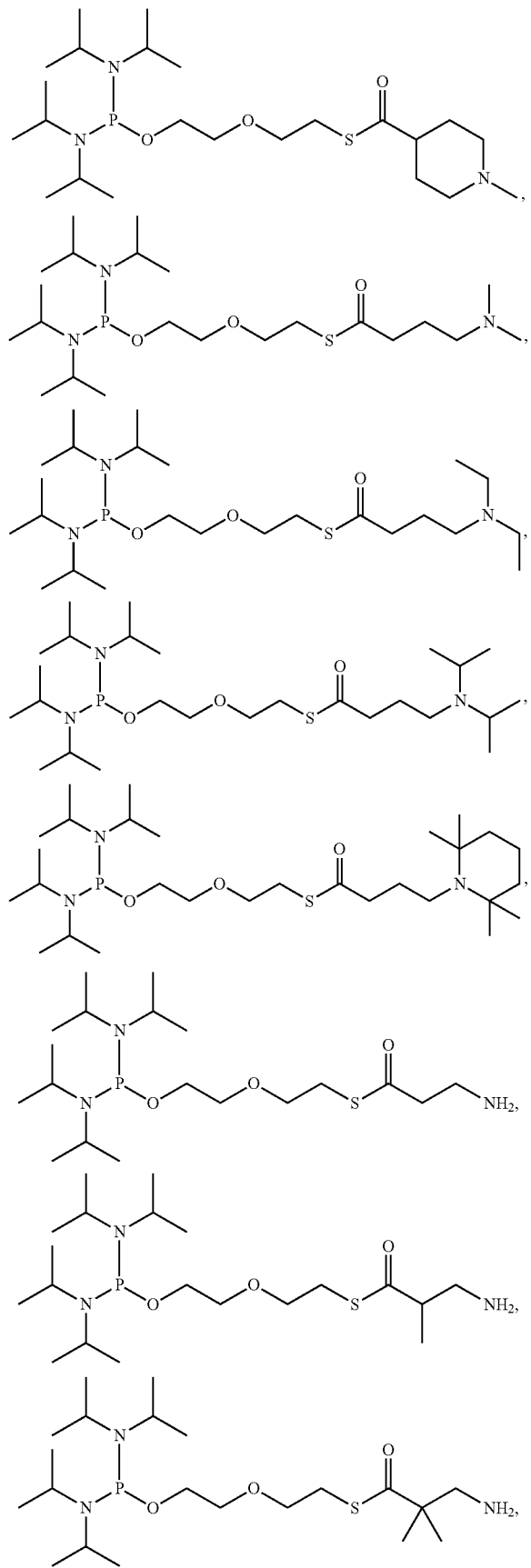
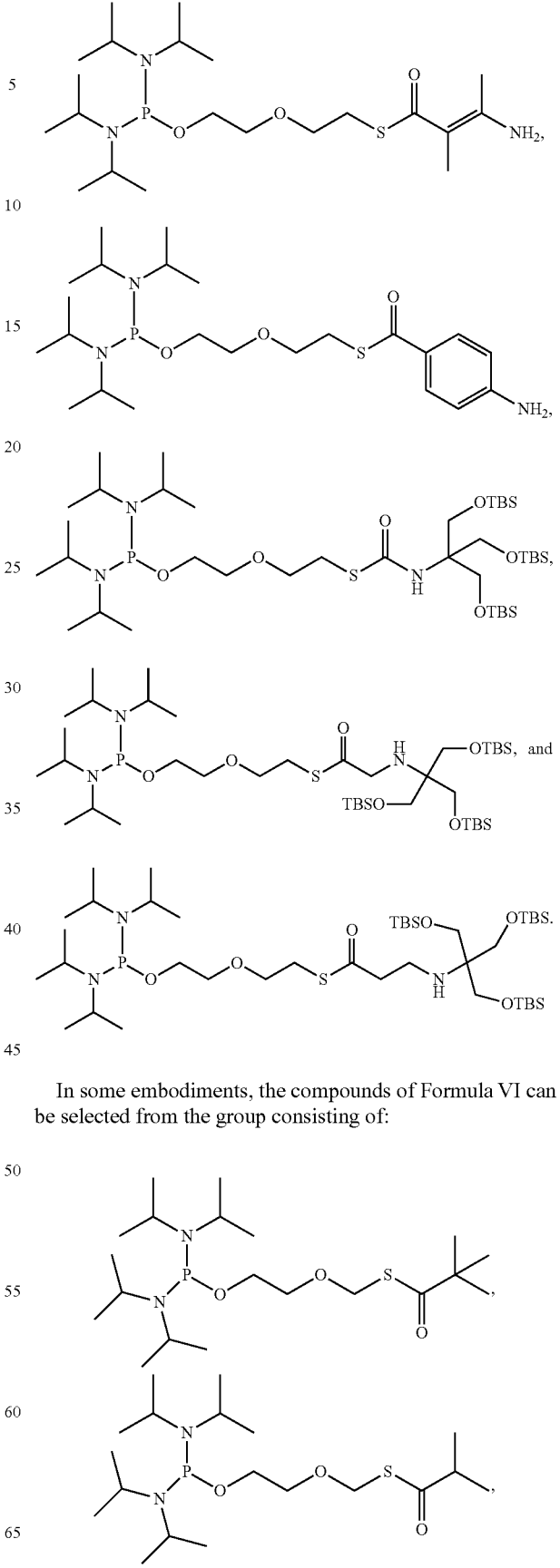
In some embodiments, the compounds of Formula VI can be selected from the group consisting of:

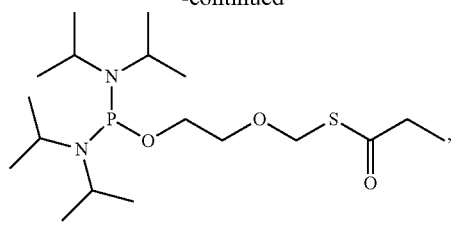
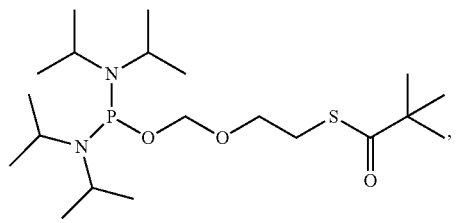
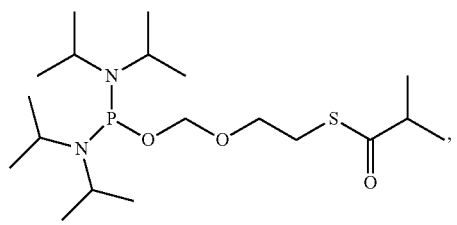
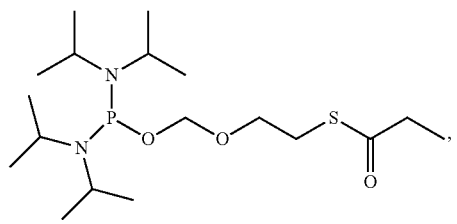
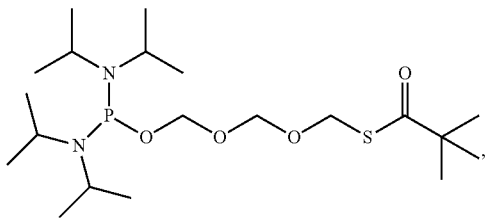
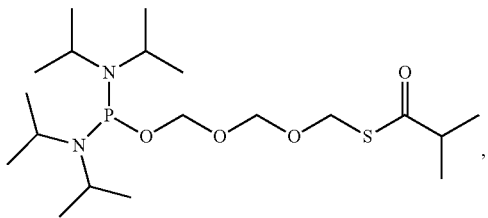
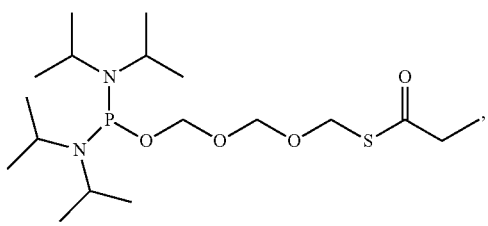
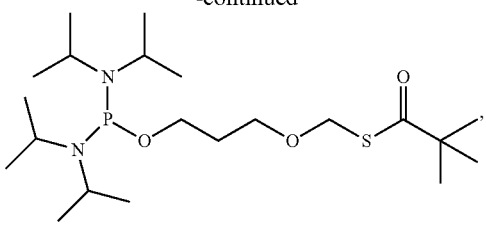
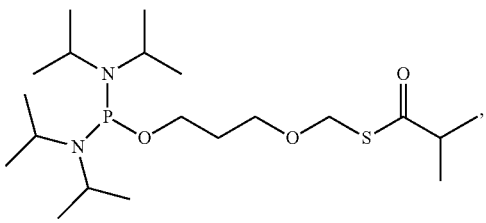
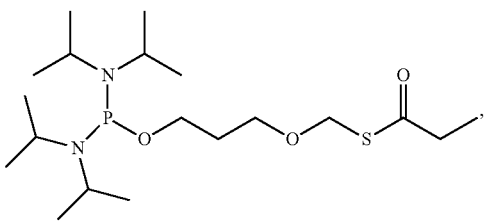
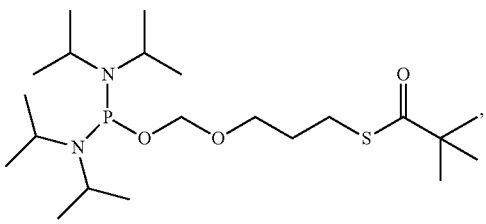
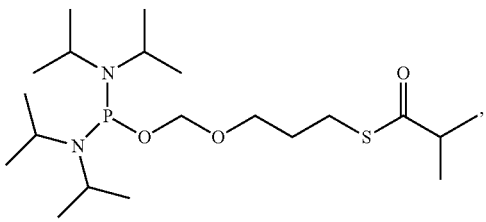
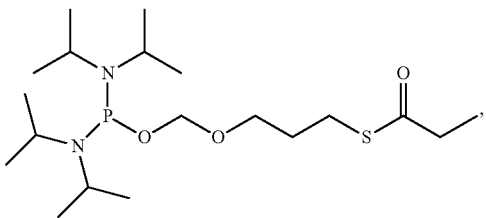
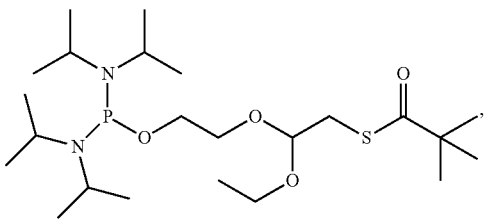

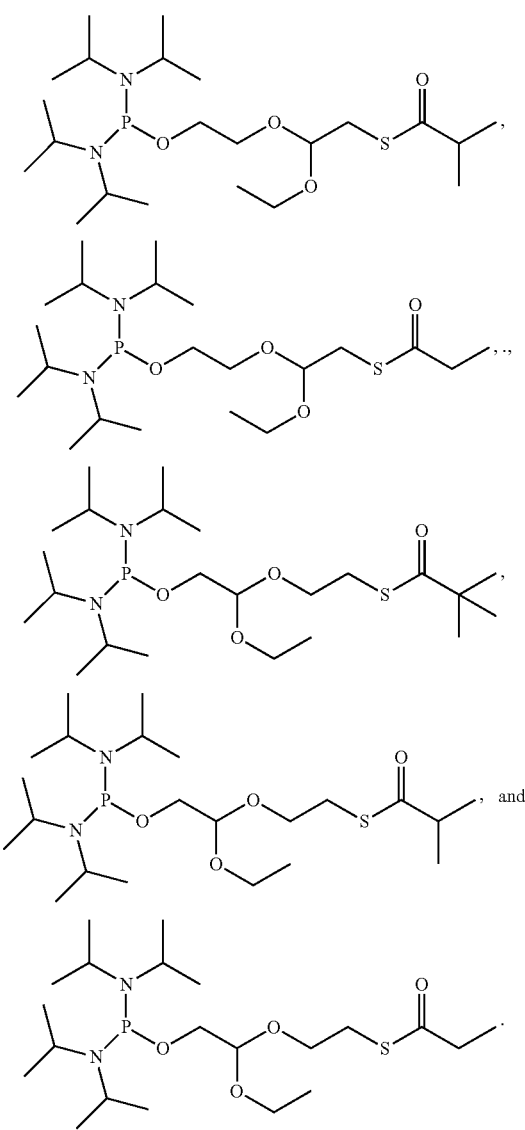
In some embodiments, the compounds of Formula VI can be selected from the group consisting of:
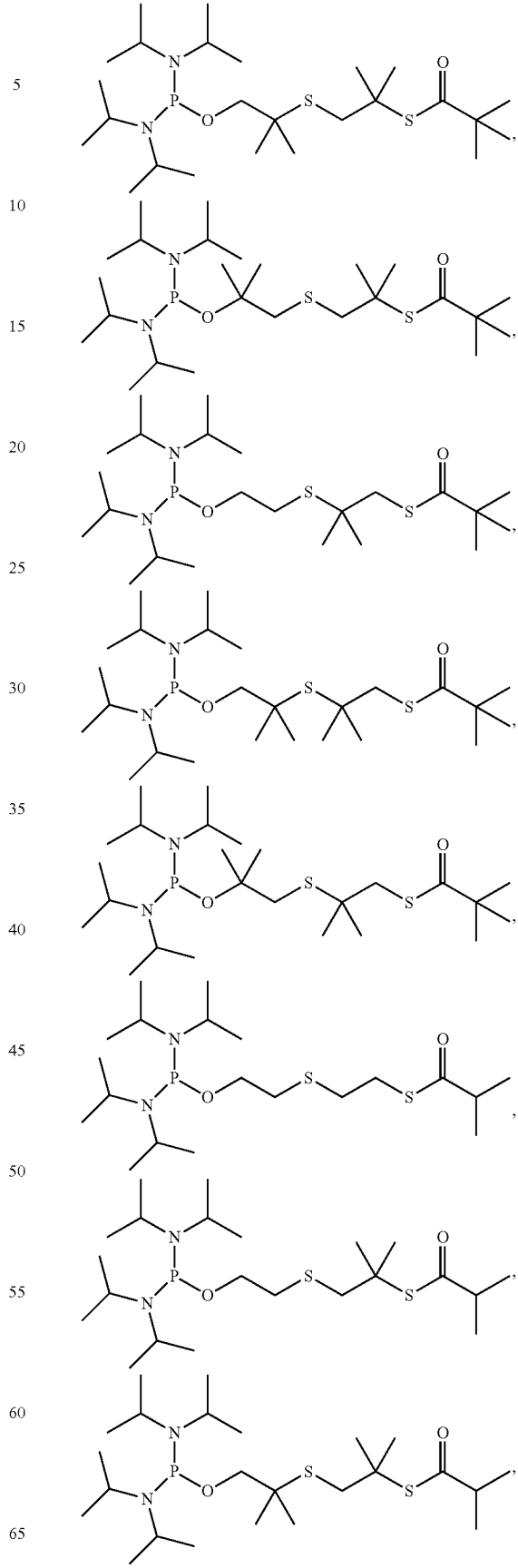

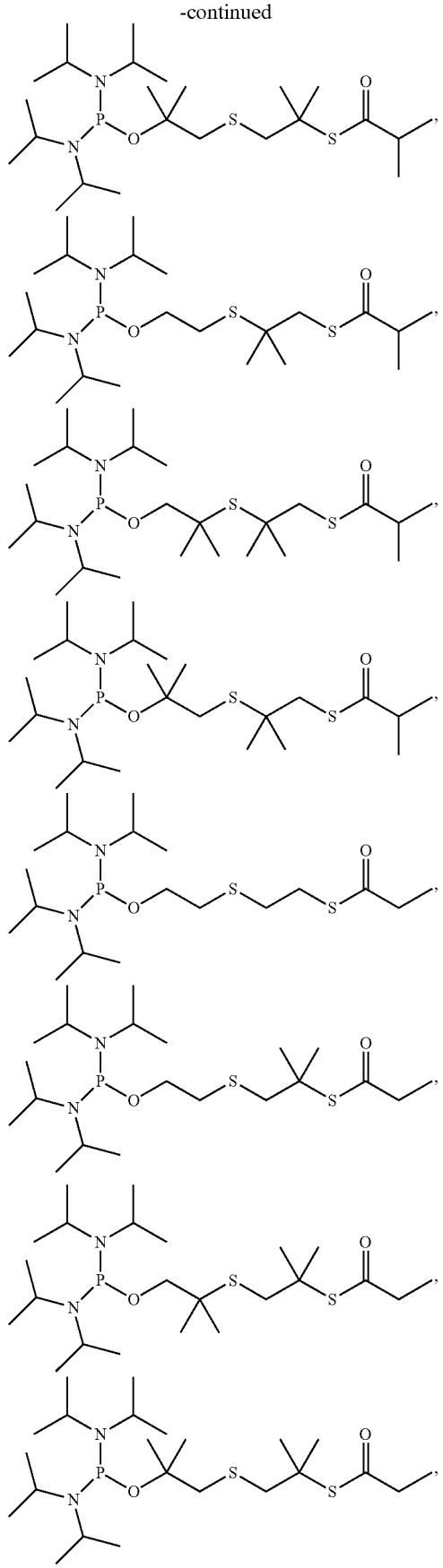
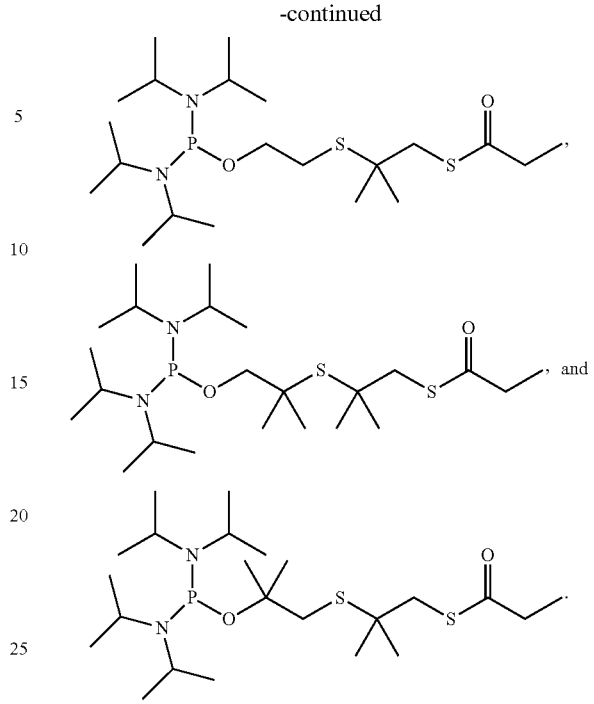
In some embodiments, the compounds of Formula VI can be selected from the group consisting of:
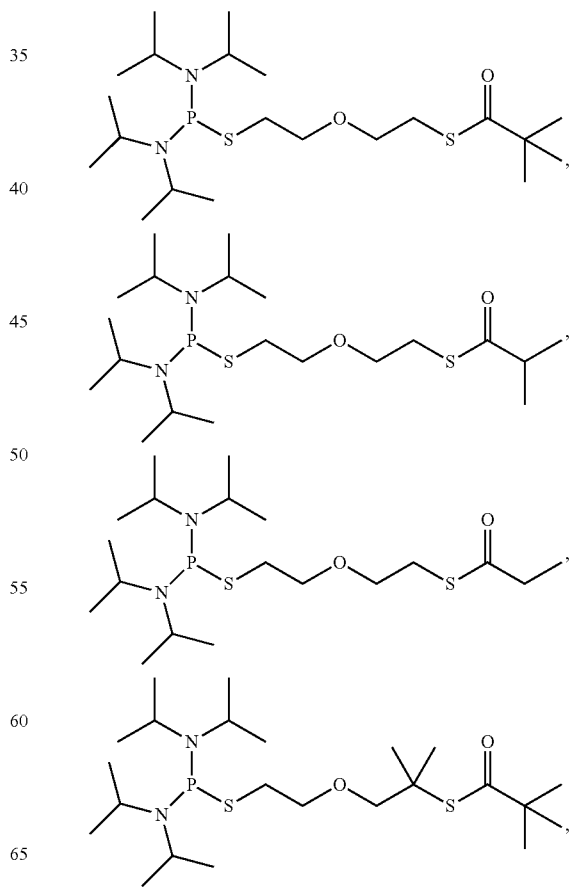

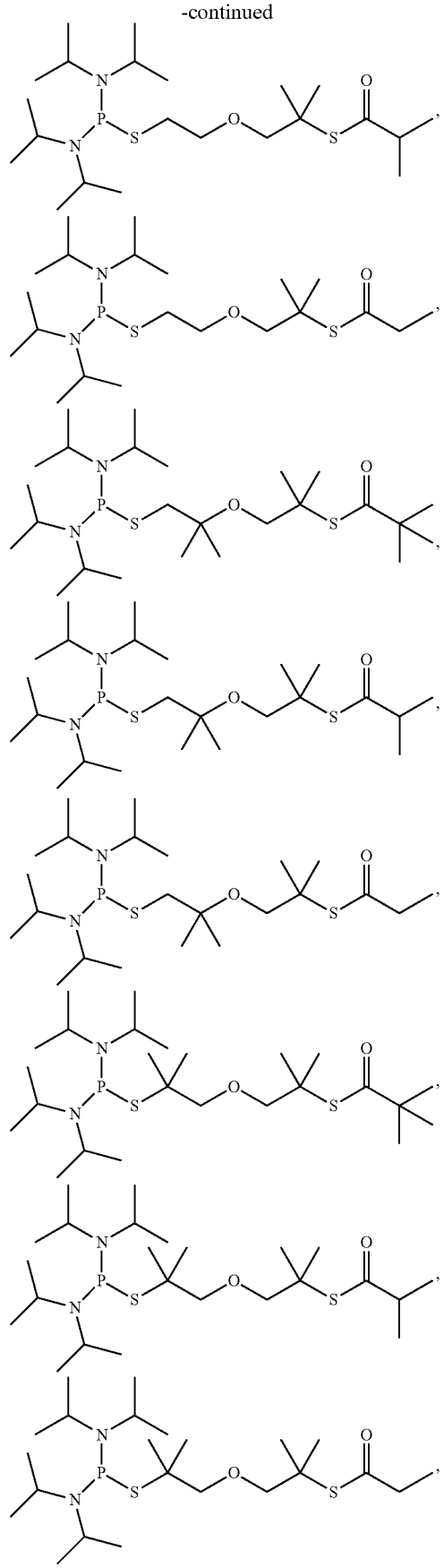
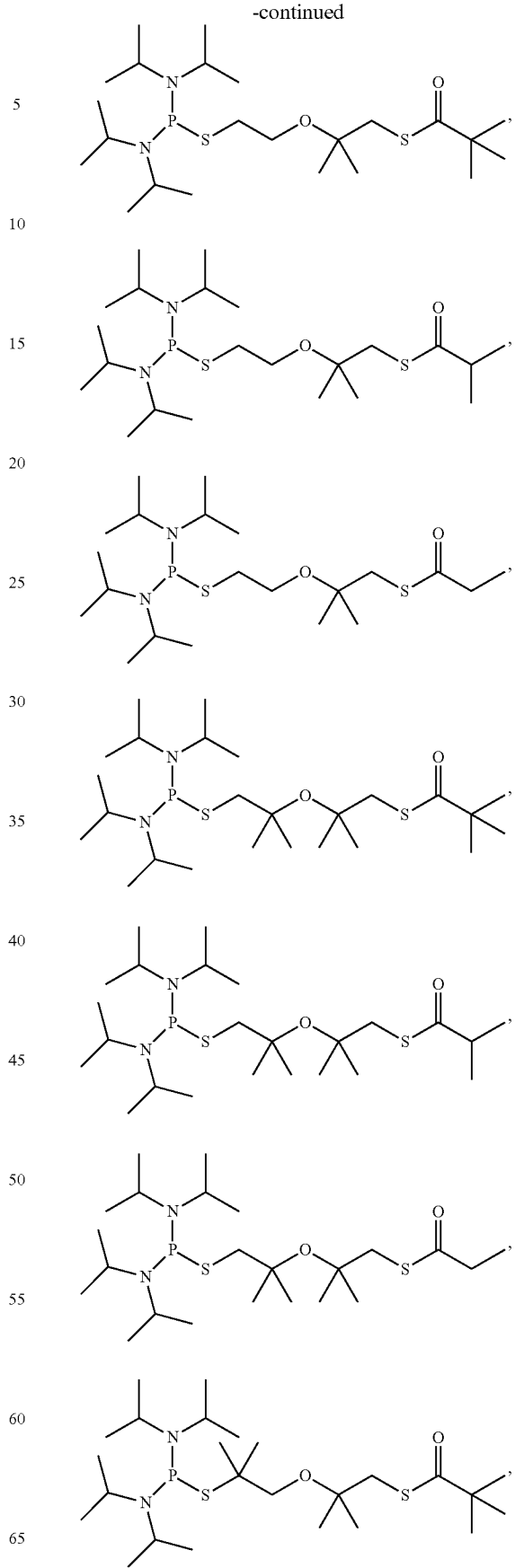

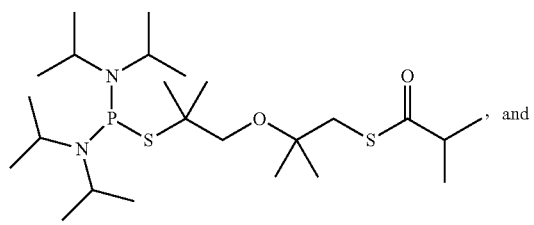, and
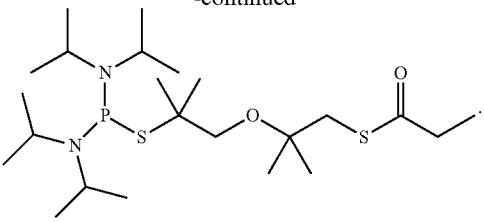
In some embodiments, the compounds of Formula VI can be selected from the group consisting of:
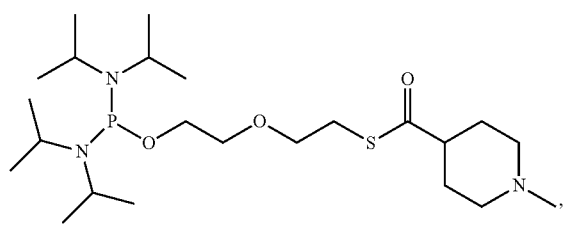
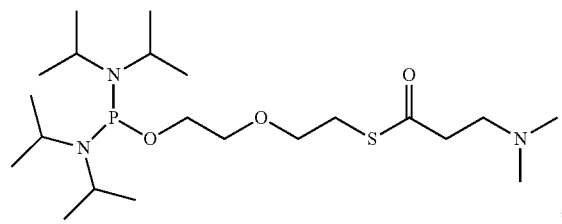,
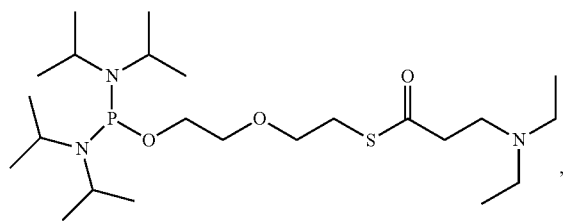,
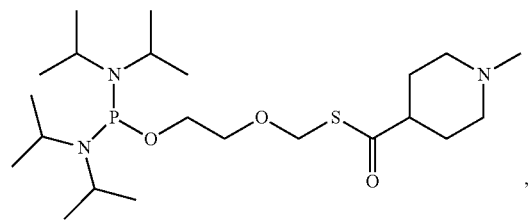,
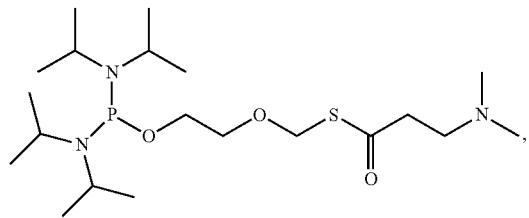,
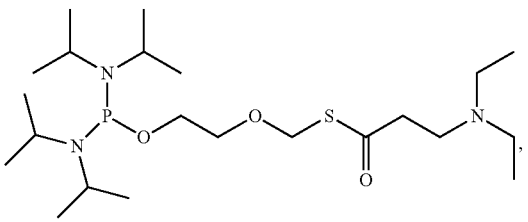,
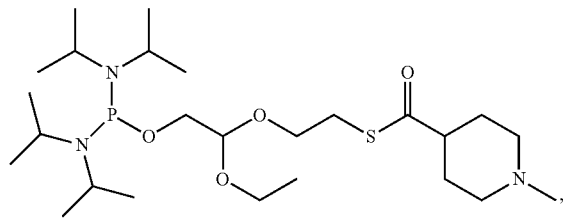,
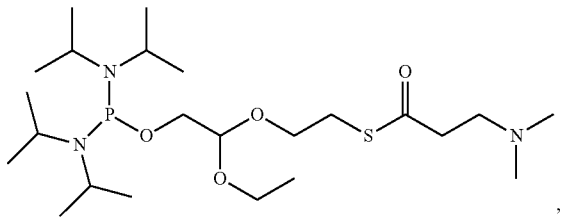,
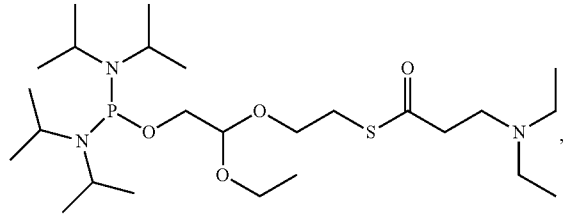,
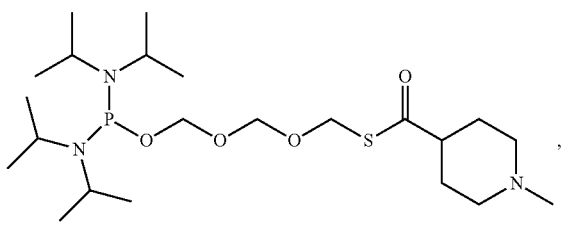,
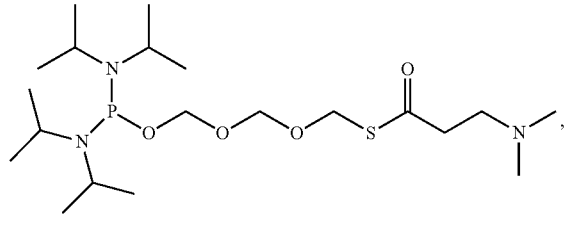,
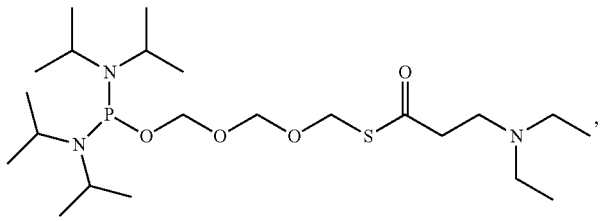, 23
24
-continued
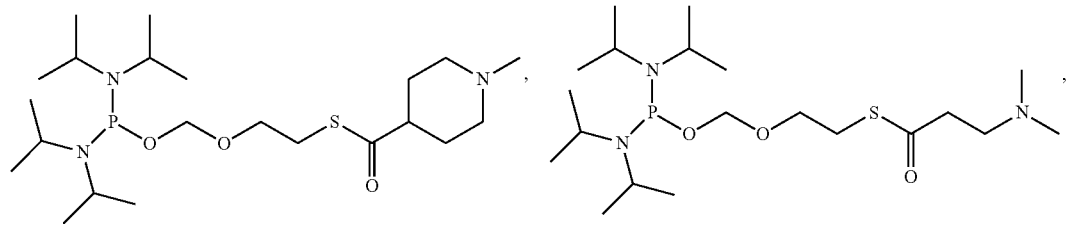
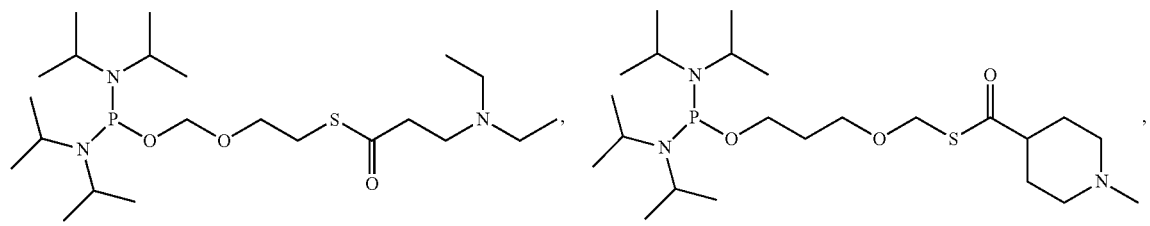
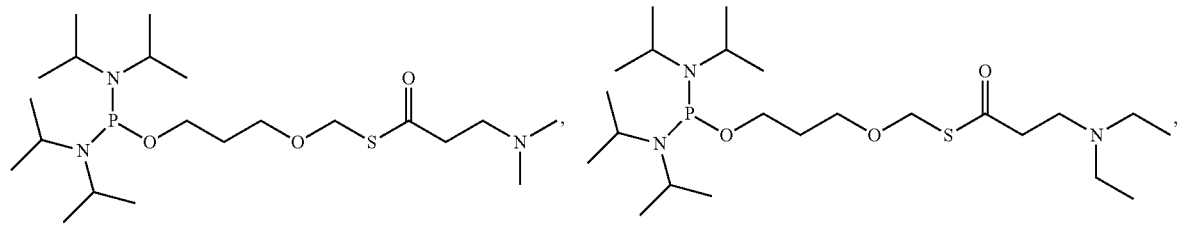
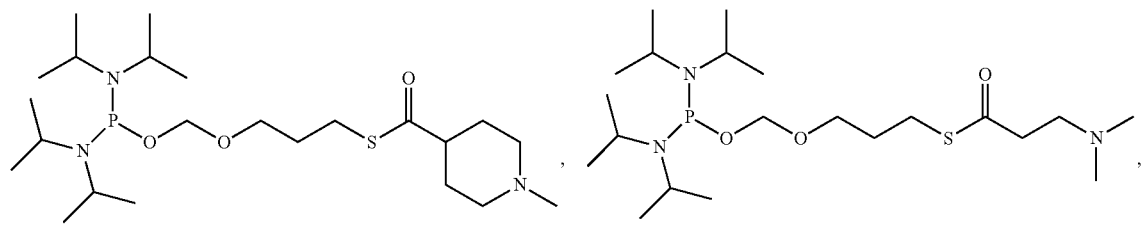
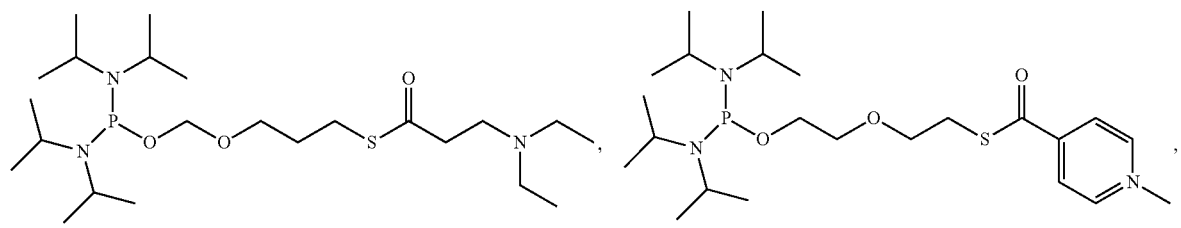
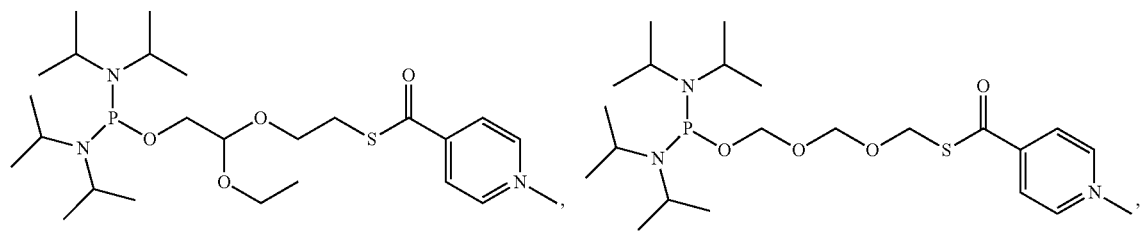
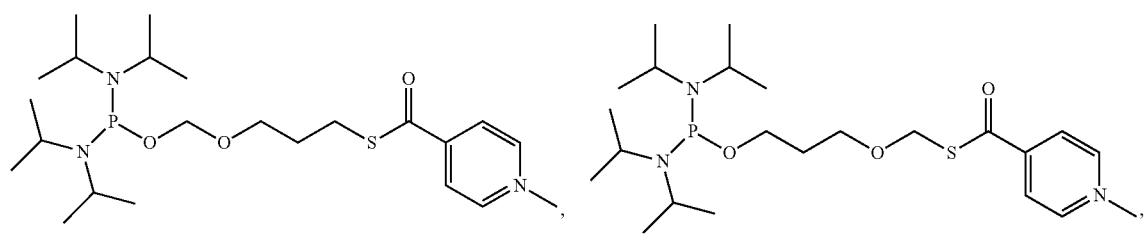

25
-continued
26
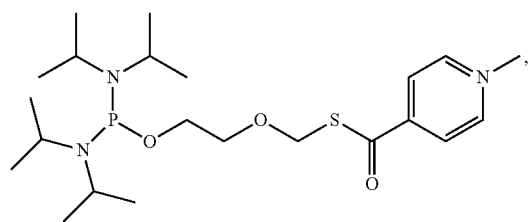
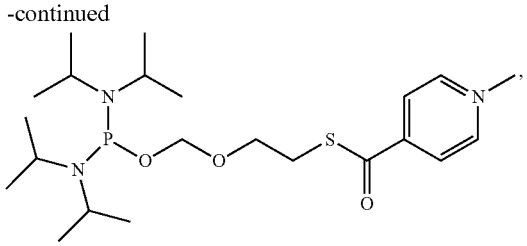
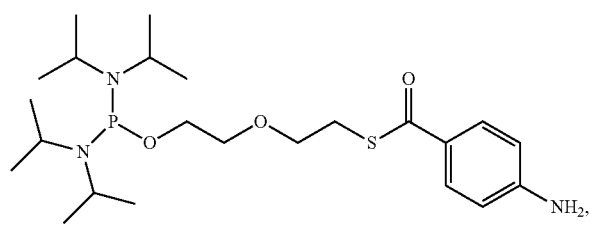
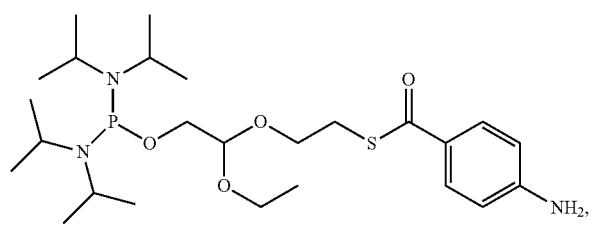
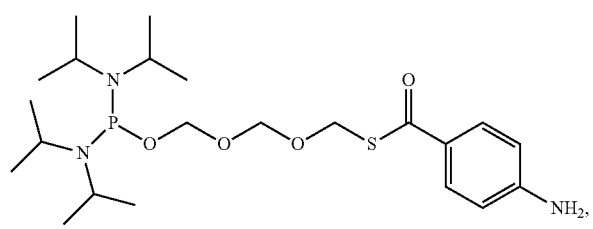
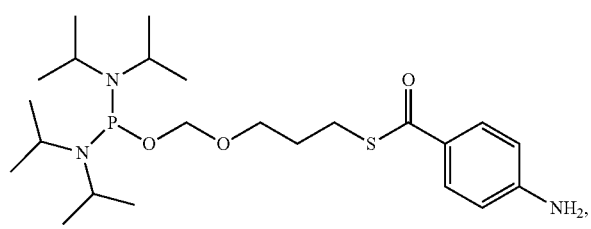
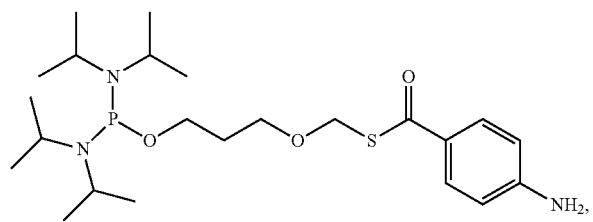
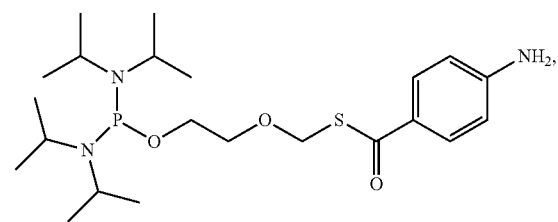
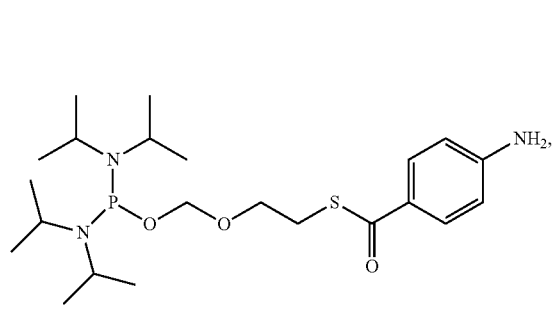
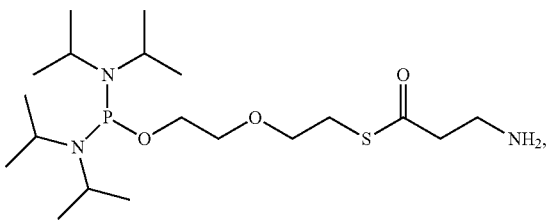
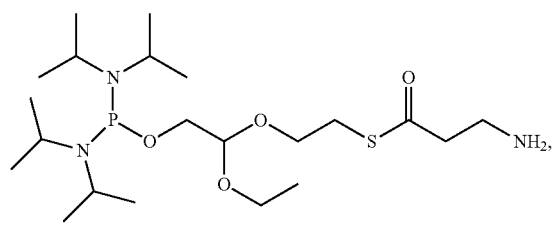
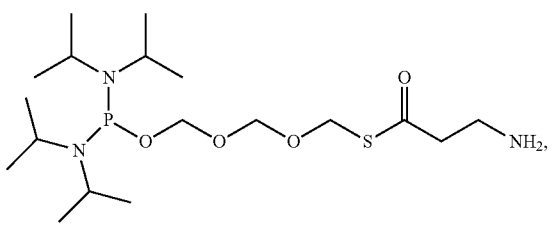

-continued
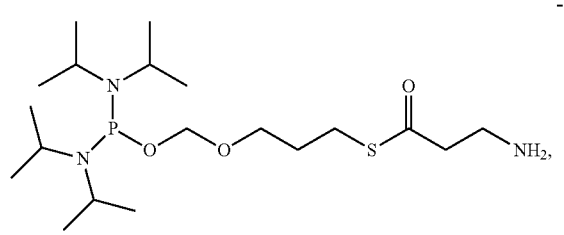
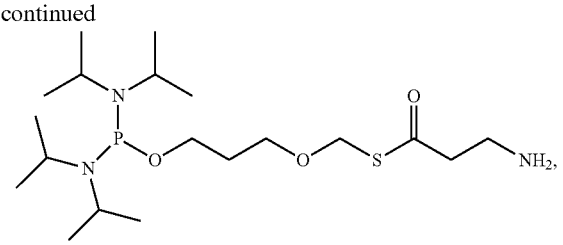
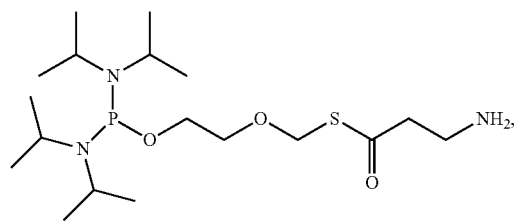
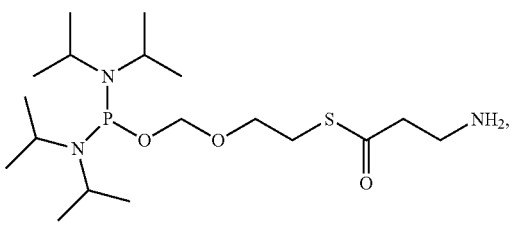
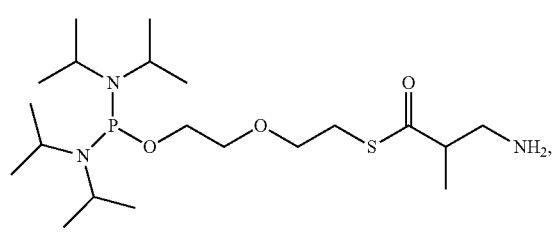
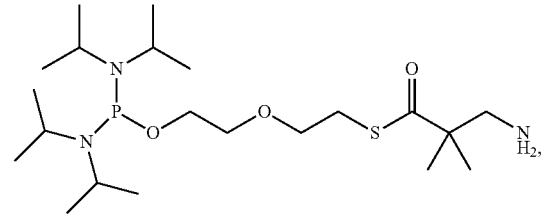
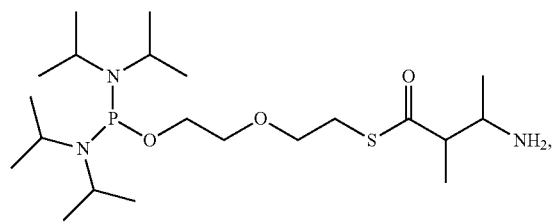
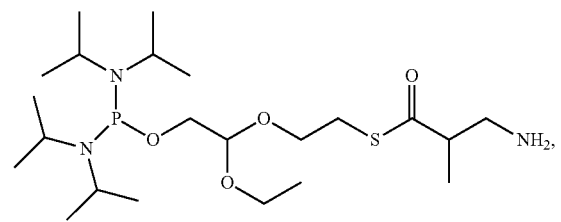
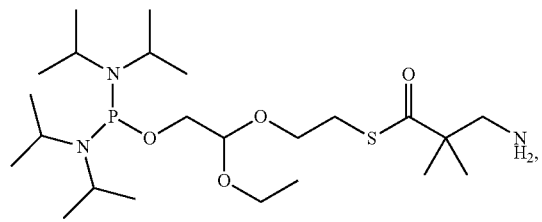
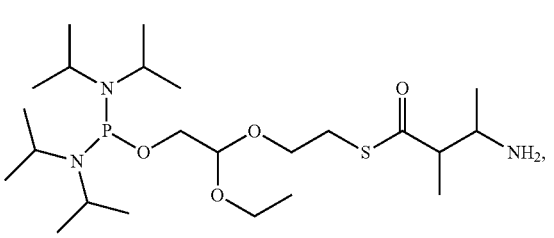
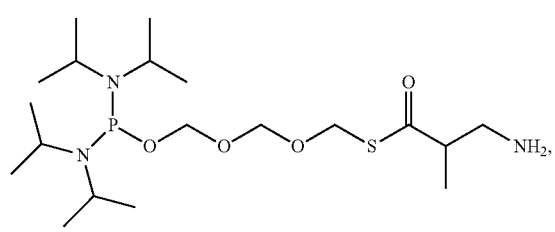
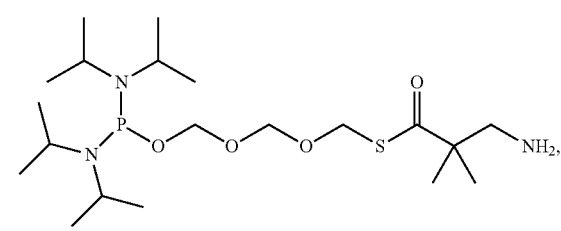
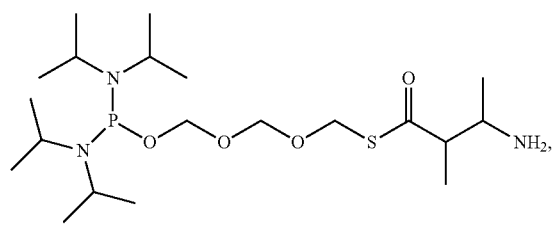
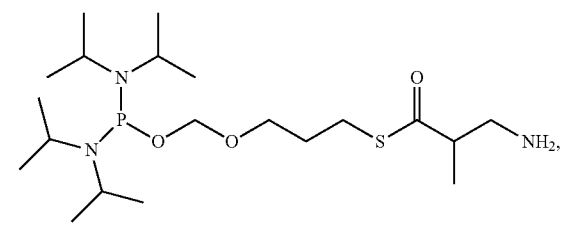

-continued
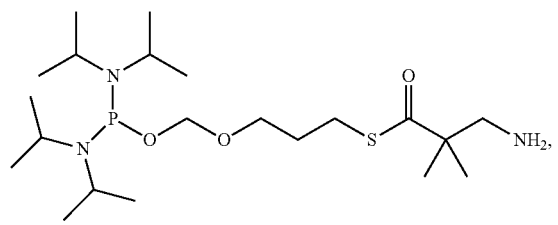
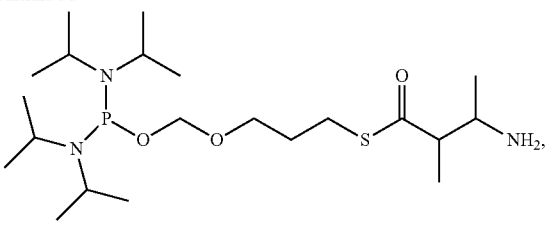
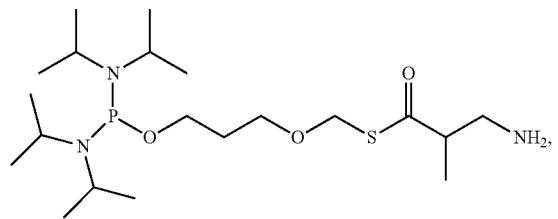
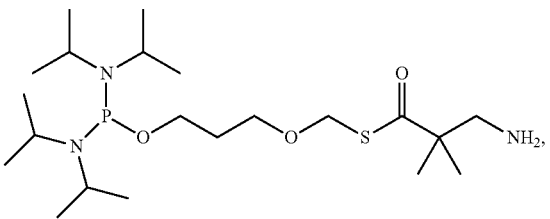
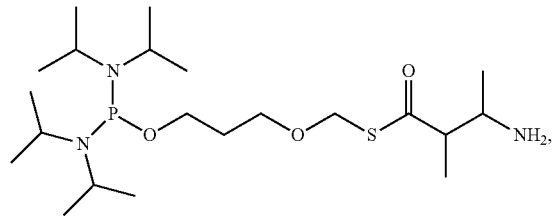
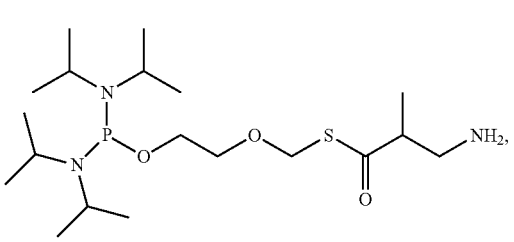
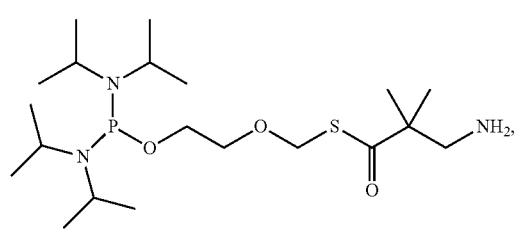
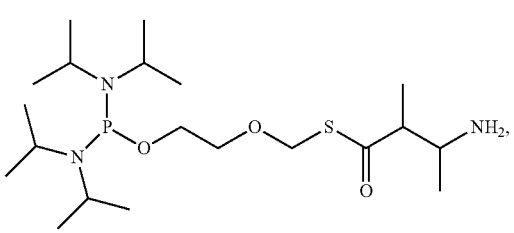
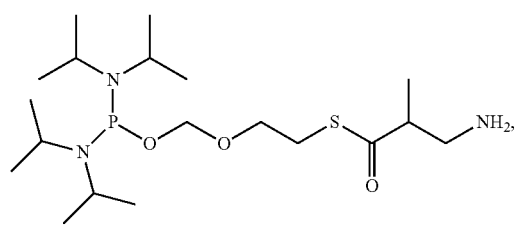
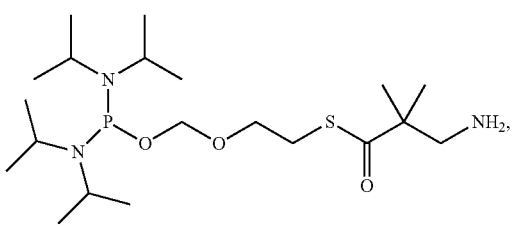
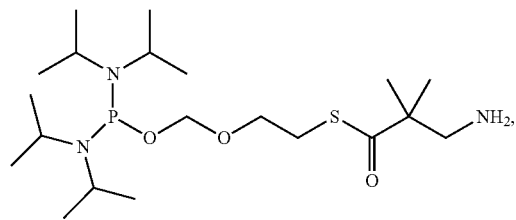
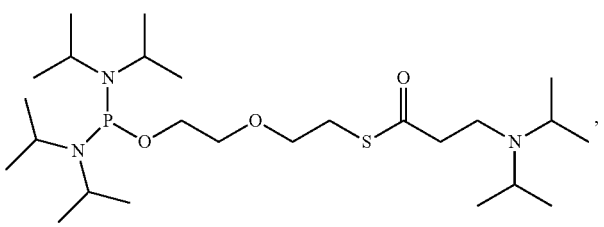
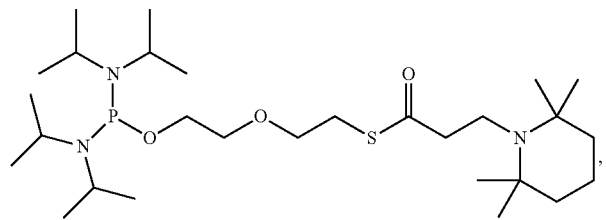
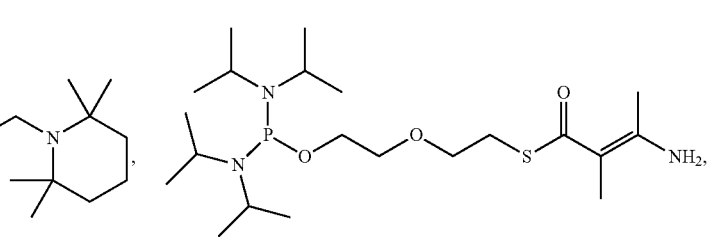

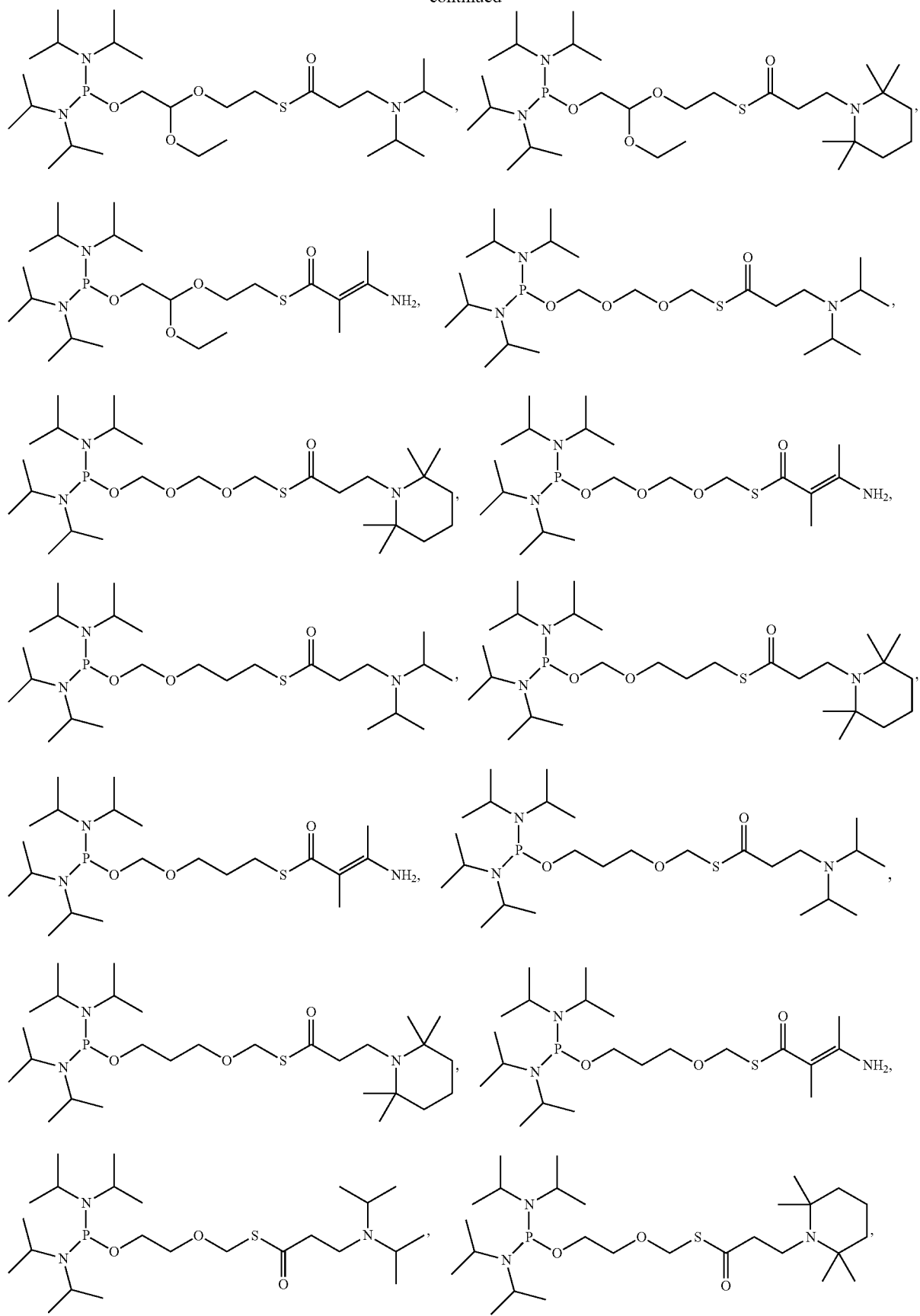

-continued
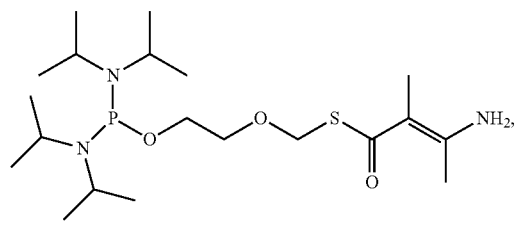
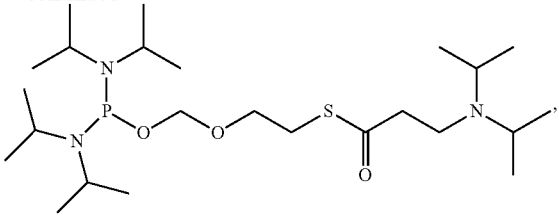
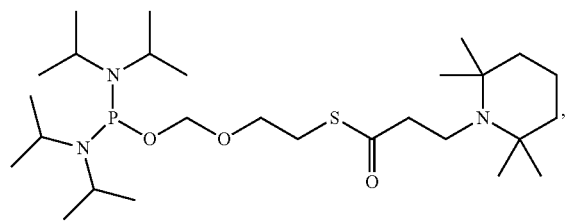
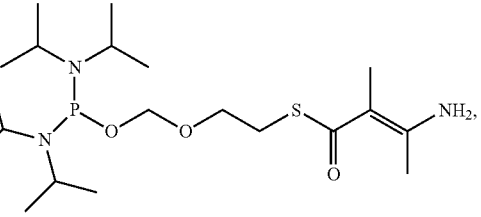
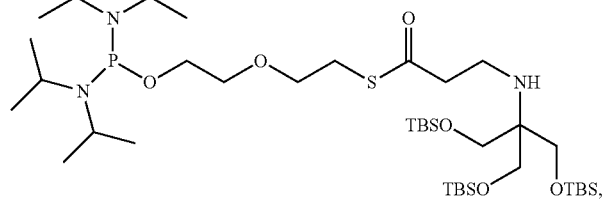
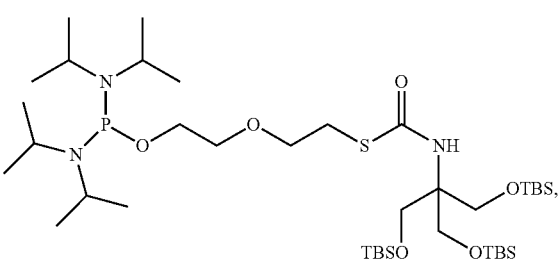
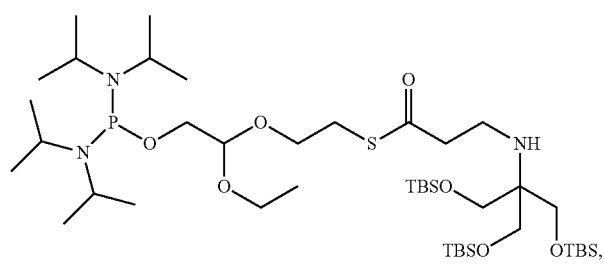
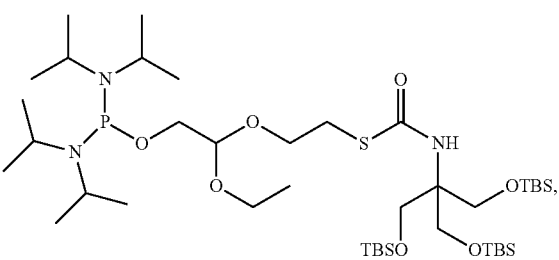
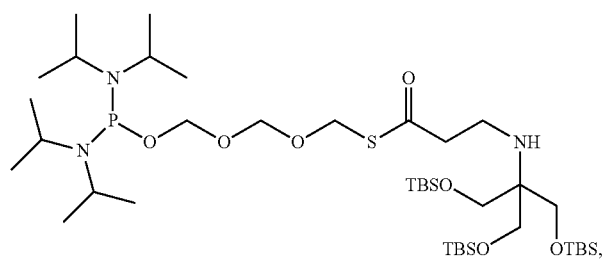
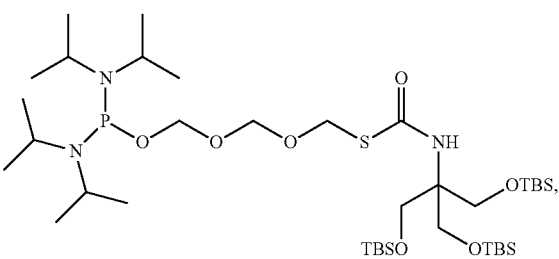
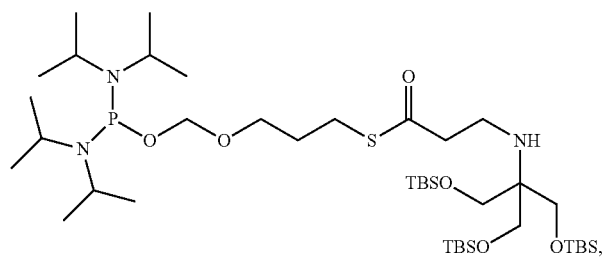
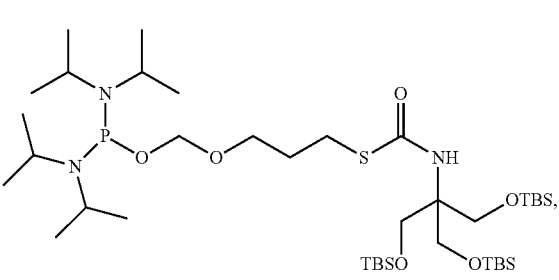

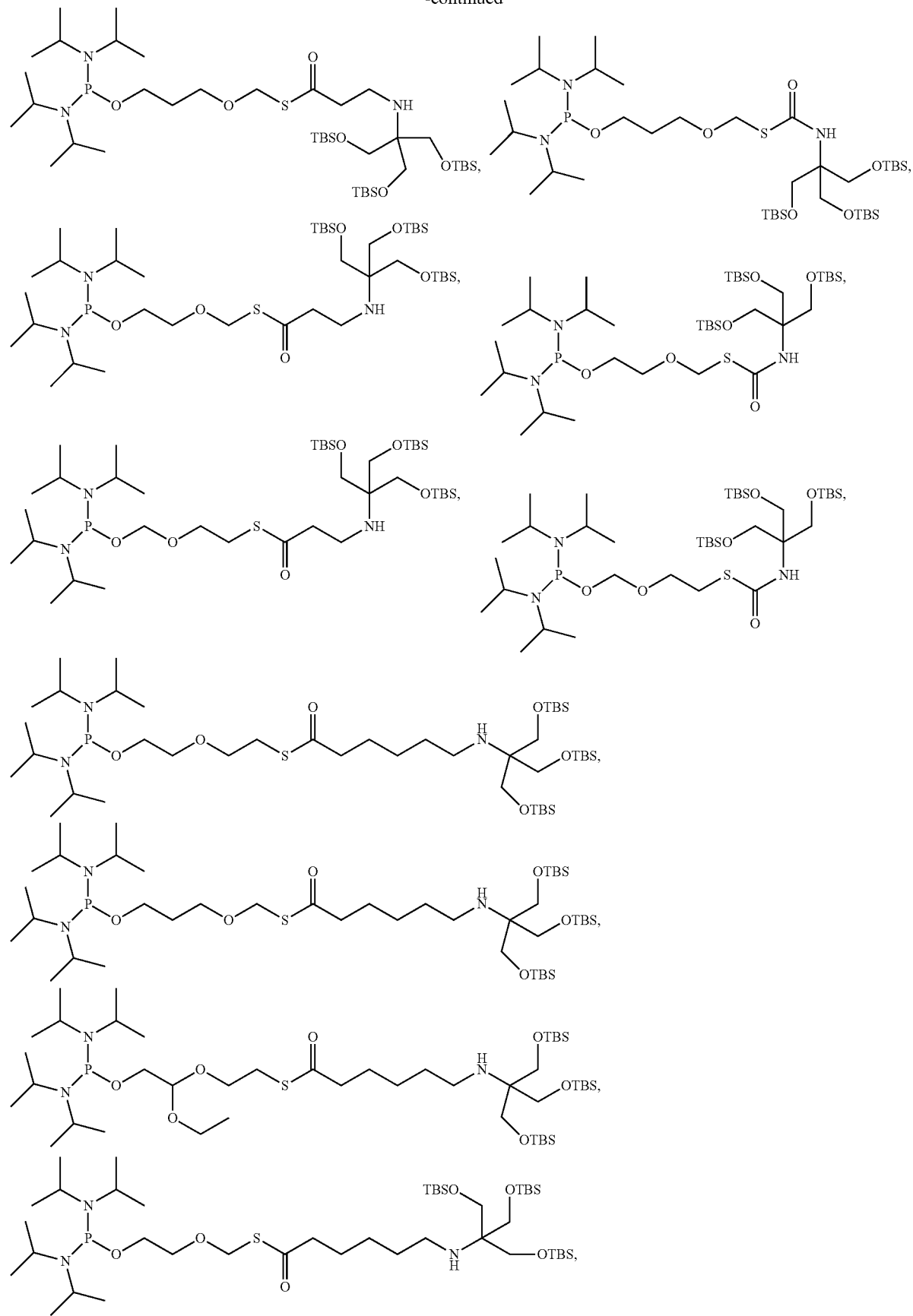

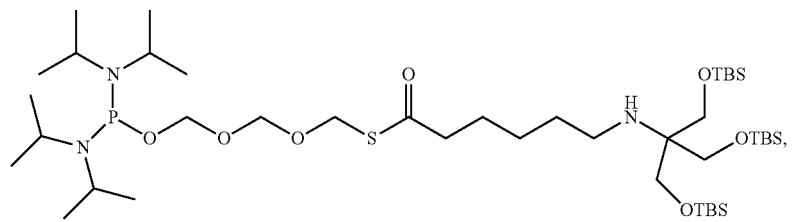
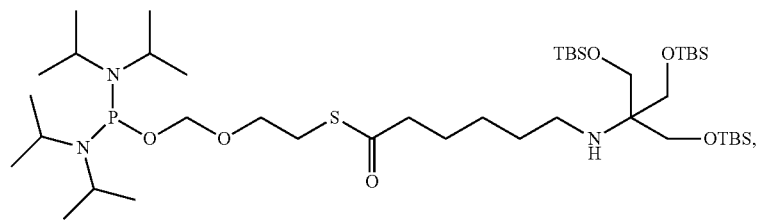
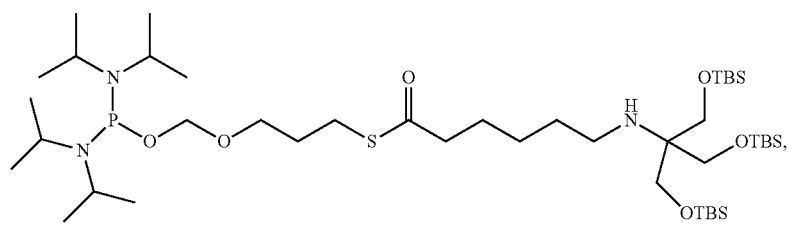
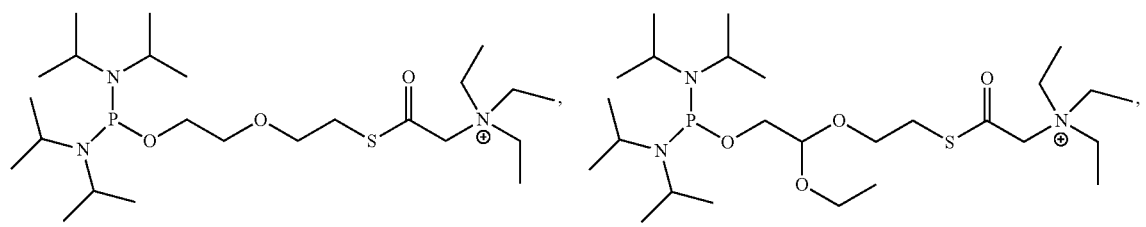
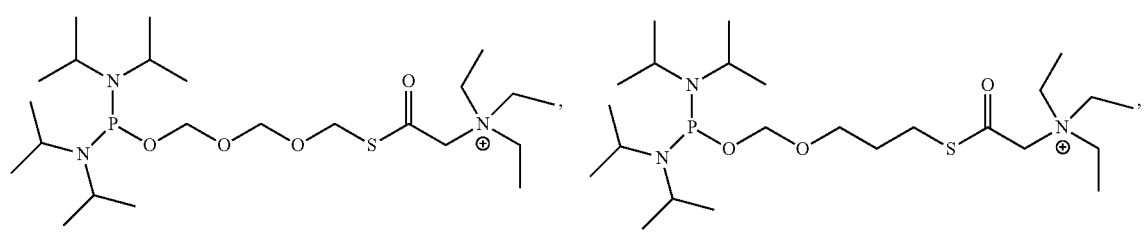
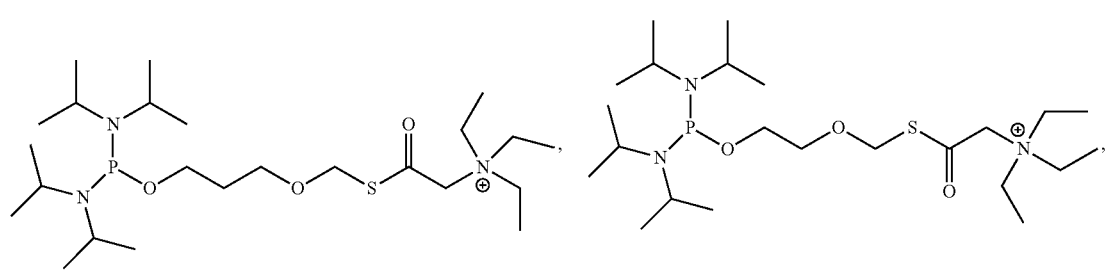
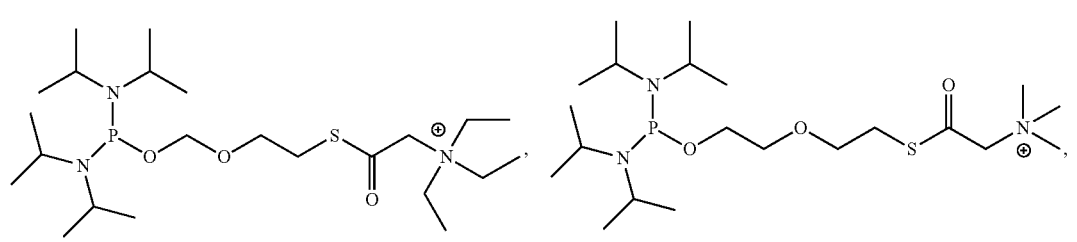

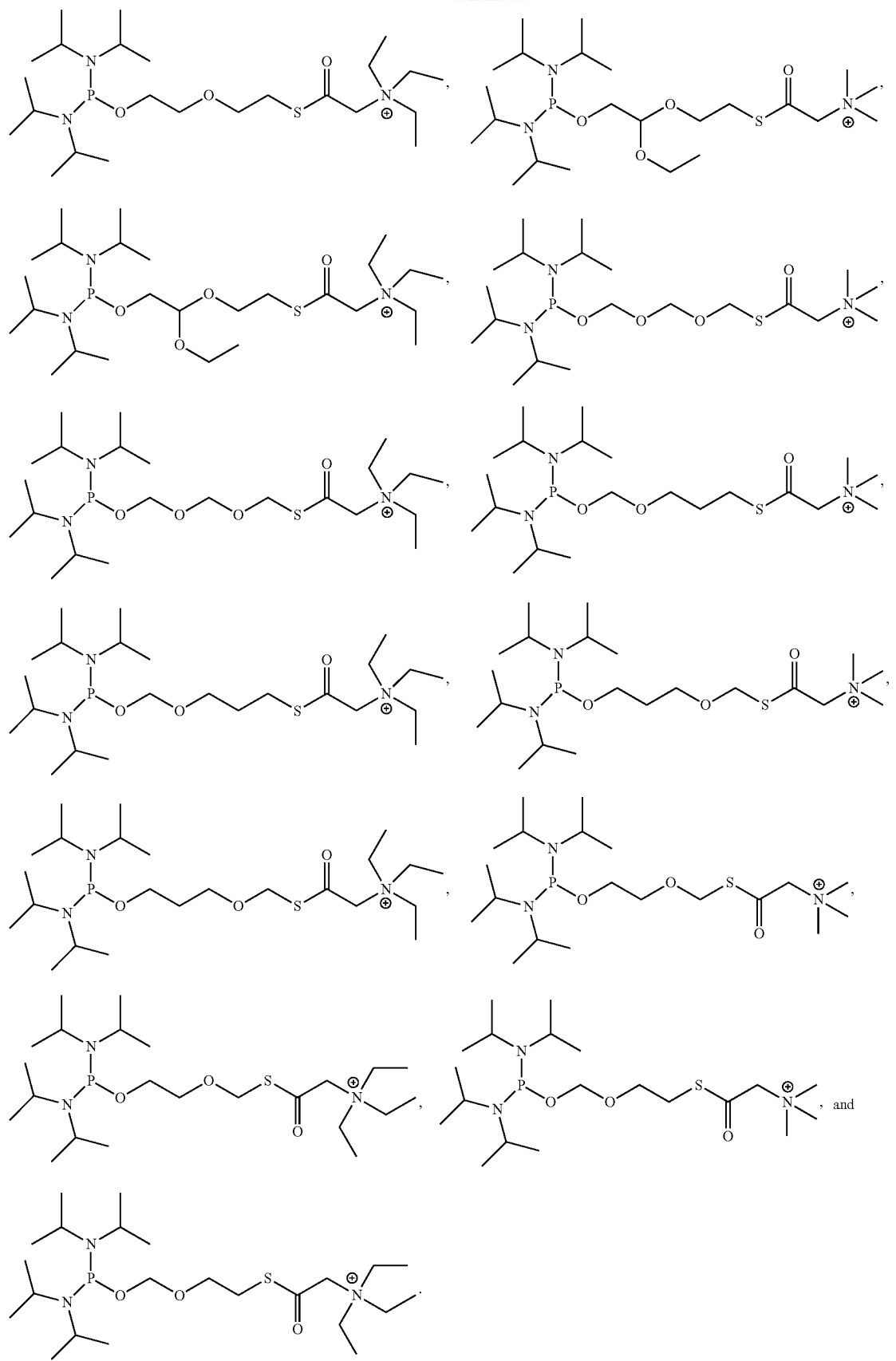

In some embodiments, $R^{31}$ can be $C_{1-6}$alkyl, $(R^{38})_4N(CH_2)_r$—, or $(R^{38})_3C(CH_2)_r$—; and each $R^{38}$ can be individually selected from the group consisting of optionally substituted $C_{1-6}$alkyl. In some embodiments, $R^{31}$ can be

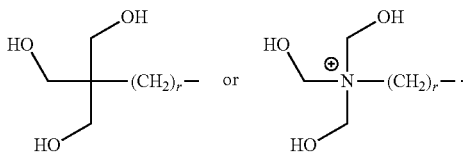

In some embodiments, each $A_5$ can be —C(Me)$_2$— or —CH$_2$—, each $A_6$ can be individually selected from the group consisting of —C(Me)$_2$O—, —C(Me)$_2$S—, —C(Me)$_2$—, —CH$_2$O—, —CH$_2$S—, and —CH$_2$—, and each $A_7$ can be —C(Me)$_2$— or —CH$_2$—.

In some embodiments,

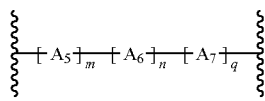

can be

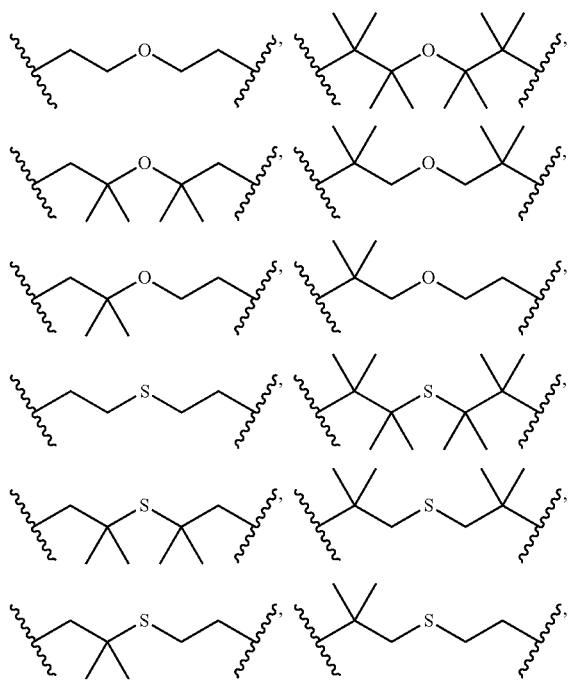

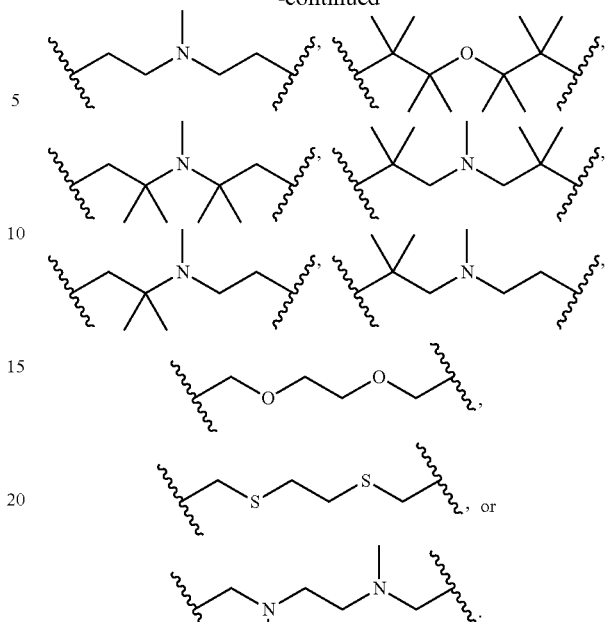

In some embodiments, the compounds can be represented by formula VII:

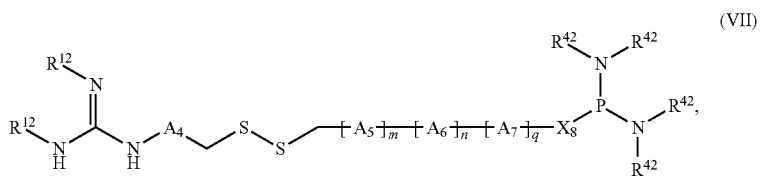

wherein:
each $R^{42}$ is individually $C_{1-6}$alkyl;
$X_8$ is O (oxygen) or S (sulfur);
$A_4$ is an optionally substituted substituent selected from the group consisting of $C_{1-15}$ $C_{1-15}$ alkoxy, $C_{1-15}$heteroalkyl, aryl, heteroaryl and heterocycle; or $A_4$ is $L_1$-$L_2$, $L_1$-$L_2$-$L_3$, $L_1$-$X_9$-$L_2$-$X_9$-$L_3$, -$X_9$-$L_1$-$X_9$-$L_2$-$X_9$-$L_3$-$X_9$-, $L_1$-$X_9$-$L_2$-$L_3$, -$X_9$-$L_1$-$X_9$-$L_2$-$X_9$-$L_3$, $L_1$-$X_9$-$L_2$-$L_3$-$X_9$, -$X_9$-$L_1$-$X_9$-$L_2$-$X_9$-$L_3$-$X_9$, and -$X_9$-$L_1$-$L_2$-$X_9$-$L_3$-$X_9$;
$L_1$ is an optionally substituted substituent selected from the group consisting of $C_{1-5}$alkyl, $C_{1-5}$alkoxy, $C_{1-5}$heteroalkyl, aryl, heteroaryl and heterocycle;
$L_2$ is an optionally substituted substituent selected from the group consisting of $C_{1-5}$alkyl, $C_{1-5}$alkoxy, $C_{1-5}$heteroalkyl, aryl, heteroaryl and heterocycle;
$L_3$ is an optionally substituted substituent selected from the group consisting of $C_{1-5}$alkyl, $C_{1-5}$alkoxy, $C_{1-5}$heteroalkyl, aryl, heteroaryl and heterocycle;
each $X_9$ is independently selected from the group consisting of O (oxygen), $NR^{43}$, Se (selenium), or S (sulfur);
each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $A_5$ is $—C(R^{44})_2—$;

each $A_6$ is individually selected from the group consisting of $—NR^{46}—$, $—C(R^{45})_2NR^{46}—$, $—C(R^{45})_2O—$, $—C(R^{45})_2S—$, $—C(R^{45})_2Se—$, $—OC(R^{45})_2O—$, $—SC(R^{45})_2S—$, $—SeC(R^{45})_2Se—$, $—C(R^{45})_2C(R^{45})_2NR^{46}—$, $—C(R^{45})_2C(R^{45})_2O—$, $—C(R^{45})_2C(R^{45})_2S—$, $—C(R^{45})_2C(R^{45})_2Se—$, and $—C(R^{45})_2—$;

each $A_7$ is $—C(R^{47})_2—$;

m is an integer selected from 1, 2, or 3;

n is an integer selected from 1, 2, or 3;

q is an integer selected from 1, 2, or 3;

each $C(R^{44})_2$ is independently selected, wherein each $R^{44}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{44}$ groups are taken together with the carbon to which they are attached to form an optionally substituted $C_{3-7}$cycloalkyl group;

each $C(R^{45})_2$ is independently selected, wherein each $R^{45}$ is individually selected from the group consisting of H (hydrogen), halo, $C_{1-6}$alkyl, $C_{1-6}$alkoxy, and $C_{1-6}$alkyl substituted with up to 5 fluorine; or two $R^{45}$ are optionally taken together to form an oxo group;

each $R^{46}$ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $C(R^{47})_2$ is independently selected, wherein each $R^{47}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{47}$ groups are taken together with the carbon to which they are attached to form an optionally substituted $C_{3-7}$cycloalkyl group;

each $R^{12}$ is individually selected from the group consisting of H (hydrogen), $R^{13}OC(O)—$, $R^{13}C(O)—$, $R^{13}C(O)CH_2—$, $R^{13}SO_2—$, alkylOC(O)—, or an optionally substituted arylOC(O)—; and each $R^{13}$ is individually selected from the group consisting of optionally substituted $C_{1-6}$alkyl, and an optionally substituted aryl.

In some embodiments,

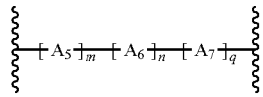

can be

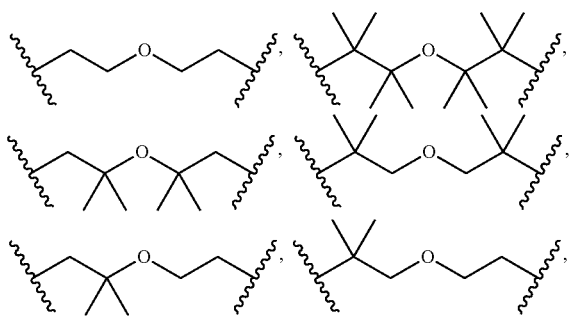

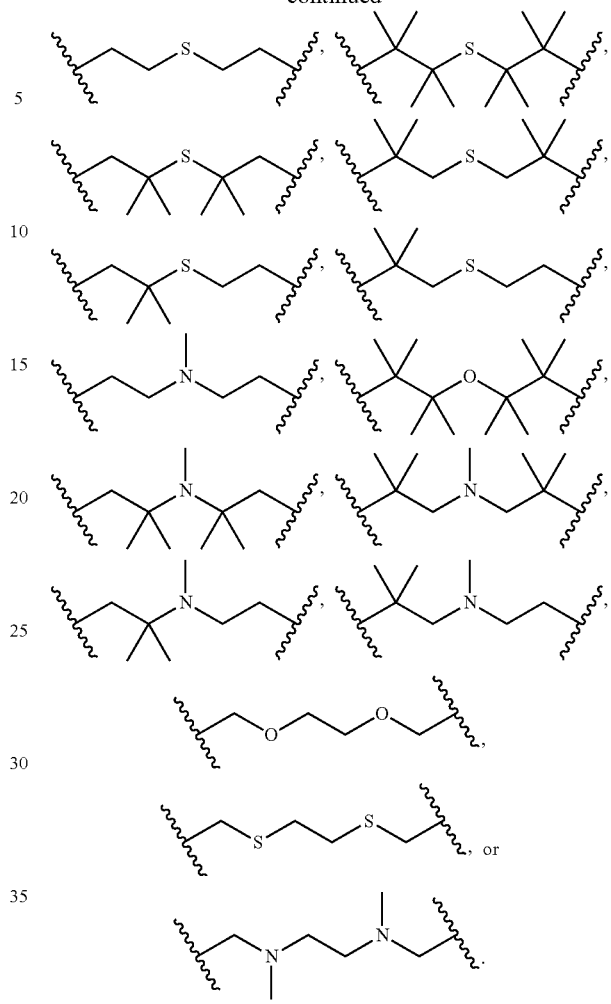

In some embodiments, the compounds of Formula VI can be selected from the group consisting of:

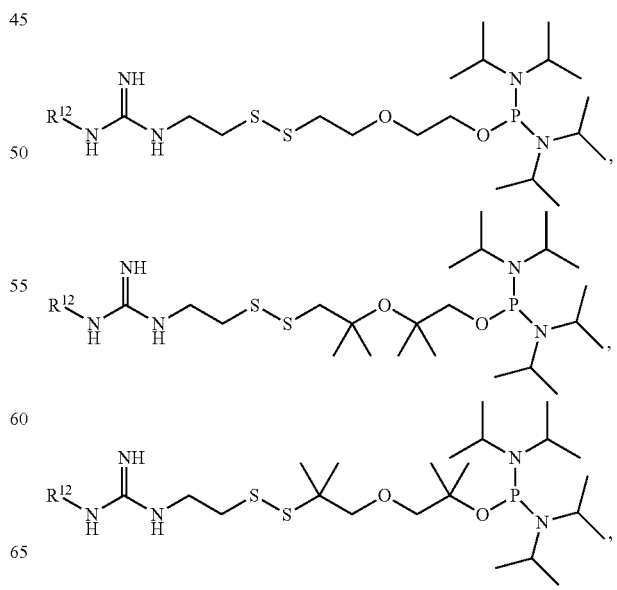

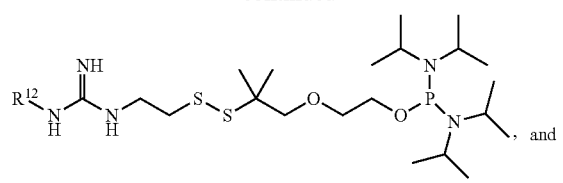
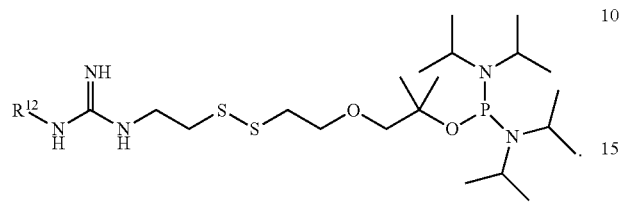
In some embodiments, the compounds of Formula VI can be selected from the group consisting of:
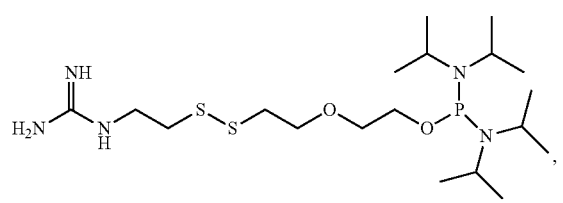
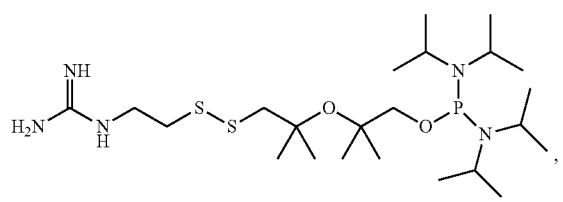
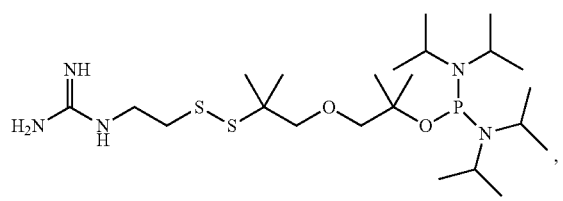
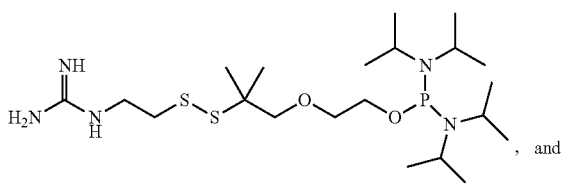
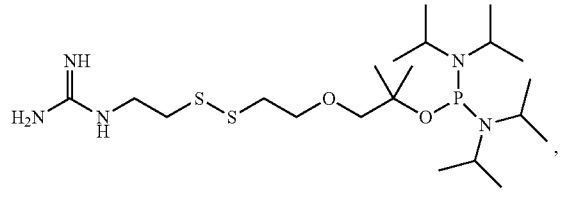
In some embodiments, the compounds of Formula VI can be selected from the group consisting of:
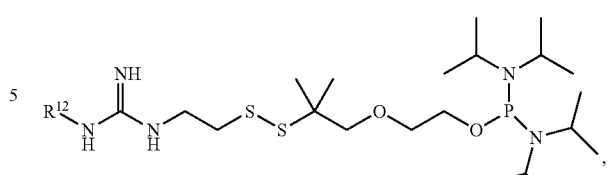
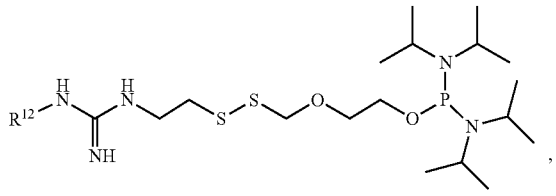
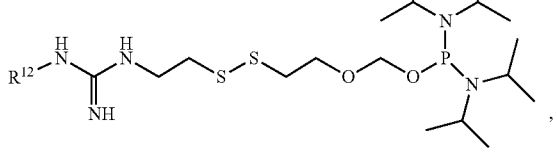
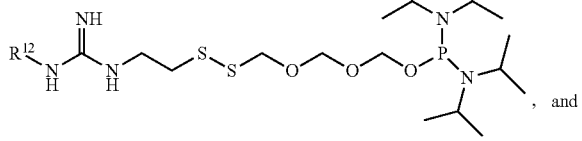
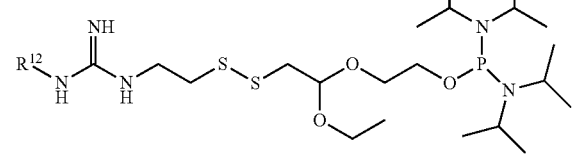
In some embodiments, the compounds of Formula VI can be selected from the group consisting of:
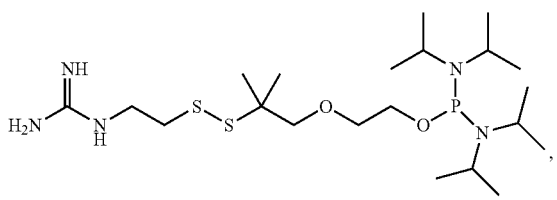
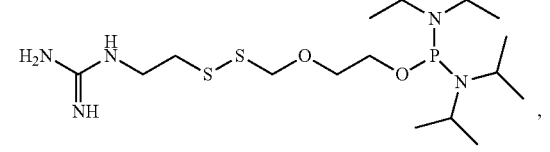
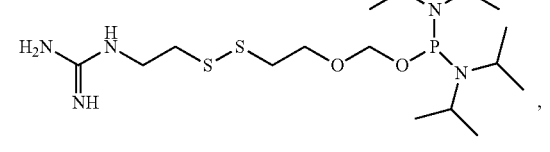

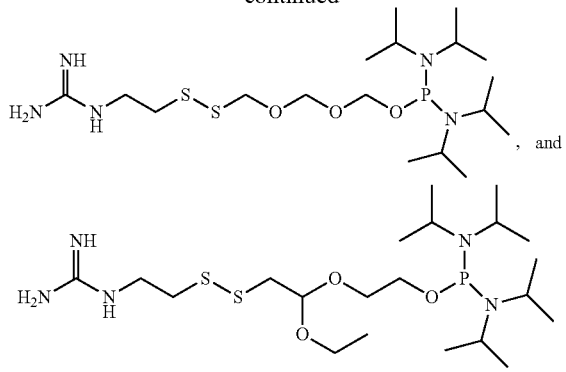
, and

Definitions

As used herein, organic abbreviations are defined as follows:
ACN Acetonitrile, Methyl cyanide
BMEG S-isobutanoyl 2-(2-mercaptoethoxy)ethoxyl
n-Bu n-Butyl
n-BuOH n-Butanol
° C. Temperature in degrees Centigrade
DIA Diisopropyl amine
DIEA Diisopropylethyl amine
DMSO Dimethylsulfoxide
DMT Dimethoxytrityl
Et Ethyl
EtOH Ethanol
ETT ethylthiotetrazole
g Gram(s)
h, hr(s) Hour (hours)
L Liter(s)
M Molar
Me Methyl
MeOH Methanol
MHz Megahertz
mL Milliliter(s)
MMT Monomethoxytrityl
mmol Millimole(s)
mol Mole(s)
NMR Nuclear magnetic resonance
PAC phenoxyacetyl, tert-Butyl-phenoxyacetyl or isopropyl-phenoxyacetyl
Pixyl 9-phenylxanthenyl
PMEG S-Pivaloyl 2-(2-mercaptoethoxy)ethoxyl
PrMEG S-Propanoyl 2-(2-mercaptoethoxy)ethoxyl
py Pyridine
rt Room temperature
SATE S-Acyl-2-thioethyl
SPTE S-Pivaloyl-2-thioethyl
TEA Triethyl amine
Tert, t tertiary
THF Tetrahydrofuran
TLC Thin layer chromatography
μL Microliter(s)
wk week(s)

The term "alkyl" refers to a branched or unbranched fully saturated acyclic aliphatic hydrocarbon group. An alkyl may be branched or straight chain. Alkyls may be substituted or unsubstituted. "Substituted alkyl" refers to alkyl substituted with one or more substituent groups. Alkyls include, but are not limited to, methyl, ethyl, propyl, isopropyl, butyl, isobutyl, tertiary butyl, pentyl, hexyl, and the like, each of which may be optionally substituted.

In certain embodiments, an alkyl comprises 1 to 20 carbon atoms (whenever it appears herein, a numerical range such as "1 to 20" refers to each integer in the given range; e.g., "1 to 20 carbon atoms" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). An alkyl may be designated as "$C_1$-$C_6$ alkyl" or similar designations. By way of example only, "$C_1$-$C_4$ alkyl" indicates an alkyl having one, two, three, or four carbon atoms, e.g., the alkyl is selected from methyl, ethyl, propyl, iso-propyl, butyl, iso-butyl, sec-butyl, and tert-butyl.

The term "heteroalkyl" refers to a group comprising an alkyl and one or more heteroatoms. Examples of heteroalkyls include, but are not limited to, $CH_3CH_2OCH_2$—, $CH_3CH_2SCH_2$—, $CH_3CH_2NHCH_2$—, $CH_3CH_2SCH_2CH_2$—, $CH_3CH_2CH_2OCH_2CH_2$—, $CH_3CH_2OCH_2CH_2OCH_2CH_2$—, $CH_3CH_2SCH_2CH_2OCH_2CH_2$—, $CH_3CH_2OCH_2CH_2SCH_2CH_2$—, $CH_3CH_2NHCH_2CH_2OCH_2CH_2$—, $CH_3CH_2OCH_2CH_2NHCH_2CH_2$—, $CH_3OCH_2CH_2$—, $CH_3NHCH_2$—, and the like.

The term "halo" used herein refers to fluoro, chloro, bromo, or iodo.

The term "alkoxy" used herein refers to straight or branched chain alkyl radical covalently bonded to the parent molecule through an —O— linkage. Examples of alkoxy groups include, but are not limited to, methoxy, ethoxy, propoxy, isopropoxy, butoxy, n-butoxy, sec-butoxy, t-butoxy and the like.

The term "alkenyl" used herein refers to a monovalent straight or branched chain radical of from two to twenty carbon atoms containing a carbon double bond including, but not limited to, 1-propenyl, 2-propenyl, 2-methyl-1-propenyl, 1-butenyl, 2-butenyl, and the like.

The term "alkynyl" used herein refers to a monovalent straight or branched chain radical of from two to twenty carbon atoms containing a carbon triple bond including, but not limited to, 1-propynyl, 1-butynyl, 2-butynyl, and the like.

The term "aryl" used herein refers to homocyclic aromatic radical whether fused or not fused. Examples of aryl groups include, but are not limited to, phenyl, naphthyl, phenanthrenyl, naphthacenyl, and the like. The aryl may be fused to other aryl rings, heteroaryl rings, cycloalkyl rings, cycloalkenyl rings, or heterocyclyl rings.

The term "cycloalkyl" used herein refers to saturated aliphatic ring system radical having three to twenty carbon atoms including, but not limited to, cyclopropyl, cyclopentyl, cyclohexyl, cycloheptyl, and the like. The cycloalkyl may be fused to other cycloalkyl rings, aryl rings, heteroaryl rings, cycloalkenyl rings, or heterocyclyl rings.

The term "cycloalkenyl" used herein refers to aliphatic ring system radical having three to twenty carbon atoms having at least one carbon-carbon double bond in the ring. Examples of cycloalkenyl groups include, but are not limited to, cyclopropenyl, cyclopentenyl, cyclohexenyl, cycloheptenyl, and the like. The cycloalkenyl may be fused to other cycloalkenyl rings, aryl rings, heteroaryl rings, cycloalkyl rings, or heterocyclyl rings The term "polycycloalkyl" used herein refers to saturated aliphatic ring system radical having at least two rings that are fused with or without bridgehead carbons. Examples of polycycloalkyl groups include, but are not limited to, bicyclo[4.4.0]decanyl, bicyclo[2.2.1]heptanyl, adamantyl, norbornyl, and the like.

The term "polycycloalkenyl" used herein refers to aliphatic ring system radical having at least two rings that are fused with or without bridgehead carbons in which at least one of the rings has a carbon-carbon double bond. Examples of polycycloalkenyl groups include, but are not limited to, norbornylenyl, 1,1'-bicyclopentenyl, and the like.

The term "polycyclic hydrocarbon" used herein refers to a ring system radical in which all of the ring members are carbon atoms. Polycyclic hydrocarbons can be aromatic or can contain less than the maximum number of non-cumulative double bonds. Examples of polycyclic hydrocarbon include, but are not limited to, naphthyl, dihydronaphthyl, indenyl, fluorenyl, and the like.

The term "heterocyclic" or "heterocyclyl" used herein refers to non-aromatic cyclic ring system radical having at least one ring system in which one or more ring atoms are not carbon, namely heteroatom. Examples of heterocyclic groups include, but are not limited to, morpholinyl, tetrahydrofuranyl, dioxolanyl, pyrrolidinyl, pyranyl, pyridyl, pyrimidinyl, and the like. The heterocyclyl may be fused to other heterocyclyl rings, aryl rings, heteroaryl rings, cycloalkyl rings, or cycloalkenyl rings The term "heteroaryl" used herein refers to heterocyclic group, whether one or more rings, formally derived from an arene by replacement of one or more methine and/or vinylene groups by trivalent or divalent heteroatoms, respectively, in such a way as to maintain the aromatic system in one or more rings. Examples of heteroaryl groups include, but are not limited to, pyridyl, pyrrolyl, oxazolyl, indolyl, and the like. The heteroaryl may be fused to other heteroaryl rings, aryl rings, cycloalkyl rings, cycloalkenyl rings, or heterocyclyl rings.

The phrase "ring or ring system" used herein refers to a cycloalkyl, cycloalkenyl, polycycloalkyl, polycycloalkenyl, heterocyclyl, or heteroaryl radical.

The term "arylalkyl" or "aralkyl" used herein refers to one or more aryl groups appended to an alkyl radical. Examples of arylalkyl groups include, but are not limited to, benzyl, phenethyl, phenpropyl, phenbutyl, and the like.

The term "cycloalkylalkyl" used herein refers to one or more cycloalkyl groups appended to an alkyl radical. Examples of cycloalkylalkyl include, but are not limited to, cyclohexylmethyl, cyclohexylethyl, cyclopentylmethyl, cyclopentylethyl, and the like.

The term "heteroarylalkyl" or "heteroaralkyl" used herein refers to one or more heteroaryl groups appended to an alkyl radical. Examples of heteroarylalkyl include, but are not limited to, pyridylmethyl, furanylmethyl, thiophenylethyl, and the like.

The term "heterocyclylalkyl" used herein refers to one or more heterocyclyl groups appended to an alkyl radical. Examples of heterocyclylalkyl include, but are not limited to, morpholinylmethyl, morpholinylethyl, morpholinylpropyl, tetrahydrofuranylmethyl, pyrrolidinylpropyl, and the like.

The term "aryloxy" used herein refers to an aryl radical covalently bonded to the parent molecule through an —O— linkage.

The term "alkylthio" used herein refers to straight or branched chain alkyl radical covalently bonded to the parent molecule through an —S— linkage. Examples of alkoxy groups include, but are not limited to, methoxy, ethoxy, propoxy, isopropoxy, butoxy, n-butoxy, sec-butoxy, t-butoxy and the like.

The term "arylthio" used herein refers to an aryl radical covalently bonded to the parent molecule through an —S— linkage.

The term "alkylamino" used herein refers to nitrogen radical with one or more alkyl groups attached thereto. Thus, monoalkylamino refers to nitrogen radical with one alkyl group attached thereto and dialkylamino refers to nitrogen radical with two alkyl groups attached thereto.

The term "cyanoamino" used herein refers to nitrogen radical with nitrile group attached thereto.

The term "carbamyl" used herein refers to RNHCOO—.

The term "keto" and "carbonyl" used herein refers to C=O.

The term "carboxy" used herein refers to —COOH.

The term "sulfamyl" used herein refers to —SO$_2$NH$_2$.

The term "sulfonyl" used herein refers to —SO$_2$—.

The term "sulfinyl" used herein refers to —SO—.

The term "thiocarbonyl" used herein refers to C=S.

The term "thiocarboxy" used herein refers to CSOH.

The term "C-amido" used herein refers to —C(O)NR$_2$, where each R is independently H or C$_1$-C$_6$ alkyl.

The term "N-amido" used herein refers to —NRC(O)R, where each R is independently H or C$_1$-C$_6$ alkyl.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, a substituted group is derived from the unsubstituted parent structure in which there has been an exchange of one or more hydrogen atoms for another atom or group. When substituted, the substituent group(s) is (are) one or more group(s) individually and independently selected from C$_1$-C$_6$ alkyl, C$_1$-C$_6$ alkenyl, C$_1$-C$_6$ alkynyl, C$_3$-C$_6$ cycloalkyl, C$_3$-C$_6$ heterocycloalkyl (e.g., tetrahydrofuryl), aryl, aralkyl, heteroaryl, halo (e.g., chloro, bromo, iodo and fluoro), cyano, hydroxy, hydroxy-C$_1$-C$_6$ alkyl, halogenated C$_1$-C$_6$ alkyl, C$_1$-C$_6$ alkoxy, halogenated C alkoxy (e.g., perhalogenated C$_1$-C$_6$ alkoxy), aryloxy, sulfhydryl (mercapto), C$_1$-C$_6$ alkylthio, arylthio, amino, mono- and di-(C$_1$-C$_6$)alkyl amino, quaternary ammonium salts, amino(C$_1$-C$_6$)alkoxy, hydroxy(C$_1$-C$_6$)alkylamino, amino(C$_1$-C$_6$)alkylthio, C$_1$-C$_6$ alkylamino-C$_1$-C$_6$ alkylamino, acyanoamino, nitro, N-carbamyl (e.g., —NHC(O)O-t-butyl, —N(cyclopropyl)C(O)O-t-butyl, etc.), C-carbamate, keto (oxy), carbonyl, O-carboxy (e.g., —OC(O)CH$_3$, etc.), urea, C-carboxy (e.g., —C(O)OCH$_3$, —C(O)O-alkyl, etc.), C$_1$-C$_6$-alkylcarboxy, C-amido (e.g., —C(O)N(CH$_3$)$_2$, —C(O)NH$_2$, etc.), N-amido (e.g., —N(CH$_3$)C(O)CH$_3$, —NHC(O)CH$_3$, —N(CH$_3$)C(O)H, —N(CH$_2$CH$_3$C(O)H, etc.), C$_1$-C$_6$-alkyl-OC(O)NH—C$_1$-C$_6$-alkyl, glycolyl, glycyl, hydrazino, guanyl, guanidine, sulfamyl, sulfonyl (e.g., C$_1$-C$_6$-alkylsulfonyl, hydroxy-C$_1$-C$_6$-alkylsulfonyl), sulfonylamino (e.g., C$_1$-C$_6$-alkylsulfonylamino (e.g., —N(CH$_3$)SO$_2$CH$_3$)), sulfinyl, thiocarbonyl, thiocarboxy, PAC (i.e. phenoxyacetyl, tert-Butyl-phenoxyacetyl or iPr-phenoxyacetyl) and combinations thereof. When the group contains a nitrogen, or a sulfur, an oxo as a substituent also includes oxides, for example pyridine-N-oxide, thiopyran sulfoxide and thiopyran-S,S-dioxide. When the group contains an nitrogen, an C$_1$-C$_6$ alkyl as a substituent includes substitution on the nitrogen providing a salt, for example N-methyl-pyridinium, the counter ion is understood to be present. When the group is amino (i.e. —NH$_2$) it is understood that the amino can further be optionally in a protected form. The amino can be protected with trifluoroacetyl, tert-butoxycarbonyl (i.e. Boc), 9H-fluoren-9-ylmethoxycarbonyl (i.e. Fmoc), 2-cyanoethyloxycarbonyl (i.e. CEOC), phenacyl (i.e. PAC), and the like in a manner understood by those of skill in the art. When the group is guanidino (i.e. —NHC(=NH)NH$_2$) it is understood that the guanidino can further be optionally in a protected form. The guanidino can be protected with one or two protecting groups selected from the group including, but not limited to, trifluoroacetyl, tert-butoxycarbonyl (i.e. Boc), 9H-fluoren-9-yl-methoxycarbonyl (i.e. Fmoc), 2-cyanoethyloxycarbonyl i.e. (CEOC), phenacyl (i.e. PAC), and the like in a manner understood by those of skill in the art. Further protecting groups for the amino and guanidino group can be found in references such as Greene and Wuts *Protective Groups in Organic Synthesis*; John Wiley and Sons: New York, 1999. In embodiments in which two or more hydrogen atoms have been substituted, the substituent groups may together form a ring. The protecting groups that can form the protective derivatives of the above substituents are known to those of skill in the art and can be found in references such as Greene and Wuts *Protective Groups in Organic Synthesis*; John Wiley and Sons: New York, 1999. Wherever a substituent is described as "optionally substituted" that substituent can be substituted with the above substituents.

Asymmetric carbon atoms may be present in the compounds described. All such isomers, including diastereomers and enantiomers, as well as the mixtures thereof are intended to be included in the scope of the recited compound. In certain cases, compounds can exist in tautomeric forms. All tautomeric forms are intended to be included in the scope. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated. Thus, reference herein to a compound includes all of the aforementioned isomeric forms unless the context clearly dictates otherwise.

In some embodiments, $X_3$ can be O (oxygen). In some embodiments, $X_3$ can be S (sulfur).

In some embodiments, $R^1$ can be a $C_{1-6}$alkyl group. For example, $R^1$ can be a tert-butyl group, methyl group, ethyl group, propyl group, butyl group and the like. In some embodiments, $R^1$ can be $C_{1-6}$alkyl substituted with one or more hydroxy groups. For example, $R^1$ can be a tert-butyl group substituted with three hydroxy groups (e.g. 2-hydroxymethyl-propan-2-yl-1,3-diol). In some embodiments, $R^1$ can be $C_{1-6}$alkoxy. For example, $R^1$ can be a methoxy group, ethoxy group, propoxy group, 2-propoxy group, butoxy group, 2-butoxy group, tert-butoxy group and the like. In some embodiments, $R^1$ can be —NHC$_{1-6}$alkyl group. For example, $R^1$ can be a methylamino group, ethylamino group, propylamino group, 2-propylamino group, butylamino group, 2-butylamino group, tert-butylamino group and the like. In some embodiments, $R^1$ can be guanidinyl. In some embodiments, $R^1$ can be $C_{1-6}$alkylC(O)O—. For example, $R^1$ can be a acetoxy group, propanoyloxy group, butanoyloxy group, isobutanoyloxy group, pivalyloxy group, and the like In some embodiments, $R^1$ can be optionally substituted arylC(O)O—. For example, $R^1$ can be a benzoyloxy group, 4-tert-butyl-benzoyloxy group, 4-methyl-benzoyloxy group, 4-nitro-benzoyloxy group, 4-cyano-benzoyloxy group, 4-chloro-benzoyloxy group, 4-bromo-benzoyloxy group, 2-tert-butyl-benzoyloxy group, 2-methyl-benzoyloxy group, 2-nitro-benzoyloxy group, 2-cyano-benzoyloxy group, 2-chloro-benzoyloxy group, 2-bromo-benzoyloxy group, 3-tert-butyl-benzoyloxy group, 3-methyl-benzoyloxy group, 3-nitro-benzoyloxy group, 3-cyano-benzoyloxy group, 3-chloro-benzoyloxy group, 3-bromo-benzoyloxy group, 3,5-di-tert-butyl-benzoyloxy group, 3,5-dimethyl-benzoyloxy group, 3,5-dinitro-benzoyloxy group, 3,5-dicyano-benzoyloxy group, 3,5-dichloro-benzoyloxy group, 3,5-dibromo-benzoyloxy group, 3-chloro-5-methyl-benzoyloxy group, 3-bromo-5-nitro-benzoyloxy group, 3-tert-butyl-5-cyano-benzoyloxy group, 3-tert-butyl-5-methyl-benzoyloxy group, 3-bromo-5-chloro-benzoyloxy group and the like, In some embodiments, $R^1$ can be a heteroarylC(O)O— group. For example, $R^1$ can be a pyrimidine-5-carbonyloxy group, pyrimidine-2-carbonyloxy group, pyrimidine-4-carbonyloxy group, pyridine-5-carbonyloxy group, pyridine-2-carbonyloxy group, pyridine-3-carbonyloxy group, pyridine-4-carbonyloxy group, imidazole-2-carbonyloxy group, oxazole-2-carbonyloxy group, thiazole-2-carbonyloxy group, imidazole-4-carbonyloxy group, oxazole-4-carbonyloxy group, thiazole-4-carbonyloxy group, imidazole-5-carbonyloxy group, oxazole-5-carbonyloxy group, thiazole-5-carbonyloxy group, benzo[d]thiazole-2-carbonyloxy group and the like. In some embodiments, $R^1$ can be heterocyclylC(O)O—. For example, $R^1$ can be a piperidine-1-carbonyloxy group, morpholine-4-carbonyloxy group and the like.

In some embodiments, the compound of formula I is:

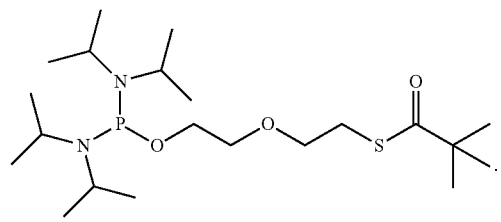 [SMILES: CC(C)N(C(C)C)P(OCCOCCSC(=O)C(C)(C)C)N(C(C)C)C(C)C]

In some embodiments, the compound of formula I is:

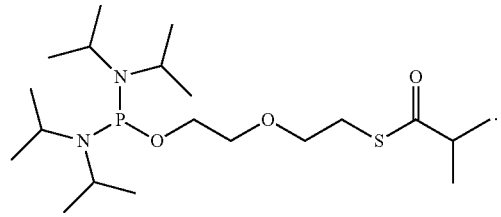 [SMILES: CC(C)C(=O)SCCOCCOP(N(C(C)C)C(C)C)N(C(C)C)C(C)C]

In some embodiments, the compound of formula I is:

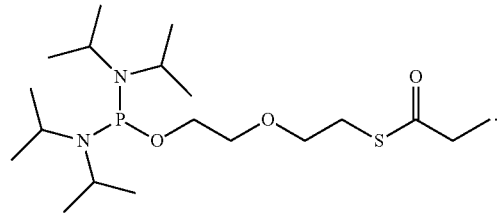 [SMILES: CCC(=O)SCCOCCOP(N(C(C)C)C(C)C)N(C(C)C)C(C)C]

In some embodiments, the compound of formula I can be selected from the group consisting of:
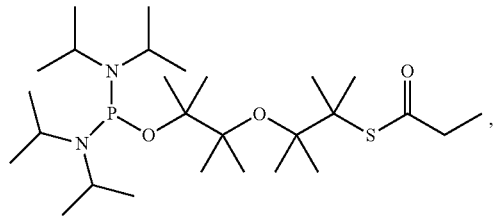
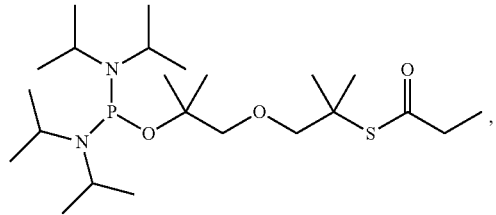
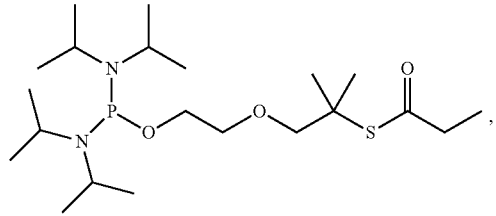
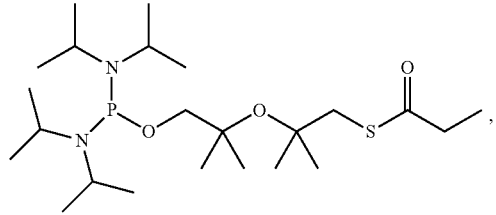
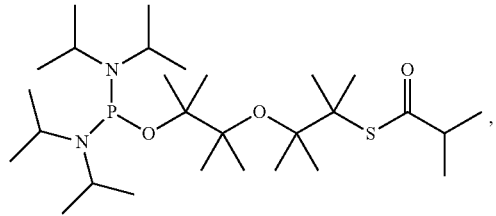
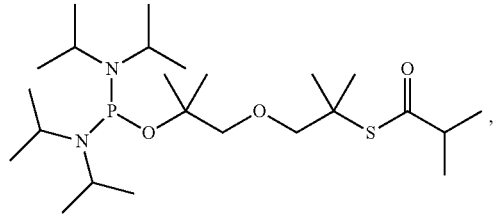
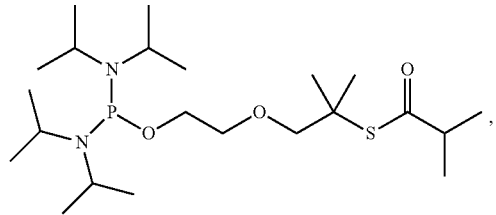
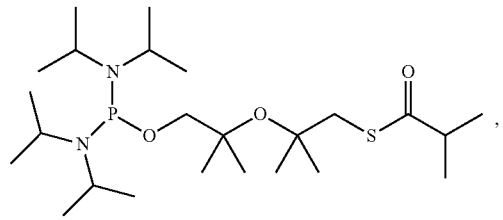
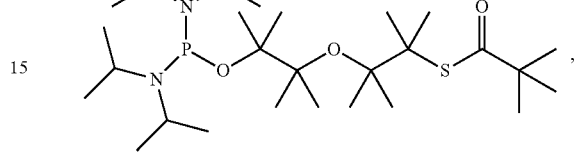
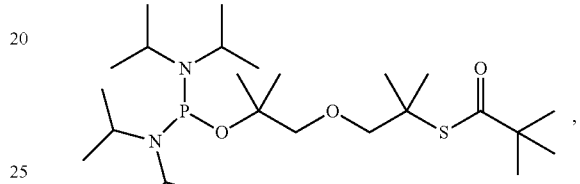
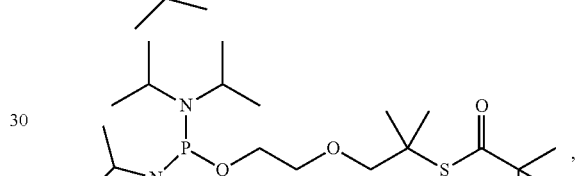
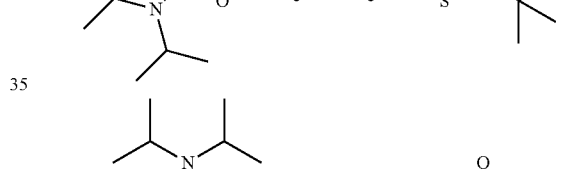
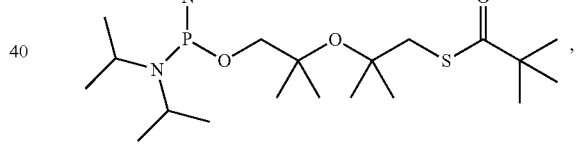
and the like.
In some embodiments, the compound of formula VI can be selected from the group consisting of:
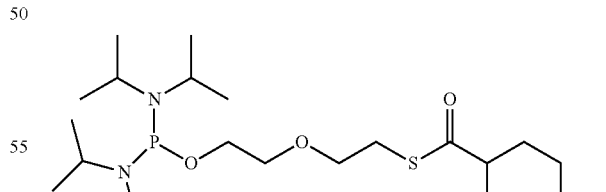
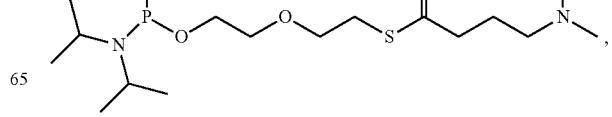

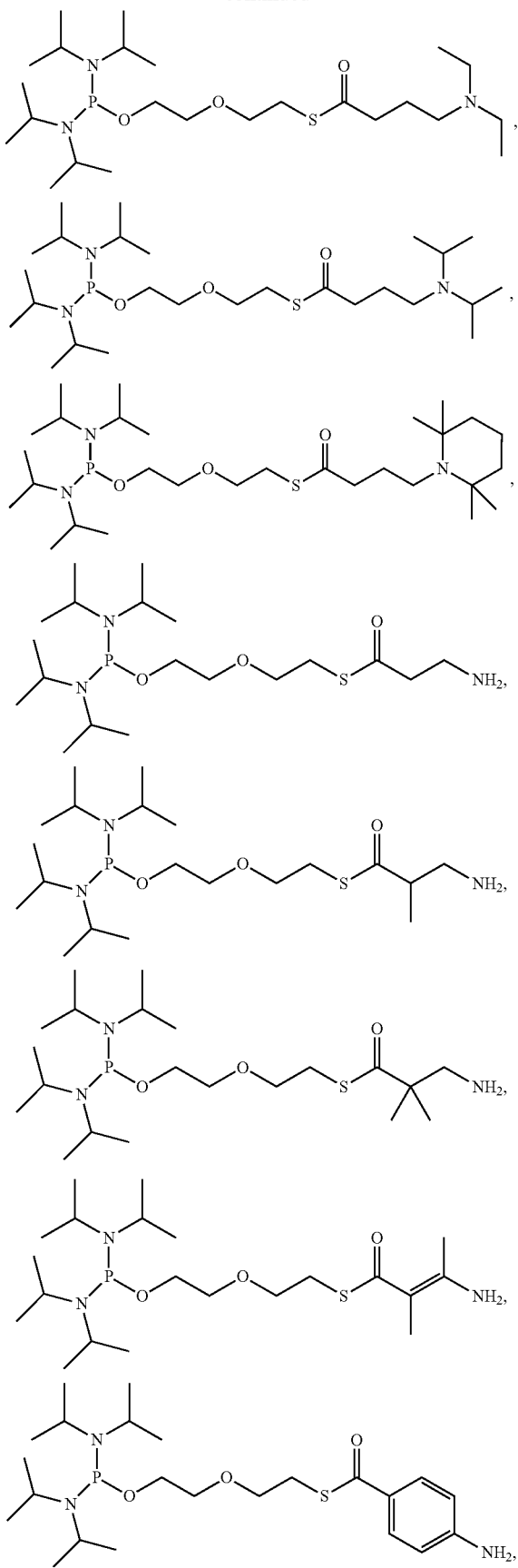

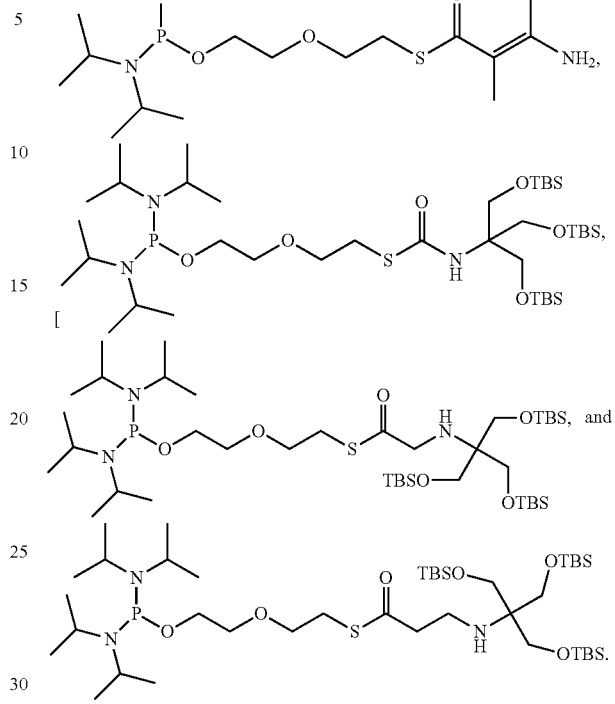

The compounds disclosed herein provide an extended length between the anionic biomolecule and the distal end of the charge-neutralizing compounds disclosed herein, in comparison to the compounds disclosed, for example, in PCT Publication No. WO2008/008476. Preferably, the linker is a straight-chain linker having 7 or more chain atoms, preferably with no side groups, extending from the biomolecule (e.g., a polynucleotide). The extended length of the protecting group provides unexpected enhanced flexibility, increased solubility in water, improved double stranding capability when used in connection with polynucleotides, and a reduction in reversal byproduct toxicity when compared to other "protecting groups" known in the art. As such, the compounds disclosed herein provide unforeseen advantages over protecting groups described in the art, particularly in the context of modification of antisense molecules such as siRNA, shRNA, miRNA and the like.

In some embodiments, $A_1$ can be —$C(R^4)_2$—. In some embodiments, $A_3$ can be —$C(R^7)_2$—. For example, $A_1$ and $A_3$ can each individually be selected from the group consisting of —$CH_2$— and —$CMe_2$—. In some embodiments, $A_2$ can be selected from the group consisting of —$NR^6$—, —$C(R^5)_2NR^6$—, —$C(R^5)_2O$—, —$C(R^5)_2S$—, —$C(R^5)_2C(R^5)_2NR^6$—, —$C(R^5)_2C(R^5)_2O$—, and —$C(R^5)_2C(R^5)_2S$—. For example, $A_2$ can be selected from the group consisting of —NH—, —NMe—, —$CH_2$NH—, —$CH_2CH_2$NH—, —$CMe_2$NH—, —$CMe_2CH_2$NH—, —$CH_2CMe_2$NH—, —$CH_2$NMe—, —$CH_2CH_2$NMe—, —$CMe_2$NMe—, —$CMe_2CH_2$NMe—, —$CH_2CMe_2$NMe—, —$CH_2$O—, —$CH_2CH_2$O—, —$CMe_2$O—, —$CMe_2CH_2$O—, —$CH_2CMe_2$O—, —$CH_2$S—, —$CH_2CH_2$S—, —$CMe_2$S—, —$CMe_2CH_2$S—, —$CH_2CMe_2$S—, and the like.

In some embodiments, the total length of $A_1$, $A_2$ and $A_3$ is such that, when dissociated from the biomolecule, e.g., in vivo, the protecting group forms a heterocyclic decomposition product that is thermodynamically or kinetically favored, e.g., a five, six or seven membered heterocycle ring. For example, the decomposition product can be thiazolidine, 3-methylthiazolidine, 1,3-oxathiolane, 1,3-dithiolane, thiomorpholine, 4-methylthiomorpholine, 1,4-oxathiane, 1,4-dithiane, 1,4-thiazepane, 4-methyl-1,4-thiazepane, 1,4-oxathiepane, 1,4-dithiepane and the like.

Modified Nucleosides, Oligonucleotides, and Polynucleotides

In some embodiments, the compounds or protecting groups disclosed herein are operably linked to a nucleoside, oligonucleotide, polynucleotide. Accordingly, some embodiments disclosed herein provide compositions that comprise, consist essentially of, or consist of a nucleoside, oligonucleotide, or polynucleotide that includes at least one protecting group disclosed herein linked thereto.

As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g. the individual units of a peptide nucleic acid, each containing a base, are referred to herein as a nucleoside. The nucleosides, oligonucleotides, and polynucleotides disclosed herein can include any bases, including uracil, adenine, thymine, cytosine, guanine, inosine, xanthine hypoxanthine, isocytosine, isoguanine, etc., known in the art.

Some embodiments herein relate to modified nucleosides of formula III $$D_1 \!-\!\!\left[\!A_1\!\right]_{\!m}\!\!-\!\!\left[\!A_2\!\right]_{\!n}\!\!-\!\!\left[\!A_3\!\right]_{\!q}\!\!-\!X_1 \quad (III)$$

(with $R^8\!-\!O\!-\!$ attached to sugar bearing B and $R^9$, and phosphorus $P$ bearing $N(R^2)_2$)

wherein:

$D_1$ is $$R^{12}\!-\!N(H)\!-\!C(=\!NH)\!-\!N(H)\!-\!CH_2CH_2\!-\!S\!-\!S\!-\!\{ \quad \text{or} \quad R^1\!-\!C(X_3)\!-\!X_2\!-\!\{;$$

$R^1$ is an optionally substituted substituent selected from the group consisting of $C_{1-6}$alkyl, $C_{1-6}$alkoxyl, aryl, heteroaryl, heterocyclyl, $-\!NHC_{1-6}$alkyl, aryl$C_{1-6}$alkyl, heteroaryl$C_{1-6}$alkyl, heterocyclyl$C_{1-6}$alkyl, guanidinyl, $C_{1-6}$alkylC(O)O$-\!$, arylC(O)O$-\!$, heteroarylC(O)O$-\!$, and heterocyclylC(O)O$-\!$;

$R^{12}$ is H (hydrogen), alkylOC(O)$-\!$, or an optionally substituted arylOC(O)$-\!$;

each $R^2$ is individually $C_{1-6}$alkyl;

$X_1$ is O (oxygen) or S (sulfur);

$X_2$ is O (oxygen), $NR^3$, or S (sulfur);

$R^3$ is selected from the group consisting of H (hydrogen), $C_{1-6}$alkyl, $Cl_{1-6}$alkylC(O)$-\!$, $C_{1-6}$alkylOC(O)$-\!$, $C_{1-6}$alkylNHC(O)$-\!$, $C_{1-6}$alkylS(O)$_2\!-\!$, optionally substituted arylC(O)$-\!$, optionally substituted heteroarylC(O)$-\!$, optionally substituted arylOC(O)$-\!$, optionally substituted heteroarylOC(O)$-\!$, optionally substituted arylNHC(O)$-\!$, optionally substituted heteroarylNHC(O)$-\!$, and optionally substituted arylS(O)$_2\!-\!$;

$X_3$ is O (oxygen), NH, or S (sulfur);

each $A_1$ is $-\!C(R^4)_2\!-\!$;

each $A_2$ is individually selected from the group consisting of $-\!NR^6\!-\!$, $-\!C(R^5)_2NR^6\!-\!$, $-\!C(R^5)_2O\!-\!$, $-\!C(R^5)_2S\!-\!$, $-\!C(R^5)_2Se\!-\!$, $-\!C(R^5)_2C(R^5)_2NR^6\!-\!$, $-\!C(R^5)_2C(R^5)_2O\!-\!$, $-\!C(R^5)_2C(R^5)_2S\!-\!$, $-\!C(R^5)_2C(R^5)_2Se\!-\!$, and $-\!C(R^5)_2\!-\!$;

each $A_3$ is $-\!C(R^7)_2\!-\!$;

m is an integer selected from 1, 2, or 3;

n is an integer selected from 1, 2, or 3;

q is an integer selected from 1, 2, or 3;

each $C(R^4)_2$ is independently selected, wherein each $R^4$ is individually selected from the group consisting of H (hydrogen), halo, $C_{1-6}$alkyl, and $C_{1-6}$alkyl substituted with up to 5 fluorine, or optionally two $R^4$ groups are taken together with the carbon to which they are attached to form an optionally substituted $C_{3-7}$cycloalkyl group;

each $C(R^5)_2$ is independently selected, wherein each $R^5$ is individually selected from the group consisting of H (hydrogen), halo, $C_{1-6}$alkyl, and $C_{1-6}$alkyl substituted with up to 5 fluorine; or two $R^5$ are optionally taken together to form an oxo group;

each $R^6$ is individually selected from the group consisting of H (hydrogen), $C_{1-6}$alkyl, $C_{1-6}$alkylC(O)$-\!$, $C_{1-6}$alkylOC(O)$-\!$, $C_{1-6}$alkylNHC(O)$-\!$, $C_{1-6}$alkylS(O)$_2\!-\!$, optionally substituted arylC(O)$-\!$, optionally substituted heteroarylC(O)$-\!$, optionally substituted arylOC(O)$-\!$, optionally substituted heteroarylOC(O)$-\!$, optionally substituted arylNHC(O)$-\!$, optionally substituted heteroarylNHC(O)$-\!$, and optionally substituted arylS(O)$_2\!-\!$;

each $C(R^7)_2$ is independently selected, wherein each $R^7$ is individually selected from the group consisting of H (hydrogen), halo, $C_{1-6}$alkyl, and $C_{1-6}$alkyl substituted with up to 5 fluorine, or optionally two $R^7$ groups are taken together with the carbon to which they are attached to form an optionally substituted $C_{3-7}$cycloalkyl group;

$R^8$ is selected from the group consisting of H (hydrogen), optionally substituted trityl, optionally substituted pixyl (9-phenylxanthenyl), and optionally substituted S-pixyl (9-phenylthioxanthyl);

$R^9$ is selected from the group consisting of H (hydrogen), halo, $-\!OR^{10}$, and optionally substituted $C_{1-6}$alkoxyl;

$R^{10}$ is selected from the group consisting of H (hydrogen), triisopropylsilylOCH$_2\!-\!$, tert-butyldimethylsilylOCH$_2\!-\!$, triethylsilylOCH$_2\!-\!$, trimethylsilylethylOCH$_2\!-\!$, triisopropylsilyl-, tert-butyldimethylsilyl-, trimethylsilylethyl$-\!$, triethylsilyl-, optionally substituted trimethylsilyl-, and optionally substituted trimethylsilylOCH$_2\!-\!$; and each B can individually be an optionally substituted substituent selected from the group consisting of a pyrimidine, a purine or heterocyclic base, including but not limited to uracil, thymine, cytosine, adenine, guanine, inosine, xanthine hypoxanthine, isocytosine, isoguanine, etc. and non-natural nucleobase analogs such as difluorotolyl, nitroindolyl, nitropyrrolyl, or nitroimidazolyl.

Some embodiments herein relate to modified nucleosides of formula VIII

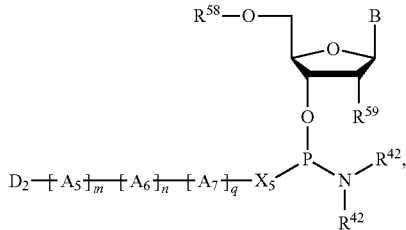

wherein:
$D_2$ is

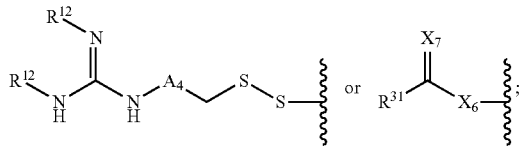

$R^{31}$ is an optionally substituted substituent selected from the group consisting of $C_{1-8}$alkyl, $C_{1-8}$ alkenyl, $C_{1-6}$alkoxyl, aryl, heteroaryl, heterocyclyl, —$NHC_{1-6}$alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroarylC(O)O—, heterocyclylC(O)O—, and $C_{1-8}$alkyl substituted with one or more hydroxyl groups; or $R^{31}$ is selected from the group consisting of $(R^{48})_4N(CH_2)_r$—, $(R^{48})_3C(CH_2)_r$—, $(R^{48})_3CNH(CH_2)_r$—, $HS(CH_2)_r$—, $C_{1-8}$heteroalkyl, and guanidiny$(CH_2)_r$—;

$R^{48}$ is selected from the group consisting of H (hydrogen), $R^{49}(CH_2)_r$—, optionally substituted $C_{1-6}$alkyl, optionally substituted $C_{3-7}$alkyl, optionally substituted arylalkyl, and optionally substituted aryl;

$R^{49}$ is selected from the group consisting of H (hydrogen), halo, $R^{50}$O—, and optionally substituted $C_{1-6}$alkoxyl; and $R^{50}$ is selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$— each $R^{12}$ is individually selected from the group consisting of H (hydrogen), $R^{13}OC(O)$—, $R^{13}C(O)$—, $R^{13}C(O)CH_2$—, $R^{13}SO_2$—, alkylOC(O)—, or an optionally substituted arylOC(O)—;

each $R^{13}$ is individually selected from the group consisting of optionally substituted $C_{1-6}$alkyl, and an optionally substituted aryl;

each $R^{42}$ is individually $C_{1-6}$alkyl;

$X_5$ is O (oxygen) or S (sulfur);

each $X_6$ is independently selected from the group consisting of O (oxygen), $NR^{33}$, Se (selenium), or S (sulfur);

$R^{33}$ is selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

$X_7$ is O (oxygen), NH, or S (sulfur);

each $A_5$ is —$C(R^{44})_2$—;

each $A_6$ is individually selected from the group consisting of —$NR^{46}$—, —$C(R^{45})_2NR^{46}$—, —$C(R^{45})_2O$—, —$C(R^{45})_2S$—, —$C(R^{45})_2Se$—, —$OC(R^{45})_2O$—, —$SC(R^{45})_2S$—, —$SeC(R^{45})_2Se$—, —$C(R^{45})_2C(R^{45})_2NR^{46}$—, —$C(R^{45})_2C(R^{45})_2O$—, —$C(R^{45})_2C(R^{45})_2S$—, —$C(R^{45})_2C(R^{45})_2Se$—, and —$C(R^{45})_2$—;

each $A_7$ is —$C(R^{47})_2$—;

$A_4$ is an optionally substituted substituent selected from the group consisting of $C_{1-15}$alkyl, $C_{1-15}$alkoxy, $C_{1-15}$heteroalkyl, aryl, heteroaryl and heterocycle; or $A_4$ is $L_1$-$L_2$, -$X_9$-$L_1$-$X_9$-$L_2$-$X_9$-, -$X_9$-$L_1$-$L_2$-$X_9$-, $L_1$-$L_2$-$L_3$, $L_1$-$X_9$-$L_2$-$X_9$-$L_3$, -$X_9$-$L_1$-$X_9$-$L_2$-$X_9$-$L_3$-$X_9$-, $L_1$-$X_9$-$L_2$-$L_3$, -$X_9$-$L_1$-$X_9$-$L_2$-$X_9$-$L_3$, -$X_9$-$L_1$-$L_2$-$X_9$-$L_3$, $L_1$-$X_9$-$L_2$-$L_3$-$X_9$, -$X_9$-$L_1$-$X_9$-$L_2$-$X_9$-$L_3$-$X_9$, and -$X_9$-$L_1$-$L_2$-$X_9$-$L_3$-$X_9$;

$L_1$ is an optionally substituted substituent selected from the group consisting of $C_{1-5}$alkyl, $C_{1-5}$alkoxy, $C_{1-5}$heteroalkyl, aryl, heteroaryl and heterocycle;

$L_2$ is an optionally substituted substituent selected from the group consisting of $C_{1-5}$alkyl, $C_{1-5}$alkoxy, $C_{1-5}$heteroalkyl, aryl, heteroaryl and heterocycle;

$L_3$ is an optionally substituted substituent selected from the group consisting of $C_{1-5}$alkyl, $C_{1-5}$alkoxy, $C_{1-5}$heteroalkyl, aryl, heteroaryl and heterocycle;

each $X_9$ is independently selected from the group consisting of O (oxygen), $NR^{43}$, Se (selenium), or S (sulfur);

each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

m is an integer selected from 1, 2, or 3;
n is an integer selected from 1, 2, or 3;
q is an integer selected from 1, 2, or 3;
r is an integer selected from 0, 1, 2, 3, 4, 5, or 6;

each $C(R^{44})_2$ is independently selected, wherein each $R^{44}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{44}$ groups are taken together with the carbon to which they are attached to form an optionally substituted $C_{3-7}$cycloalkyl group;

each $C(R^{45})_2$ is independently selected, wherein each $R^{45}$ is individually selected from the group consisting of H (hydrogen), halo, $C_{1-6}$alkyl, $C_{1-6}$alkoxy, and Cl_6alkyl substituted with up to 5 fluorine; or optionally two $R^{45}$ are optionally taken together to form an oxo group;

each $R^{46}$ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $C(R^{47})_2$ is independently selected, wherein each $R^{47}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{47}$ groups are taken together with the carbon to which they are attached to form an optionally substituted $C_{3-7}$cycloalkyl group;

$R^{58}$ is selected from the group consisting of H (hydrogen), optionally substituted trityl, optionally substituted pixyl (9-phenylxanthenyl), and optionally substituted S-pixyl (9-phenylthioxanthyl);

$R^{59}$ is selected from the group consisting of H (hydrogen), halo, $R^{60}O(CH_2)_r$—, and optionally substituted $C_{1-6}$alkoxyl;

$R^{60}$ is selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—; and B is an optionally substituted substituent selected from the group consisting of a pyrimidine, a purine, and a heterocyclic base.

In some embodiments,

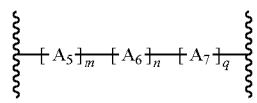

can be

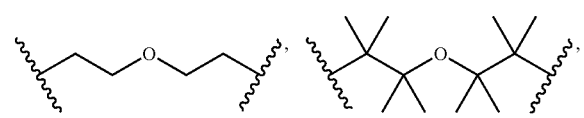

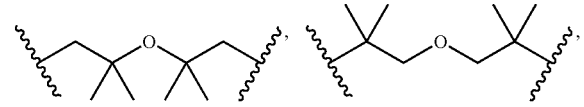

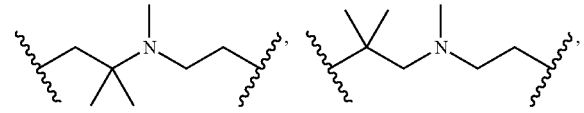

In some embodiments, the compounds of Formula VIII can be selected from the group consisting of:

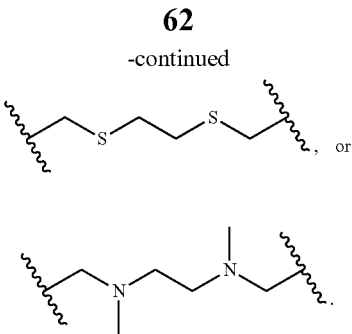

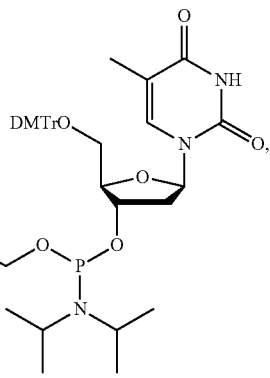

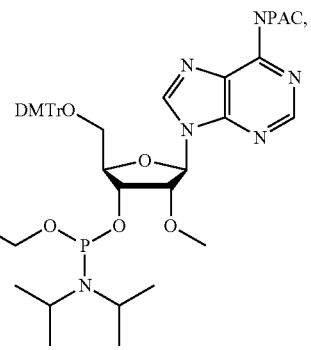

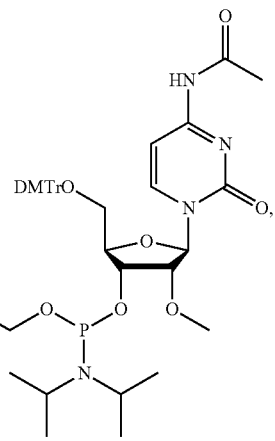

63
-continued
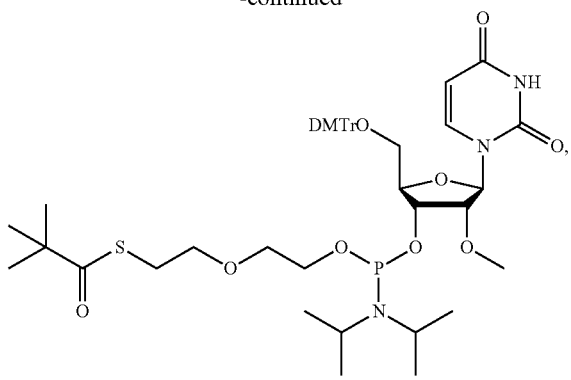
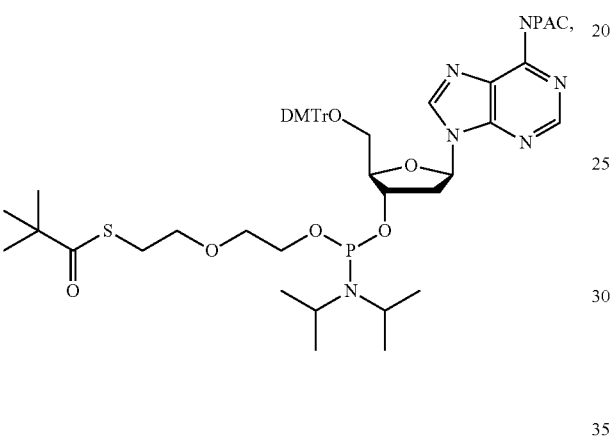
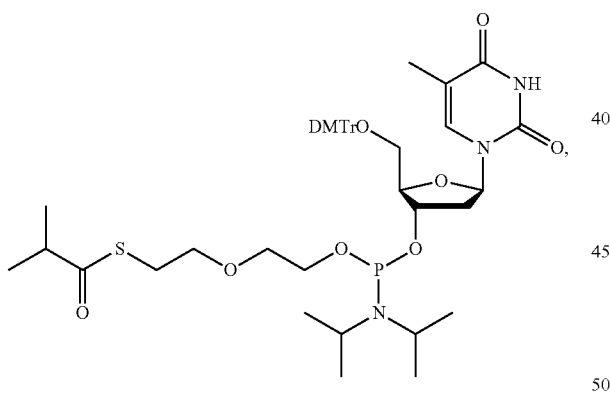
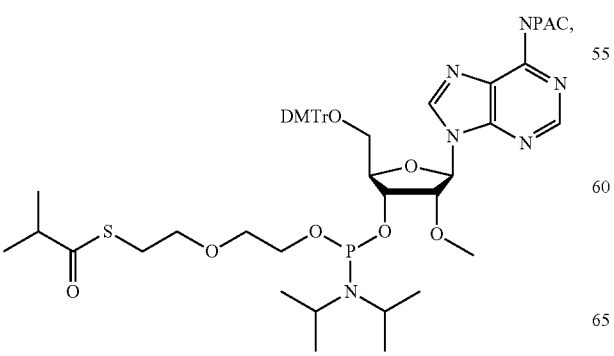
64
-continued
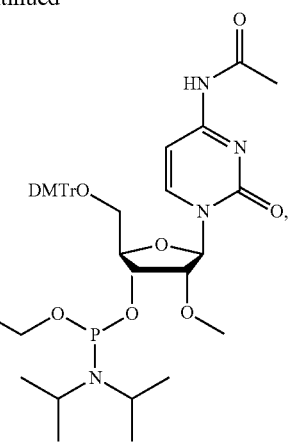
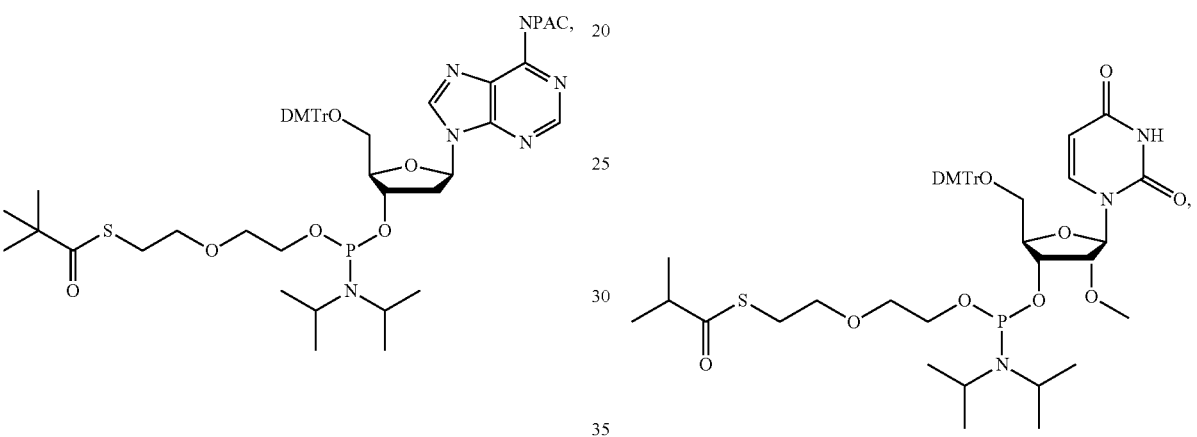
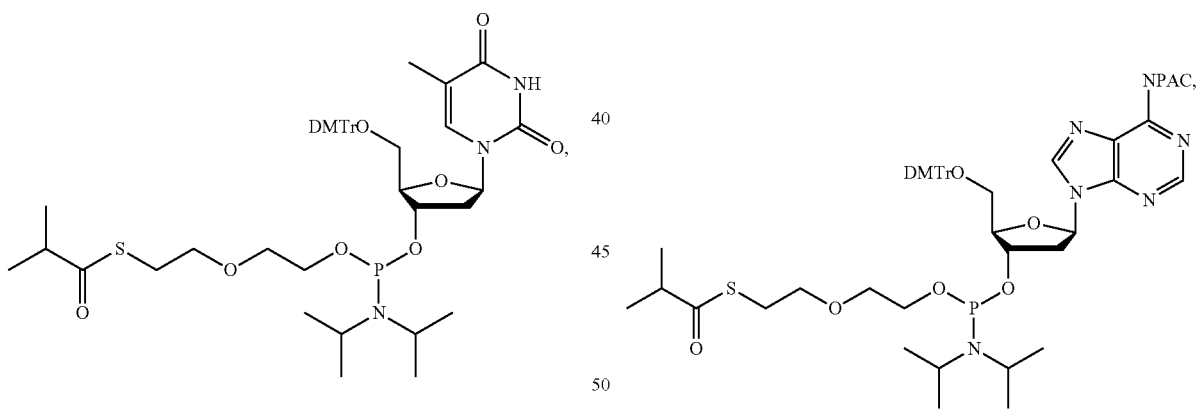
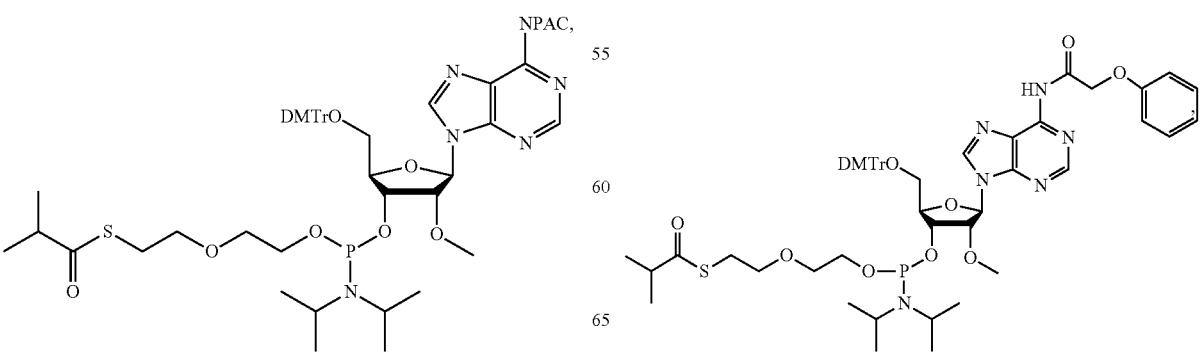

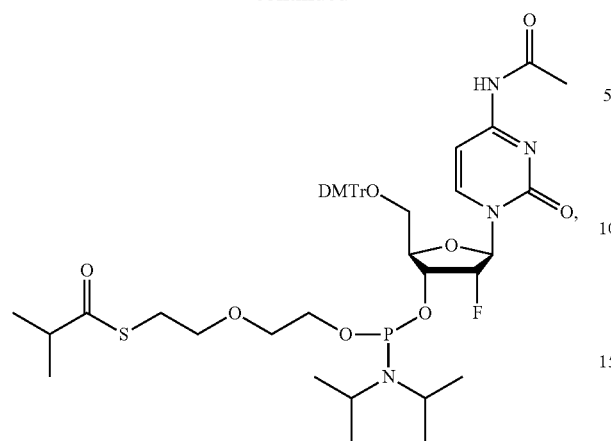
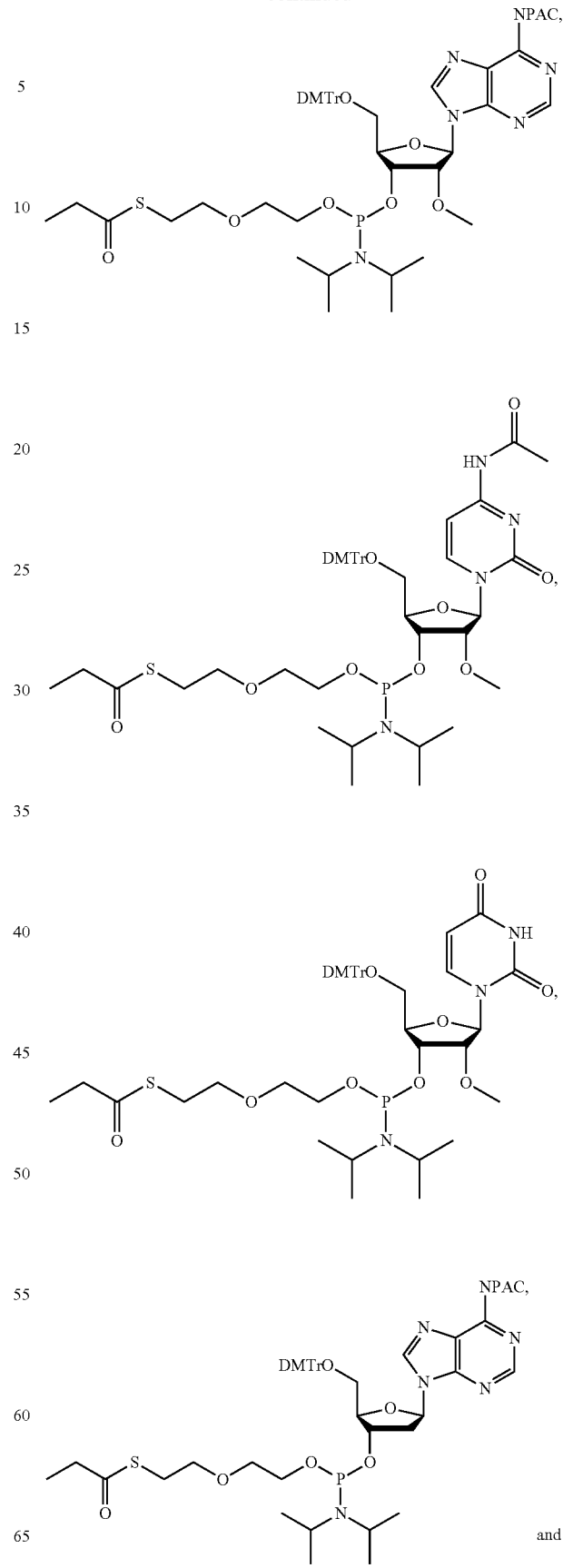

-continued

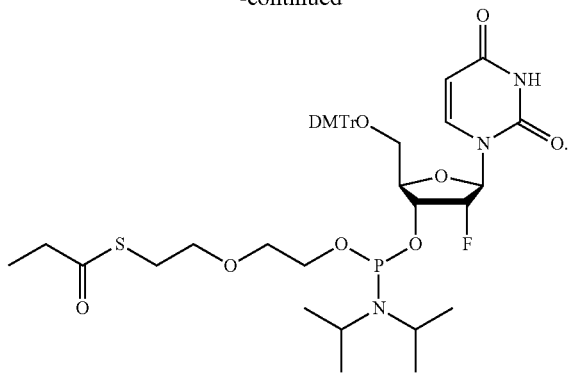

In some embodiments, the modified nucleosides disclosed herein can be incorporated into an oligonucleotide or polynucleotide. As used herein, a the term "polynucleotide," or "oligonucleotide" can refer to any molecule that includes a polynucleotide or oligonucleotide, or analog thereof, such as a ribozyme, an antisense molecule (e.g., siRNA, miRNA, shRNA, or the like), RNA or DNA aptamers, or the like. Polynucleotides are polymeric compounds made up of any number of covalently bonded nucleotide monomers, including nucleic acid molecules such as DNA and RNA molecules, including single- double- and triple-stranded molecules, and is expressly intended to embrace that group of polynucleotides commonly referred to as "oligonucleotides," which are typically distinguished as having a relatively small number (no more than about 30, e.g., about 5-10, 10-20 or 20-30) of nucleotide constituents. The term "polynucleotide" also encompasses molecules that contain both deoxyribo- and ribo-nucleotides, and combinations of bases including uracil, adenine, thymine, cytosine, guanine, inosine, xanthine, thypoxanthine, isocysteine, isoguaninne, and the like.

The terms "RNN" and "DNN" refer to "Ribo-Nucleic Neutral" polyribonucleotides and "$\overline{\text{Deoxyribo}}$-$\overline{\text{N}}$ucleic-$\overline{\text{N}}$eutral" polynucleotides or analogs thereof, that $\overline{\text{are}}$ modified, for example with the protecting groups disclosed herein, or other modifying groups, such that the modified RNA or DNA, i.e., the RNN or DNN, respectively, has less negative total charge when compared to a an RNA or DNA of the same sequence that is not modified with a compound/protecting group described herein. Note that the charge-neutralized individual residues of these biopolymers are no longer nucleic acids, so the traditional terminology of DNA and RNA are, in a strict sense, inaccurate and inapplicable.

Polynucleotides generally contain phosphodiester bonds, although nucleic acid analogs are known in the art that have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. The terms "polynucleotide" and "oligonucleotide" encompass mixtures of naturally occurring nucleic acids and analogs are encompassed by the term oligonucleotide and polynucleotide; alternatively, mixtures of different nucleic acid analogs, and mixtures of naturally occurring nucleic acids and analogs can be made. The terms "polynucleotide" and "oligonucleotide" also encompass hybrids of RNN, RNB, RNA, DNA, including but not limited to dsDNA, ssDNA, dsRNA, siRNA, shRNA, miRNA.

As used herein, the term "siRNA" is an abbreviation for "short interfering RNA," also sometimes known as "small interfering RNA" or "silencing RNA," and refers to a class of about 19-25 nucleotide-long double-stranded ribonucleic acid molecules that in eukaryotes are involved in the RNA interference (RNAi) pathway that results in post-transcriptional, sequence-specific gene silencing. siRNAs are processed by the RNase III enzyme dicer. siRNAs hybridize to cognate mRNAs having sequences homologous to the siRNA sequence, and, as part of a large protein complex, and induce mRNA cleavage and degradation.

As used herein, the term "dsRNA" is an abbreviation for "double-stranded RNA" and as used herein refers to a ribonucleic acid molecule having two complementary RNA strands and which stands distinct from siRNA in being at least about 26 nucleotides in length, and more typically is at least about 50 to about 100 nucleotides in length.

As used herein, the term "miRNA" is an abbreviation for "microRNA," and refers to a class of single-stranded RNA molecules of about 21-23 nucleotides in length, which regulate gene expression. miRNA is complementary to a part of one or more messenger RNAs (mRNAs). MicroRNAs negatively regulate the expression of genes with sequences that are complementary to the miRNAs.

As used herein, the term "shRNA" is an abbreviation for "small hairpin RNA" or "short hairpin RNA." shRNA is a sequence of ribonucleic acid that contains a sense sequence, antisense sequence, and a short loop sequence between the sense and antisense sequences. Due to the complementarity of the sense and antisense sequences, shRNA molecules tend to form hairpin-shaped double-stranded RNA (dsRNA). shRNA can be processed by dicer into siRNA which then get incorporated into the siRNA induced silencing complex (RISC).

The polynucleotides and oligonucleotides described herein can include both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

Polynucleotides and oligonucleotide derivatives, such as RNN and DNN polynucleotides and oligonucleotides containing one or more of the protecting groups disclosed herein, can be prepared using routine synthetic methods, including phosphoramidite chemistry, phosphonate chemistry and the like. The practice of phosphoramidite chemistry to prepare oligonucleotides is known from the published work of M. Caruthers and S. Beaucage and others. U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference, describe methods of oligonucleotide synthesis. Additionally, the practice of phosphoramidite chemistry has been systematically reviewed by Beaucage and Iyer in Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein, all of which are herein incorporated by reference.

Phosphonate chemistry can be used to prepare oligonucleotides and polynucleotides. For example, the following cycle can be utilized in an automated synthesizer:

Step 1: The resin attached to a protected nucleotide can be washed with solvent (e.g. acetonitrile) several times. Step 2: The protecting group (e.g. DMT (dimethoxytrityl)) on 5' hydroxy group can be under appropriate conditions (e.g. by 2.5% dichloroacetic acid in dichloromethane). Step 3: The resin can be washed with solvent (e.g. acetonitrile) several times. Step 4: The resin can be washed with solvent (e.g. pyridine/acetonitrile) several times. Step 5: 5'-protected Nucleoside H-phosphonate monomer (e.g. DMT protected) can be added to the resin with the free 5'-hydroxy group under appropriate conditions (e.g. (2-3 eq. solution in pyridine/acetonitrile), benzoic anhydride (6-9 eq. solution in pyridine/acetonitrile), triphosgene (0.6-0.9 eq. solution in acetonitrile) can be sequentially added to the reaction vessel. Step 6: The resin can be washed with solvent (e.g. pyridine/acetonitrile) several times. Step 7: Repeat Steps 1-6 using automated synthesizer until sequence is complete. Step 8: Oxidation. An $I_2$ solution or sulfur solution can be used to oxidize the H-phosphonate linkages to provide phosphate (PO or PS) linkages, respectively. The oxidation reaction can be performed in a reaction vessel and, therefore, need not be conducted in an automated synthesizer.

Nucleic acid synthesizers are commercially available and their use is generally understood by persons of ordinary skill in the art as being effective in generating nearly any oligonucleotide of reasonable length which may be desired.

In practicing phosphoramidite chemistry, useful 5'OH sugar blocking groups (abbreviated to DMT in the schematics and figures herein), include, but are not limited to trityl, monomethoxytrityl, dimethoxytrityl and trimethoxytrityl, especially dimethoxytrityl (DMTr). In practicing phosphoramidite chemistry, useful phosphite activating groups include but are not limited to dialkyl substituted nitrogen groups and nitrogen heterocycles. For example, in some embodiments, the methods disclosed herein include the use of a di-isopropylamino activating group.

Various nucleoside units, including the modified nucleosides of formula III disclosed herein, can be can be activated as amidites and incorporated in to biomolecules such as polynucleotides and oligonucleotides, including deoxynucleotides, ribonucleotides, 2'-alkoxy nucleotides, substituted 2'-O-alkyl nucleotides, and the like. Exemplary 2'-O-alkyl nucleotides that can be modified by the compounds disclosed herein are described in U.S. Pat. No. 5,466,786, herein incorporated by reference. In some embodiments, the amidites disclosed herein are used to modify nucleotides wherein the 2'-O-alkyl group, the methoxyethoxy group, described by Martin, P., Hely. Chim. Acta, 1995, 78, 486-504, also herein incorporated by reference.

Nucleosides comprising a protecting group as disclosed herein can be used in solid phase automated oligonucleotide synthesizer to generate the protected polynucleotides and oligonucleotides disclosed herein, e.g., the RNN, DNN, RNNi, dsRNN, shRNN, siRNN, compositions. By way of example, polynucleotides and oligonucleotides comprising the protecting groups disclosed herein can be synthesized by a MERMADE-6 solid phase automated oligonucleotide synthesizer (Bioautomation, Plano, Tex.), or any commonly available automated oligonucleotide synthesizer. Triester, phosphoramidite, or hydrogen phosphonate coupling chemistries described in, for example, M. Caruthers, Oligonucleotides: Antisense Inhibitors of Gene Expression, pp. 7-24, J. S. Cohen, ed. (CRC Press, Inc. Boca Raton, Fla., 1989) or Oligonucleotide synthesis, a practical approach, Ed. M. J. Gait, IRL Press, 1984; "Oligonucleotides and Analogues, A Practical Approach", Ed. F. Eckstein, IRL Press, 1991, are employed by these synthesizers to provide the desired oligonucleotides. The Beaucage reagent, as described in, for example, Journal of American Chemical Society, 1990, 112, 1253-1255, or elemental sulfur, as described in Beaucage et al., Tetrahedron Letters, 1981, 22, 1859-1862, is used with phosphoramidite or hydrogen phosphonate chemistries to provide substituted phosphorothioate oligonucleotides. For example, the reagents comprising the protecting groups recited herein can be used in numerous applications where protection is desired. Such applications include, but are not limited to, both solid phase and solution phase, oligo-synthesis, polynucleotide synthesis and the like.

Accordingly, some embodiments provide a compound of formula IV:

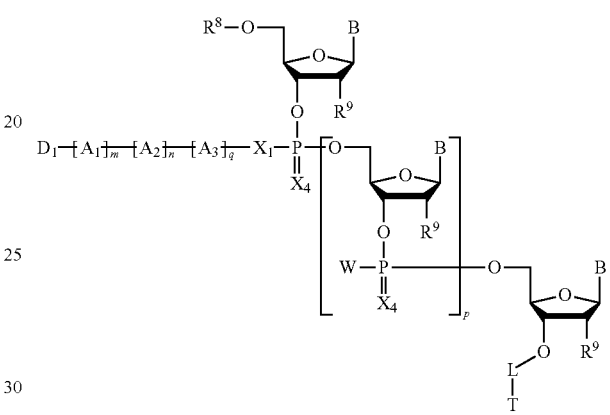

wherein:
each $D_1$ is independently

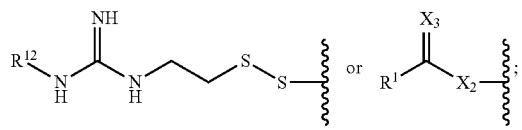

each $R^1$ is independently an optionally substituted substituent selected from the group consisting of $C_{1-6}$alkyl, $C_{1-6}$alkoxyl, aryl, heteroaryl, heterocyclyl, —NH$C_{1-6}$alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroarylC(O)O—, and heterocyclylC(O)O—;

L is a linker;

T is a solid support;

each $R^{12}$ is independently H (hydrogen), alkylOC(O)—, or an optionally substituted arylOC(O)—;

each $X_1$ is independently O (oxygen) or S (sulfur);

each $X_2$ is independently O (oxygen), NR$^3$, or S (sulfur);

each $R^3$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $X_3$ is independently O (oxygen), NH, or S (sulfur);

each $A_1$ is —C(R$^4$)$_2$—;

each $A_2$ is individually selected from the group consisting of —NR$^6$—, —C(R$^5$)$_2$NR$^6$—, —C(R$^5$)$_2$O—, —C(R$^5$)$_2$S—, —C(R⁵)₂Se—, —C(R⁵)₂C(R⁵)₂NR⁶—, —C(R⁵)₂C(R⁵)₂ O—, —C(R⁵)₂C(R⁵)₂S—, —C(R⁵)₂C(R⁵)₂Se—, and —C(R⁵)₂—;

each $A_3$ is —C(R⁷)₂—;
each m is independently an integer selected from 1, 2, or 3;
each n is independently an integer selected from 1, 2, or 3;
each q is independently an integer selected from 1, 2, or 3;
each C(R⁴)₂ is independently selected, wherein each R⁴ is independently selected from the group consisting of H (hydrogen), halo, $C_{1-6}$alkyl, and $C_{1-6}$alkyl substituted with up to 5 fluorine, or optionally two R⁴ groups are taken together with the carbon to which they are attached to form an optionally substituted $C_{3-7}$cycloalkyl group;
each C(R⁵)₂ is independently selected, wherein each R⁵ is independently selected from the group consisting of H (hydrogen), halo, $C_{1-6}$alkyl, and $C_{1-6}$alkyl substituted with up to 5 fluorine; or two R⁵ are optionally taken together to form an oxo group;
each R⁶ is independently selected from the group consisting of H (hydrogen), $C_{1-6}$alkyl, $C_{1-6}$alkylC(O)—, $C_{1-6}$alkyl OC(O)—, $C_{1-6}$alkylNHC(O)—, $C_{1-6}$alkylS(O)₂—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)₂—;
each C(R⁷)₂ is independently selected, wherein each R⁷ is independently selected from the group consisting of H (hydrogen), halo, $C_{1-6}$alkyl, and $C_{1-6}$alkyl substituted with up to 5 fluorine, or optionally two R⁷ groups are taken together with the carbon to which they are attached to form an optionally substituted $C_{3-7}$cycloalkyl group;
R⁸ is selected from the group consisting of H (hydrogen), optionally substituted trityl, optionally substituted pixyl (9-phenylxanthenyl), optionally substituted S-pixyl (9-phenylthioxanthenyl);
each R⁹ is independently selected from the group consisting of H (hydrogen), halo, —OR¹⁰, and optionally substituted $C_{1-6}$alkoxyl;
each R¹⁰ is independently selected from the group consisting of H (hydrogen), triisopropylsilylOCH₂—, tert-butyldimethylsilylOCH₂—, triethylsilylOCH₂—, trimethylsilylethylOCH₂—, triisopropylsilyl-, tert-butyldimethylsilyl-, trimethylsilylethyl-, triethylsilyl-, optionally substituted trimethylsilyl-, and optionally substituted trimethylsilylOCH₂—;
each B can individually be an optionally substituted substituent selected from the group consisting of a pyrimidine, a purine or heterocyclic base, including but not limited to uracil, thymine, cytosine, adenine, guanine, inosine, xanthine hypoxanthine, isocytosine, isoguanine, etc. and non-natural nucleobase analogs such as difluorotolyl, nitroindolyl, nitropyrrolyl, or nitroimidazolyl;
p is an integer from 0 (zero) to about 50;
each W is independently —OR¹¹ or $$\left[D_1 \!\!-\!\! \{A_1\}_{\overline{m}} \!\!-\!\! \{A_2\}_{\overline{n}} \!\!-\!\! \{A_3\}_{\overline{q}} \!\!-\!\! X_1\right]\!\!-\!\!;$$

each $X_4$ is independently O (oxygen) or S (sulfur); and
each R¹¹ is independently H (hydrogen), $C_{1-6}$alkyl, —CH₂CH₂CN, or absent,
with the proviso that when R¹¹ is absent then —OR¹¹ is —O⁻ (anionic oxygen radical) providing an phosphate anionic diester group or anionic thiophosphate diester group.

Some embodiments provide a compound of formula IX:

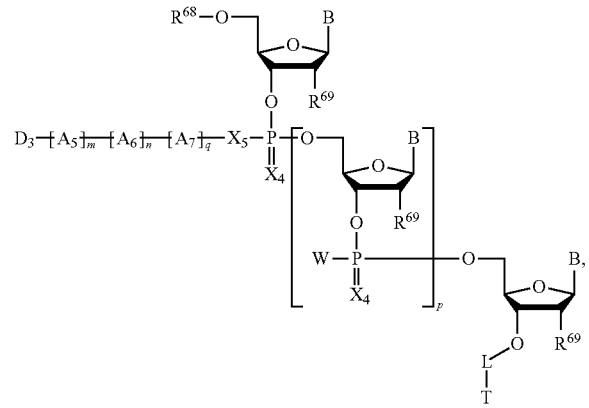

(IX)

wherein:
each $D_3$ is independently

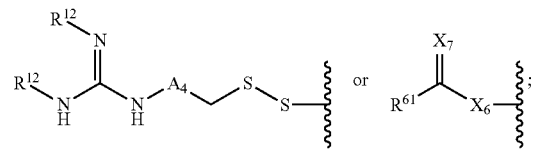

each R⁶¹ is independently an optionally substituted substituent selected from the group consisting of $C_{1-8}$alkyl, $C_{1-8}$alkenyl, $C_{1-8}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, $C_{1-6}$alkylC(O)O—, arylC(O) O—, heteroarylC(O)O—, heterocyclylC(O)O—, and $C_{1-8}$alkyl substituted with one or more hydroxyl groups; or R⁶¹ is selected from the group consisting of (R⁷⁸)₄N (CH₂)$_r$—, (R⁷⁸)₃C(CH₂)$_r$—, (R⁷⁸)₃CNH(CH₂)$_r$—, HS (CH₂)$_r$—, $C_{1-8}$heteroalkyl, and guanidiny(CH₂)$_r$—;
L is a linker arm;
T is a solid support;
each R¹² is individually selected from the group consisting of H (hydrogen), R¹³OC(O)—, R¹³C(O)—, R¹³C(O)CH₂—, R¹³SO₂—, alkylOC(O)—, or an optionally substituted arylOC(O)—;
each R¹³ is individually selected from the group consisting of optionally substituted $C_{1-6}$alkyl, and an optionally substituted aryl;
each $X_5$ is independently O (oxygen) or S (sulfur);
each $X_6$ is independently selected from the group consisting of O (oxygen), NR⁶³, Se (selenium), or S (sulfur);
each R⁶³ is independently selected from the group consisting of H (hydrogen), $C_{1-6}$alkyl, $C_{1-6}$alkylC(O)—, $C_{1-6}$alkyl OC(O)—, $C_{1-6}$alkylNHC(O)—, $C_{1-6}$alkylS(O)₂—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)₂—;
each $X_7$ is independently O (oxygen), NH, or S (sulfur);
each $A_4$ is independently an optionally substituted substituent selected from the group consisting of $C_{1-15}$alkyl, $C_{1-15}$alkoxy, $C_{1-15}$heteroalkyl, aryl, heteroaryl and heterocycle; or $A_4$ is $L_1$-$L_2$, $L_1$-$X_9$-$L_2$, -$X_9$-$L_1$-$X_9$-$L_2$-$X_9$-, $L_1$-$X_9$-$L_2$-$X_9$-$L_3$, -$X_9$-$L_4$-$X_9$-$L_2$-$X_9$-$L_3$-$X_9$-, $L_1$-$X_9$-$L_2$-$L_3$, -$X_9$-$L_1$-

$X_9-L_2-X_9-L_3$, $-X_9-L_1-L_2-X_9-L_3$, $L_1-X_9-L_2-L_3-X_9$, $-X_9-L_1-X_9-L_2-X_9-L_3-X_9$, and $-X_9-L_1-L_2-X_9-L_3-X_9$;

each $L_1$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $L_2$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $L_3$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $X_9$ is independently selected from the group consisting of O (oxygen), $NR^{43}$, Se (selenium), or S (sulfur);

each $NR^{43}$ is independently selected, wherein each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$ alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $A_5$ is —C($R^{64}$)$_2$—;

each $A_6$ is individually selected from the group consisting of —$NR^{66}$—, —C($R^{65}$)$_2$$NR^{66}$—, —C($R^{65}$)$_2$O—, —C($R^{65}$)$_2$S—, —C($R^{65}$)$_2$Se—, —OC($R^{65}$)$_2$O—, —SC($R^{65}$)$_2$S—, —SeC($R^{65}$)$_2$Se—, —C($R^{65}$)$_2$C($R^{65}$)$_2$$NR^{66}$, C($R^{65}$)$_2$C($R^{65}$)$_2$O—, C($R^{65}$)$_2$C($R^{65}$)$_2$S—, —C($R^{65}$)$_2$C($R^{65}$)$_2$Se—, and —C($R^{65}$)$_2$—;

each $A_7$ is —C($R^{67}$)$_2$—;

each m is independently an integer selected from 1, 2, or 3;

each n is independently an integer selected from 1, 2, or 3;

each q is independently an integer selected from 1, 2, or 3;

each r is independently an integer selected from 0, 1, 2, 3, 4, 5, or 6;

each C($R^{64}$)$_2$ is independently selected, wherein each $R^{64}$ is independently selected from the group consisting of H (hydrogen), halo, $C_{1-6}$alkyl, $C_{1-6}$alkoxy, and $C_{1-6}$alkyl substituted with up to 5 fluorine, or optionally two $R^{64}$ groups are taken together with the carbon to which they are attached to form an optionally substituted $C_{3-7}$cycloalkyl group;

each C($R^{65}$)$_2$ is independently selected, wherein each $R^{65}$ is independently selected from the group consisting of H (hydrogen), halo, $C_{1-6}$alkyl, $C_{1-6}$alkoxy, and $C_{1-6}$alkyl substituted with up to 5 fluorine; or two $R^{65}$ are optionally taken together to form an oxo group;

each $R^{66}$ is independently selected from the group consisting of H (hydrogen), $C_{1-6}$alkyl, $C_{1-6}$alkylC(O)—, $C_{1-6}$alkyl OC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each C($R^{67}$)$_2$ is independently selected, wherein each $R^{67}$ is independently selected from the group consisting of H (hydrogen), halo, $C_{1-6}$alkyl, $C_{1-6}$alkoxy, and $C_{1-6}$alkyl substituted with up to 5 fluorine, or optionally two $R^{67}$ groups are taken together with the carbon to which they are attached to form an optionally substituted $C_{3-7}$cycloalkyl group;

$R^{68}$ is selected from the group consisting of H (hydrogen), optionally substituted trityl, optionally substituted pixyl (9-phenylxanthenyl), and optionally substituted S-pixyl (9-phenylthioxanthyl);

each $R^{69}$ is independently selected from the group consisting of H (hydrogen), halo, $R^{60}$O(CH$_2$)$_r$—, and optionally substituted $C_{1-6}$alkoxyl;

each $R^{60}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

each $R^{78}$ is independently selected from the group consisting of H (hydrogen), $R^{79}$(CH$_2$)$_r$, optionally substituted $C_{1-6}$alkyl, optionally substituted $C_{3-7}$alkyl, optionally substituted arylalkyl, and optionally substituted aryl;

each $R^{79}$ is independently selected from the group consisting of H (hydrogen), halo, $R^{80}$O—, and optionally substituted $C_{1-6}$alkoxyl;

each $R^{80}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

each B is independently an optionally substituted substituent selected from the group consisting of a pyrimidine, a purine, and a heterocyclic base;

p is an integer from 0 (zero) to about 50;

each $W_1$ is independently —$OR^{11}$ or

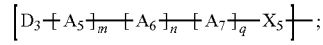

each $X_4$ is independently O (oxygen) or S (sulfur); and each $R^{11}$ is independently H (hydrogen), $C_{1-6}$alkyl, —CH$_2$CH$_2$CN, or absent, with the proviso that when $R^{11}$ is absent then —$OR^{11}$ is —O$^-$ (anionic oxygen radical) providing an phosphate anionic diester group or anionic thiophosphate diester group.

As used herein, the term "linker arm" refers to any group that attaches a nucleotide to a solid support. For example, linker can be 1,4-phenylenedioxydiacetyl, or any other group known in the art for solid phase DNA or RNA synthesis, including but not limited to those disclosed in U.S. Pat. Nos. 5,112,962; 6,015,895, each of which is herein incorporated by reference in its entirety.

As used herein, the term "solid support" can refers to any composition known in the art for solid phase DNA or RNA synthesis. Accordingly, the term solid support can refer to an aminomethyl-polystyrene support, a long chain alkylamino-CPG support, an aminomethyl-polystyrene support, or the like.

Some embodiments provide compositions that consist of, consist essentially of, or comprise an RNN or DNN phosphate protected oligonucleotide or polynucleotide derivative of formula V:

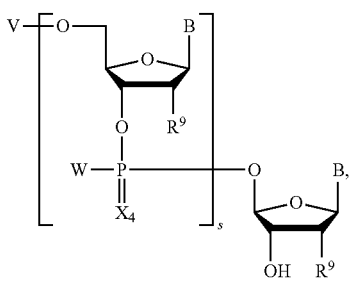

(V)

wherein:

each $X_4$ is individually O (oxygen) or S (sulfur);

s is an integer from 1 to about 5000, preferably 10 to about 100, and including siRNA where s is about 19-24 and is double-stranded (with or without a hairpin loop) and miRNA wherein s is 20-22;

each $R^9$ is individually selected from the group consisting of H (hydrogen), halo, —$OR^{10}$, and optionally substituted $C_{1-6}$alkoxyl;

each $R^{10}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

each B can individually be an optionally substituted substituent selected from the group consisting of a pyrimidine, a purine or heterocyclic base, including but not limited to uracil, thymine, cytosine, adenine, guanine, inosine, xanthine, hypoxanthine, isocytosine, isoguanine, etc. and non-natural nucleobase analogs such as difluorotolyl, nitroindolyl, nitropyrrolyl, or nitroimidazolyl;

V is H (hydrogen) or a transduction domain, nuclear localization sequence, cell penetrating peptide, receptor ligand, cholesterol, antibody, protamine, hormone, etc. optionally attached via a linker to a single strand of RNN, DNN, RNA or DNA wherein said linker is a covalent or non-covalent linker each W is independently $R^{11}$O— or

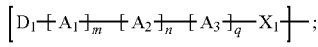

each $R^{11}$ is independently H (hydrogen), $C_{1-6}$alkyl, —$CH_2CH_2CN$, or absent;

each $D_1$ is independently

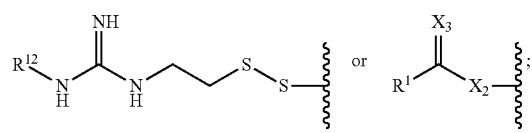

each $R^1$ is independently an optionally substituted substituent selected from the group consisting of $C_{1-6}$alkyl, $C_{1-6}$alkyl substituted with one or more hydroxyl groups, $C_{1-6}$alkoxyl, aryl, heteroaryl, heterocyclyl, —NH$C_{1-6}$alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroarylC(O)O—, and heterocyclylC(O)O—;

each $R^{12}$ is independently is H (hydrogen), alkylOC(O)—, or an optionally substituted arylOC(O)—;

each $X_1$ is independently O (oxygen) or S (sulfur);

each $X_2$ is independently O (oxygen), $NR^3$, or S (sulfur);

each $R^3$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C1_6$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

$X_3$ is O (oxygen), NH, or S (sulfur);

each $A_1$ is —$C(R^4)_2$—;

each $A_2$ is individually selected from the group consisting of —$NR^6$—, —$C(R^5)_2NR^6$—, —$C(R^5)_2O$—, —$C(R^5)_2S$—, —$C(R^5)_2Se$—, —$C(R^5)_2C(R^5)_2NR^6$—, —$C(R^5)_2C(R^5)_2O$—, —$C(R^5)_2C(R^5)_2S$—, —$C(R^5)_2C(R^5)_2Se$—, and —$C(R^5)_2$—;

each $A_3$ is —$C(R^7)_2$—;

m is an integer selected from 1, 2, or 3;

n is an integer selected from 1, 2, or 3;

q is an integer selected from 1, 2, or 3;

each $C(R^4)_2$ is independently selected, wherein each $R^4$ is individually selected from the group consisting of H (hydrogen), halo, $C_{1-6}$alkyl, and $C_{1-6}$alkyl substituted with up to 5 fluorine, or optionally two $R^4$ groups are taken together with the carbon to which they are attached to form an optionally substituted $C_{3-7}$cycloalkyl group;

each $C(R^5)_2$ is independently selected, wherein each $R^5$ is individually selected from the group consisting of H (hydrogen), halo, $C_{1-6}$alkyl, and $C_{1-6}$alkyl substituted with up to 5 fluorine; or two $R^5$ are optionally taken together to form an oxo group;

each $R^6$ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—; and each $C(R^7)_2$ is independently selected, wherein each $R^7$ is individually selected from the group consisting of H (hydrogen), halo, $C_{1-6}$alkyl, and $C_{1-6}$alkyl substituted with up to 5 fluorine, or optionally two $R^7$ groups are taken together with the carbon to which they are attached to form an optionally substituted $C_{3-7}$cycloalkyl group;

with the proviso that at least one W is

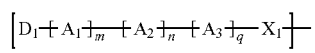

and when $R^{11}$ is absent then $R^{11}$O— is —O$^-$ (anionic oxygen radical) providing an phosphate anionic diester group or anionic thiophosphate diester group.

In some embodiments, V is an optionally linked to a transduction domain, nuclear localization sequence, cell penetrating peptide, receptor ligand, cholesterol, antibody, protamine, hormone, etc. optionally attached via a linker to a single strand of RNN, DNN, RNA or DNA wherein said linker is a covalent or non-covalent linker. This construct can be referenced as a carrier strand. The carrier strand can be comprised of combinations or plurality of the mentioned targeting motifs, for example a 3× PTD of natural or synthetic sources attached to the optionally protected oligonucleotide or analog thereof.

Some embodiments provide compositions that consist of, consist essentially of, or comprise an RNN or DNN phosphate protected oligonucleotide or polynucleotide derivative of formula X:

$$V-\left[O-\begin{array}{c}B\\\\O\\\\O\quad R^{89}\\\\W_2-P-O\\\\X_4\end{array}\begin{array}{c}B,\\\\O\\\\OH\quad R^{89}\end{array}\right]_s \quad (X)$$

wherein:
each $X_4$ is individually O (oxygen) or S (sulfur);
s is an integer from 1 to about 5000;
each $R^{89}$ is individually selected from the group consisting of H (hydrogen), halo, —$OR^{90}$, and optionally substituted $C_{1-6}$ alkoxyl;
each $R^{90}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;
each B is individually an optionally substituted substituent selected from the group consisting of a pyrimidine, a purine, and a heterocyclic base;
V is H (hydrogen) or a transducing moiety;
each $W_2$ is independently $R^{11}$O— or $$\left[D_3+A_5\right]_m+A_6\right]_n+A_7\right]_q-X_5\right]-;$$

each $R^{11}$ is independently H (hydrogen), $C_{1-6}$alkyl, —CH$_2$CH$_2$CN, or absent;
each $D_3$ is independently <br/>

$$\begin{array}{c}R^{12}\\\\\quad N\\\\R^{12}\!-\!N\quad\quad N\!-\!A_4\!-\!S\!-\!S\!-\!\xi\\\\H\quad\quad H\end{array}\quad\text{or}\quad\begin{array}{c}X_7\\\\\parallel\\\\R^{61}\!-\!X_6\!-\!\xi\end{array};$$

each $R^{61}$ is independently an optionally substituted substituent selected from the group consisting of $C_{1-8}$alkyl, $C_{1-8}$alkenyl, $C_{1-6}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, $C_{1-6}$alkylC(O)O—, arylC(O)O—, heteroarylC(O)O—, heterocyclylC(O)O—, and $C_{1-8}$alkyl substituted with one or more hydroxyl groups; or $R^{61}$ is selected from the group consisting of $(R^{78})_4N(CH_2)_r$—, $(R^{78})_3C(CH_2)_r$—, $(R^{78})_3CNH(CH_2)_r$—, HS$(CH_2)_r$—, $C_{1-8}$heteroalkyl, and guanidiny$(CH_2)_r$—;

each $R^{78}$ is independently selected from the group consisting of H (hydrogen), $R^{79}(CH_2)_r$—, optionally substituted $C_{1-6}$alkyl, optionally substituted $C_{3-7}$alkyl, optionally substituted arylalkyl, and optionally substituted aryl;
each $R^{79}$ is independently selected from the group consisting of H (hydrogen), halo, $R^{80}$O—, and optionally substituted $C_{1-6}$alkoxyl;
each $R^{80}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;
each $R^{12}$ is individually selected from the group consisting of H (hydrogen), $R^{13}$OC(O)—, $R^{13}$C(O)—, $R^{13}$C(O)CH$_2$—, $R^{13}$SO$_2$—, alkylOC(O)—, or an optionally substituted arylOC(O)—;
each $R^{13}$ is individually selected from the group consisting of optionally substituted $C_{1-6}$alkyl, and an optionally substituted aryl;
each $X_5$ is independently O (oxygen) or S (sulfur);
each $X_6$ is independently selected from the group consisting of O (oxygen), $NR^{63}$, Se (selenium), or S (sulfur);
each $R^{63}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
each $X_7$ is independently O (oxygen), NH, or S (sulfur);
each $A_4$ is independently an optionally substituted substituent selected from the group consisting of $C_{1-15}$alkyl, $C_{1-15}$alkoxy, $C_{1-15}$heteroalkyl, aryl, heteroaryl and heterocycle; or $A_4$ is $L_1$-$L_2$, $L_1$-$X_9$-$L_2$, -$X_9$-$L_1$-$X_9$-$L_2$-$X_9$-, -$X_9$-$L_1$-$L_2$-$X_9$-, $L_1$-$L_2$-$L_3$, $L_1$-$X_9$-$L_2$-$X_9$-$L_3$, -$X_9$-$L_1$-$X_9$-$L_2$-$X_9$-$L_3$-$X_9$-, $L_1$-$X_9$-$L_2$-$L_3$, -$X_9$-$L_1$-$X_9$-$L_2$-$X_9$-$L_3$, -$X_9$-$L_1$-$L_2$-$X_9$-$L_3$, $L_1$-$X_9$-$L_2$-$L_3$-$X_9$, -$X_9$-$L_1$-$X_9$-$L_2$-$X_9$-$L_3$-$X_9$, and -$X_9$-$L_1$-$L_2$-$X_9$-$L_3$-$X_9$;
each $L_1$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $L_2$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $L_3$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $X_9$ is independently selected from the group consisting of O (oxygen), $NR^{43}$, Se (selenium), or S (sulfur);
each $NR^{43}$ is independently selected, wherein each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
each $A_5$ is —$C(R^{84})_2$—;
each $A_6$ is individually selected from the group consisting of —$NR^{86}$—, —$C(R^{85})_2NR^{86}$—, —$C(R^{85})_2O$—, —$C(R^{85})_2S$—, —$C(R^{85})_2Se$—, —$OC(R^{85})_2O$—, —$SC(R^{85})_2S$—, —SeC($R^{85}$)$_2$Se—, —C($R^{85}$)$_2$C($R^{85}$)$_2$N$R^{86}$—, —C($R^{85}$)$_2$C($R^{85}$)$_2$O—, —C($R^{85}$)$_2$C($R^{85}$)$_2$S—, —C($R^{85}$)$_2$C($R^{85}$)$_2$Se—, and —C($R^{85}$)$_2$—;

each $A_7$ is —C($R^{87}$)$_2$—;
each m is independently an integer selected from 1, 2, or 3;
each n is independently an integer selected from 1, 2, or 3;
each q is independently an integer selected from 1, 2, or 3;
each r is independently an integer selected from 0, 1, 2, 3, 4, 5, or 6;
each C($R^{84}$)$_2$ is independently selected, wherein each $R^{84}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{84}$ groups are taken together with the carbon to which they are attached to form an optionally substituted $C_{3-7}$cycloalkyl group;
each C($R^{85}$)$_2$ is independently selected, wherein each $R^{85}$ is individually selected from the group consisting of H (hydrogen), halo, $C_{1-6}$alkyl, $C_{1-6}$alkoxy, and $C_{1-6}$alkyl substituted with up to 5 fluorine; or two $R^{85}$ are optionally taken together to form an oxo group;
each $R^{86}$ is individually selected from the group consisting of H (hydrogen), $C_{1-6}$alkyl, $C_{1-6}$alkylC(O)—, $C_{1-6}$alkyl OC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—; and
each C($R^{87}$)$_2$ is independently selected, wherein each $R^{87}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{87}$ groups are taken together with the carbon to which they are attached to form an optionally substituted $C_{3-7}$cycloalkyl group;

with the proviso that at least one $W_2$ is

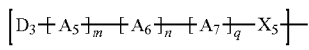

and when $R^{11}$ is absent then $R^{11}$O— is —O⁻ (anionic oxygen radical) providing an phosphate anionic diester group or anionic thiophosphate diester group.

Compositions that consist of, consist essentially of, or comprise an RNN or DNN phosphate protected oligonucleotide or polynucleotide derivative of formula V or X, include embodiments where V can be a transducing moiety, wherein said transducing moiety is a protein transduction domain. In some embodiments, an RNN or DNN phosphate protected oligonucleotide or polynucleotide derivative of formula V or X, can further include a plurality of transducing moieties. In some embodiments, s can be an integer between about 10 and 100. In some embodiments, s can be an integer between about 19 and 24. In some embodiments, s can be an integer between 20 and 22. In some embodiments, an RNN or DNN phosphate protected oligonucleotide or polynucleotide derivative of formula V or X, in double-stranded form, wherein in each strand, s can be an integer between about 19 and 24. In some embodiments, s can be an integer between about 42 and 55, comprising a hairpin loop.

Some embodiments include method of delivering a biomolecule to a target cell, comprising:
providing a phosphate-protected oligonucleotide derivative of formula V or X,
providing a target cell; and
contacting said target cell with said phosphate-protected oligonucleotide derivative to deliver the derivative into the cell. In some embodiments, the contacting step can be performed in vitro. In some embodiments, the contacting step can be performed in vivo. In some embodiments, the phosphate-protected oligonucleotide can be an siRNA derivative. In some embodiments, the phosphate-protected oligonucleotide can be an miRNA derivative. In some embodiments, V can be a transducing moiety. In some embodiments, said transducing moiety can be a protein transduction domain.

Some embodiments include a composition comprising the nucleic acid molecule of formula V or X, in a pharmaceutically acceptable carrier, salt or diluents buffer. In some embodiments, the sense strand, the antisense strand, or both the sense strand and the antisense strand include a 3'-overhang.

The attachment of the delivery and targeting domain to the oligo construct can be accomplished by numerous techniques well known to those skilled in the art. In some embodiments, the attachment can be either covalent or non-covalent. Examples of non-covalent attachment include, but are not limited to, a biotin streptavidin association, hydrogen bonding, non covalent metal/ligand association, a nucleotide overhang that allows attachment to by base pairing, or the noncovalent attachment of a fusion protein containing a combination of delivery and targeting domains with a oligonucleotide binding domain of the general design described in U.S. Pat. Nos. 6,376,248B1, and 6,835,810B2. These examples are by no means intended to limit the scope of the invention, a vast wealth of non-covalent linkage approaches are available to choose from and are obvious extensions to those practicing in the field. Examples of covalent linkages include, but are not limited to, disulfide formation, free thiol bromoacetyl reactions, azide alkynyl addition reactions (Click chemistry, Huisgen reaction), via homo-bifunctional linkers, hetero-bifunctional linkers and the like. Bio-condensations of this type are well established in the field and the previous examples are not provided with the intent of limiting the scope of the invention.

In some embodiments, the attachment to the oligonucleotide can occur through the nucleobase, the 2' position, or the 5' position of the nucleoside and can be optionally formed at the 3', 5' or both terminal nucleosides or from any nucleobase within the carrier strand. Multiple linkers can be applied to this technology to generate branched or unbanked combinations of delivery and cell targeting domains. Examples of this type of linker include, but are not limited to, commercially available (Glen Research) Trebler linkages, doubling linkers and combinations thereof. Branching of the delivery and targeting domains can also be accomplished during peptide synthesis by for example using appropriately protected lysine in the peptide synthesizer and using both of the resulting primary amines as extension points.

The modified oligonucleotides and polynucleotides described herein (e.g., RNN and DNN oligonucleotides) are not limited by any particular sequence. Any number of oligonucleotide or polynucleotides useful for diagnostics, therapeutics and research can be used in the methods and compositions of the disclosure, to generate cognate RNN and DNN oligonucleotides and polynucleotides. Various sources of oligonucleotides and polynucleotides are available to one of skill in the art. For example, fragments of a genome may be isolated and the isolated polynucleotides modified in accordance with the disclosure to reduce the overall net anionic charge using phosphodiester and/or phosphorothioate protecting groups or may be used as a source for extension of the oligonucleotide or polynucleotide using, for example, nucleic acid synthesis techniques known in the art.

In preferred embodiments wherein the compounds or protecting groups disclosed herein are linked to a polynucleotide or oligonucleotide, to produce an RNN or DNN, the RNN or DNN has a pH between about 7 to 12. For example, in some embodiments, the RNN or DNN has a pH of 7.0-7.5, 7.5-8.0, 8.0-8.5, 8.5-9.0, 9.0-9.5, 9.5-10.0, 10.0-10.5, 10.5-11.0, 11.0-11.5, 11.5-12.0, 12.0, or any number in between.

In some embodiments, the compounds/protecting groups described herein are linked to polynucleotides that are 5-10-mers, 10-15-mers, 15-20mers, 20-25 mers, 25-30-mers, 30-40-mers, 40-45-mers, 45-50-mers, 50-55-mers, 55-60-mers, 60-65-mers, 65-70-mers, 70-75-mers, 75-80-mers, 80-85-mers, 85-90-mers, 90-95-mers, 95-100-mers, 100-120-mers, 120-140-mers, 140-160-mers, 160-180-mers, 180-200-mers, or greater, or any number in between, including full length genes or RNA transcripts thereof. In some embodiments the polynucleotide can be, for example, a 43-69-mer that forms a hairpin, wherein about 4-5 of the nucleotide/modified subunits form the turn with a preferred length of 18-32 nucleobases participating in the double stranded portion of the complex. Alternate configurations include constructs where both ends form loops as in a dumbbell structure with a preferred double stranded region of between 18-32 nucleotides In some embodiments, only one protecting group disclosed herein is present within a polynucleotide. In other embodiments, a plurality of protecting groups is present within a polynucleotide. In some embodiments, a protecting group disclosed herein is present on every phosphate group of a polynucleotide. In some embodiments, a protecting group disclosed herein is present on every other phosphate group of a polynucleotide. In some embodiments, a protecting group disclosed herein is positioned at regularly occurring intervals, e.g., at every $3^{rd}$, $4^{th}$, $5^{th}$, $6^{th}$, $7^{th}$, $8^{th}$, $9^{th}$, or $10^{th}$ phosphate group of a polynucleotide. In some embodiments, polynucleotides can comprise a plurality of protecting groups disclosed herein, wherein the protecting groups are not positioned in regularly occurring intervals. In some embodiments only pyrimidines or purines will be protected generating a pattern directed by the pro-oligo target sequence The skilled artisan will appreciate that the polynucleotides (e.g., RNN, DNN, siRNN, dsRNN, shRNN, miRNN, and the like) are not limited by any particular sequence. Any number of oligonucleotides or polynucleotides useful for diagnostics, therapeutics and research can be used in the methods and compositions disclosed herein.

Non-limiting examples of siRNA, shRNA and miRNA molecules useful in the embodiments described herein include those disclosed in U.S. Pat. Nos. 7,414,125; 7,414,109, 7,410,944; 7,405,292; 7,399,586; 7,304,042; 7,288,531; 7,235,654; 7,268,227; 7,173,015; 7,148,342; 7,199,109; 7,022,028; 6,974,680; 7,005,254; 7,307,067; 7,232,806; e.g., Let 7a, let 7a-1, let 7b, let 7b-1, let-7c, let-7d, let 7g, miR-1, miR-1-d, miR-1-2, miR-9, miR-10a, miR-10b, miR-15a, miR-16, miR-17, miR-17-3p, miR-18, miR-19a, miR-20, miR-21, miR-22, miR-23, miR-23a, miR-23b, miR-24, miR-25, miR-26a, miR-27a, miR-28, miR-29a, miR-29b, miR-30a-3p, miR-30a, miR-30e-5p, miR-31, miR-32, miR-34a, miR-92, miR-93, miR-95, miR-96, miR-98, miR-99a, miR-100, miR-101, miR-105, miR-106, miR-107, miR-108, miR-122, miR-124, miR-125, miR-125b, miR-126, miR-127, miR-128, miR-129, miR-130, miR-130a, miR-133, miR-133a, miR-133a-2, miR-133b, miR-134, miR-135, miR-137, miR-138, miR-139, miR-140, miR-141, miR-142, miR-143, miR-145, miR-147, miR-148, miR-149, miR-150, miR-152, miR-153, miR-154, miR-155, miR-181, miR-182, miR-183, miR-184, miR-186, miR-187, miR-188, miR-190, miR-191, miR-192, miR-193, miR-194, miR-195, miR-196, miR-197, miR-198, miR-199, miR-199a-1, miR-200b, miR-201, miR-203, miR-204, miR-206, miR-207, miR-208, miR-210, miR-211, miR-212, miR-213, miR-214, miR-215, miR-216, miR-217, miR-218, miR-222, miR-223, miR-224, miR-291-3p, miR-292, miR-292-3p, miR-293, miR-294, miR-295, miR-296, miR-297, miR-298, miR-299, miR-320, miR-321, miR-322, miR-324, miR-325, miR-326, miR-328, miR-329, miR-330, miR-331, miR-333, miR-335, miR-337, miR-338, miR-340, miR-341, miR-342, miR-344, miR-345, miR-346, miR-350, miR-367, miR-368, miR-369, miR-370, miR-371, miR-373, miR-380-3p, miR-409, miR-410, miR-412, or the like. Although exemplary antisense polynucleotides are described herein, the skilled artisan will readily appreciate that the compositions and methods disclosed herein are useful for any polynucleotides such as siRNAs, miRNAs, shRNAs, dsRNAs, RNAi's, and oligonucleotides now known or discovered in the future. In a general sense, the operability of the methods and compounds disclosed herein is not dependent on the sequence or function of the oligonucleotide; rather, the disclosed methods and compounds are useful for delivering oligonucleotides (as a generic class) into cells.

Transduction Moieties

In some embodiments, the compounds disclosed herein include a transduction moiety. Transduction moieties can include, but are not limited to, cell-penetrating peptide (CPP), peptide transduction domain (PTD), nucleic acid binding proteins, such as RNA binding proteins, or any combination thereof.

Nucleic acid binding proteins, such as double-stranded RNA binding domains, have been used to enhance delivery of oligonucleotides into cells. (See, e.g., Eguchi et al. Nat. Biotech. 27:567-571 (2009)). Exemplary nucleic acid binding domains useful in the embodiments disclosed herein include, but are not limited to, those listed in U.S. Patent Application Publication No. US 2009/0093026.

Cell-penetrating peptides (CPPs) or peptide transfer domains (PTDs) have been used successfully to induce intracellular uptake of DNA (Abu-Amber, supra), antisense oligonucleotides (Astriab-Fisher et al., Pharm. Res. 19:744-54, 2002), small molecules (Polyakov et al. Biocong. Chem. 11:762-71, 2000), and iron particles (Dodd et al. J. Immunol. Methods 256:89-105, 2001; Wunderbaldinger et al., Bioconjug. Chem. 13:264-8, 2002; Lewin et al., Nat. Biotechnol. 18:410-4, 2000; Josephson et al., Bioconjug. Chem. 10:186-91, 1999), suggesting that the size of the cargo is not a limiting factor.

In some embodiments, PTD can be defined as one or more cationic peptides that are able to interact with the cell membrane in a manner that enhances macromolecular uptake. In some embodiments, these peptides can be configured in a linear sequence or attached via a branched linker. Alternatively the branching mechanism can be built into the peptide by having multiple cysteines or lysines that are specifically used to form linkages. The methods for synthesizing branched amino acid constructs are well established in the field. In some embodiments, a transduction moiety can be a cell penetrating peptide (CPP), a cationic polymer, an antibody, a cholesterol or cholesterol derivative, a Vitamin E compound, a tocol, a tocotrienol, a tocopherol, glucose, receptor ligand, antibody or the like capable of cell type specific targeting, to further facilitate the uptake of the anionic biomolecule, such as oligonucleotides and polynucleotides (e.g., RNN or DNN oligonucleotides and polynucleotides).

In some embodiments, the PTD domain comprises a peptide represented by the following general formula: B1-X1-

X2-X3-B2-X4-X5-B3, wherein B1, B2, and B3 are each independently a basic amino acid, the same or different; and X1, X2, X3, X4 and X5 are each independently an alpha-helix enhancing amino acid, the same or different.

In some embodiments, the PTD domain comprises a polypeptide represented by the following general formula: X-X-R-X-(P/X)-(B/X)-B-(P/X)-X-B-(B/X), wherein X is any alpha helical promoting residue such as alanine; P/X is either proline or X as previously defined; B is a basic amino acid residue, e.g., arginine (Arg) or lysine (Lys); R is arginine (Arg) and B/X is either B or X as defined herein.

In some embodiments, the PTD can be cationic. For example, in some embodiments, the PTD can include between 7 and 10 amino acids and have the general formula K-X1-R-X2-X1 wherein X1 is R or K and X2 is any amino acid. An example of such a cationic polypeptide can include the sequence RKKRRQRRR (SEQ ID NO: 16), or functional fragments and variants thereof.

A number of protein transduction domains/peptides are known in the art and facilitate uptake of heterologous molecules linked to the transduction domains (e.g., cargo molecules). Such peptide transduction domains (PTD's) facilitate uptake through a process referred to as macropinocytosis. Macropinocytosis is a nonselective form of endocytosis that all cells perform.

PTDs and CPPs useful in the embodiments disclosed herein include the PTDs and CPPs described in, for example, Langel, Ulo, "Cell Penetrating Peptides, Processes and Applications," In Langel, Ulo; (Ed.); Handbook of Cell-Penetrating Peptides, $2^{nd}$ Ed (2007); Langel, Ulo, (Ed.). "Cell-Penetrating Peptides, Mechanisms and Applications;" In Curr. Pharm. Des.; 2005, 11(28)(2005); Langel, Ulo, "Cell-Penetrating Peptides: Processes and Applications" (2002); Wadia, Jehangir S.; Becker-Hapak, Michelle; Dowdy, Steven F. Protein transport. Cell-Penetrating Peptides (2002), pp. 365-375, each of which is herein incorporated by reference.

Exemplary peptide transduction domains (PTD's) can be derived from the *Drosophila* homeoprotein Antennapedia transcription protein (AntHD) (Joliot et al., New Biol. 3:1121-34, 1991; Joliot et al., Proc. Natl. Acad. Sci. USA, 88:1864-8, 1991; Le Roux et al., Proc. Natl. Acad. Sci. USA, 90:9120-4, 1993), the herpes simplex virus structural protein VP22 (Elliott and O'Hare, Cell 88:223-33, 1997), the HIV-1 transcriptional activator TAT protein (Green and Loewenstein, Cell 55:1179-1188, 1988; Frankel and Pabo, *Cell* 55:1189-1193, 1988), and more recently the cationic N-terminal domain of prion proteins. Other exemplary peptide transduction domains are described in International Patent Application Publication No. WO 08/008,476. Preferably, the peptide transduction domain increases uptake of the biomolecule to which it is fused in a receptor independent fashion, is capable of transducing a wide range of cell types, and exhibits minimal or no toxicity (Nagahara et al., Nat. Med. 4:1449-52, 1998).

In some embodiments, the compositions disclosed herein (e.g., modified RNN and DNN oligonucleotides and polynucleotides) include PTDs that are cationic in nature. Cationic protein transduction domains track into lipid raft endosomes carrying with them their linked cargo and release their cargo into the cytoplasm by disruption of the endosomal vesicle. The disclosure provides, in one aspect, methods and compositions that combine the use of PTDs such as TAT and poly-Arg, with a charge neutralized nucleic acids or analogs thereof, such as RNN and DNN polynucleotides disclosed herein. By charge neutralized is meant that the anionic charge of the nucleic acid (e.g., oligonucleotide or polynucleotide) is reduced, neutralized or more cationic than the same nucleic acid in the absence of a phosphodiester and/or phosphorothioate protecting group or a phosphodiester and/or phosphorothioate protecting group and a binding domain capable of neutralizing the anionic charge on a nucleic acid (i.e., the "cargo") domain.

In general, protein transduction domains of the embodiments disclosed herein can be any synthetic or naturally-occurring amino acid sequence that can transduce or assist in the transduction of the fusion molecule. For example, transduction can be achieved in accord with the disclosure by use of a nucleic acid construct including phosphodiester and/or phosphorothioate protecting groups and a protein sequence such as an HIV TAT protein or fragment thereof that is linked at the N-terminal or C-terminal end to an oligonucleotide or polynucleotide comprising a phosphodiester and/or phosphorothioate protecting group. In some aspects, the nucleic acid may comprise a phosphodiester and/or phosphorothioate protecting group and may also comprise a nucleic acid binding domain (e.g., a DRBD). The transducing protein domain, for example, can be the Antennapedia homeodomain or the HSV VP22 sequence, the N-terminal fragment of a prion protein or suitable transducing fragments thereof such as those known in the art.

In some embodiments, the compositions disclosed herein can include a PTD that has substantial alpha-helicity, for example, to optimize transduction of the biomolecule. In another embodiment, the PTD comprises a sequence containing basic amino acid residues that are substantially aligned along at least one face of the peptide. By "substantial" alpha-helicity, it is meant that the circular dichroism (CD) of the peptide show appropriate Cotton effects at key wavelengths. Alpha-helicity of a peptide can be determined by measuring its circular dichroism (CD), and CD data is normally presented as mean residue ellipticies $[\theta]_m$. Alpha-helical peptides can show two negative Cotton effects at 208 nm and 222 nm, and a positive Cotton effect at 193 nm, while the CD spectra of peptides with random coil secondary structure are dominated by the increasing negative Cotton effect at shorter wavelength. Alpha-helicity may be estimated from the value at 222 nm, and by comparing the negative Cotton effects at 222 nm and 208 nm. Increasing fraction of $[\theta]_m$ (222 nm) divided by $[\theta]_m$ (208 nm) correlates with increasing alpha-helicity. High values for $[\theta]_m$ (208 nm) compared to $[\theta]_m$ (222 nm) and a shifting minimum from 208 nm to shorter wavelengths indicate random coil conformation.

In some embodiments, the compositions described herein, e.g., RNN and DNN oligonucleotides modified with one or more protecting groups disclosed herein, the PTD is one of those described in PCT Pub. Nos. WO 08/008,476 and WO 07/095,152, the PTD disclosure of which is hereby expressly incorporated by this reference. Additional transducing domains useful in the embodiments disclosed herein include but are not limited to a TAT fragment that comprises at least amino acids 49 to 56 of TAT up to about the full-length TAT sequence as described in PCT Pub. No. WO 08/008,476. In some embodiments, a TAT fragment can include one or more amino acid changes sufficient to increase the alpha-helicity of the fragment. In some embodiments, amino acid changes are introduced in the PTDs that add a recognized alpha-helix enhancing amino acid. In some embodiments, amino acids are introduced in the PTD's that remove one or more amino acids from the TAT fragment that impede alpha helix formation or stability. In some embodiments, for example, the PTD can be a TAT fragment that includes at least one amino acid substitution with an alpha-helix enhancing amino acid.

Additional transduction proteins (PTDs) useful in the embodiments disclosed herein include a TAT fragment in which the TAT 49-56 sequence has been modified so that at least two basic amino acids in the sequence are substantially aligned along at least one face of the TAT fragment. Exemplary TAT fragments useful as PTDs in the embodiments disclosed herein can include at least one specified amino acid substitution in at least amino acids 49-56 of TAT which substitution aligns the basic amino acid residues of the 49-56 sequence along at least one face of the segment.

In some embodiments, the PTD used in the embodiments disclosed herein can be a naturally occurring PTD, such as include the homeodomain of the *Drosophila melanogaster* protein *Antennapedia* (Lindsay (2002) *Curr. Op. Pharmacol.* 2:587-94; Derossi et al. (1994) *J. Biol. Chem.* 269:10444-50), HSV-1 VP22 (Bennett et al. (2002) *Nat. Biotechnol.* 20:20), and Buforin II (Park et al. (2000) *Proc. Natl. Acad. Sci. U.S.A.* 97:8245-50), or the like, or fragments thereof.

In some embodiments, the PTD used in the embodiments disclosed herein can be a recombinant or synthetic PTD designed to mimic and/or enhance the translocating properties of known PTDs, based on consideration of parameters such as electrostatic and hydrophobic properties or secondary structure (Wender et al. (2000) *Proc. Natl. Acad. Sci. U.S.A.* 97:13003-8; Futaki et al. (2001) *J. Biol. Chem.* 276:5836-40). An exemplary artificial PTD is transportan (Pooga et al. (1998) *FASEB J.* 12:67-77; Soomets et al. (2000) *Biochim. Biophys. Acta* 1467:165-76). Synthetic PTDs such as polylysine, polyarginine, and polyhistidine (which can be positively charged based on the pH of the formulation) e.g., polyarginine (6-15 amino acids) are useful in the embodiments disclosed herein.

Other PTDs useful in the embodiments disclosed herein include, but are not limited to those provided in Table 1 below:

TABLE 1

| SEQUENCE | SEQ ID NO: |
| --- | --- |
| YGRKKRRQRRR | 17 |
| RQIKIWFQNRRMKWKK | 18 |
| TRSSRAGLQFPVGRVHRLLRK | 19 |
| GWTLNSAGYLLGKINKALAALAKKIL | 20 |
| KLALKLALKALKAALKLA | 21 |
| AAVALLPAVLLALLAP | 22 |
| VPMLK | 23 |
| PMLKE | 24 |
| MANLGYWLLALFVTMWTDVGLCKKRPKP | 25 |
| LLIILRRRIRKQAHAHSK | 26 |
| KETWWETWWTEWSQPKKKRKV | 27 |
| RGGRLSYSRRRFSTSTGR | 28 |
| SDLWEMMMVSLACQY | 29 |
| TSPLNIHNGQKL | 30 |
| KRRQRRR | 31 |
| RKKRRQR | 32 |
| RKKRRQRR | 33 |
| GRKKRRQRRRPPQ | 34 |

TABLE 1-continued

| SEQUENCE | SEQ ID NO: |
| --- | --- |
| TRQARRNRRRRWRERQR | 35 |
| TRRQRTRRARRNR | 36 |
| TRRNKRNRIQEQLNRK | 37 |
| TAKTRYKAEEAELIAERR | 38 |
| MDAQTRRRERRAEKQAQWKAAN | 39 |
| RRRRNRTRRNRRRVR | 40 |
| KMTRAQRRAAARRNRWTAR | 41 |
| TRRQRTRRARRNR | 42 |
| TRQARRNRRRRWRERQR | 43 |
| GRKKRRQRRRPPQ | 44 |
| RRRQRRKKR | 45 |
| AGRKKRRQRRR | 46 |
| YARKARRQARR | 47 |
| YARAAARQARA | 48 |
| YARAARRAARR | 49 |
| YARAARRAARA | 50 |
| YARRRRRRRRR | 51 |
| YAAARRRRRRR | 52 |
| KKRPKPG | 53 |
| KRPAATKKAGQAKKL | 54 |
| PKKKRKV | 55 |

Yet other PTDs useful in the embodiments described herein include PTDs derived from protamine (AAA39985), penetratin (1OMQ_A), TAT (NP_057853), pVEC, Cationic prion protein domains, P101 (ACT78456), MATa2 (Q6B184), HIV-1 rev (CAA41586), Polyomavirus Vp1 (AAP14004), NF-kappaB (NP_003989), M9 (BAA76626), Vpr (BAH97661), FP_NLS (MPG), Sp-NPS (ACU27162), SN50, Importins and Karyopherins, e.g., Karyopherin alpha (NP_002255), and Karyopherin beta (NP_002256), and the like. Other PTDs useful in the embodiments disclosed herein include those found in International Patent Application Publication No's: WO 09/041,902, WO 05/084158; WO 00/062067, WO 00/034308, and WO 99/55899, each of which is herein incorporated by reference.

In some embodiments, the transduction moiety can be a chimeric PTD domain comprising sequences derived from at least two different transducing proteins. For example, chimeric transducing proteins useful in the embodiments disclosed herein include a chimera between two different TAT fragments, e.g., one from HIV-1 and the other from HIV-2 or one from a prion protein and one from HIV. S. Deshayes, M. C. Morris, G. Divita and F. Heitz Cell-penetrating peptides: tools for intracellular delivery of therapeutics 2005, V62, N 16, p 1839.

In some embodiments, the transduction moiety can be a nucleic acid binding polypeptide, such as an RNA binding protein, or the like optionally linked to a PTD selected from the examples listed above. Exemplary RNA binding proteins (e.g., DRBD) include histone, RDE-4 protein, or protamine. Exemplary dsRNA binding proteins (with Accession numbers listed in parenthesis) include but are not limited to: PKR (AAA36409, AAA61926, Q03963), TRBP (P97473, AAA36765), PACT (AAC25672, AAA49947, NP609646), Staufen (AAD17531, AAF98119, AAD17529, P25159), NFAR1 (AF167569), NFAR2 (AF167570, AAF31446, AAC71052, AAA19960, AAA19961, AAG22859), SPNR (AAK20832, AAF59924, A57284), RHA (CAA71668, AAC05725, AAF57297), NREBP (AAK07692, AAF23120, AAF54409, T33856), kanadaptin (AAK29177, AAB88191, AAF55582, NP499172, NP198700, BAB19354), HYL1 (NP563850), hyponastic leaves (CAC05659, BAB00641), human rhinovirus polyprotein (ACT09659), ADAR1 (AAB97118, P55266, AAK16102, AAB51687, AF051275), ADAR2P78563, P51400, AAK17102, AAF63702), ADAR3 (AAF78094, AAB41862, AAF76894), TENR (XP059592, CAA59168), RNaseIII (AAF80558, AAF59169, Z81070Q02555/S55784, PO5797), and Dicer (BAA78691, AF408401, AAF56056, 544849, AAF03534, Q9884), RDE-4 (AY071926), F1120399 (NP060273, BAB26260), CG1434 (AAF48360, EAA12065, CAA21662), CG13139 (XP059208, XP143416, XP110450, AAF52926, EEA14824), DGCRK6 (BAB83032, XP110167) CG1800 (AAF57175, EAA08039), F1120036 (AAH22270, XP134159), MRP-L45 (BAB14234, XP129893), CG2109 (AAF52025), CG12493 (NP647927), CG10630 (AAF50777), CG17686 (AAD50502), T22A3.5 (CAB03384) and Accession number EAA14308. Nucleic acid binding polypeptides can comprise any of the full length polypeptides of the foregoing accession numbers, as well as fragments or variants thereof, including as modified polypeptides comprising from 1-14 amino acid substitutions.

The skilled artisan will readily appreciate that the CPP and PTD domains described herein include modified peptides such as glycoproteins, the L-optical isomer or the D-optical isomer of amino acids or a combination of both, as well as retro-inverso polypeptides. As used herein, the term "retro-inverso" refers a peptide that comprises an amino-carboxy inversion as well as enantiomeric change in one or more amino acids (i.e., levorotatory (L) to dextrorotary (D)). The CPP and PTD domains described herein encompass D-amino acid modified polypeptides, amino-carboxy inversions of the amino acid sequence, amino-carboxy inversions containing one or more D-amino acids, naturally occurring proteins, recombinantly or synthetically synthesized peptides, non-inverted sequence containing one or more D-amino acids, peptidomimetics, Beta-amino acid analogs, gamma amino acid analogs, and the like.

The CPP or PTD peptides disclosed herein encompass peptide fragments. As used herein, the term "fragment" refers to a portion of a polypeptide which exhibits at least one useful functional domain, such that the peptide fragment retains an activity of the polypeptide, e.g., transduction activity.

Linking Moieties

In some embodiments, in addition to including one or more protecting groups disclosed herein, anionic biomolecules disclosed herein can be operably linked to an additional transduction moiety. In some embodiments, the transduction moiety can be a synthetic or non-synthetic, linear or branched peptide transduction domain (PTD). The PTD can be a cationic peptide optionally connected via a branching linker installed during automated nucleotide synthesis. These linkers have been established and are described by Horn et al., 1989: Chang et al., 1991; Foldesi et al, 1991, M. S. Shchepinov, I. A. Udalova, A. J. Bridgman, and E. M. Southern, Nucleic Acids Res, 1997, 25, 4447-4454, T. Horn, C. A. Chang, and M. S. Urdea, Nucleic Acids Res, 1997, 25, 4842-4849, M. S. Shchepinov, K. U. Mir, J. K. Elder, M.D. Frank-Kamenetskii, and E. M. Southern, Nucleic Acids Res, 1999, 27, 3035-41 The branching linker can be trebler, symmetrical or combinations thereof. The transduction moieties disclosed herein can be linked or fused with another transduction moiety (e.g., PTD, cationic polymer, an antibody, a cholesterol or cholesterol derivative, a Vitamin E compound, a tocol, a tocotrienol, or a tocopherol, glucose, receptor ligand or the like), a linker, such as a peptide linker or a nucleotide linker, or can be directly linked to an anionic biomolecule comprising a protecting group disclosed herein, e.g., a modified oligonucleotide or polynucleotide, such as an RNN or DNN derivative disclosed herein. Non-limiting examples of linkers useful in the embodiments disclosed herein include, but are not limited to GG (SEQ ID NO: 1), GGGGS (SEQ ID NO: 2), GGGGSN (SEQ ID NO: 3), GKSSGSGSESKS (SEQ ID NO: 4), GSTSGSGKSSEGKG (SEQ ID NO: 5), GSTSGSGKS-SEGSGSTKG (SEQ ID NO: 6), GSTSGSGKPGSGEG-STKG (SEQ ID NO: 7), or EGKSSGSGSESKEF (SEQ ID NO: 8) Linking moieties are described, for example, in Huston et al., Proc. Nat'l Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference.

In some embodiments, the compositions disclosed herein comprise targeting moieties and the like.

For example, in some embodiments, two or more transduction moieties, such as PTDs (e.g., 1-5, 2-4, typically 3) can be linked in series or separated by one or more other domains (e.g., a nucleic acid domain or peptide linkers). Transduction moieties, anionic biomolecules comprising one or more of the protecting groups disclosed herein (e.g., RNN and DNN oligonucleotide/polynucleotides), and peptide linkers, can be organized in nearly any fashion provided that the construct has the function for which it was intended (e.g., sufficiently cationic or having reduced anionic charge). Each of several domains (e.g., transduction moieties and RNN and/or DNN oligonucleotides and polynucleotides) may be directly linked or may be separated by a linker peptide. The domains may be presented in any order. Additionally, the fusion polypeptides may include tags, e.g., to facilitate identification and/or purification of the fusion polypeptide, such as a 6×HIS tag, a maltose binding protein domain, a GST tag, or the like.

In some embodiments, the compositions described herein include a peptide linker. For example, in some embodiments, a peptide linker comprises up to about 20 or 30 amino acids, commonly up to about 10 or 15 amino acids, and still more often from about 1 to 5 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more amino acids. In some embodiments, the amino acid sequence of the linker is engineered to be flexible so as not to hold the fusion molecule in a single rigid conformation. Peptide linker sequences can be used, e.g., to space the transduction moieties from the polynucleotides or oligonucleotides. For example, the peptide linker sequence can be positioned between a transduction moiety, and a polynucleotide or oligonucleotide domain, e.g., to provide molecular flexibility. The length of the linker moiety is chosen to optimize the biological activity of the polypeptide comprising a PTD domain fusion construct and can be determined empirically without undue experimentation. The linker moiety should be long enough and flexible enough to allow a nucleic acid binding domain to freely interact with a nucleic acid or vice versa. Exemplary peptide linkers and linker moieties are described in Int. Pub. No. WO/2008/

008476, in Huston et al., Proc. Natl. Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are incorporated herein by reference.

Formulations

The compounds disclosed herein encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds described herein: i.e., salts that retain the desired biological activity of the parent compound and do not impart undesired toxicological effects thereto. For the compounds disclosed herein, preferred examples of pharmaceutically acceptable salts and their uses are further described in U.S. Pat. No. 6,287,860, which is incorporated herein in its entirety.

Another embodiment is pharmaceutical compositions and formulations which include the compounds described herein. The pharmaceutical compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflations of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compounds with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions include, but are not limited to, solutions, emulsions, foams and liposome-containing formulations. The pharmaceutical compositions and formulations may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are also contemplated. Emulsions and their uses are well known in the art and are further described in U.S. Pat. No. 6,287,860, which is incorporated herein in its entirety.

The pharmaceutical formulations and compositions may also include surfactants. The use of surfactants in drug products, formulations and in emulsions is well known in the art. Surfactants and their uses are further described in U.S. Pat. No. 6,287,860, which is incorporated herein in its entirety.

In one embodiment, various penetration enhancers are employed to affect the efficient delivery of the compositions disclosed herein. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the compounds disclosed herein are in admixture with a topical delivery agent such as lipids, fatty acids, fatty acid esters, steroids, chelating agents and surfactants. Preferred lipids and include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. The compositions disclosed herein may be delivered orally, in granular form including sprayed dried particles, or complexed to form micro or nanoparticles. Complexing agents and their uses are further described in U.S. Pat. No. 6,287,860, which is incorporated herein in its entirety. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

In another related embodiment, the compositions may contain one or more compounds disclosed herein compounds, targeted to a first nucleic acid and one or more additional compounds targeted to a second nucleic acid target. Alternatively, compositions may contain two or more antisense compounds targeted to different regions of the same nucleic acid target. Numerous examples of antisense compounds are known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

Having generally described this invention, a further understanding can be obtained by reference to certain specific examples which are provided herein for purposes of illustration only, and are not intended to be limiting.

General Methods:

All reactions were carried out under an argon atmosphere. Glassware was cleaned overnight in a KOH/EtOH base bath, rinsed with MeOH and flame dried under vacuum before use in all anhydrous systems. Reactions were run with solvents that were either purchased sure-sealed over molecular sieves or were distilled using protocols listed in Purification of Laboratory Chemicals 4th ed. and stored over sieves.

Tetrahydrofuran (THF) was distilled from sodium metal and benzophenone, triethyl amine ($Et_3N$), diisopropylethyl amine (DIEA) and pyridine (py) were distilled from sodium metal. Dichloromethane ($CH_2Cl_2$), methanol (MeOH) and toluene were distilled from calcium hydride. All other solvents and reagents were purchased from Fisher Chemical Co., Aldrich Chemical Co., EMD or Acros Organics and used without further purification. Reactions were cooled to −78° C. via dry ice-acetone baths.

Flash column chromatography was performed using Merck grade 60 silica gel (230-400 mesh) and TLC analysis was carried out using Merck 60E-254 pre-coated silica sheets. Visualization of TLC plates was achieved using ultraviolet light, p-anisaldehyde in ethanol with sulfuric acid, polyphosphomolybdic acid and cerium sulfate in EtOH with $H_2SO_4$, ninhydrin in EtOH with $H_2SO_4$, potassium permanganate or iodine. Solvent removal was effected by Büchi rotary evaporator equipped with a dry ice isopropanol cold finger trap, and a $H_2O$ aspirator was used to concentrate in vacuo. Samples were further dried under reduced pressure on a high vacuum line over $P_2O_5$ and KOH.

$^1H$ NMR spectra were taken on a Varian Unity Inova 400 in $CDCl_3$ or $d_6$Benzene at ambient temperature unless otherwise noted. Mestre-C was used to visualize and measure J couplings. $^1H$ chemical shifts in $CDCl_3$ were reported in ppm; (δunits) downfield from tetramethylsilane. $^1H$ NMR splitting patterns are designated as a singlet (s), doublet (d), triplet (t) or quartet (q). All first order splitting patterns were assigned based on the appearance of the multiplet as interpreted by the program. Splitting patterns that could not be easily interpreted are designated as multiplet (m) or (br). In cases where broad or multiplet splitting patterns are clearly centered on one peak the chemical shift for that peak was reported instead of a range. The solvent peak at 2.49 was used as an internal reference in DMSO-$d_6$, and the solvent peak at 3.30 was used as an internal reference in $CD_3OD$. Solvent peaks were used as internal references for all $^{13}C$ NMR. NMR spectral data is tabulated as follows: chemical shift, multiplicity, coupling constant and number of protons. $^{31}P$ NMR chemical shifts were measured relative to a phosphoric acid standard and spectra were acquired in d6 benzene unless otherwise noted. NMR $^{13}C$ and $^1H$ data were not reported when the product was a racemic mixture.

Mass spectroscopy was obtained at Nu Mega Laboratories, San Diego, Calif.

Oligonucleotides of 17-29 nt in length were synthesized on an MerMade 6 automated DNA/RNA synthesizer. Glen Research Q CPG support was used with ethylthiotetrazole as the coupling reagent during 3 coupling steps of 7 minutes each. Phosphine was oxidized to phosphate by the standard iodine method and capping was performed with phenoxyacetic anhydride. All amidites and materials used on the MerMade 6 synthesizer were either synthesized or purchased from EMD, ChemGenes or Glen Research.

EXAMPLES

Generalized Protecting Group Synthesis

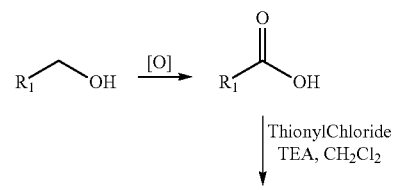

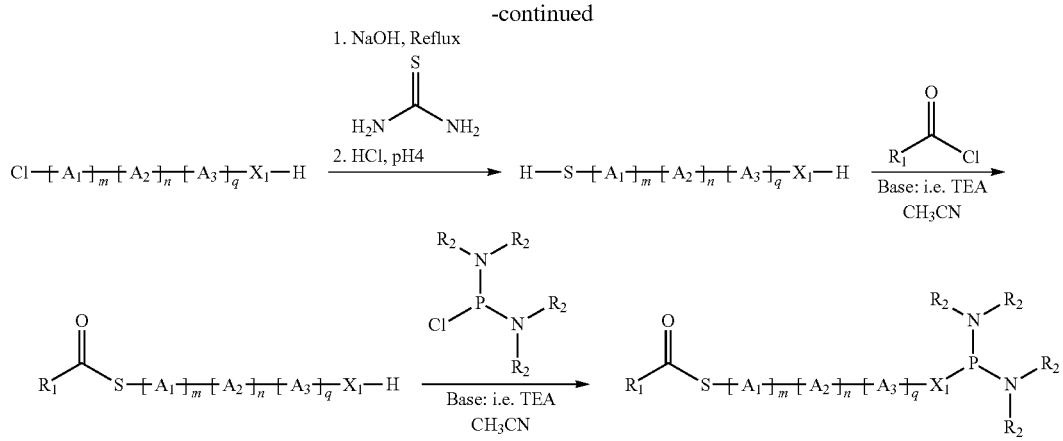

The general synthetic scheme for the synthesis of a reversible protecting group includes the oxidation of an appropriately protected alcohol or the formation of acid chloride from its carboxylic acid precursor. When starting with an alcohol oxidation to generate a carboxylic acid is achieved using one of the well established protocols including but not limited to potassium permanganate oxidation, Jones oxidation, Swern oxidation, single electron based Tempo mediated oxidation procedures. When starting with an oxidized alcohol or an appropriately protected carboxylic acid the acid chloride is generated for example by exposure to thionyl chloride under basic conditions, phosphorous (III) or (V) chloride, $C_3N_3Cl_3$ TEA or any number of well established methods. Thio alcohols are both commercially available and can be readily synthesized from their commercially available halo-alcohol precursors by first substituting the halide with thiourea under basic conditions to form the isothiuronium salt intermediate and then under controlled acidic conditions to eliminate ammonia to yield the free thiol. This free thiol when added to the acid chloride, described above under basic conditions in an aprotic solvent results in the formation of a biolabile thioester linkage. The alcohol can then be converted, in quantitative yield, to the activated phosphorodiamidite by the addition of excess chloro phosphorodiamidite under basic conditions in an appropriate solvent, preferably anhydrous acetonitrile or methylene chloride. The resulting phosphorodiamidite protecting group can be used to generate a phosphoramidite center, or nucleotide phosphoramidite at primary or secondary alcohol containing sites, that can in turn be applied to the practice of automated oligonucleotide synthesis. It is to be understood that the generation of nucleotide phosphoramidite synthesis can occur at the 5' position or the 3' position of a ribose containing structure or at the 5' or 3' position of a deoxyribose containing structure. It is also considered obvious to those skilled in the art that the nucleobase attached to the sugar can be appropriately or optionally protected, purine, pyrimidine or heterocyclic analog of the naturally or un-naturally occurring duplex forming nucleobases. Alternate embodiments of the invention include the use of this protecting group for the generation of phosphate containing small molecule prodrugs to improve the pharmacological properties, of tyrosine kinase activated antiviral agents for example Valaciclovir, AZT, acyclovir, ganciclovir, etc. and pyrophosphate analogs like foscarnet, etc.

The following example describes the synthesis of exemplary protecting groups disclosed in this application.

Example 1

Exemplary Synthesis of Pivaloyl MercaptoEthyl Glycol (PMEG)

An exemplary synthetic route for the synthesis of PMEG is described below. Scheme 1 shows the synthesis of 2-(2-mercaptoethoxy)ethanol form 2-(2-chloroethoxy)ethanol.

Scheme 1

Cl~~O~~OH
Chemical Formula: $C_4H_9ClO_2$
Exact Mass: 124.03
Molecular Weight: 124.57

1. Thiourea, water 100° C., 18 h
2. NaOH, 100° C., 3 h
3. HCl to pH 4

HS~~O~~OH
Chemical Formula: $C_4H_{10}O_2S$
Exact Mass: 122.04
Molecular Weight: 122.19

A solution of 2-(2-chloroethoxy)ethanol (90 mL, 125 mmol) and thiourea (95.2 g, 1.25 mol) were dissolved in water that had been sparged with argon for 30 min. The reaction was then heated to reflux for 18 h under argon. The resulting mixture was cooled to room temperature and sodium hydroxide (211.4 g, 5.3 mol) in deoxygenated water (1 L) was added. The mixture was refluxed for another 3 h before it was poured onto ice and carefully brought to pH 4 with concentrated HCl under argon. The aqueous layer was extracted with $CHCl_3$. The combined organic fractions were extracted with brine, dried over anhydrous sodium sulfate, filtered, and evaporated to dryness under reduced pressure to leave 51.7 g (49%) of the thiol as a colorless oil. $^1$H NMR (300 MHz, $CDCl_3$): d 3.76 (t, 2H, J) 4.5), 3.64 (t, 2H, J) 6.0), 3.59 (t, 2H, J) 4.5), 2.72 (q, 2H, J) 6.0), 2.13 (br, 1H), 1.57 (t, 1H, J) 8.1). $^{13}$C NMR (75 MHz, $CDCl_3$): d 72.82, 72.16, 61.91, 24.52.

Scheme 2 depicts the synthesis of S-2-(2-hydroxyethoxy) ethyl 2,2-dimethylpropanethioate from Mercaptoethoxy ethanol.

Scheme 2:

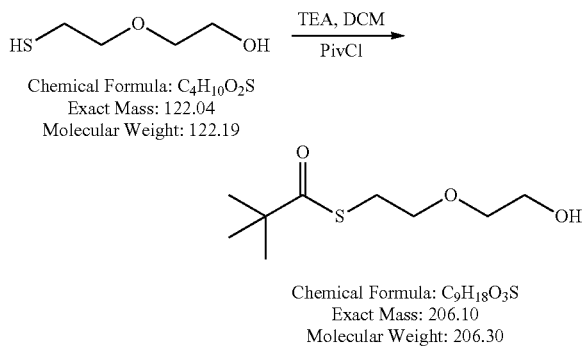

Mercaptoethoxy ethanol (42.5 g, 348 mmol) and Triethyl amine (50.9 mL, 365 mmol) were dissolved in dichloromethane and cooled to −78° C. Pivaloyl chloride (42.9 mL, 348 mmol) was added dropwise to the stirring solution. The reaction was allowed to proceed for one hour at −78° C. then it was warmed to rt and stirred for an additional 1 h before quenching with water. The aqueous was washed (3× dichloromethane) and dried with magnesium sulfate. Quantitative conversion was observed by TLC crude was distilled from a 1 L flask at 100° C. on the rotory evaporator using, highvac and a large (250 mL) ice/MeOH cooled bump trap to collect 65.9 g of a colorless oil at 92% yield.

Scheme 3 depicts the synthesis of PMEG from S-2-(2-hydroxyethoxy)ethyl 2,2-dimethylpropanethioate.

Scheme 3:

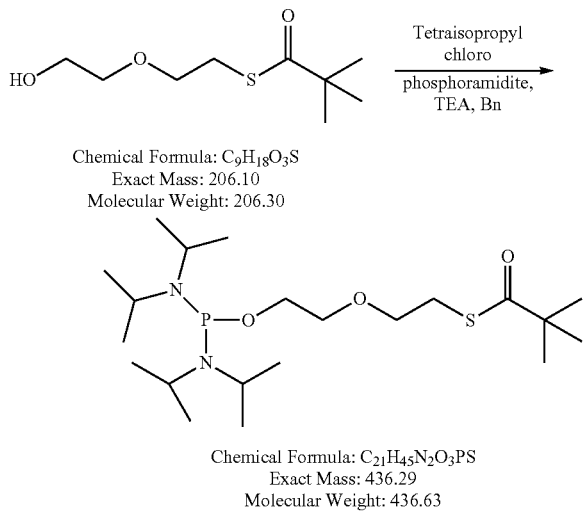

Tetraisopropyl chlorophosphoramidite (10 g, 37.6 mmol) and triethylamine (5.2 mL, 37.7 mmol) were dissolved in benzene and placed in a flask equipped with a stir bar at room temperature. To the stirring solution was added the thioester (7.0 g, 37.6 mmol). The reaction was monitored for complete conversion by TLC, 1.5 h. Solvent was removed from the mixture and the resulting oil was applied directly to a TEA pretreated silica flash column. Solvent was removed from fractions containing product and the resulting oil was co-evaporated 2× with toluene and lyophilized from benzene a give a colorless solid. Full characterization of the highly unstable product was not attempted and the product was used directly (within 1 wk) in the next reaction.

Example 1A

Synthesis of BMEG and PMEG Mercaptoesters of Formula I

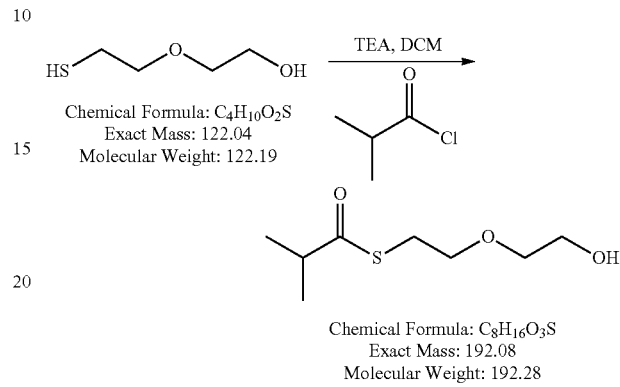

Using 2-(2-mercaptoethoxy)ethanol from scheme 1 addition of a Mercaptoethoxy ethanol (42.5 g, 348 mmol) and Triethyl amine (50.9 mL, 365 mmol) were dissolved in dichloromethane and cooled to −78° C. Isobutyroyl chloride (42.9 mL, 348 mmol) was added dropwise to the stirring solution. The reaction was allowed to proceed for one hour at −78° C. then it was warmed to rt and stirred for an additional 1 h before quenching with water. The aqueous was washed (3× dichloromethane) and dried with magnesium sulfate. Quantitative conversion was observed by TLC crude was distilled from a 1 L flask at 100° C. on the rotory evaporator using, highvac and a large (250 mL) ice/MeOH cooled bump trap to collect 65.9 g of a colorless oil at 92% yield.

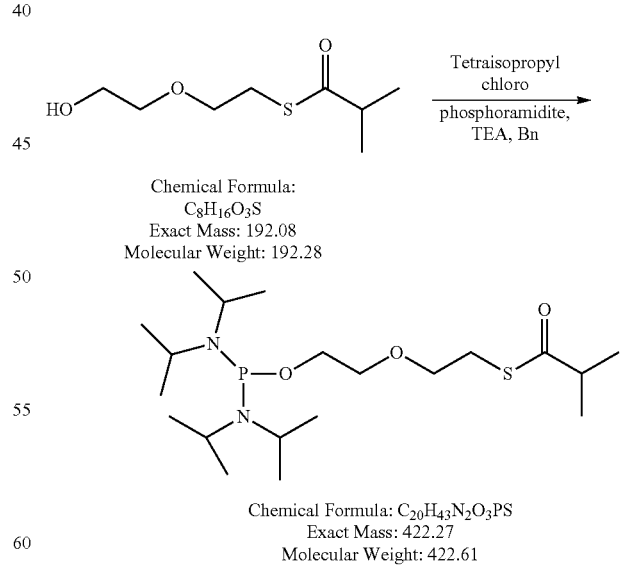

Tetraisopropyl chlorophosphoramidite (10 g, 37.6 mmol) and triethylamine (5.2 mL, 37.7 mmol) were dissolved in benzene and placed in a flask equipped with a stir bar at room temperature. To the stirring solution was added the thioester (7.0 g, 37.6 mmol). The reaction was monitored for complete conversion by TLC, 1.5 h. Solvent was removed from the mixture and the resulting oil was applied directly to a TEA pretreated silica flash column. Solvent was removed from fractions containing product and the resulting oil was co-evaporated 2× with toluene and lyophilized from benzene a give a colorless solid. Full characterization of the highly unstable product was not attempted and the product was used directly (within 1 wk) in the next reaction.

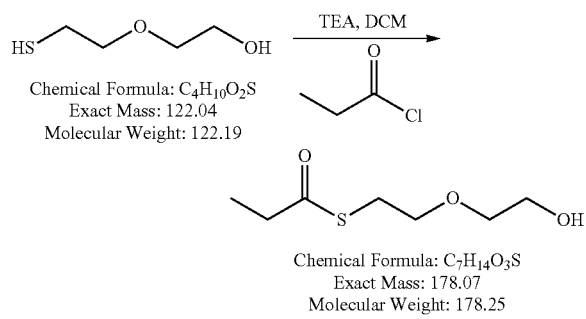

Using 2-(2-mercaptoethoxy)ethanol from scheme 1 addition of a Mercaptoethoxy ethanol (42.5 g, 348 mmol) and Triethyl amine (50.9 mL, 365 mmol) were dissolved in dichloromethane and cooled to −78° C. Propionoyl chloride (42.9 mL, 348 mmol) was added dropwise to the stirring solution. The reaction was allowed to proceed for one hour at −78° C. then it was warmed to rt and stirred for an additional 1 h before quenching with water. The aqueous was washed (3× dichloromethane) and dried with magnesium sulfate. Quantitative conversion was observed by TLC crude was distilled from a 1 L flask at 100° C. on the rotory evaporator using, highvac and a large (250 mL) ice/MeOH cooled bump trap to collect 65.9 g of a colorless oil at 92% yield.

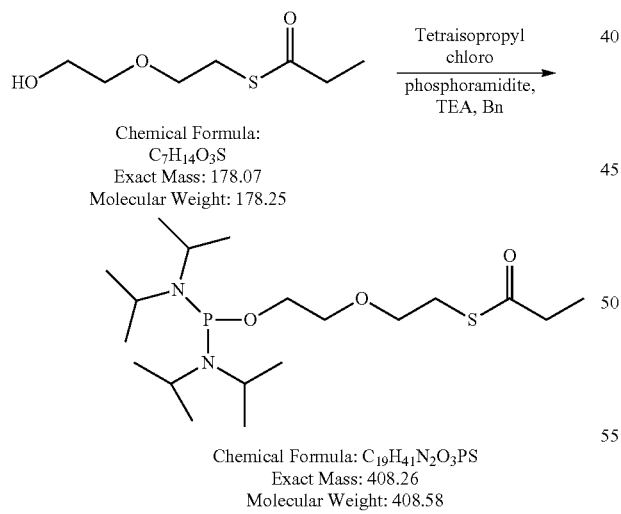

Tetraisopropyl chlorophosphoramidite (10 g, 37.6 mmol) and triethylamine (5.2 mL, 37.7 mmol) were dissolved in benzene and placed in a flask equipped with a stir bar at room temperature. To the stirring solution was added the thioester (7.0 g, 37.6 mmol). The reaction was monitored for complete conversion by TLC, 1.5 h. Solvent was removed from the mixture and the resulting oil was applied directly to a TEA pretreated silica flash column. Solvent was removed from fractions containing product and the resulting oil was co-evaporated 2× with toluene and lyophilized from benzene a give a colorless solid. Full characterization of the highly unstable product was not attempted and the product was used directly (within 1 wk) in the next reaction.

Figure 1:
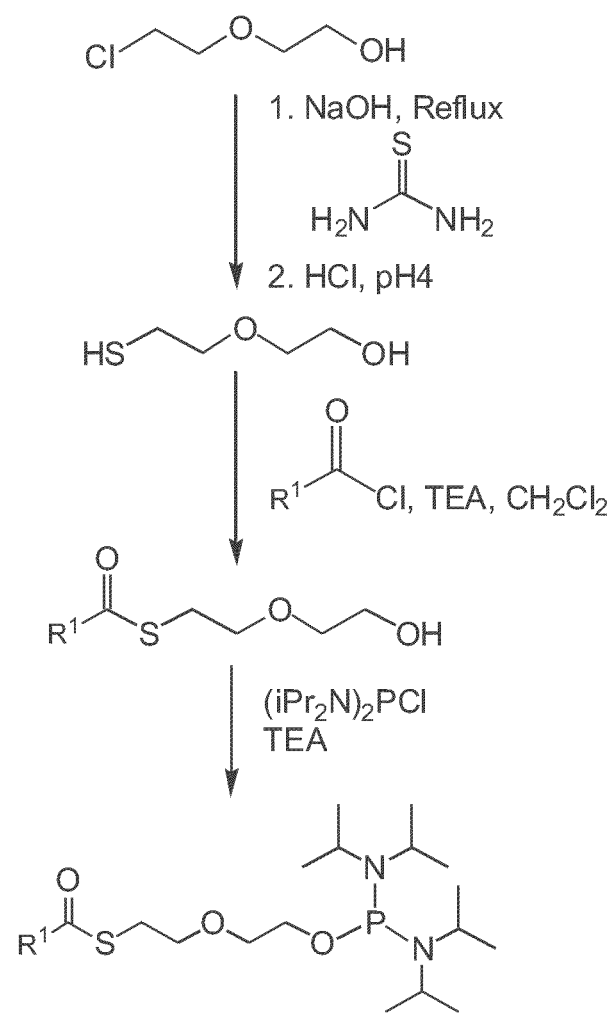
FIG. 1 is a schematic showing exemplary synthetic pathways for the production of select Phosphoramidite Mercaptoethyl Glycol monomers.

In these examples the phosphorodiamidites were synthesized, as shown in FIG. 1, from the readily available chloroethyl glycol. Chloride substitutions are accomplished using thiourea under basic conditions and completed generation of the thiol under acidic conditions. The resulting Thioethylglycol was selectively reacted with an acid chloride to generate a thioester linkage.

Alternate A1, A2, A3 Linkers

Several alternate linkers are readily generated by straight forward reaction scheme. When starting from an alcohol feed stock the Appel Reaction or the like is used to substitute the alcohol with a chloride. The chloride can then be substituted with thiourea under basic conditions to give the isothiuronium salt. The salt is decomposed under acidic conditions to generate ammonia and the desired thiol containing product.

Retrosynthetic Approach to Alternate Examples of Phosphate Thioester Linkers

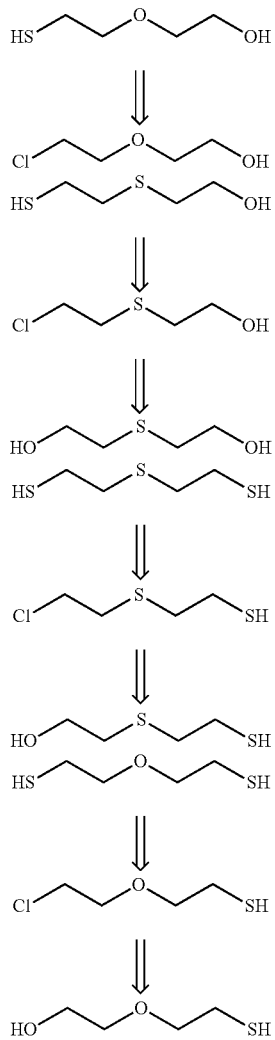

(Mercaptomethoxy)methanol

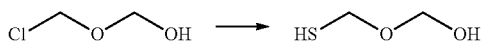

Conversion of (chloromethoxy)methanol to (mercaptomethoxy)methanol is readily accomplished using the general protocol and from starting materials described by: Katzhendler, Jehoshua; Ringel, Israel; Karaman, Rafik; Zaher, Hisham; Breuer, Eli. Acylphosphonate hemiketals—formation rate and equilibrium. The electron-withdrawing effect of dimethoxyphosphinyl group. Journal of the Chemical Society, Perkin Transactions 2: Physical Organic Chemistry (1997), (2), 341-349. CODEN: JCPKBH ISSN:0300-9580. CAN 126:238418 AN 1997:134060 CAPLUS 2-(2-Mercaptoethoxy)-2-ethoxyethanol

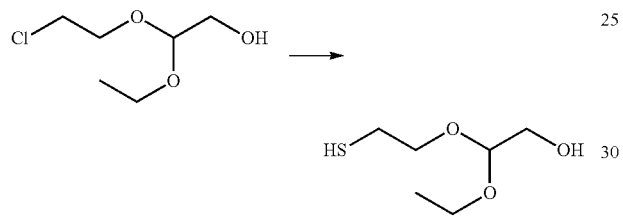

Conversion of 2-(2-chloroethoxy)-2-ethoxyethanol to (2-(2-mercaptoethoxy)-2-ethoxyethanol is readily accomplished using the general protocol and from starting materials described by: Ilcock, Harry R.; Dodge, Jeffrey A.; Van Dyke, Leon S.; Martin, Charles R. Polyphosphazenes bearing polymerizable pyrrole, thiophene, and furan side groups: synthesis and chemical oxidation. Chemistry of Materials (1992), 4(4), 780-8.

2-(Mercaptomethoxy)ethanol

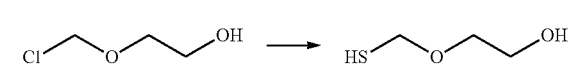

Conversion of 2-(chloromethoxy)ethanol to 2-(mercaptomethoxy)ethanol is readily accomplished using the general protocol and from starting materials described by: Sato, Kenichiro; Aogo, Toshiaki. Positively-working photoresist composition for far-ultraviolet ray exposure. Jpn. Kokai Tokkyo Koho (1999)

(2-Mercaptoethoxy)methanol

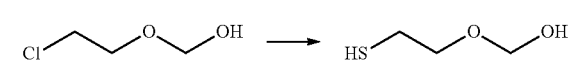 [SMILES: OCOCCCl ; OCOCCS]

Conversion of (2-chloroethoxy)methanol to (2-mercaptoethoxy)methanolis readily accomplished using the general protocol and from commercially available starting material.

((Mercaptomethoxy)methoxy)methanol

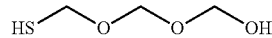

Formation of ((mercaptomethoxy)methoxy)methanol is readily accomplished using the general protocol and from commercially available starting material.

(2-Mercaptoethoxy)methanol

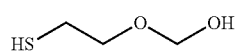

(2-Mercaptoethoxy)methanol is available from commercial sources.

3-(Mercaptomethoxy)propan-1-ol

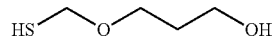

3-(Mercaptomethoxy)propan-1-ol is available as described by several authors: Ranu, B et. Al Piers, E et al. Vasickova, S et al.

These select examples are given in order to demonstrate the potential variability of this approach and are in no way intended to limit the scope of the above previously described embodiments.

Thioester Class Phosphoramidites:

Preparation of Thioester Protecting Groups from Alcohol Feed Stocks:

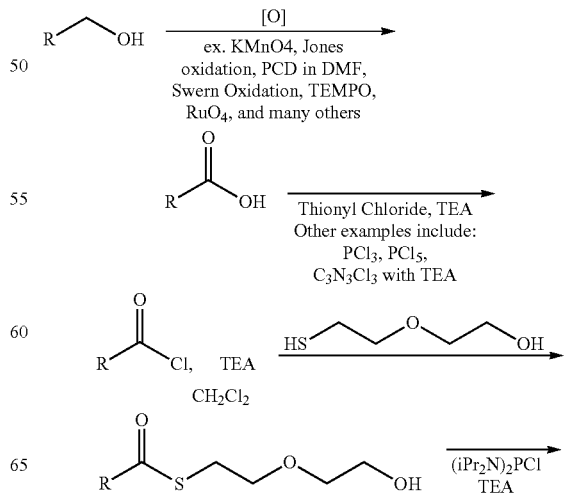

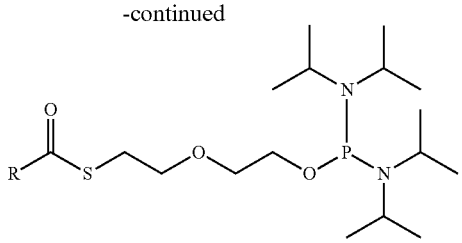

One can readily synthesize phosphoramidite constructs from a wide variety of commercially available alcohols to create a great deal of diversity at the R position. The pool of available alcohols may contain appropriately protected amines, guanidine, thiol or other functionality. Additionally, one can draw from the vast array of readily available alcohol containing precursors that include the following functionally; alkyl, heteroalkyl, alkoxy, alkyl rings, and heteroalkyl rings. The free alcohol can be converted to a carboxylic acid through a large number of commonly practiced oxidation reactions. The acid chloride can be formed under many different conditions including thionyl chloride, TEA, Phosphorus(III) Chloride, etc. and then combined selectively with any number of thioalcohols or dithiols to generate the requisite biolabile thioester center. Tetraisopropyl chlorophosphoramidite or the like is used to activate the protecting group as the diamidite. The diamidite is then reacted with the free 3'OH or 5'OH of an appropriately protected nucleoside in the presence of ETT, DCI, tetrazole or the like to generate nucleoside amidites that are able to be used in automated oligonucleotide synthesis.
Preparation of Thioester Protecting Groups from Amino Acid and Carboxylic Acid Containing Feed Stocks:

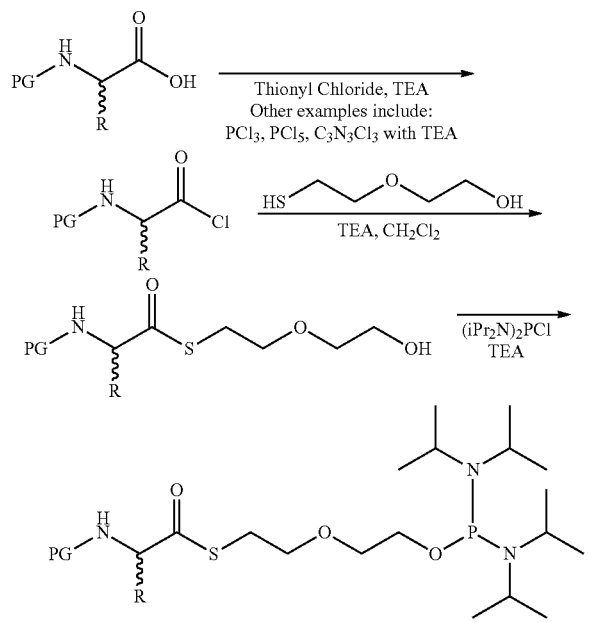

Alternatively, appropriately Boc, Fmoc, etc. (further examples of protecting groups can be found in Greene and Wuts "Protective Groups in Organic Synthesis) protected commercially available amino acids containing a free carboxylic acid can be fed directly into the reaction scheme to generate a diverse array of acyl chlorides. Thioester formation is readily accomplished under basic conditions and formation of the pivotal diamidite is accomplished with tetraisopropyl chlorophosphoramidite. The amino acid feed stock pool can be natural or synthetic in nature and in either the D or L configuration. Additionally, beta amino acids and gamma amino acids can be used. Amino acids as feed stock for formation of phosphoramidites, include but are not limited to, lysine, arginine, serine, threonine, isoleucine, alanine, glycine and cysteine to both enhance solubility and to optionally provide an attachment point for polypeptides.

A very comprehensive review of amino acid protecting groups, preferably base labile or photolabile, strategies can be found in Isidro-Llobet, A. et al. Chem. Rev. 2009 109, 2455. Additional protecting groups can be found in Green and Wuts Protective Groups in Organic synthesis.
Preparation of Guanidinyl Groups for Thioester Protecting Groups:

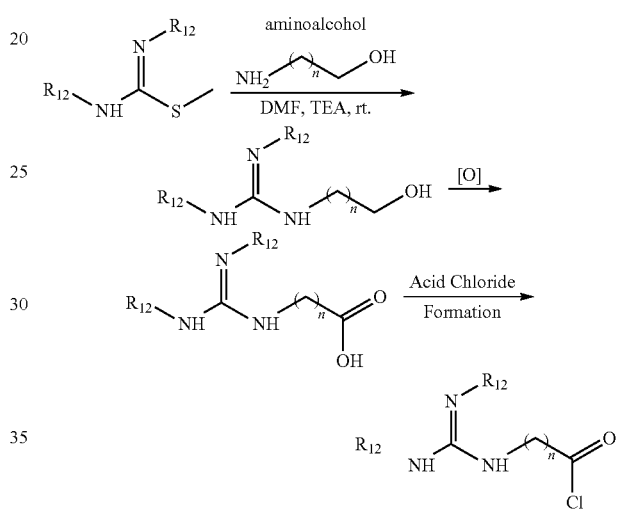

$R_{12}$=Preferred embodiments include tfa (Trifluoroacetyl), CEOC, PAC, FMOC, BOC, HCl salt Comprehensive review of guanidinyl protecting group strategies can be found in Isidro-Llobet, A. et al. Chem. Rev. 2009 109, 2455 additionally the practice of installation of those protecting groups is well described in Green and Wuts Protective groups in organic synthesis. The protected methyl thiourea is reacted with an amino alcohol to generate the guanidinyl alcohol. The resulting alcohol is oxidized via one of the many oxidation routes described in earlier in the document and the acid chloride is generated using thionyl chloride or the like. The resulting acid chloride can then be reacted with any one of the previously described thioalcohols and can be further elaborated to provide phosphoramidites.
Disulfide Class Phosphoramidites:
Generic Disulfide Bond Containing Reversible Protecting Group Strategy

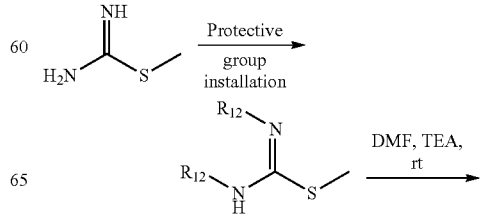

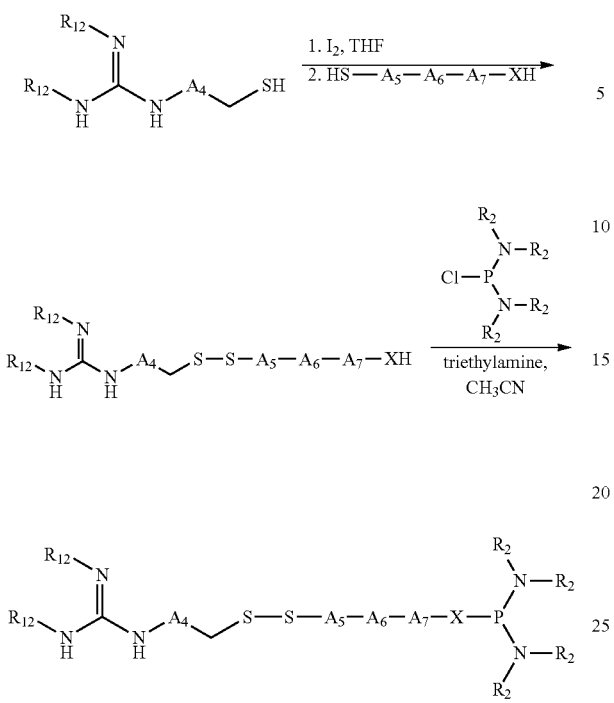

S-methylisothiourea can be readily protected by one of ordinary skill in the art via a large number of reactions as described above. The protected thiourea in the presence of an appropriate amino thiol linker, selected from the library described above, under basic conditions in a polar solvent will readily generate the desired thiol adduct. (Thazha P. Prakash, Ask Pu schl, and Muthiah Manoharan, N',N'-Bis-(2-(cyano) ethoxycarbonyl)-2-methyl-2-thiopseudourea: A Guanylating Reagent for Synthesis of 2'-O-[2-(Guanidinium)ethyl]-Modified Oligonucleotides', Nucleosides, Nucleotides and Nucleic Acids, 26:2, 149-159). The resulting thiol is activated for oxidation by example the addition of iodine in THF, by NPyS chloride, Cu(II), Fe(III) or the like then added to a second thiol containing linker selected from the library described earlier in this document. The final diamidite is achieved by the addition of the appropriate chlorophosphine to generate the desired reversible protecting group.

General Synthetic Routes to PMEG Nucleoside Amidites:

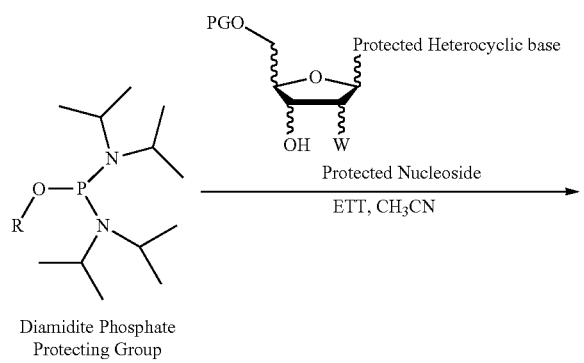

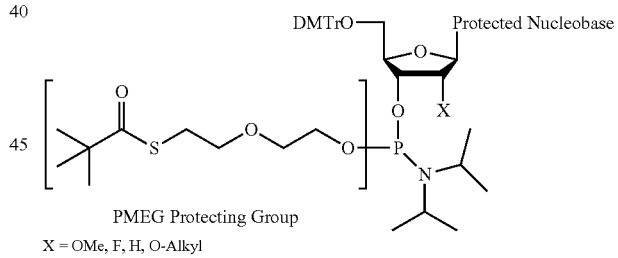

RNN or RNB Nucleoside Amidite

The general method for the synthesis of RNN or RNB nucleoside amidites for use in automated oligonucleotide synthesis begins with the synthesis of the central diamidite with an appropriate biolabile and reversible protecting group. Formation of the phosphate bond is selectively formed in high yield at the free 3'OH of any appropriately protected nucleoside construct in the presence of ethylthiotetrazole, tetrazole, DCI, or other phosphate coupling reagent. Appropriately protected nucleosides will have an acid labile protecting group on the 5' position, base labile or photolabile protection on the nucleobase and optionally F-labile or base labile protection on the 2' position. One skilled in the art can appreciate the enormous amount of diversity that can be generated from this single straight forward reaction scheme.

Example 2

PMEG (Pivaloyl MercaptoEthyl Glycol) Protected Amidites

Figure 2:
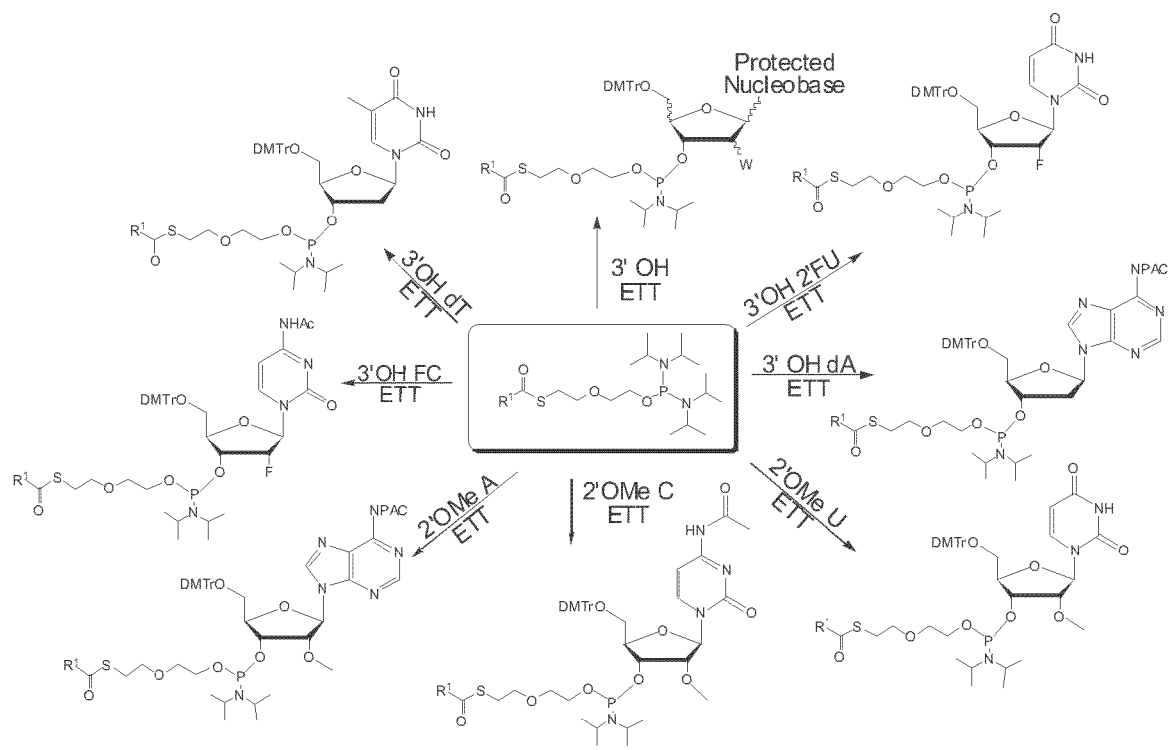
FIG. 2 is a schematic showing exemplary synthetic pathways for the production of nucleoside amidites with biolabile protecting groups.

PMEG phosphorodiamidites can be synthesized using routine synthetic chemistry. Exemplary synthetic pathways for the synthesis of Pivaloyl Mercaptoethyl Glycol monomers are shown in FIG. 1. The resulting diamidite can be used to form nucleoside amidites from any available or synthesized appropriately protected 3'OH containing nucleoside as depicted in FIG. 2.

3'OH phosphotidylation can be achieved with, ethylthiotetrazole (ETT) or any other method of 3' phosphotidylation known in the art.

Using the methods described herein, the following PMEG amidites have been successfully synthesized: 5' DMT protected 2'F-Cytidine, 5' DMT protected 2'F'-Uridine and 5' DMT protected 2' OMe-Adenosine. Appropriate base protecting groups can be used where appropriate.

Specific Protocol 1

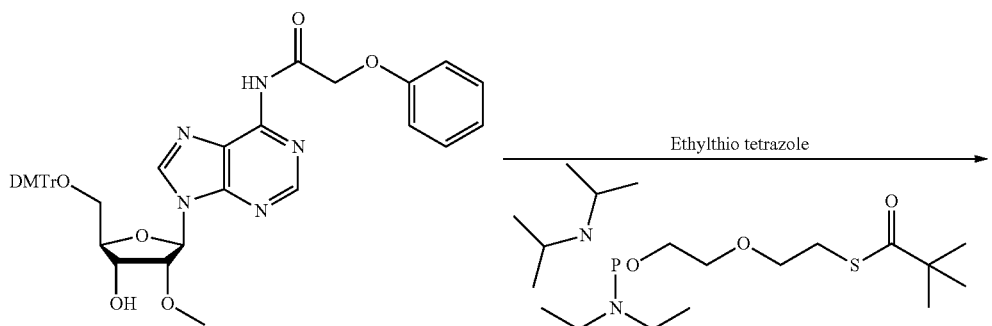

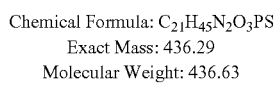

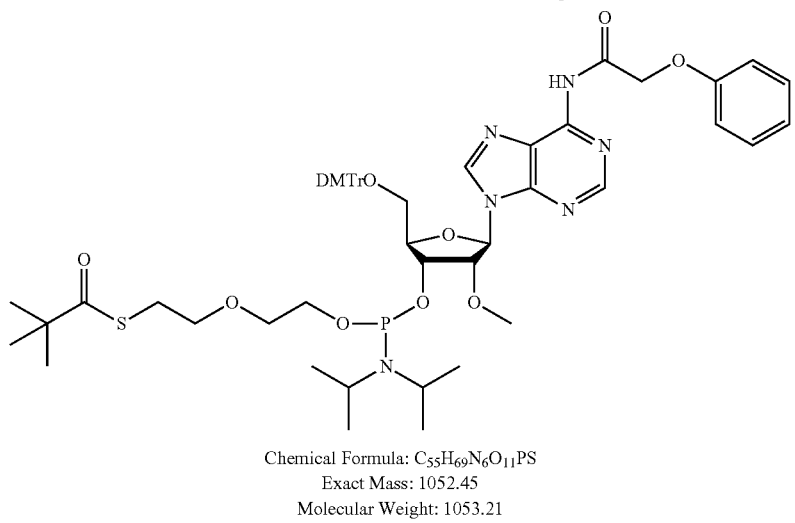

Nucleoside (3.07 g, 4.28 mmol), 0.45M Ethylthiotetrazole/acetonitrile (17.1 mL), and dichloromethane (17.1 mL) were added to a flame dried vial. To the stirring solution was added the PMEG phosphorodiamidite (1.96 g, 4.5 mmol) and the reaction was allowed to proceed for 3 h. The reaction was quenched by addition of TEA (1 mL). Solvent was removed from the reaction by rotary evaporation and the resulting slurry was applied directly to a TEA pretreated column. Fractions containing product were evaporated to a foam followed by transfer/filtration through a 0.2 μm filter in acetonitrile. The product was dried to again to a foam, re-dissolved in benzene, frozen and lyophilized from benzene overnight to ensure complete removal of water and residual triethyl amine to give 2.5 g of a colorless lyophilate.

Specific Protocol 2

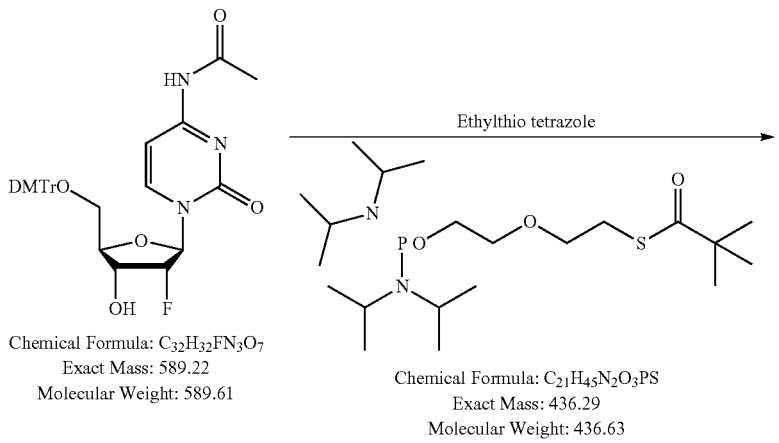

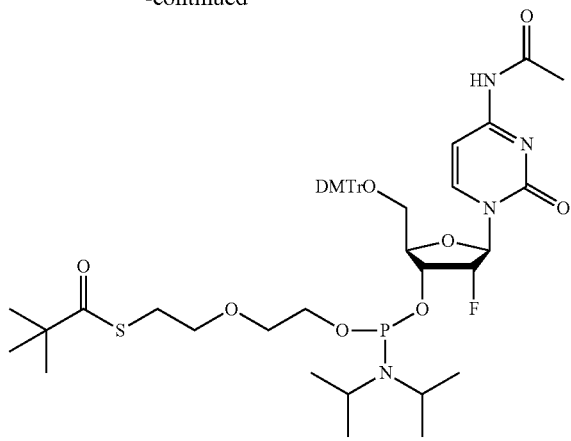

Chemical Formula: $C_{47}H_{62}FN_4O_{10}PS$
Exact Mass: 924.39
Molecular Weight: 925.05

Nucleoside (3.5 g, 5.94 mmol), 0.45M Ethylthiotetrazole/acetonitrile (23.8 mL), and dichloromethane (23.8 mL) were added to a flame dried vial. To the stirring solution was added the PMEG phosphorodiamidite (2.73 g, 6.25 mmol) and the reaction was allowed to proceed for 4.5 h. The reaction was quenched by addition of TEA (1 mL). Solvent was removed from the reaction by rotary evaporation and the resulting slurry was applied directly to a TEA pretreated column. Fractions containing product were evaporated to a foam followed by transfer/filtration through a 0.2 μm filter in acetonitrile. The product was dried to again to a foam, re-dissolved in benzene, frozen and lyophilized from benzene overnight to ensure complete removal of water and residual triethyl amine to give 1.93 g of a colorless lyophilate at 35% yield.

Specific Protocol 3

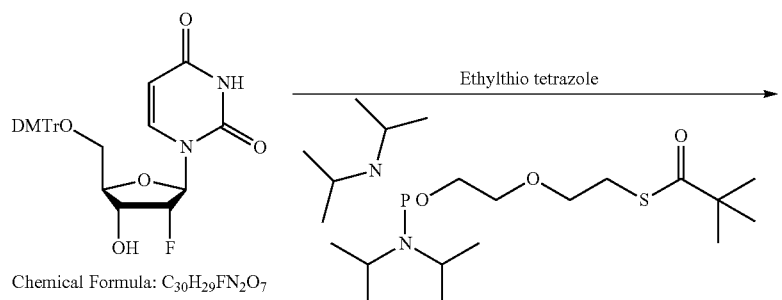

Chemical Formula: $C_{30}H_{29}FN_2O_7$
Exact Mass: 548.20
Molecular Weight: 548.56

Chemical Formula: $C_{21}H_{45}N_2O_3PS$
Exact Mass: 436.29
Molecular Weight: 436.63

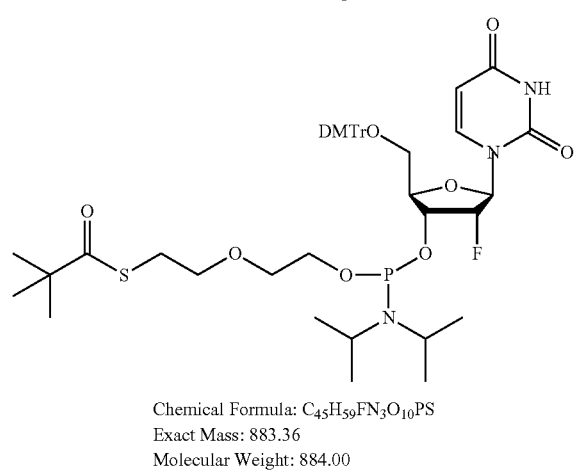

Chemical Formula: $C_{45}H_{59}FN_3O_{10}PS$
Exact Mass: 883.36
Molecular Weight: 884.00

Nucleoside (2.6 g, 4.75 mmol), 0.45-Methylthiotetrazole/acetonitrile (19 mL), and dichloromethane (19 mL) were added to a flame dried vial. To the stirring solution was added the PMEG phosphorodiamidite (2.18 g, 5.0 mmol) and the reaction was allowed to proceed for 2.5 h. The reaction was quenched by addition of TEA (1 mL). Solvent was removed from the reaction by rotary evaporation and the resulting slurry was applied directly to a TEA pretreated column. Fractions containing product were evaporated to a foam followed by transfer/filtration through a 0.2 µm filter in acetonitrile. The product was dried to again to a foam, re-dissolved in benzene, frozen and lyophilized from benzene overnight to ensure complete removal of water and residual triethyl amine to give 2.6 g of a colorless lyophilate at 65% yield.

Nucleoside (2.76 g, 5.03 mmol) and activator (20 mL, 0.45M) were added to a flame dried vial. To the stirring solution was added the BMEG phosphorodiamidite (2.5 g, 5.93 mmol) and the reaction was allowed to proceed for 3 h. The reaction was quenched by addition of 1 mL neat TEA. Solvent was removed from the reaction and the resulting slurry was applied directly to a TEA pretreated column, 120 g Si 20 mL TEA. Solvent was removed from fractions containing product and was then co-evaporated with anhydrous toluene to generate a foam. Following overnight exposure to high vac the product was transferred and filtered under argon through a 0.45 µm filter in acetonitrile into amber vials. Rotory evaporation of fractions resulted in the generation of a foam, the solid was re-dissolved in benzene, frozen and lyophilized from benzene overnight to ensure complete removal of water and residual amine. To give 3.96 g of lyophilate at 90% yield.

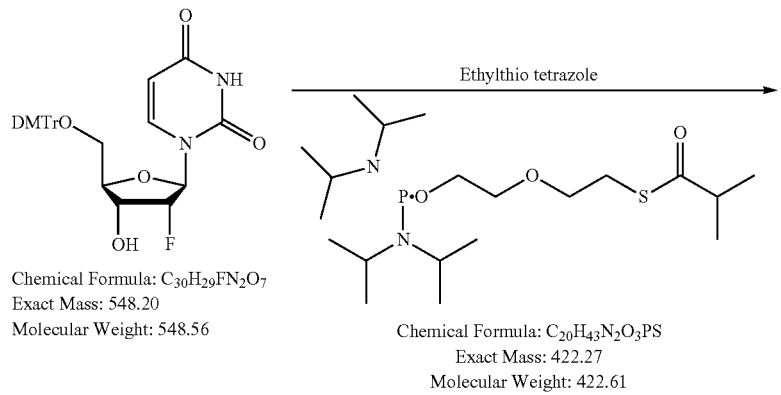

Chemical Formula: $C_{30}H_{29}FN_2O_7$
Exact Mass: 548.20
Molecular Weight: 548.56

Chemical Formula: $C_{20}H_{43}N_2O_3PS$
Exact Mass: 422.27
Molecular Weight: 422.61

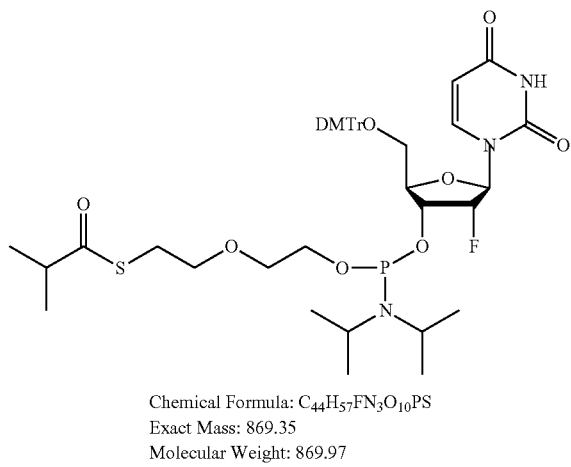

Chemical Formula: $C_{44}H_{57}FN_3O_{10}PS$
Exact Mass: 869.35
Molecular Weight: 869.97

Specific Protocol 4

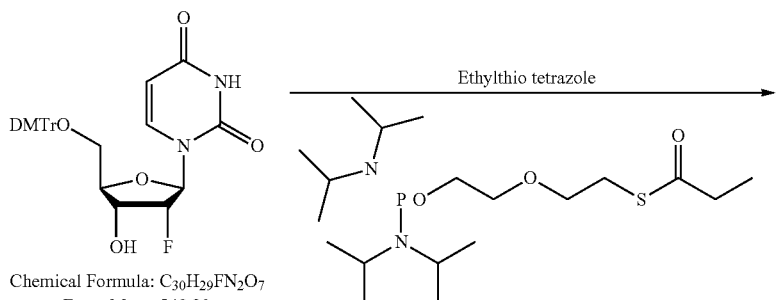

Chemical Formula: C$_{30}$H$_{29}$FN$_2$O$_7$
Exact Mass: 548.20
Molecular Weight: 548.56

Chemical Formula: C$_{19}$H$_{41}$N$_2$O$_3$PS
Exact Mass: 408.26
Molecular Weight: 408.58

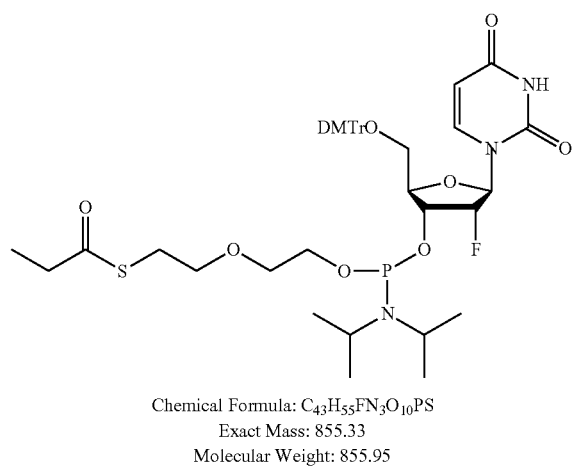

Chemical Formula: C$_{43}$H$_{55}$FN$_3$O$_{10}$PS
Exact Mass: 855.33
Molecular Weight: 855.95

Nucleoside (2.86 g, 5.2 mmol) and activator in acetonitrile (20.8 mL, 0.45M) were added to a flame dried vial. To the stirring solution was added the phosphorodiamidite (2.5 g, 6.13 mmol) and the reaction was allowed to proceed for 3 h. The reaction was quenched by addition of TEA. Solvent was removed from the reaction and the resulting slurry was applied directly to a TEA pretreated column 120 g Si 20 mL TEA. Solvent was removed from fractions containing product and was then co-evaporated with Anhydrous Toluene to generate a foam. Following overnight exposure to high vac the product was transferred and filtered under argon through a 0.45 μm filter in Acetonitrile into amber vials. Solvent was removed from the product to generate a foam, the foam was re-dissolved in benzene, frozen and lyophilized from the benzene overnight to ensure complete removal of water and residual amine. Final yield was 3.6 g of colorless lyophilate at 81%.

PMEG phosphorodiamidite Reaction with 3'-OH

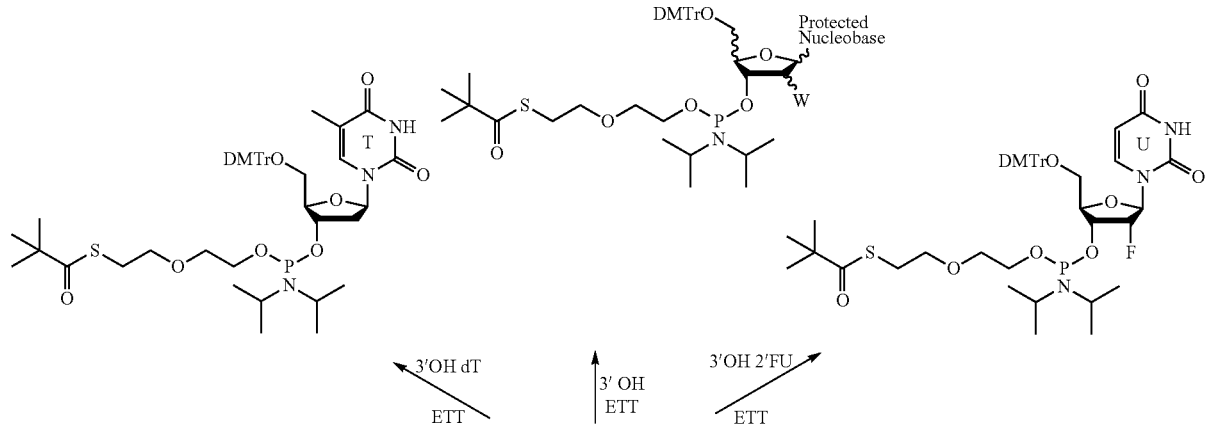

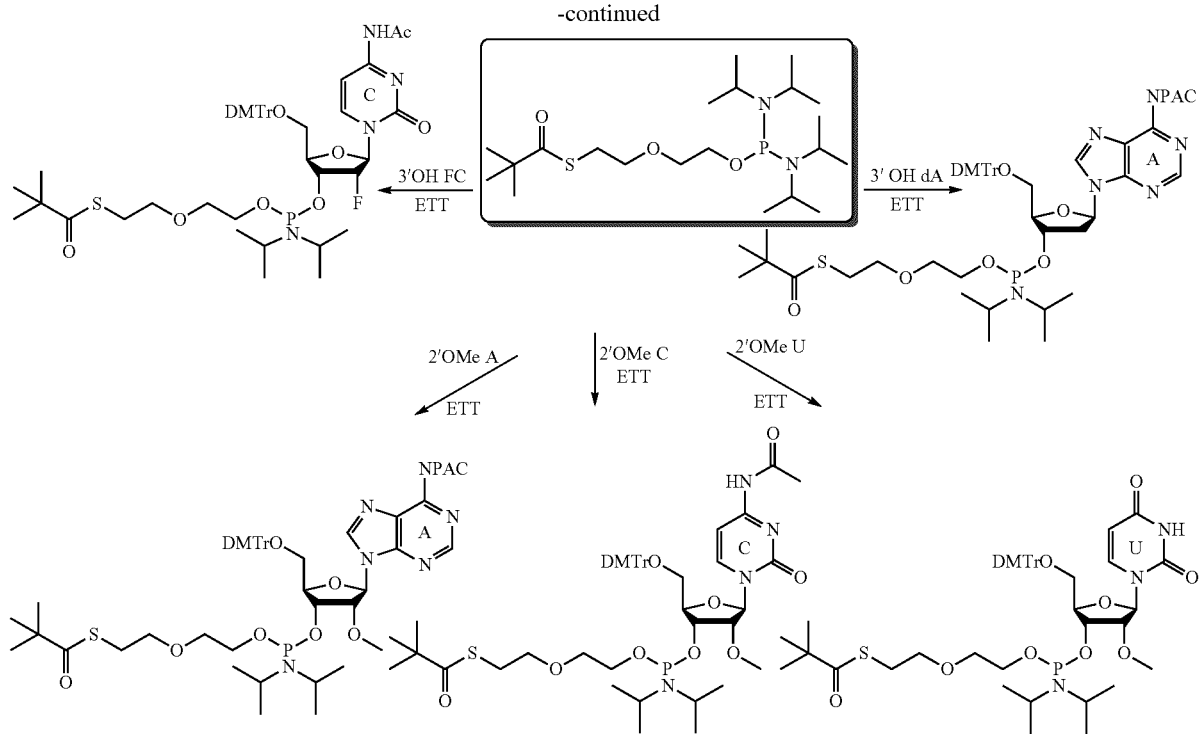

Starting with the PMEG phosphorodiamidite protecting group and any one of a host of 3'OH appropriately protected nucleosides the desired nucleotide phosphoramidites can be easily generated by one of ordinary skill in the art in high yield. The standard method for this reaction is accomplished by adding the solid phosphorodiamidite in slight excess 0.5% to the appropriately protected nucleoside in a reaction vessel equipped with a stirbar. The reaction vessel is evacuated and filled with dry argon several times to purge water vapor and air from the flask. Acetonitrile and optionally dichloromethane is added to the flask to achieve dissolution. Ethylthiotetrazole 0.45 M in acetonitrile is added in a 0.5% excess in 3 equal aliquots to the stirring solution under argon over 45 m. The reaction is allowed to proceed until consumption of nucleoside is observed by TLC, this is usually observed between 1 and 4 h. The ethylthiotetrazole is quenched with an equimolar amount of TEA and the solvent is removed from the reaction vessel by low temperature rotory evaporation. The resulting slurry is applied directly to a TEA pretreated silica chromatographic column and fractionated. Fractions containing the desired product are pooled, the solvent is removed, the resulting oil or foam is brought up in acetonitrile and 0.45 µm filtered. The filtrate is placed on a rotory evaporator to remove the acetonitrile, brought up in benzene, aliquoted into tared storage flasks and then frozen with dry ice. Prior to long term storage under argon at −20° C. benzene is removed by lyophilization. The example above demonstrates the synthesis of seven nucleoside amidites with PMEG protecting groups, however this approach is not limited to the listed examples. A person of ordinary skills in the art will recognize that this approach is readily diversified into any nucleoside that has protecting groups amenable to automated oligonucleotide synthesis and either a free 3' OH or 5'OH in the case of 5' to 3' synthesis.

BMEG phosphorodiamidite Reaction with 3'-OH

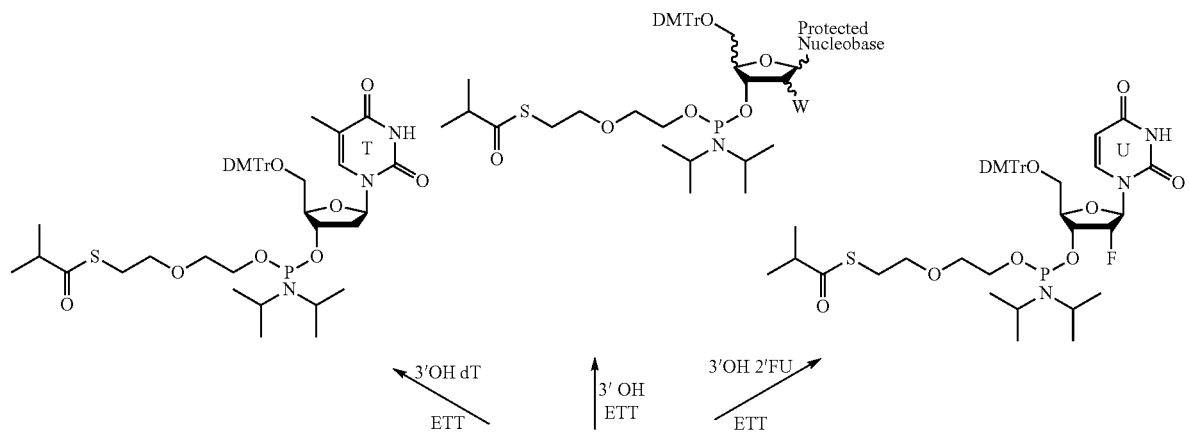

-continued

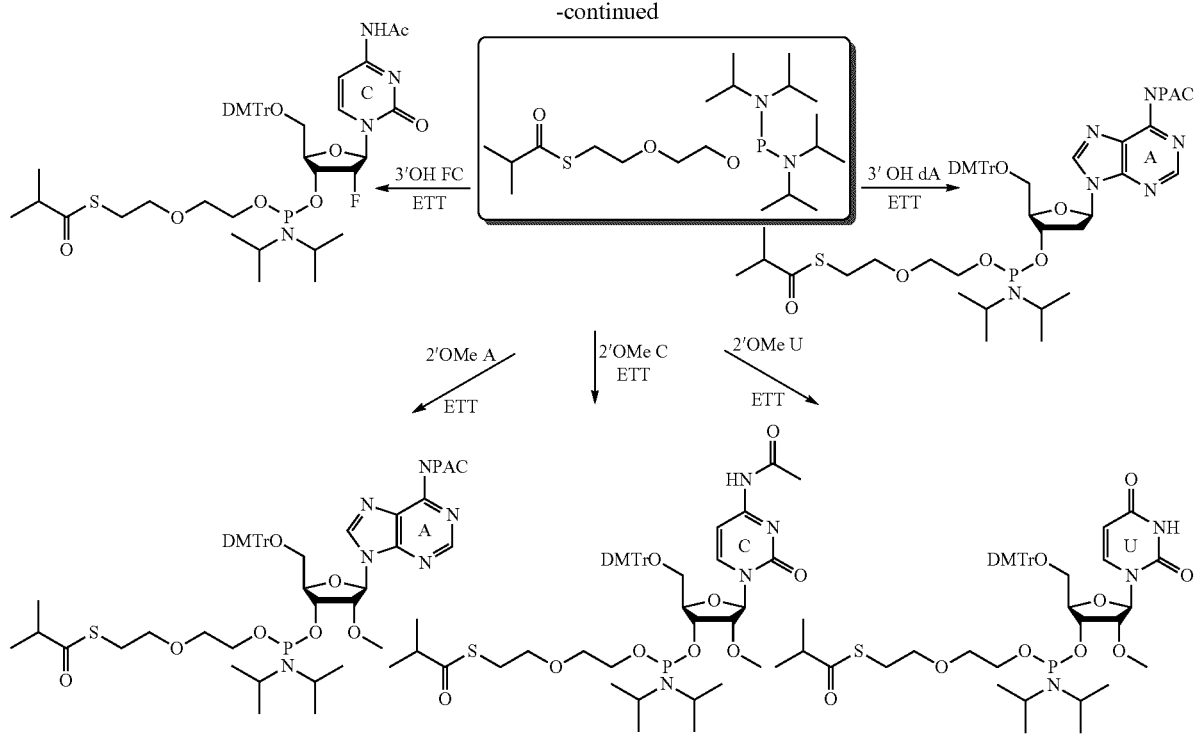

Starting with the BMEG phosphorodiamidite protecting group and any one of a host of 3'OH appropriately protected nucleosides the desired nucleotide phosphoramidites can be generated in high yield. The standard method for this reaction is accomplished by adding the solid phosphorodiamidite in slight excess 0.5% to the appropriately protected nucleoside in a reaction vessel equipped with a stirbar. The reaction vessel is evacuated and filled with dry argon several times to purge water vapor and air from the flask. Acetonitrile and optionally dichloromethane is added to the flask to achieve dissolution. Ethylthiotetrazole 0.45M in acetonitrile is added in a 0.5% excess in 3 equal aliquots to the stirring solution under argon over 45 m. The reaction is allowed to proceed until consumption of nucleoside is observed by TLC, this is usually observed between 1 and 4 h. The ethylthiotetrazole is quenched with an equimolar amount of TEA and the solvent is removed from the reaction vessel by low temperature rotory evaporation. The resulting slurry is applied directly to a TEA pretreated silica chromatographic column and fractionated. Fractions containing the desired product are pooled, the solvent is removed, the resulting oil or foam is brought up in acetonitrile and 0.45 μm filtered. The filtrate is placed on a rotory evaporator to remove the acetonitrile, brought up in benzene, aliquoted into tared storage flasks and then frozen with dry ice. Prior to long term storage under argon at −20° C. benzene is removed by lyophilization. The example above demonstrates the synthesis of seven nucleoside amidites with BMEG protecting groups, however this approach is not limited to the listed examples. A person of ordinary skills in the art will recognize that this approach is readily diversified into any nucleoside that has protecting groups amenable to automated oligonucleotide synthesis and either a free 3' OH or 5'OH in the case of 5' to 3' synthesis.

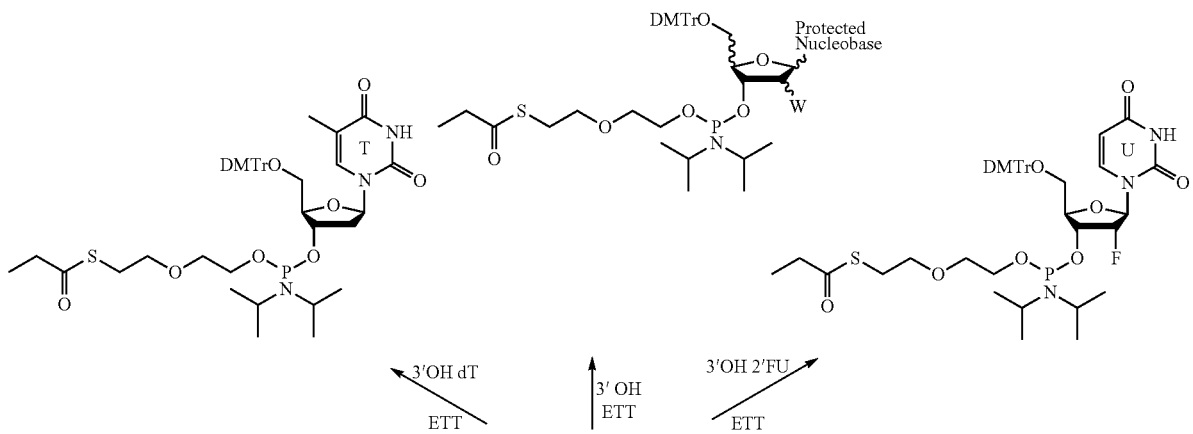

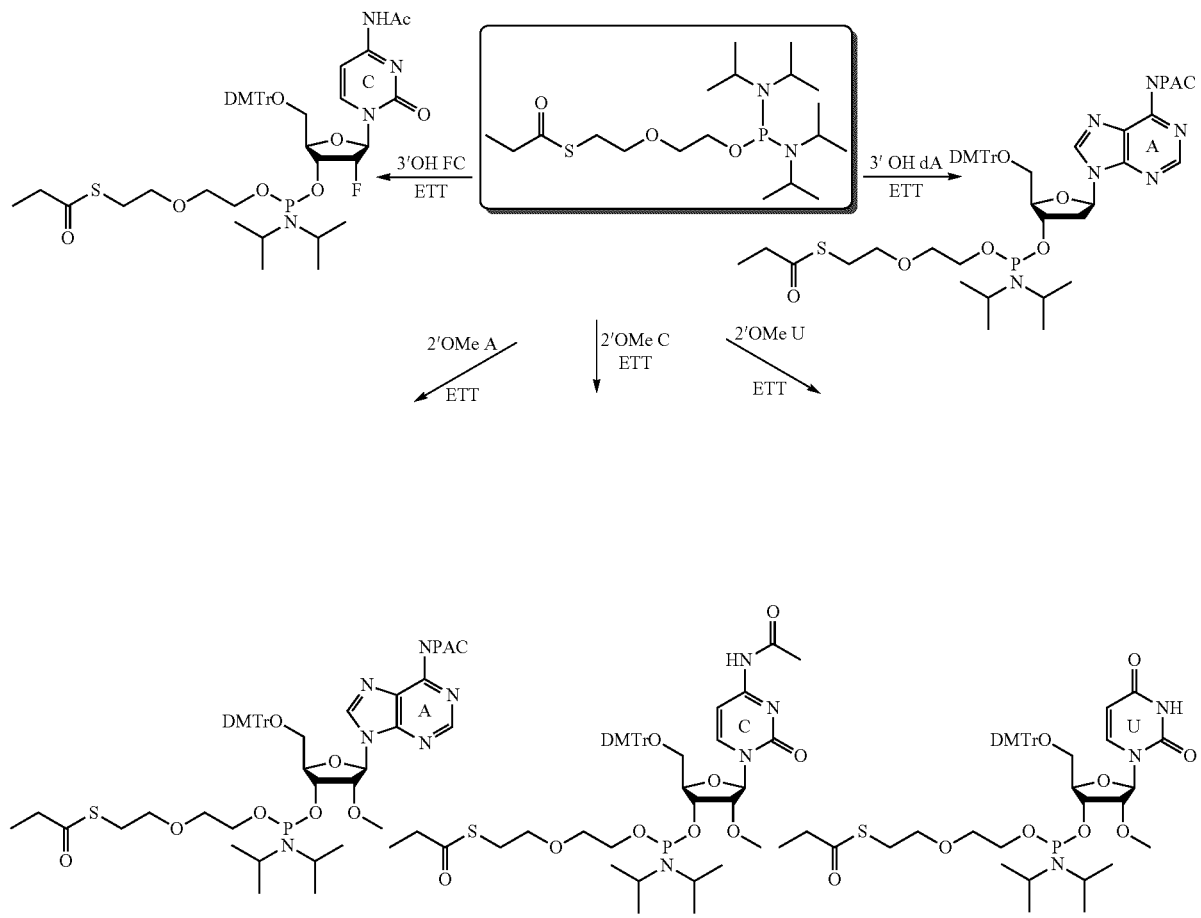

Starting with the PrMEG phosphorodiamidite protecting group and any one of a host of 3'OH appropriately protected nucleosides the desired nucleotide phosphoramidites can be easily generated in high yield. The standard method for this reaction is accomplished by adding the solid phosphorodiamidite in slight excess 0.5% to the appropriately protected nucleoside in a reaction vessel equipped with a stirbar. The reaction vessel is evacuated and filled with dry argon several times to purge water vapor and air from the flask. Acetonitrile and optionally dichloromethane is added to the flask to achieve dissolution. Ethylthiotetrazole 0.45 M in acetonitrile is added in a 0.5% excess in 3 equal aliquots to the stirring solution under argon over 45 m. The reaction is allowed to proceed until consumption of nucleoside is observed by TLC, this is usually observed between 1 and 4 h. The ethylthiotetrazole is quenched with an equimolar amount of TEA and the solvent is removed from the reaction vessel by low temperature rotory evaporation. The resulting slurry is applied directly to a TEA pretreated silica chromatographic column and fractionated. Fractions containing the desired product are pooled, the solvent is removed, the resulting oil or foam is brought up in acetonitrile and 0.45 μm filtered. The filtrate is placed on a rotory evaporator to remove the acetonitrile, brought up in benzene, aliquoted into tared storage flasks and then frozen with dry ice. Prior to long term storage under argon at −20° C. benzene is removed by lyophilization. The example above demonstrates the synthesis of seven nucleoside amidites with PrMEG protecting groups, however this approach is not limited to the listed examples. A person of ordinary skills in the art will recognize that this approach is readily diversified into any nucleoside that has protecting groups amenable to automated oligonucleotide synthesis and either a free 3' OH or 5'OH in the case of 5' to 3' synthesis.

Capping and Repeat of the Synthesis Cycle

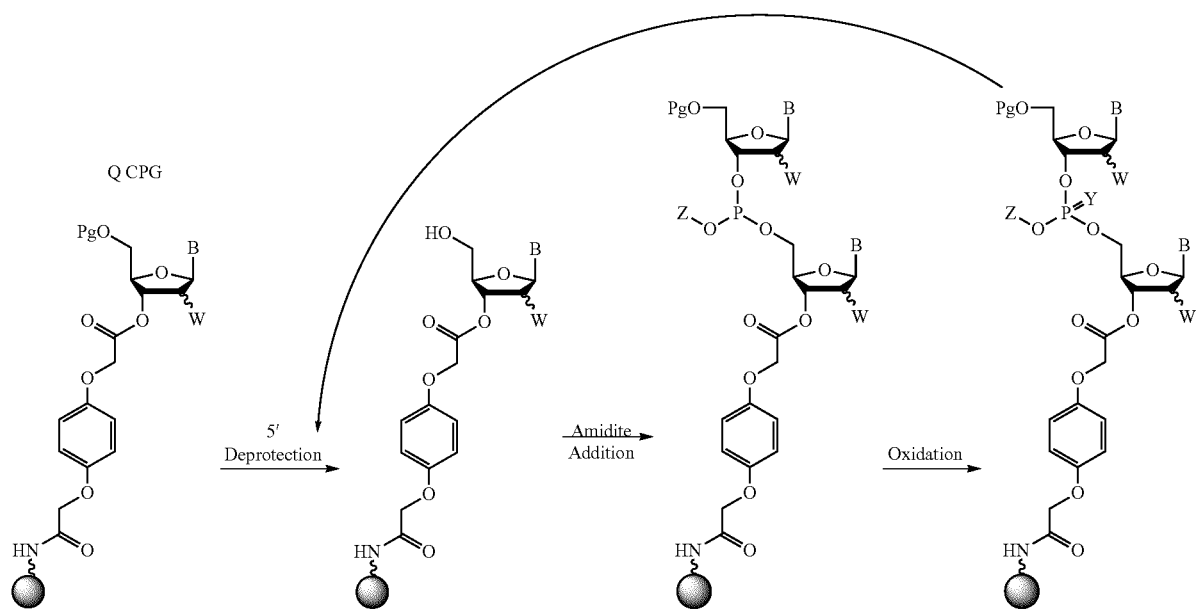

Pg = Acid Labile protecting group such as DMT, Pixyl, MMT
X = O-Alkyl, H or F
Z = Alkyl, cyanoethyl, SPTE, PMEG
Y = O or S
R = Alkyl
B = Pyrimidine, Purine or heterocyclic base with suitable exocylic N protection Automated oligonucleotide synthesis as described by Caruthers, et al. can readily be applied to RNN technologies. The oligonucleotide is grown from the 5' position of a base labile or photolabile solid support tethered nucleoside, from the free 3' position in reverse synthesis or from the free alcohol found on a universal support. This first addition is accomplished by unmasking the alcohol by the treatment with acid using standard 5' trityl deprotection. The resulting support bound intermediate is washed with solvent and the amidite addition step is accomplished by the addition of a suitably base and 2' protected RNA nucleoside amidite, 2' halide or DNA amidite commonly in the presence of tetrazole, ethylthioltetrazole, DCI or any of a number of other coupling agents well known to those that practice the art. The newly formed phosphine center is oxidized commonly with iodine in pyridine to return a phosphate center with the desired Z group in place. Alternatively the oxidation step can be modified to incorporate the use of a Sulfurizing Reagent (Beaucage Reagent or (3' ((Dimethylamino-methylidene) amino)-3H-1,2,4-dithiazole-3-thione, DDTT) reagent to return a phosphorothioate in the Y position, the prior two thiolation reagents are intended to demonstrate common examples of thiolation and are not intended to limit the scope of the invention, many alternate methods of phosphorothioate linkage generation are known in the field. By repeating this process a nucleotide of any reasonable length containing any combination of nucleobases, phosphorothioate linkages, Triester modifications, DNA or RNA can be attained. Alternatively additional functionality can be installed at the 2' position, including by not limited to alkynes for use in Click chemistry, thiols for disulfide and thioether linkage points. The practice of phosphoramidite chemistry to prepare oligonucleotides is known from the published work of M. Caruthers, S. Beaucage and others. U.S. Pat. Nos. 4,458,066, 4,500,707, 5,132,418, 4,415,732, 4,668,777, 4,973,679, 5,278,302, 5,153,319, 5,218,103, 5,268,464, 5,000,307, 5,319,079, 4,659,774, 4,672,110, 4,517,338, 4,725,677 and Re. 34,069, each of which is herein incorporated by reference, describe methods of oligonucleotide synthesis. Additionally, the practice of phosphoramidite chemistry has been systematically reviewed by Beaucage and Iyer in Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein, all of which are herein incorporated by reference. Alternatively those skilled in the art will recognize that automated synthesis approaches include phosphonate based synthesis and reverse oligonucleotide synthesis both of which are included in the scope of this invention.

The example below describes a deprotection strategy useful with RNN or DNN oligonucleotides synthesized using a Q based support from Glen Research.

Example 2A

PMEG (Pivaloyl MercaptoEthyl Glycol) Protected Amidites (Reverse Protocol)

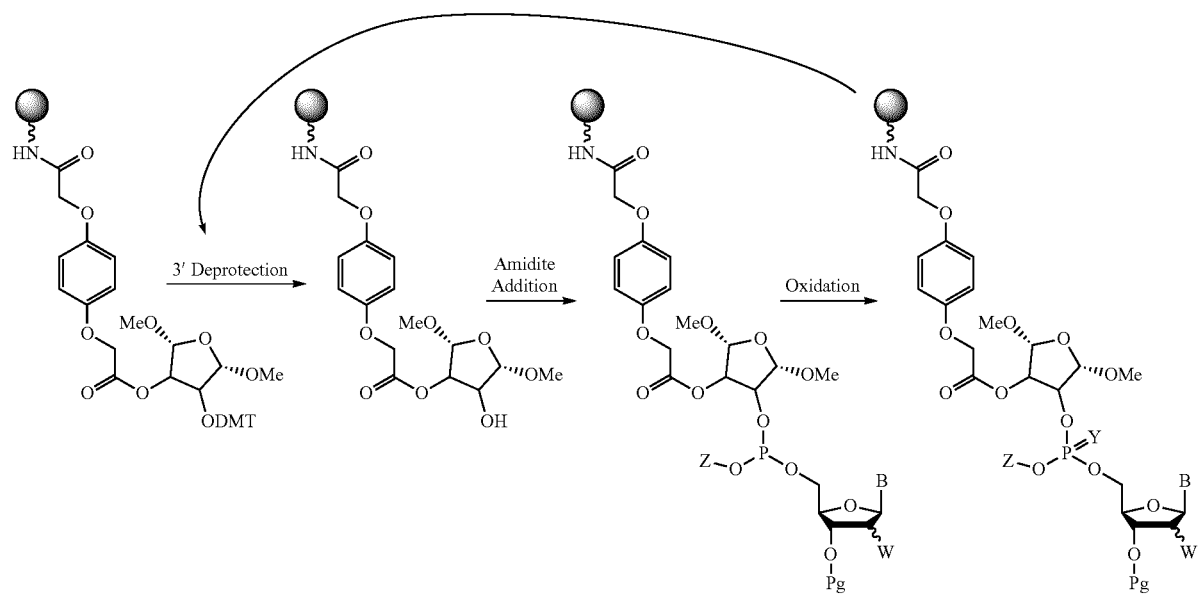

Pg = Acid Labile protecting group such as DMT, Pixyl, MMT
X = O-Alkyl, H or F
Z = Alkyl, cyanoethyl, BMEG, PrMeg, PMEG, etc.
Y = O or S
R = Alkyl
B = Pyrimidine, Purine or heterocyclic base with suitable exocylic N protection 5' to 3' Synthesis (Reverse synthesis)

Oligonucleotide synthesis is routinely carried out from the 3' to the 5' terminus for no other reason than the ease of synthesis of the monomer units. The 5'-hydroxyl group, a primary hydroxyl, is significantly more reactive than the secondary 3'-hydroxyl (or 2'-hydroxyl) group, making it straightforward to protect with the DMT group and leaving the 3'-hydroxyl available to form the phosphoramidite. However, a few situations make it necessary to synthesize oligonucleotides in the opposite sense. The design of antisense oligo-nucleotides as therapeutics has stimulated significant research activity on backbone modification. Modifying the natural phosphodiester linkage is essential to protect the oligonucleotide from intracellular nuclease degradation. However, an interesting addition to the protection of antisense oligonucleotides is to modify the terminal linkages from the natural 3'-5' to 3'-3' and/or 5'-5' linkages. In this way, the oligonucleotides are protected against exonuclease activity, especially 3'-exonuclease activity which is by far the most significant enzymatic degradation route. Moreover, once degradation has occurred, the products are normal nucleosides with no toxicity concerns. Although this strategy has been applied successfully (M. Koga, M. F. Moore, and S. L. Beaucage, J. Org. Chem., 1991, 56, 3757) to the protection of internal linkages using alternating a,b nucleosides to maintain effective hybridization, the most simple strategy is to modify only the linkage at the 3' terminus (J. F. R. Ortigao, H. Rosch, H. Selter, A. Frohlich, A. Lorenz, M. Montenarh, and H. Seliger, Antisense Res. & Dev., 1992, 2, 129-146) resulting in effective nuclease resistance with minimal disruption of hybridization.

Example 3

Solid Phase Synthesis

Deprotection Strategy for Q Based Supports

The deprotection strategy is depicted in Scheme 1, below:

Scheme 1:

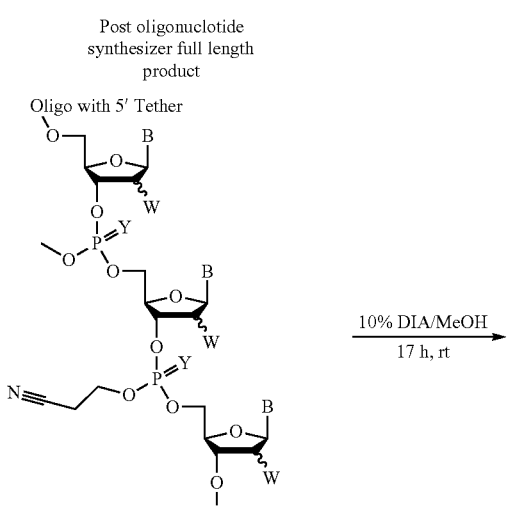

-continued

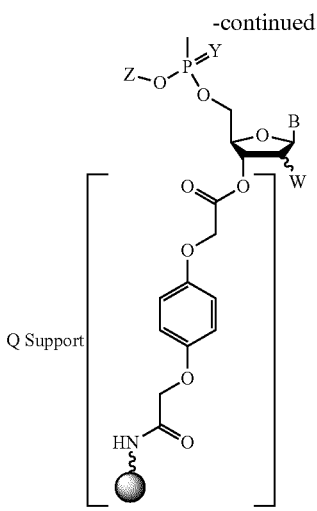

Oligo released from CPG,
Bases are deprotected
and cyanoethyl group is
removed from phosphates

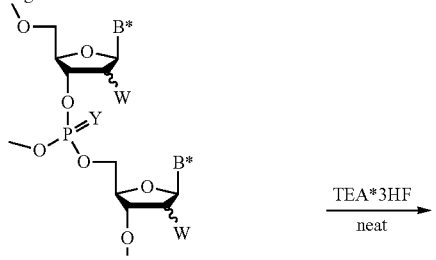

TEA*3HF
neat
→

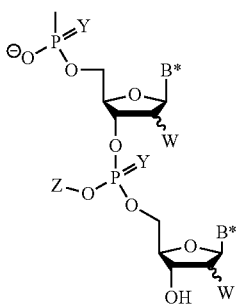

2' O-sily groups
are removed to
generate 2' OH

Oligo with 5' Tether

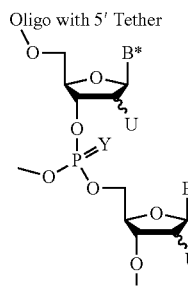

-continued

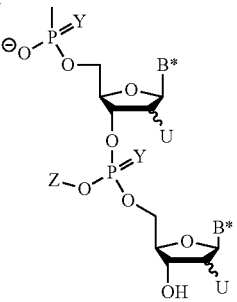

Pg = Acid Labile 5' hydroxyl protecting group such as DMT, Pixyl, MMT
W = O-Alkyl, O-Silyl, H or F
U = O-Alkyl, OH, H or F
Z = Alkyl, cyanoethyl, SPTE, SATE, or thiophenone derivative
Y = O or S
B* = Pyrimidine, Purine or heterocyclic base
B = Pyrimidine, Purine or heterocyclic base with suitable exocylic N protection A 20mer RNN oligonucleotide was synthesized as described below. A standard etch-labeled QT standard support was used RNN synthesis was carried out using the RNN-triester-containing nucleotides described in Example 2. Synthesis of the RNN polynucleotide was carried out on a MERMADE™ oligonucleotide synthesizer, according to manufacturer's instructions. The synthesis uses etch labeled QT standard support. The RNA synthesis is accomplished using the dimethoxytrityl (DMT) Off mode on a MerMade™ synthesizer from Bioautomation. Following the addition to the final triester-containing nucleotide, the dry controlled-pore glass (CPG) was transferred to 2 mL screw cap tubes.

Scheme 1 demonstrates how the primary deprotection step was performed to release the polynucleotide from the solid support, to deprotect the bases, and to remove any cyanoethyl groups present on phosphates. The standard primary deprotection step is accomplished by the addition of 1 mL 10% DIA/MeOH to the 2 mL screw cap tubes, and the sample was incubated at room temperature 8 hours to overnight. The supernatant was transferred to fresh 2 mL tubes, and washed twice with 400 µL methanol. The methanol was evaporated by vacuum centrifugation of the open tubes at room temperature to 35° C., at 2 Ton until evaporation was complete, e.g., 3 hours to overnight.

A secondary deprotection step was performed if necessary to remove 2' silyl groups. The pellet from the primary deprotection step was completely resuspended in 250 µL neat triethylamine-hydrogen fluoride (TEA●3HF) and rotated on an end over end rotator for 8 hrs. 3M sodium acetate (30 µL) was added to the liquid and mixed. 1.5 mL n-BuOH was added, and the mixture was vortexed. Samples were placed at −80° C. for >1 hr, followed by centrifugation for 30 minutes, at 14400 rpm, at 4° C. The supernatant was aspirated via vacuum. The resulting pellet was dissolved in 1 mL 20% acetonitrile.

The sample was loaded onto NAP-10 columns (available from GE Healthcare) equilibrated with 20% acetonitrile. The eluate was collected in 2 mL tubes. (Optional: aliquot and take $A_{260}$ of eluant, usually 1:100 dilution to reach linear range).

Centrifugal evaporation 3 hrs at 35° C. or overnight with no heat and ramp set at 3 to provide the final lyophilate.

The example below describes a deprotection strategy useful with RNN or DNN oligonucleotides synthesized using a 3' thiol-based CPG support.

Example 4

Deprotection Strategy for 3' Thiol Based CPG Supports

The following deprotection strategy invokes the use of an anhydrous 10% diisopropyl amine methanol solution to effect cleavage from the support and removal of the protecting groups from the exocyclic amines of the nucleobases. The deprotection strategy is depicted in Scheme 2, below:

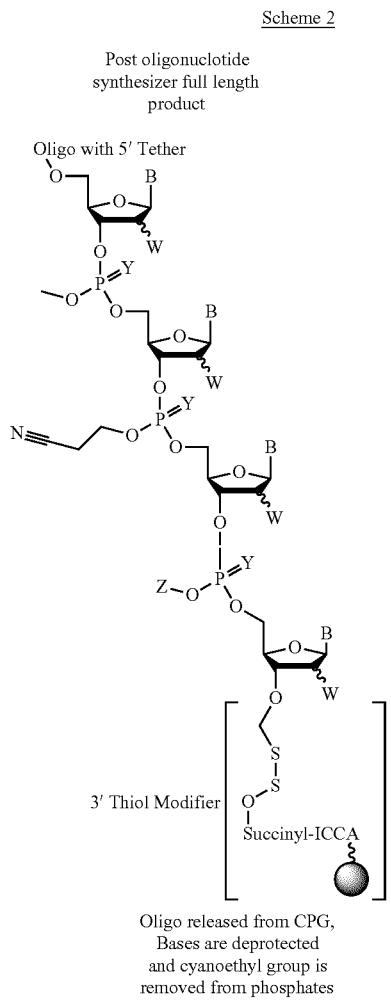

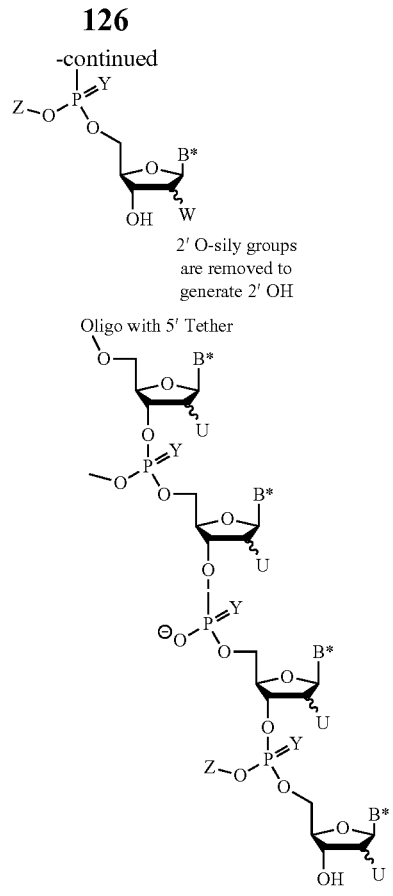

Pg = Acid Labile 5' hydroxyl protecting group such as DMT, Pixyl, MMT
W = O-Alkyl, O-Silyl, H or F
U = O-Alkyl, OH, H or F
Z = Alkyl, cyanoethyl, SPTE, SATE, or thiophenone derivative
Y = O or S
B* = Pyrimidine, Purine or heterocyclic base
B = Pyrimidine, Purine or heterocyclic base with suitable exocylic N protection A 20mer RNN oligonucleotide was synthesized as described below. A standard 3' thiol based CPG support was used.

RNN synthesis was carried out following the protocol described in Example 3.

A primary deprotection step was performed to release the polynucleotide from the solid support, to deprotect the base, and to remove cynao ethyl groups present on phosphates. 10% diisopropyl amine/MeOH (1 mL) was added to the 2 mL screw cap tubes, and incubated at room temperature overnight. The supernatant was transferred to fresh 2 mL screw cap tubes, and washed twice with 400 µL methanol. The methanol was evaporated by centrifuging the open tubes at room temperature to 35° C., until evaporation was complete.

A secondary deprotection step was performed to remove 2' silyl groups. The pellet from the primary deprotection step was completely resuspended in 250 µL neat TEA*3HF and rotated on an endo over end rotator for 8 hrs. Subsequently, 30 µL 3M sodium acetate was added to the tube and mixed. 1.5 mL n-BuOH was added to the tube, followed by vortexing. The tubes containing the samples were placed in −80° C. for >1 hr, followed by centrifugation for 30 min at 14400 at 4° C. The supernatant was aspirated, and the resulting pellet was dissolved in 1 mL 20% acetonitrile.

Next, the sample was loaded onto NAP-10 sephadex columns (GE Healthcare, Piscataway, N.J.) equilibrated with 20% acetonitrile, the eluate was collected in 2 mL tubes. The final lyophilate was obtained by centrifugal evaporation for 3 hrs—overnight at room temperature to 35° C.

Example 5

PMEG Construct Stability

In order to evaluate PMEG construct stability towards the requisite high temperature annealing conditions necessary to generate an a RNN/RNA duplex, a 21mer containing 9 PMEG insertions was synthesized and isolated as essentially described in specific Protocol 4 described above. The RNN strand was placed in a salt water bath and heated to 103° C. for up to 6 minutes, run on an agarosepolyacrylamide gel, and stained with ethidium bromide. The gel is shown in FIG. 7. The results demonstrate that there was no evidence of decomposition of the test strand even after 6 minutes at 103° C. This finding is a striking improvement over previously described phosphate protecting groups that significantly decompose after 1 minute at 100° C. Efficient duplex formation of neutralized constructs with more than 7 phosphate protecting groups per strand requires heating to 100° C. for a minimum of 1.5 minutes, and in some cases for longer periods of time, e.g., 2 minutes, 3 minutes, 4 minutes, or longer.

The data demonstrate that the PMEG constructs described herein are stable under conditions required for duplex formation.

Example 6

RNN and RNN/RNA Duplexes

In order to evaluate whether the protecting groups interfered with the generation of double stranded constructs, a dGFP guide strand having the sequence 5' CCACUAC-CUGAGCACCCAGUT 3' (SEQ ID NO: 9) was synthesized and isolated according the QT support protocol described in Examples 1-4. The guide strand contained 9 reversible PMEG phosphotriester protecting groups, shown below as 9Ng. All single stranded constructs were normalized to 1 mM in water and were added to the corresponding complementary strand (TUGGUGAUGGACUCGUGGGUC—SEQ ID NO: 10) in an equal volume to give a final 500 uM concentration. The 9Ng strand was hybridized to its complementary passenger strands containing 10, 11, and 12 PMEG protecting groups shown below as 10Np, 11Np and 12Np. 3 µL of each sample was added to each well to ensure that the total amount of oligonucleotide added to gel was normalized. An image of the ethidium bromide stained gel is shown in FIG. 8.

FIG. 8 shows the single stranded constructs on either side of the resulting double stranded product. Complete hybridization was observed as evidenced by the absence of bands corresponding to single strands in the hybridization lanes 9N/10N, 9N/11N and 9N/12N. As double stranded oligonucleotides more readily take up ethidium bromide and appear brighter than single stranded oligonucleotide, the increase in the band intensity in the hybridization lanes is also indicative of duplex formation.

Example 7

Lipofectamine Transfection Assay

General Protocol for Transfection with Lipofectamine® 2000

Transfections are performed in reverse transfection format to knock down dGFP in expressing adherent H1299 human lung adenocarcinoma cells. Lipofectamine is diluted in optimem per the manufacturer's instructions; and incubated for 5 minutes room temperature. The siRNA or siRNN is diluted to the appropriate concentration usually starting at 1 mM and serial diluting across a 96 well plate. The siRNA or siRNN dilutions 200 µL and 200 µL of Lipofectamine 2K are mixed and incubated for 20 m at room temperature. 100 µL of the siRNA lipid complex is added to wells containing 100 µL of H1299 cells at 150000 cells/mL for 24 h time points, 100000 cells/mL for 48 h time points, 50000 cells/mL for 72 h time points and 25000 cells/mL for the 96 h time points. On days of data collection, 48, 72, and 96 h the media is removed from the plate and the cells are washed with PBS. Adherent cells are released from the plate with 50 µL 1× trypsin at 37° C. for 5-10m the cells are transferred to a round bottom 96 well plate and dGFP expression was quantified by FACS analysis on a Guava instrument.

In order to test whether the nucleotide modifications of PMEG RNN™ oligonucleotides were reversed intracellularly, an siRNA with a guide strand sequence of 5' CUGGGUGCUCAGGUAGUGGTT 3' (SEQ ID NO: 11) and a passenger strand sequence of 5' CUGGGUGCUCAG-GUAGUGGTT 3' (SEQ ID NO: 12) in examples containing siRNN protecting groups all uridine sites were substituted within the experimental strand. The constructs were transfected into H1299 cells grown in 96 well plates with Lipofectamine 2000 according to the general protocol, at 2 nM, 4 nM, 8 nM, 16 nM, 31 nM, 62.5, 125 M, or 250 nM. Reversal was measured at 24, 48, and 72 h with this sequence. The results are shown in FIG. 4A. The results demonstrate that PMEG modified siRNN were able to elicit a detectable reduction in dGFP expression at concentrations as low as 2 nM.

FIG. 4A shows the dose response curve at 72 h of a positive control wild type siRNA containing no 2' modifications, a siRNN comprised of seven PMEG insertions on the passenger strand that is completely 2' OMe modified over a wild type guide strand, a second siRNN construct with six PMEG insertions containing 2' F modifications on nucleosides containing the protecting group hybridized to a wild type passenger strand, and a negative control siRNN construct containing six irreversible protecting group POEt insertions with adjacent 2' OMe modifications. Maximal response for the PMEG 7N p2OMe construct was 63% knockdown of dGFP expression observed at a concentration of 8 nM. PMEG 6N g2OH gave a maximal knock down of 67% at 31 nM. 6NPOEt irreversible siRNN constructs resulted in negligible reduction in dGFP expression levels. These data support the reversibility of the protecting group when exposed to an intra-cellular environment.

Levels of observed knockdown with a siRNN construct comprising a wild type passenger strand and a guide strand containing 6 phosphotriester linkages were plotted at 4 nM, 8 nM, 16 nM and 31 nM vs. 3 time points 24, 48 and 72 h. Knockdown was first observed at 24 h and appeared to reach a maximum at 72 h with the 31 nM dose giving a 68% reduction in dGFP expression.

Figure 3:
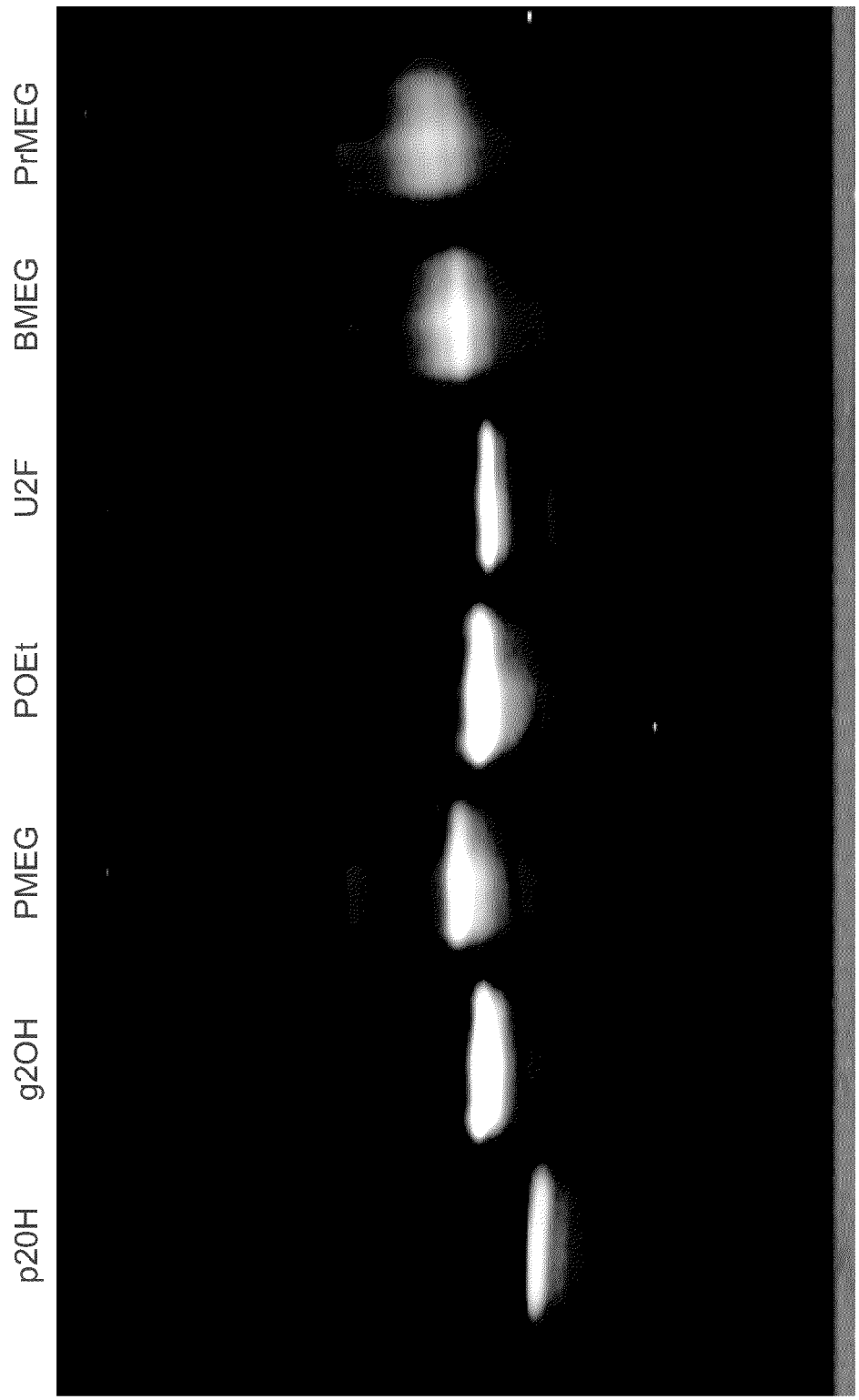
FIG. 3 is a photograph of a polyacrylamide gel of complete double stranded 21mer siRNN constructs with controls.

A second in-vitro experimental approach was carried out with an optimized dGFP oligonucleotide sequence containing a passenger strand of 5' AGCUGACCCUGAAGUU-CAUTT 3' (SEQ ID NO: 13) and the corresponding guide strand 5' AUGAACUUCAGGGUCAGCUTT 3' (SEQ ID NO: 14). In these experiments, all uridine sites within the guide strand were modified and all 2' positions of the oligonucleotides were either 2' deoxy 2' fluoro in the case of pyrimidine insertion sites and 2' OMe modified in the case of purine insertions. FIG. 3 shows full length 21mer siRNN dGFP oligonucleotide synthesis products containing 5 neutralizing group insertions per duplex. P₂OH is a normal passenger strand siRNA single stranded construct, g2OH is a normal guide strand single stranded siRNA. PMEG is a double stranded siRNN guide strand with 5 strategically placed biolabile reversible neutralizing groups hybridized to the p2OH strand. POEt is a double stranded construct containing a siRNN guide strand with 5 strategically placed phosphate protected irreversible neutralizing groups hybridized to the p2OH. U2F is a double stranded siRNA guide strand with 5 strategically placed 2' deoxyfluoro substitutions over p2OH to simulate a prematurely reversed double stranded siRNN. BMEG is a double stranded siRNN guide strand with 5 strategically placed biolabile reversible neutralizing groups hybridized to the p2OH strand. PrMEG is a double stranded siRNN guide strand with 5 strategically placed biolabile reversible neutralizing groups hybridized to the p2OH strand. The changes in mobility in the gel are associated with the reduction in charge and polarity of the double stranded constructs. Double stranded constructs with neutralizing groups have a slower migration rate.

FIG. 5 is a FACs analysis histogram of the levels of dGFP expression in H1299 cells challenged with 21mer siRNN constructs, negative controls and positive controls. The histograms appear on the graph from left to right in the order of g2OH/p2OH, U2F, BMEG, PrMEG PMEG, POEt and Lipofectamine only control. The positive controls are shown at the far left of the plot, and show maximum knockdown. The negative controls are shown on the far right and show no reduction of dGFP expression. Oligonucleotides were delivered into the cells using the Invitrogen product Lipofectamine 2000® (Invitrogen, Carlsbad, Calif.) according to the manufacturer's protocol.

Oligonucleotide constructs bearing 5 reversible protecting groups at all uridine sites on the guide strand are labeled as BMEG, PrMEG, and PMEG according to the protocols described herein and all five siRNN reversible uridine amidites were 2' deoxy 2' fluoro. The product of intracellular protecting group reversal retains the 2' fluoro modification. This oligonucleotide was synthesized de novo as the positive control U2F. Wild type unmodified siRNA, g2OH/p2OH was also synthesized and used as another positive control. An siRNN with irreversible POEt insertions at all uridine sites within the dGFP siRNA sequence was used as a negative control, as was treatment with lipofectamine only.

The data of FIG. 5 demonstrate that sites modified with irreversible phosphate protecting groups in the uridine positions gave in no reduction in dGFP expression. In contrast to the irreversible phosphate protecting group, the reversible phosphate protecting groups resulted in knockdown of dGFP expression in the 87% to 94% range, when compared to Lipofectamine® only controls, consistent with intracellular reversal. These levels of knockdown were also observed at the 72 h and 96 h timepoints. The plots of forward scatter vs side scatter indicate that the reduction of expression of dGFP is not due to cytotoxicity.

FIG. 4B depicts knockdown of dGFP expression with the tested constructs over 96 h. U2F 5N g2 Mod is a positive control that demonstrates the maximum achievable level of reduction of dGFP expression by a construct that does not have phosphotriester protecting groups. PMEG, BMEG and PrMEG constructs all contain five reversibly protected siRNN insertions on the guide strand. POEt 5N g2 Mod is an irreversibly protected siRNN negative control. The results of this experiment indicated that all three reversibly protected constructs were able to load into the RISC complex and elicit a reduction in protein expression intracellularly in the range of 87% to 94%. This effect was observed at the first time point of 48 h and continued for all time points evaluated. All constructs tested except the irreversible phosphotriester gave high levels of knockdown, up to 99% in the case of wild type siRNA. This effect was observed immediately at the first 48 h time point and continued through 96 h, the entire length of the experiment.

Example 8

PTD siRNN Construct Synthesis

This example demonstrates the formation of oligonucleotide-peptide conjugates via disulfide linkage. FIG. 9 shows three different peptide oligonucleotide disulfide bond formation. The active oligonucleotides were incubated with DNA 21mer model system. The disulfide bond forming reactions between highly cationic peptides and highly anionic oligonucleotides is typically very low yielding due to the formation of an undesired charge/charge non-covalently bound side product. After an extraordinary number of trials a method was developed to successfully and repeatedly generate the elusive disulfide linkage. The starting oligo is a 5' thiol modified DNA 21mer oligonucleotide purchased from IDT that was protected as a C6 disulfide, show in lane 1 of FIG. 9. The multiple bands observed in lane one are generated by non specific disulfide exchange. The starting oligo was converted to the active oligo by treatment with TCEP to cleave the disulfide bound protecting group. The crude material was placed on a NAP 10 size exclusion column in water to remove reaction byproducts and excess TCEP, the eluant was lyophilized, normalized to 1 mM in water and stored over solid phase TCEP to prevent oxidation and dimer formation. Aliquots of active oligo were reacted in formamide with an 8 fold molar excess of terminal cysteine NPyS modified PTD polypeptides. Each of the reactions were allowed to proceed for 12 h to yield products that were positively charged. In a manner similar to the methods described in Current Protocols in Nucleic Acid Chemistry. The increase in charge significantly retards mobility into the gel. (See, FIG. 9, lanes labeled RXN). In the case of 2×PTD-NPyS reactions the disappearance of starting material indicates successful reaction completion. Samples of each of the reactions RxN were taken at 12 h and were incubated with DTT at 65° C. to cleave the newly formed disulfide bond. The return of activated oligo starting material further supports the presence of the correct linkage. To demonstrate that the bond was in fact a covalent linkage, aliquots of NPyS modified peptides were deactivated by the addition of beta mercaptothiol prior to the addition to the active oligo. These samples were incubated under the same conditions as the RxN lanes to intentionally form non-covalently bound control products. The deactivated peptide negative control lanes can be found for each of the oligo peptide combination. The NPyS control contains only 3 charged arginine residues, 1×PTD contains 7 Arg, 2×PTD contains 14arg residues. Three arginines is effective at producing a shift in mobility when covalently bound however it is not charged enough to form charge/charge side products this control further supports the formation of the desired disulfide bond under the reaction conditions.

As a final demonstration of the usefulness of the embodiments disclosed herein, the covalent linkage, of a PTD to a siRNN based passenger strand via a disulfide bond, was followed by hybridization to a complementary siRNN modified guide strand. The resulting carrier strand, peptide bound to siRNN, was accomplished using methods similar to those described in Current Protocols in Nucleic Acid Chemistry. The crude material was combined with the complementary guide strands and dialyzed against water with a 4000 MW cutoff membrane to remove solvent, reaction byproducts, salts and excess free PTD. Dialysis from the chaotropic solvent in the presence of the complementary strand effected hybridization. The gel below depicts the results of the experiment. The lanes are labeled as, 10Nc a PTD bound dGFP single stranded siRNN containing 10 PMEG insertions, 9Nc a PTD bound dGFP single stranded siRNN containing 9 PMEG insertions, 8Nc a PTD bound dGFP single stranded siRNN containing 8 PMEG insertions, and 7Nc a PTD bound dGFP single stranded siRNN containing 7 PMEG insertions. The lane with the header 2×PTD is a synthetic PTD peptide comprised of two cationic peptide domains activated towards coupling with a terminal NPyS modified terminal cysteine and an amino acid sequence of CGGGYAAAR-RRRRRRGSGSGYAAARRRRRRRG (SEQ ID NO: 15) that was loaded onto the gel to provide a size and migration standard. The photograph of the gel in FIG. 10 shows single strand carriers and final duplexed constructs containing up to 20 siRNN modifications and 50% neutralization (See, lanes 10Nc/10Ng, 10Nc/9Ng, 9Nc/10Ng, 9Nc/9Ng).

I claim:
1. A compound of formula III:

(III)

wherein:
$D_1$ is or ;

$R^1$ is an optionally substituted substituent selected from the group consisting of $C_{1-6}$alkyl, $C_{1-6}$alkyl substituted with one or more hydroxyl groups, $C_{1-6}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, $C_{1-6}$alkylC(O)O—, arylC(O)O—, heteroarylC(O)O—, and heterocyclylC(O)O—;
$R^{12}$ is H (hydrogen), alkylOC(O)—, or an optionally substituted arylOC(O)—;
each $R^2$ is individually $C_{1-6}$alkyl;
$X_1$ is O (oxygen) or S (sulfur);
$X_2$ is O (oxygen), NR$^3$, or S (sulfur);
$R^3$ is selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
$X_3$ is O(oxygen), NH, or S (sulfur);
each $A_1$ is —C(R$^4$)$_2$—;
each $A_2$ is individually selected from the group consisting of —NR$^6$—, —C(R$^5$)$_2$NR$^6$—, —C(R$^5$)$_2$O—, —C(R$^5$)$_2$S—, —C(R$^5$)$_2$C(R$^5$)$_2$NR$^6$—, —C(R$^5$)$_2$C(R$^5$)$_2$O—, and —C(R$^5$)$_2$C(R$^5$)$_2$S—
each $A_3$ is —C(R$^7$)$_2$—;
m is an integer selected from 1, 2, or 3;
n is an integer selected from 1, 2, or 3;
q is an integer selected from 1, 2, or 3;
each C(R$^4$)$_2$ is independently selected, wherein each $R^4$ is individually selected from the group consisting of H (hydrogen), halo, $C_{1-6}$alkyl, and $C_{1-6}$alkyl substituted with up to 5 fluorine, or optionally two $R^4$ groups are taken together with the carbon to which they are attached to form an optionally substituted $C_{3-7}$cycloalkyl group;
each C(R$^5$)$_2$ is independently selected, wherein each $R^5$ is individually selected from the group consisting of H (hydrogen), halo, $C_{1-6}$alkyl, and $C_{1-6}$alkyl substituted with up to 5 fluorine; or two $R^5$ are optionally taken together to form an oxo group;

each $R^6$ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
each C(R$^7$)$_2$ is independently selected, wherein each $R^7$ is individually selected from the group consisting of H (hydrogen), halo, $C_{1-6}$alkyl, and $C_{1-6}$alkyl substituted with up to 5 fluorine, or optionally two $R^7$ groups are taken together with the carbon to which they are attached to form an optionally substituted $C_{3-7}$cycloalkyl group;
$R^8$ is selected from the group consisting of H (hydrogen), optionally substituted trityl, optionally substituted pixyl (9-phenylxanthenyl), and optionally substituted S-pixyl (9-phenylthioxanthyl);
$R^9$ is selected from the group consisting of H (hydrogen, halo, —OR$^{10}$, and optionally substituted $C_{1-6}$alkoxyl;
$R^{10}$ is selected from the group consisting of H (hydrogen), triisopropylsilylOCH$_2$—, tert-butyldimethylsilylOCH$_2$—, triethylsilylOCH$_2$—, trimethyisitylethylOCH$_2$—, triisopropylsilyl-, tert-butyidimethylsily-, trimethyisitylethyl-, triethylsilyl-, optionally substituted trimethylsilyl-, and optionally substituted trimethylsilylOCH$_2$—; and
B is an optionally substituted substituent selected from the group consisting of a pyrimidine, a purine, and a heterocyclic base.

2. A compound of formula IV:

(IV)

wherein:
each $D_1$ is independently or ;

each $R^1$ is independently an optionally substituted substituent selected from the group consisting of $C_{1-6}$alkyl, $C_{1-6}$alkyl substituted with one or more hydroxyl groups, $C_{1-6}$alkoxyl aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, C$_{1-6}$alkylC(O)O—, arylC(O)O—, heteroarylC(O)O—, and heterocyclylC(O)O—, L is a linker arm;

T is a solid support;

each R$^{12}$ is independently H (hydrogen), alkylOC(O)—, or an optionally substituted arylOC(O)—;

each X$_1$ is independently O (oxygen) or S (sulfur);

each X$_2$ is independently O (oxygen), NR$^3$, or S (sulfur);

each R$^3$ is independently selected from the group consisting of H(hydrogen), C$_{1-6}$alkyl, C$_{1-6}$alkylC(O)—, C$_{1-6}$alkylOC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each X$_3$ is independently O (oxygen), NH, or S (sulfur);

each A$_1$ is —C(R$^4$)$_2$—;

each A$_2$ is individually selected from the group consisting of —NR$^6$—, —C(R$^5$)$_2$NR$^6$—, —C(R$^5$)$_2$O—, —C(R$^5$)$_2$S—, —C(R$^5$)$_2$C(R$^5$)$_2$NR$^6$—, —C(R$^5$)$_2$C(R$^5$)$_2$O—, and —C(R$^5$)$_2$C(R$^5$)$_2$S;

each A$_3$ is —C(R$^7$)$_2$—;

each m is independently an integer selected from 1, 2, or 3;

each n is independently an integer selected from 1, 2, or 3;

each q is independently an integer selected from 1, 2, or 3;

each C(R$^4$)$_2$ is independently selected, wherein each R$^4$ is independently selected from the group consisting of H (hydrogen), halo, C$_{1-6}$alkyl, and C$_{1-6}$alkyl substituted with up to 5 fluorine, or optionally two R$^4$ groups are taken together with the carbon to which they are attached to form an optionally substituted C$_{3-7}$cycloalkyl group;

each C(R$^5$)$_2$ is independently selected, wherein each R$^5$ is independently selected from the group consisting of H (hydrogen), halo, C$_{1-6}$alkyl, and C$_{1-6}$alkyl substituted with up to 5 fluorine; or two R$^5$ are optionally taken together to form an oxo group;

each R$^6$ is independently selected from the group consisting of H (hydrogen), C$_{1-6}$alkyl, C$_{1-6}$alkylC(O)—, C$_{1-6}$alkylOC(O)—, C$_{1-6}$alkylNHC(O)—, C$_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each C(R$^7$)$_2$ is independently selected, wherein each R$^7$ is independently selected from the group consisting of H (hydrogen), halo, C$_{1-6}$alkyl, and C$_{1-6}$alkyl substituted with up to 5 fluorine, or optionally two R$^7$ groups are taken together with the carbon to which they are attached to form an optionally substituted C$_{3-7}$cycloalkyl group;

R$^8$ is selected from the group consisting of H (hydrogen), optionally substituted trityl, optionally substituted pixyl (9-phenyixanthenyl), and optionally substituted S-pixyl (9-phenylthioxanthyl);

each R$^9$ is independently selected from the group consisting of H (hydrogen), halo, —OR$^{10}$, and optionally substituted C$_{1-6}$alkoxyl;

each R$^{10}$ is independently selected from the group consisting of H (hydrogen), triisopropylsilylOCH$_2$—, tert-butyldimethylsilylOCH$_2$—, triethylsilylOCH$_2$—, trimethylsitylethylOCH$_2$—, triisopropylsilylOCH$_2$-tert-butyldimethylsilyl-, trimethyisitylethyl-, triethylsilyl-, optionally substituted trimethylsilyl-, and optionally substituted trimethylsilylOCH$_2$—;

each B is independently an optionally substituted substituent selected from the group consisting of a pyrimidine, a purine, and a heterocyclic base;

p is an integer from 0 (zero) to about 50;

each W is independently —OR$^{11}$ or

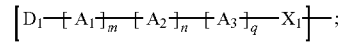

each X$_4$ is independently O (oxygen) or S (sulfur); and each R$^{11}$ is independently H (hydrogen), C$_{1-6}$alkyl, —CH$_2$CH$_2$CN, or absent, with the proviso that when R$^{11}$ is absent then —OR$^{11}$ is —O$^{31}$ (anionic oxygen radical) providing an phosphate anionic diester group or anionic thiophosphate diester group.

3. A phosphate-protected oligonucleotide derivative of formula V:

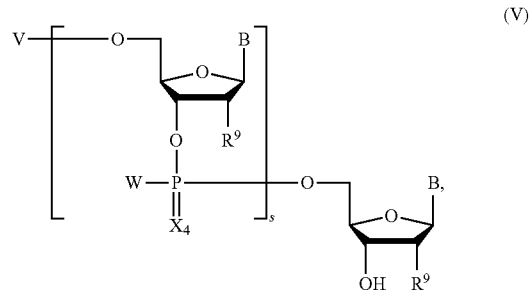

(V)

wherein:

each X$_4$ is individually O (oxygen) or S (sulfur);

s is an integer from 1 to about 5000;

each R$^9$ is individually selected from the group consisting of H (hydrogen), halo, —OR$^{10}$, and optionally substituted C$_{1-6}$ alkoxyl;

each R$^{10}$ is independently selected from the group consisting of H (hydrogen), triisopropylsilylOCH$_2$—, tert-butyldimethylsilylOCH$_2$—, triethylsitylOC$_2$—, trimethylsilylethylOCH$_2$—, triisopropylsilyl-, tert-butyldimethylsilyl-, trimethylsilylethyl-, triethylsilyl-, optionally substituted trimethylsityl-, and optionally substituted trimethylsilylOCH$_2$—;

each B is individually an optionally substituted substituent selected from the group consisting of a pyrimidine, a purine, and a heterocyclic base;

V is H (hydrogen) or a transducing moiety;

each W is independently R$^{11}$O—or

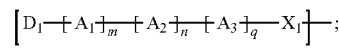

each R$_{11}$ is independently H (hydrogen), C$_{1-6}$alkyl, —CH$_2$CH$_2$CN, or absent;

each D₁ is independently

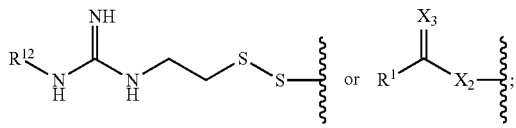

each R¹ is independently an optionally substituted substituent selected from the group consisting of $C_{1-6}$alkyl, $C_{1-6}$alkyl substituted with one or more hydroxyl groups, $C_{1-6}$alkoxyl, aryl, heteroaryl, heterocyclyl, —NH$C_{1-6}$ alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroalylC(O)O—, and heterocyclylC(O)O—;

each $R^{12}$ is independently is H (hydrogen), alkylOC(O)—, or an optionally substituted arylOC(O)—;

each $X_1$ is independently O (oxygen) or S (sulfur);

each $X_2$ is independently O (oxygen), NR³, or S (sulfur);

each $R^3$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)₂—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)₂—;

each $X_3$ is independently O (oxygen), NH, or S (sulfur);

each $A_1$ is —C(R⁴)₂—;

each $A_2$ is individually selected from the group consisting of —HR⁶—, —C(R⁵)₂NR⁶—, —C(R⁵)₂O—, —C(R⁵)₂S—, —C(R⁵)₂C(R⁵)₂NR⁶—, —C(R⁵)₂C(R⁵)₂O—, and —C(R⁵)₂C(R⁵)₂S—;

each $A_3$ is —C(R⁷)₂—;

each m is independently an integer selected from 1, 2, or 3;

each n is independently an integer selected from 1, 2, or 3;

each q is independently an integer selected from 1, 2, or 3;

each C(R⁴)₂ is independently selected, wherein each R⁴ is individually selected from the group consisting of H (hydrogen), halo, $C_{1-6}$alkyl, and $C_{1-6}$alkyl substituted with up to 5 fluorine, or optionally two R⁴ groups are taken together with the carbon to which they are attached to form an optionally substituted $C_{3-7}$cycloalkyl group;

each C(R⁵)₂ is independently selected, wherein each R⁵ is individually selected from the group consisting of H (hydrogen), halo, $C_{1-6}$alkyl, and $C_{1-6}$alkyl substituted with up to 5 fluorine; or two R⁵ are optionally taken together to form an oxo group;

each R⁶ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)₂—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNEC(O)—, and optionally substituted arylS(O)₂—; and each C(R⁷)₂ is independently selected, wherein each R⁷ is individually selected from the group consisting of H (hydrogen), halo, $C_{1-6}$alkyl, and $C_{1-6}$alkyl substituted with up to 5 fluorine, or optionally two R⁷ groups are taken together with the carbon to which they are attached to form an optionally substituted $C_{3-7}$cycloalkyl group;

with the proviso that at least one W is

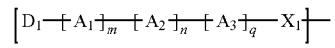

and when $R^{11}$ is absent then $R^{11}$O— is —O⁻ (anionic oxygen radical) providing an phosphate anionic diester group or anionic thiophosphate diester group.

4. A compound of formula VIII:

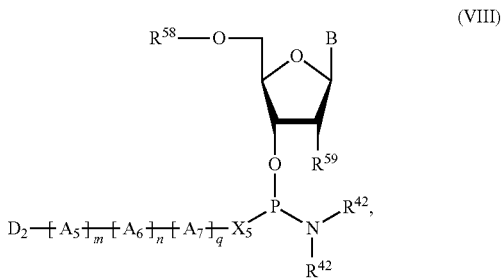

(VIII)

wherein:

D₂ is

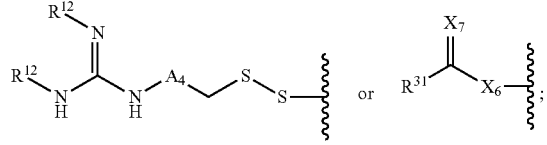

$R^{31}$ an optionally substituted substituent selected from the group consisting of $C_{1-8}$alkoxyl, $C_{1-8}$alkenyl, $C_{1-6}$alkoxyl, aryl, heteroaryl, heterocyclyl, —NH$C_{1-6}$ alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroarylC(O)O—, heterocyclylC(O)O—, and $C_{1-8}$alkyl substituted with one or more hydroxyl groups; or $R^{31}$ is selected from the group consisting of (R⁴⁸)₄N(CH₂)ᵣ—, (R⁴⁸)₃C(CH₂)ᵣ—, (R⁴⁸)₃CNH(CH₂)ᵣ—, HS(CH₂)ᵣ—, $C_{1-8}$heteroalkyl, and guanidiny(CH₂)ᵣ—, $R^{48}$ is selected from the group consisting of H (hydrogen), $R^{49}$(CH₂)ᵣ—, optionally substituted $C_{1-6}$alkyl, optionally substituted $C_{3-7}$alkyl, optionally substituted arylalkyl, and optionally substituted aryl;

$R^{49}$ is selected from the group consisting of H (hydrogen), halo, $R^{50}$O—, and optionally substituted $C_{1-6}$alkoxyl; and $R^{50}$ is selected from the group consisting of H (hydrogen), triisopropylsilylOCH₂—, tert-butyldimethylsilylOCH₂—, triethylsilylOCH₂ —, trimethylsilylethylOCH₂—, triisopropylsilyl-, tert-butyldimethylsilyl-, trimethylsilylethyl-, triethylsilyl-, optionally substituted trimethylsilyl-, and optionally substituted trimethylsilylOCH₂— each $R^{12}$ is individually selected from the group consisting of H (hydrogen), $R^{13}$OC(O)—, $R^{13}$C(O)—, $R^{13}$C(O)CH₂—, $R^{13}$SO₂—, alkylOC(O)—, or an optionally substituted arylOC(O)—;

each $R^{13}$ is individually selected from the group consisting of optionally substituted $C_{1-6}$alkyl, and an optionally substituted aryl;

each $R^{42}$ is individually $C_{1-6}$alkyl;

$X_5$ is O(oxygen) or S (sulfur);

each $X_6$ is independently selected from the group consisting of O (oxygen), $NR^{33}$, Se (selenium), or S (sulfur);

$R^{33}$ selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

$X_7$ is O (oxygen), NH, or S (sulfur);

each $A_5$ is —C($R^{44}$)$_2$—;

each $A_6$ is individually selected from the group consisting of —$NR^{46}$—, —C($R^{45}$)$_2$$NR^{46}$—, —C($R^{45}$)$_2$O—, —C($R^{45}$)$_2$S—, —C($R^{45}$)$_2$Se—, —OC($R^{45}$)$_2$O—, —SC($R^{45}$)$_2$S—, —SeC($R^{45}$)$_2$Se—, —C($R^{45}$)$_2$C($R^{45}$)$_2$$NR^{46}$—, —C($R^{45}$)$_2$C($R^{45}$)$_2$O—, —C($R^{45}$)$_2$C($R^{45}$)$_2$S—, and —C($R^{45}$)$_2$C($R^{45}$)$_2$Se—, each $A_7$ is —C($R^{47}$)$_2$—;

$A_4$ is an optionally substituted substituent selected from the group consisting of $C_{1-15}$alkoxy, $C_{1-15}$alkoxy $C_{1-15}$heteroalkyl, aryl, heteroaryl and heterocycle; or $A_4$ is $L_1$-$L_2$, $L_1$-$X_9$-$L_2$, -$X_9$-$L_1$-$X_9$-$L_2$-$X_9$-, -$X_9$-$L_1$-$L_2$-$X_9$-, $L_1$-$L_2$-$L_3$, $L_1$$X_9$-$L_2$-$X_9$-$L_3$, -$X_9$-$L_1$-$X_9$-$L_2$-$X_9$-$L_3$$X_9$-, $L_1$-$X_9$-$L_2$-$L_3$, -$X_9$-$L_1$-$X_9$-$L_2$-$X_9$-$L_3$, -$X_9$-$L_1$-$L_2$-$X_9$-$L_3$, $L_1$-$X_9$-$L_2$-$L_3$-$X_9$, -$X_9$-$L_1$-$X_9$-$L_2$-$X_9$-$L_3$-$X_9$, and -$X_9$-$L_1$-$L_2$-$X_9$-$L_3$-$X_9$;

$L_1$ is an optionally substituted substituent selected from the group consisting of $C_{1-5}$alkoxy, $C_{1-5}$alkoxy $C_{1-5}$heteroalkyl, aryl, heteroaryl and heterocycle;

$L_2$ is an optionally substituted substituent selected from the group consisting of $C_{1-5}$ alkyl, $C_{1-5}$alkoxy, $C_{1-5}$heteroalkyl, aryl, heteroaryl and heterocycle;

$L_3$ is an optionally substituted substituent selected from the group consisting of $C_{1-5}$alkyl, $C_{1-5}$alkoxy, $C_{1-5}$heteroalkyl, aryl, heteroaryl and heterocycle;

each $X_9$ is independently selected from the group consisting of O (oxygen $NR^{43}$, Se selenium), or S (sulfur);

each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)—;

m is an integer selected from 1, 2, or 3;

n is an integer selected from 1, 2, or 3;

q is an integer selected from 1, 2, or 3;

r is an integer selected from 0, 1, 2, 3, 4, 5, or 6;

each C($R^{44}$)$_2$ is independently selected, wherein each $R^{44}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{44}$ groups are taken together with the carbon to which they are attached to form an optionally substituted $C_{3-7}$cycloalkyl group;

each C($R^{45}$)$_2$ is independently selected, wherein each $R^{45}$ is individually selected from the group consisting of H (hydrogen), halo, $C_{1-6}$alkyl, $C_{1-6}$alkoxy, and $C_{1-6}$alkyl substituted with up to 5 fluorine; or optionally two $R^{45}$ are optionally taken together to form an oxo group;

each $R^{46}$ is individually selected from the group consisting of H (hydrogen), $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted h.eteroarylOC(O)—, optionally substituted arylNHC(O)—, optionally substituted heteroarylNHC(O)—, and optionally substituted arylS(O)$_2$—;

each C($R^{47}$)$_2$ is independently selected, wherein each $R^{47}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{47}$ are taken together with the carbon to which they are attached to form an optionally substituted $C_{3-7}$cycloalkyl group;

$R^{58}$ is selected from the group consisting of (hydrogen), optionally substituted trityl, optionally substituted pixyl (9-phenyixanthenyl), and optionally substituted S-pixyl (9-phenyithioxanthyl);

$R^{59}$ is selected from the group consisting of H (hydrogen), halo, $R^{60}$O(CH$_2$)$_r$—, and optionally substituted $C_{1-6}$alkoxyl;

$R^{60}$ is selected from the group consisting of H (hydrogen), triisopropylsilylOCH$_2$—, tert-butyldimethylsilylOCH$_2$—, triethyisilylOCH$_2$—, trimethylsilylethylOCH$_2$—, triisopropylsilyl-, tert-butyldimethylsilyl-, trimethyisitylethyl-, triethylsilyl-, optionally substituted trimethylsilyl-, and optionally substituted trimethylsilylOCH$_2$—; and B is an optionally substituted substituent selected from the group consisting of a pyrimidine, a purine, and a heterocyclic base.

5. The compound of claim 4, wherein:

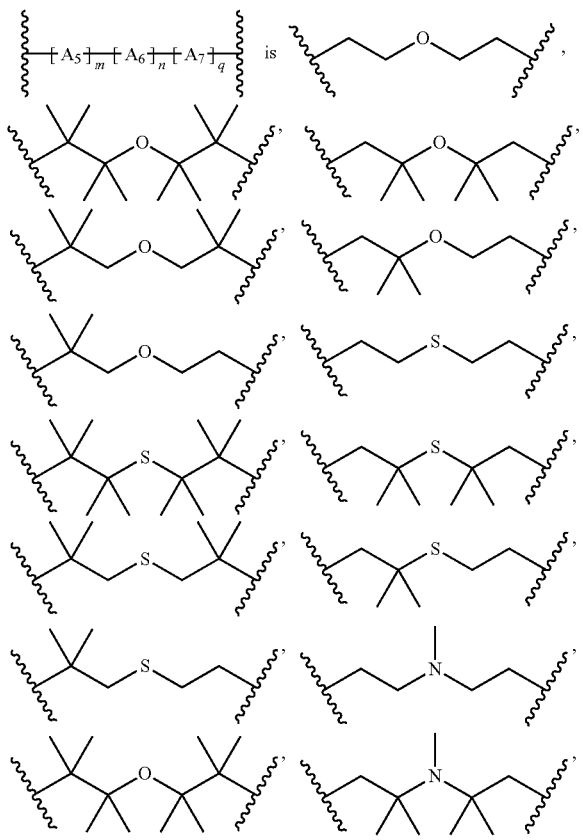

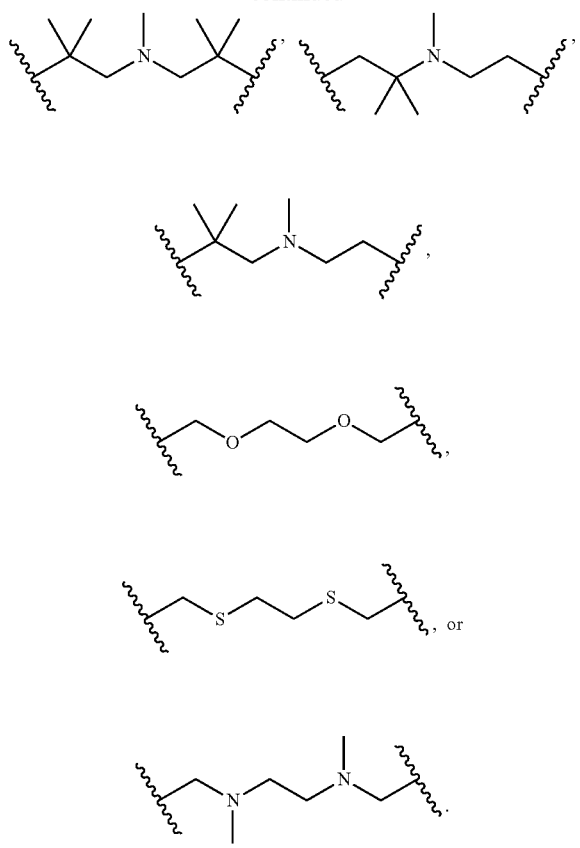
6. The compound of claim 4, wherein the compound of Formula VIII is selected from the group consisting of:
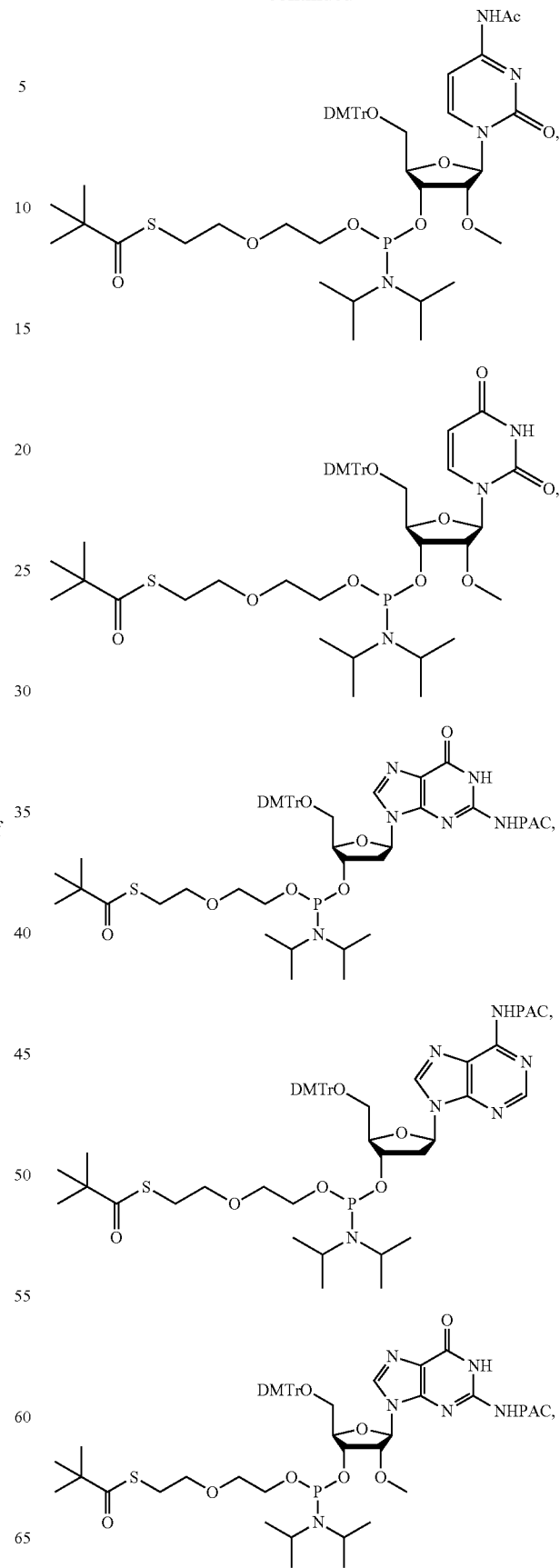

161
-continued
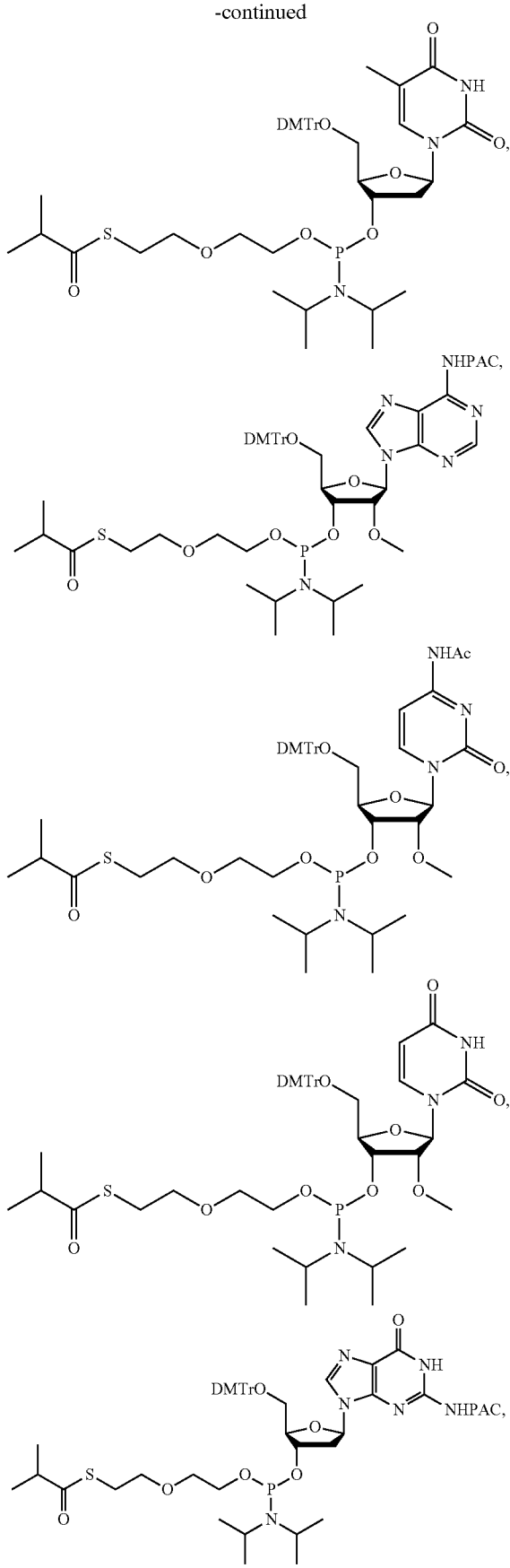
162
-continued
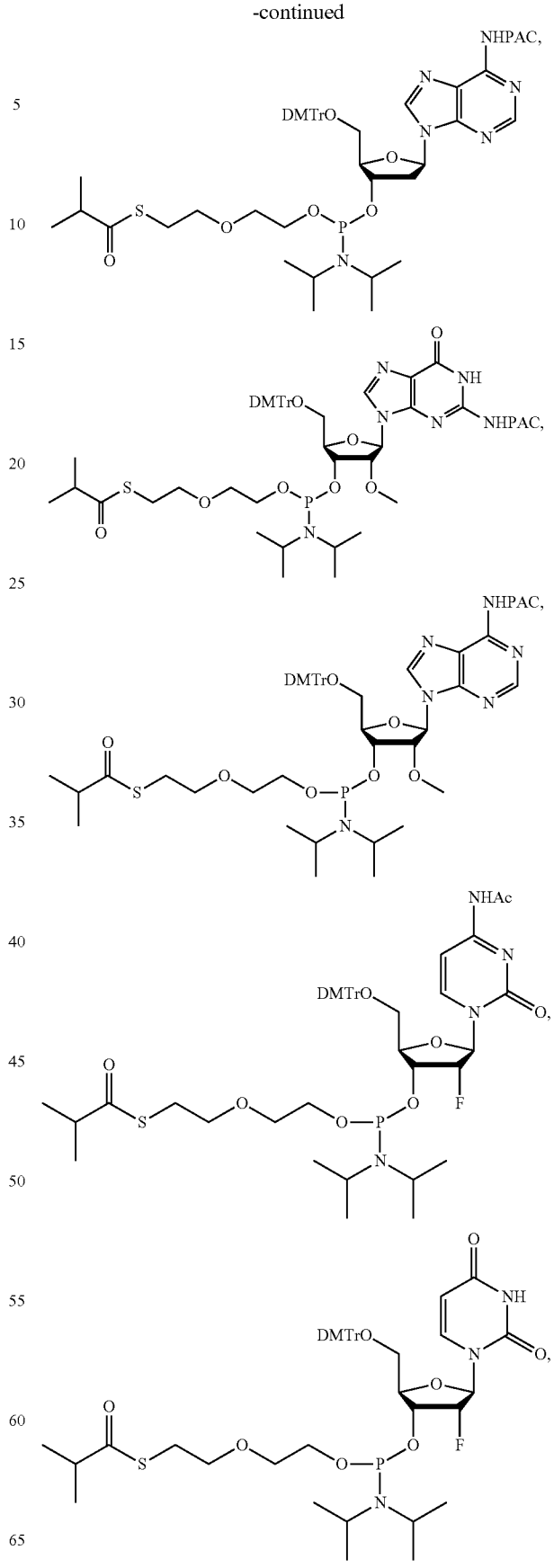

163
-continued
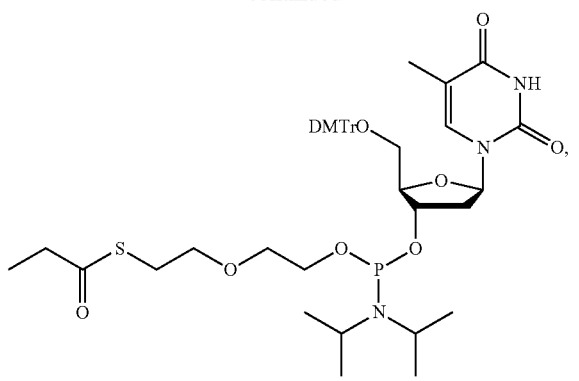
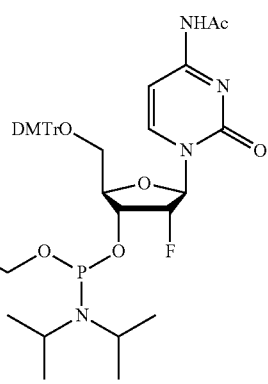
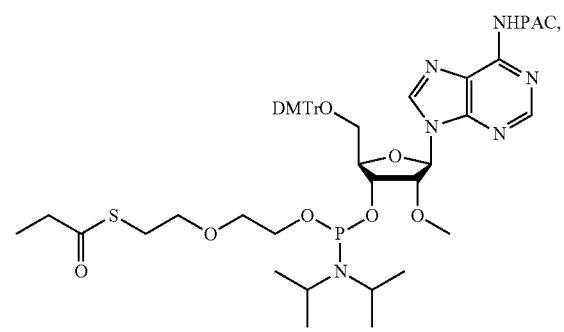
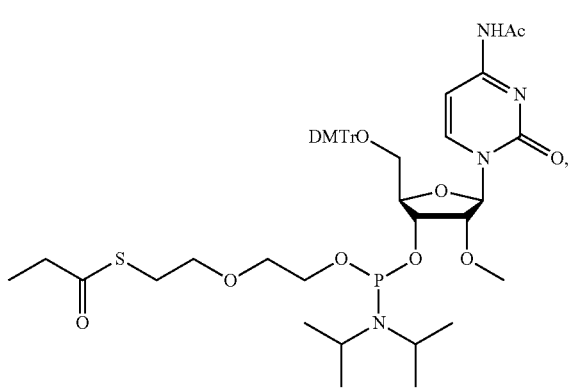
164
-continued
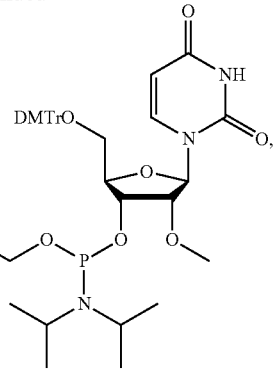
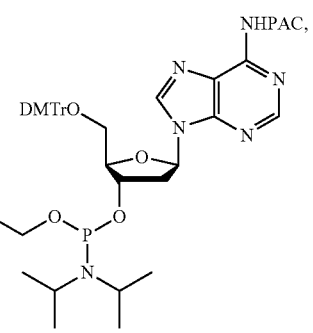
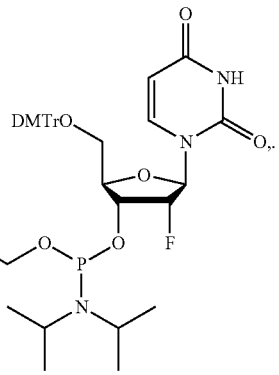
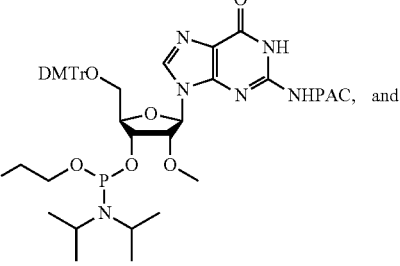
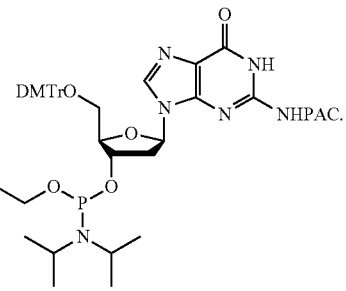

7. A compound of formula IX:

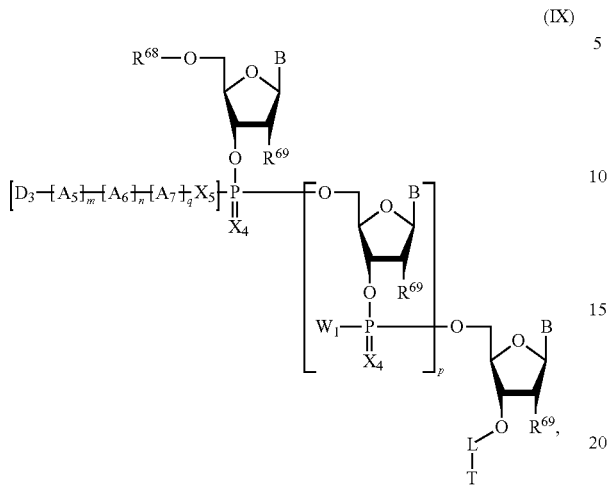

(IX)

wherein:
each $D_3$ is independently

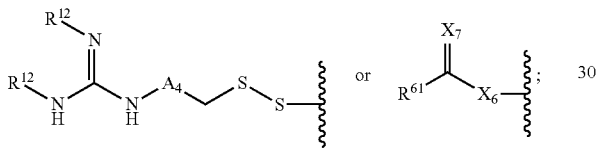

or;

each $R^{61}$ is independently an optionally substituted substituent selected from the group consisting of $C_{1-8}$alkyl, $C_{1-8}$alkenyl, $C_{1-6}$alkoxyl, aryl, heteroaryl, heterocyclyl, —$NHC_{1-6}$alkyl, aryl$C_{1-6}$alkyl, heteroaryl$C_{1-6}$alkyl, heterocyclyl$C_{1-6}$alkyl, guanidinyl, $C_{1-6}$alkylC(O)O—, arylC(O)O—, heteroarylC(O)O—, heterocyclylC(O)O—, and $C_{1-8}$alkyl substituted with one or more hydroxyl groups; or $R^{61}$ is selected from the group consisting of $(R^{78})_4N(CH_2)_r$—, $(R^{78})_3C(CH_2)_r$—, $(R^{78})_3CNH(CH_2)_r$—, $HS(CH_2)_r$—, $C_{1-8}$heteroalkyl, and guanidiny$(CH_2)_r$—;

L is a linker arm;
T is a solid support;
each $R^{12}$ is individually selected from the group consisting of H (hydrogen), $R^{13}OC(O)$—, $R^{13}C(O)$—, $R^{13}C(O)CH_2$—, $R^{13}SO_2$—, alkylOC(O)—, or an optionally substituted arylOC(O)—;
each $R^{13}$ is individually selected from the group consisting of optionally substituted $C_{1-6}$alkyl, and an optionally substituted aryl;
each $X_5$ is independently O (oxygen) or S (sulfur);
each $X_6$ is independently selected from the group consisting of O (oxygen), $NR^{63}$, Se (selenium), or S (sulfur);
each $R^{63}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
each $X_7$ is independently O (oxygen), NH, or S (sulfur);
each $A_4$ is independently an optionally substituted substituent selected from the group consisting of $C_{1-15}$alkyl, $C_{1-15}$alkoxy, $C_{1-15}$heteroalkyl, aryl, heteroaryl and heterocycle; or $A_4$ is $L_1$-$L_2$, $L_1$-$X_9$-$L_2$, -$X_9$-$L_1$-$X_9$-$L_2$-$X_9$-, -$X_9$-$L_1$- $L_2$-$X_9$-, $L_1$-$L_2$-$L_3$, $L_1$-$X_9$-$L_2$-$X_9$-$L_3$, -$X_9$-$L_1$-$X_9$-$L_2$-$X_9$-$L_3$-$X_9$-, $L_1$-$X_9$-$L_2$-$L_3$-$X_9$ $L_1$-$X_9$ $L_2$ $X_9$ $L_3$, -$X_9$-$L_1$-$L_2$-$X_9$-$L_3$, $L_1$-$X_9$-$L_2$-$L_3$ -$X_9$, -$X_9$-$L_1$-$X_9$-$L_2$-$X_9$-$L_3$-$X_9$, and -$X_9$-$L_1L_2$-$X_9$-$L_3$-$X_9$;
each $L_1$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $L_2$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $L_3$ is independently an optionally substituted substituent selected from the group consisting of $C_{1-5}$alkyl, $C_{1-5}$alkoxy, $C_{1-5}$heteroalkyl, aryl, heteroaryl and heterocycle;
each $X_9$ is independently independently selected from the group consisting of O (oxygen), $NR^{43}$, Se (selenium), or S (sulfur);
each $NR^{43}$ is independently selected, wherein each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;
each $A_5$ is —C($R^{64}$)$_2$—;
each $A_6$ is individually selected from the group consisting of —$NR^{66}$—, —C($R^{65}$)$_2$$NR^{66}$—, —C($R^{65}$)$_2$O—C($R^{65}$)$_2$S—, —C($R^{65}$)$_2$Se—, —OC($R^{65}$)$_2$O—, —SC($R^{65}$)$_2$S—, —SeC($R^{65}$)$_2$Se—, —C($R^{65}$)$_2$C($R^{65}$)$_2$$NR^{66}$—, —C($R^{65}$)$_2$O—, —C($R^{65}$)$_2$C($R^{65}$)$_2$S—, and —C($R^{65}$)$_2$C($R^{65}$)$_2$Se—;
each $A_7$ is —C($R^{67}$)$_2$—;
each m is independently an integer selected from 1, 2, or 3;
each n is independently an integer selected from 1, 2, or 3;
each q is independently an integer selected from 1, 2, or 3;
each r is independently an integer selected from 0, 1, 2, 3, 4, 5, or 6;
each C($R^{64}$)$_2$ is independently selected, wherein each $R^{64}$ is independently selected from the group consisting of H (hydrogen), halo, $C_{1-6}$alkyl, $C_{1-6}$alkoxy, and $C_{1-6}$alkyl substituted with up to 5 fluorine, or optionally two $R^{64}$ groups are taken together with the carbon to which they are attached to form an optionally substituted $C_{3-7}$cycloalkyl group;
each C($R^{65}$)$_2$ is independently selected, wherein each $R^{65}$ is independently selected from the group consisting of H (hydrogen), halo, $C_{1-6}$alkyl, $C_{1-6}$alkoxy, and $C_{1-6}$alkyl substituted with up to 5 fluorine; or two $R^{65}$ are optionally taken together to form an oxo group, each $R^{66}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS$(O)_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS$(O)_2$—;

each $C(R^{67})_2$ is independently selected, wherein each $R^{67}$ is independently selected from the group consisting of H (hydrogen), halo, $C_{1-6}$alkyl, $C_{1-6}$alkoxy, and $C_{1-6}$alkyl substituted with up to 5 fluorine, or optionally two $R^{67}$ groups are taken together with the carbon to which they are attached to form an optionally substituted $C_{3-7}$cycloalkyl group;

$R^{68}$ is selected from the group consisting of H (hydrogen), optionally substituted trityl, optionally substituted pixyl (9-phenylxanthenyl), and optionally substituted S-pixyl (9-phenyithioxanthyl);

each $R^{69}$ is independently selected from the group consisting of H (hydrogen), halo, $R^{60}O(CH_2)_r$—, and optionally substituted $C_{1-6}$alkoxyl;

each $R^{60}$ is independently selected from the group consisting of H (hydrogen), triisopropylsilylOCH$_2$—, tert-butyldimethylsilylOCH$_2$—, triethyisilylOCH$_2$—, trimethylsilylethylOCH$_2$—, triisopropylsilyl-, tert-butyldimethylsilyl-, trimethylsilylethyl-, triethylsilyl-, optionally substituted trimethylsilyl-, and optionally substituted trimethylsilylOCH$_2$—;

each $R^{78}$ is independently selected from the group consisting of H (hydrogen), $R^{79}(CH_2)_r$—, optionally substituted $C_{1-6}$alkyl, optionally substituted $C_{3-7}$alkyl, optionally substituted arylalkyl, and optionally substituted aryl;

each $R^{79}$ is independently selected from the group consisting of H (hydrogen), halo, $R^{80}O$—, and optionally substituted $C_{1-6}$alkoxyl;

each $R^{80}$ is independently selected from the group consisting of H (hydrogen), triisopropylsilylOCH$_2$—, tert-butyldimethylsilylOCH$_2$—, triethylsilylOCH$_2$—, trimethysilylethylOCH$_2$—, triisopropylsilyl-, tert-butyldimethylsilyl-, trimethysilylethyl-, triethylsilyl-, optionally substituted trimethylsilyl-, and optionally substituted trimethylsilylOC$_2$—;

each B is independently an optionally substituted substituent selected from the group consisting of a pyrimidine, a purine, and a heterocyclic base;

p is an integer from 0 (zero) to about 50;

each $W_1$ is independently —OR$^{11}$ or

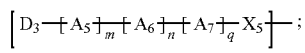

each $X_4$ is independently O (oxygen) or S (sulfur); and
each $R^{11}$ is independently H (hydrogen), $C_{1-6}$alkyl, —CH$_2$CH$_2$CN, or absent,
with the proviso that when $R^{11}$ is absent then —OR$^{11}$ is —O$^-$ (anionic oxygen radical) providing an phosphate anionic diester group or anionic thiophosphate diester group.

8. A phosphate-protected oligonucleotide derivative of formula X:

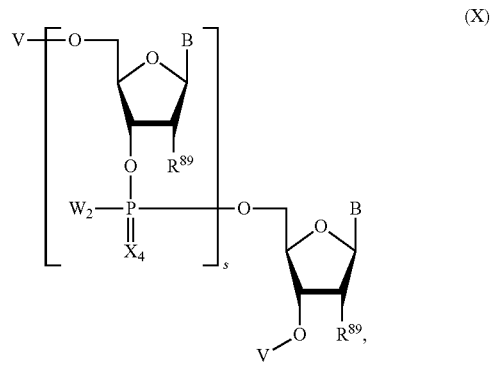

wherein:
each $X_4$ is individually O (oxygen) or S (sulfur);
s is an integer from 1 to about 5000;
each $R^{89}$ is individually selected from the group consisting of H (hydrogen), halo, —OR$^{90}$, and optionally substituted $C_{1-6}$ alkoxyl;
each R90 is independently selected from the group consisting of H (hydrogen), triisopropylsilyiOCH$_2$—, tert-butyldimethylsilylOCH$_2$—, triethylsitylOCH$_2$—, trimethyisitylethylOC$_2$—, triisopropylsilyl-, tert-butyldimethylsilyl-, trimethylsilylethyl-, triethylsilyl-, optionally substituted trimethylsityl-, and optionally substituted trimethylsilylOCH$_2$—;
each B is individually an optionally substituted substituent selected from the group consisting of a pyrimidine, a purine, and a heterocyclic base;
each V is is individually a H (hydrogen) or a transducing moiety;
each $W_2$ is independently $R^{11}O$— or

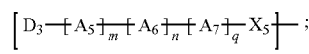

each $R^{11}$ is independently H (hydrogen), $C_{1-6}$alkyl, —CH$_2$CH$_2$CN, or absent;
each $D_3$ is independent

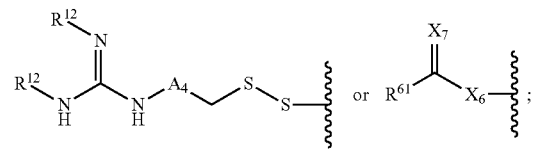

each $R^{61}$ is independently an optionally substituted substituent selected from the group consisting of $C_{1-8}$alkyl, $C_{1-8}$alkenyl, $C_{1-6}$alkoxyl, aryl, heteroaryl, heterocyclyl, —NHC$_{1-6}$alkyl, arylC$_{1-6}$alkyl, heteroarylC$_{1-6}$alkyl, heterocyclylC$_{1-6}$alkyl, guanidinyl, $C_{1-6}$alkylC(O)O—, arylC(O)O—, heteroarylC(O)O—, heterocyclylC(O)O—, and $C_{1-8}$alkyl substituted with one or more hydroxyl groups; or $R^{61}$ is selected from the group consisting of $(R^{78})_4N(CH_2)_r$—, $(R^{78})_3C(CH_2)_r$—, $(R^{78})_3CNH(CH_2)_r$—, $HS(CH_2)_r$—, $C_{1-8}$heteroalkyl, and guanidiny$(CH_2)_r$—;

each $R^{78}$ is independently selected from the group consisting of H (hydrogen), $R^{79}(CH_2)_r$—, optionally substituted $C_{1-6}$alkyl, optionally substituted $C_{3-7}$alkyl, optionally substituted arylalkyl, and optionally substituted aryl;

each $R^{79}$ is independently selected from the group consisting of H (hydrogen), halo, $R^{80}O$—, and optionally substituted $C_{1-6}$alkoxyl;

each $R^{80}$ is independently selected from the group consisting of H (hydrogen), triisopropylsilylOCH$_2$—, tert-butyldimethylsilylOCH$_2$—, triethylsilylOCH$_2$—, trimethylsilylethylOCH$_2$—, triisopropylsilyl-, tert-butyldimethylsilyl-, triinethylsilylethyl-, triethylsilyl-, optionally substituted trimethylsilyl-, and optionally substituted trimethylsilylOCH$_2$—;

each $R^{12}$ is individually selected from the group consisting of H (hydrogen), $R^{13}OC(O)$—, $R^{13}C(O)$—, $R^{13}C(O)CH_2$—, $R^{13}SO_2$—, alkylOC(O)—, or an optionally substituted arylOC(O)—;

each $R^{13}$ is individually selected from the group consisting of optionally substituted $C_{1-6}$alkyl, and an optionally substituted aryl;

each $X_5$ is independently O (oxygen) or S (sulfur);

each $X_6$ is independently selected from the group consisting of O (oxygen), $NR^{63}$, Se (selenium), or S (sulfur);

each $R^{63}$ is independently selected from the group consisting of H (hydrogen), $C_{1-6}$alkyl, $C_{1-6}$alkylC(O)—, $C_{1-6}$alkylOC(O)—, $C_{1-6}$alkyNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $X_7$ is independently O (oxygen), NH, or S (sulfur);

each $A_4$ is independently an optionally substituted substituent selected from the group consisting of $C_{1-15}$alkyl, $C_{1-15}$alkoxy, $C_{1-15}$heteroalkyl, aryl, heteroaryl and heterocycle; or $A_4$ is $L_1$-$L_2$, $L_1$-$X_9$-$L_2$,-$X_9$-$L_{19}$-$L_2$-$X_9$-, -$X_9$-$L_1$-$L_2$-$X_9$-, $L_1$-$L_2$-$L_3$, $L_1X_9$-$L_2$-$X_9$-$L_3$, -$X_9$-$L_1$-$X_9$-$L_2$-$X_9$-$L_3X_9$-, $L_1$-$X_9$-$L_2$-$L_3$, -$X_9$-$L_1$-$X_9$-$L_2$-$X_9$-$L_3$, -$X_9$-$L_1$-$L^2$-$X_9$-$L_3$, $L_1$-$X_9$-$L_2$-$L_3$-$X_9$, -$X_9$-$L_1$-$X_9$-$L_2$-$X_9$-$L_3$-$X_9$, and -$X_9$-$L_1$-$L_2$-$X_9$-$L_3$-$X_9$;

each $L_1$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $L_2$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $L_3$ is independently an optionally substituted substituent selected from the group consisting of $C_{1-5}$alkyl, $C_{1-5}$alkoxy, $C_{1-5}$heteroalkyl, aryl, heteroaryl and heterocycle;

each $X_9$ is independently independently selected from the group consisting of O (oxygen), $NR^{43}$, Se (selenium), or S (sulfur);

each $NR^{43}$ is independently selected, wherein each $R^{43}$ is independently selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—;

each $A_5$ is —C($R^{84}$)$_2$—;

each $A_6$ is individually selected from the group consisting of —$NR^{86}$—, —C($R^{85}$)$_2$$NR^{86}$—, —C($R^{85}$)$_2$O—, —C($R^{85}$)$_2$S—, —C($R^{85}$)$_2$Se—, —OC($R^{85}$)$_2$O—, —SC($R^{85}$)$_2$S—, —SeC($R^{85}$)$_2$Se—, —C($R^{85}$)$_2$C($R^{85}$)$_2$$NR^{86}$—, —C($R^{85}$)$_2$C($R^{85}$)$_2$O—, —C($R^{85}$)$_2$C($R^{85}$)$_2$S—, and —C($R^{85}$)$_2$C($R^{85}$)$_2$Se—;

each $A_7$ is —C($R^{87}$)$_2$—;

each m is independently an integer selected from 1, 2, or 3;

each n is independently an integer selected from 1, 2, or 3;

each q is independently an integer selected from 1, 2, or 3;

each r is independently an integer selected from 0, 1, 2, 3, 4, 5, or 6;

each C($R^{84}$)$_2$ is independently selected, wherein each $R^{84}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{84}$ groups are taken together with the carbon to which they are attached to form an optionally substituted $C_{3-7}$cycloalkyl group;

each C($R^{85}$)$_2$ is independently selected, wherein each $R^{85}$ is individually selected from the group consisting of H (hydrogen), halo, $C_{1-6}$alkyl, $C_{1-6}$alkoxy, and $C_{1-6}$alkyl substituted with up to 5 fluorine; or two $R^{85}$ are optionally taken together to form an oxo group;

each $R^{86}$ is individually selected from the group consisting of H (hydrogen), $C_{1-6}$alkyl, $C_{1-6}$alkylC(O)—, $C_{1-6}$alkylOC(O)—, $C_{1-6}$alkylNHC(O)—, $C_{1-6}$alkylS(O)$_2$—, optionally substituted arylC(O)—, optionally substituted heteroarylC(O)—, optionally substituted arylOC(O)—, optionally substituted heteroarylOC(O)—, optionally substituted arylNHC(O)—, optionally substituted heteroarylNHC(O)—, and optionally substituted arylS(O)$_2$—; and each C($R^{87}$)$_2$ is independently selected, wherein each $R^{87}$ is individually selected from the group consisting of H (hydrogen), halo, $C_{1-6}$alkyl, $C_{1-6}$alkoxy, and $C_{1-6}$alkyl substituted with up to 5 fluorine, or optionally two $R^{87}$ groups are taken together with the carbon to which they are attached to form an optionally substituted $C_{3-7}$cycloalkyl group;

with the proviso that at least one $W_2$ is

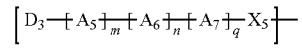

and when $R^{11}$ is absent then $R^{11}O$— is —O$^-$ (anionic oxygen radical) providing an phosphate anionic diester group or anionic thiophosphate diester group.

9. The phosphate-protected oligonucleotide derivative of claim 3 or 8, wherein V is a transducing moiety, and wherein said transducing moiety is a protein transduction domain.

10. The phosphate-protected oligonucleotide derivative of claim 9, further comprising a plurality of transducing moieties.

11. The phosphate-protected oligonucleotide derivative of claim 3 or 8, wherein s is an integer between about 10 and 100.

12. The phosphate-protected oligonucleotide derivative of claim 3 or 8, wherein s is an integer between about 19 and 24.

13. The phosphate-protected oligonucleotide derivative of claim 3 or 8, wherein s is an integer between 20 and 22.

14. The phosphate-protected oligonucleotide derivative of claim 3 or 8, in double-stranded form, wherein in each strand, s is an integer between about 19 and 24.

15. The phosphate-protected oligonucleotide derivative of claim 3 or 8, wherein s is an integer between about 42 and 55, comprising a hairpin loop.

16. A method of delivering a biomolecule to a target cell, comprising:
    providing a prosphate-protected oligonucleotide derivative of claim 3 or 8,
    providing a target cell; and
    contacting said target cell with said phosphate-protected oligonucleotide derivative to deliver the derivative into the cell.

17. The method of claim 16, wherein the contacting step is performed in vitro,

18. The method of claim 16, wherein the contacting step is performed in vivo.

19. The method of claim 16, wherein the phosphate-protected oligonucleotide is an siRNA derivative, 20. The method of claim 16, wherein the phosphate-protected oligonucleotide is an miRNA derivative.

21. The method of claim 16, wherein V is a transducing moiety.

22. The method of 21, wherein said transducing moiety is a protein transduction domain.

23. A composition comprising the nucleic acid molecule of any one of claims 3 or 4-8, in a pharmaceutically acceptable carrier, salt or diluents buffer.

24. The nucleic acid molecule of claim 3 or 8, wherein the sense strand, the antisense strand, or both the sense strand and the antisense strand include a 3'-overhang.

25. The compound of claims 1 or 2, further comprising a transduction moiety.

26. The compound of claim 25, wherein the transduction moiety is selected from a peptide transduction domain, a nucleic acid binding peptide, or a combination. thereof.

27. The compound of claim 26, wherein the nucleic acid binding peptide is an RNA binding protein.

28. The phosphate protected oligonucleotide of any one of claims 3 or 4 or 8, further comprising a transduction moiety.

29. The phosphate protected oligonucleotide of claim 28, wherein the transduction moiety is selected from a peptide transduction domain, a nucleic acid binding peptide, or a combination thereof.

30. The phosphate protected oligonucleotide of claim 29, wherein the nucleic acid binding peptide is an RNA binding protein.

* * * * *

```
                         SEQUENCE LISTING

<160> NUMBER OF SEQ ID NOS: 55

<210> SEQ ID NO 1
<211> LENGTH: 2
<212> TYPE: PRT
<213> ORGANISM: Artificial Sequence
<220> FEATURE:
<223> OTHER INFORMATION: synthetic polypeptide

<400> SEQUENCE: 1

Gly Gly
 1

<210> SEQ ID NO 2
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 2

Gly Gly Gly Gly Ser
 1               5

<210> SEQ ID NO 3
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 3

Gly Gly Gly Gly Ser Asn
 1               5

<210> SEQ ID NO 4
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 4

Gly Lys Ser Ser Gly Ser Gly Ser Glu Ser Lys Ser
 1               5                  10

<210> SEQ ID NO 5
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 5
```

```
Gly Ser Thr Ser Gly Ser Gly Lys Ser Ser Glu Gly Lys Gly
1               5                   10
```

<210> SEQ ID NO 6
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 6

```
Gly Ser Thr Ser Gly Ser Gly Lys Ser Ser Glu Gly Ser Gly Ser Thr
1               5                   10                  15

Lys Gly
```

<210> SEQ ID NO 7
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 7

```
Gly Ser Thr Ser Gly Ser Gly Lys Pro Gly Ser Gly Glu Gly Ser Thr
1               5                   10                  15

Lys Gly
```

<210> SEQ ID NO 8
<211> LENGTH: 14
<212> TYPE: PRT
<213> ORGANISM: Artificial Sequence
<220> FEATURE:
<223> OTHER INFORMATION: synthetic polypeptide

<400> SEQUENCE: 8

```
Glu Gly Lys Ser Ser Gly Ser Gly Ser Glu Ser Lys Glu Phe
1               5                   10
```

<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 9
ccacnaccng agcacccagn t                                              21

<210> SEQ ID NO 10
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 10
tnggngangg acncgngggn c                                              21

<210> SEQ ID NO 11

```
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 11
cngggngcnc aggnagnggt t                                           21

<210> SEQ ID NO 12
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 12
cngggngcnc aggnagnggt t                                           21

<210> SEQ ID NO 13
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 13
agcngacccn gaagnncant t                                           21

<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (0)...(0)
<223> OTHER INFORMATION: n = uracil

<400> SEQUENCE: 14
angaacnnca gggncagcnt t                                           21

<210> SEQ ID NO 15
<211> LENGTH: 32
<212> TYPE: PRT
<213> ORGANISM: Artificial Sequence
<220> FEATURE:
<223> OTHER INFORMATION: synthetic polypeptide

<400> SEQUENCE: 15

Cys Gly Gly Gly Tyr Ala Ala Ala Arg Arg Arg Arg Arg Arg Arg Gly
 1               5                  10                  15

Ser Gly Ser Gly Tyr Ala Ala Ala Arg Arg Arg Arg Arg Arg Arg Gly
                20                  25                  30

<210> SEQ ID NO 16
```

```
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 16

Arg Lys Lys Arg Arg Gln Arg Arg Arg
1               5

<210> SEQ ID NO 17
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 17

Tyr Gly Arg Lys Lys Arg Arg Gln Arg Arg Arg
1               5                   10

<210> SEQ ID NO 18
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 18

Arg Gln Ile Lys Ile Trp Phe Gln Asn Arg Arg Met Lys Trp Lys Lys
1               5                   10                  15

<210> SEQ ID NO 19
<211> LENGTH: 21
<212> TYPE: PRT
<213> ORGANISM: Artificial Sequence
<220> FEATURE:
<223> OTHER INFORMATION: synthetic polypeptide

<400> SEQUENCE: 19

Thr Arg Ser Ser Arg Ala Gly Leu Gln Phe Pro Val Gly Arg Val His
1               5                   10                  15

Arg Leu Leu Arg Lys
            20

<210> SEQ ID NO 20
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 20

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 21
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 21
```

```
Lys Leu Ala Leu Lys Leu Ala Leu Lys Ala Leu Lys Ala Ala Leu Lys
1               5                   10                  15
Leu Ala
```

<210> SEQ ID NO 22
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 22

```
Ala Ala Val Ala Leu Leu Pro Ala Val Leu Leu Ala Leu Leu Ala Pro
1               5                   10                  15
```

<210> SEQ ID NO 23
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 23

```
Val Pro Met Leu Lys
1               5
```

<210> SEQ ID NO 24
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 24

```
Pro Met Leu Lys Glu
1               5
```

<210> SEQ ID NO 25
<211> LENGTH: 28
<212> TYPE: PRT
<213> ORGANISM: Artificial Sequence
<220> FEATURE:
<223> OTHER INFORMATION: synthetic polypeptide

<400> SEQUENCE: 25

```
Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25
```

<210> SEQ ID NO 26
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 26

```
Leu Leu Ile Ile Leu Arg Arg Arg Ile Arg Lys Gln Ala His Ala His
1               5                   10                  15

Ser Lys
```

<210> SEQ ID NO 27
<211> LENGTH: 21
<212> TYPE: PRT
<213> ORGANISM: Artificial Sequence

```
<220> FEATURE:
<223> OTHER INFORMATION: synthetic polypeptide

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 28

Arg Gly Gly Arg Leu Ser Tyr Ser Arg Arg Phe Ser Thr Ser Thr
1               5                   10                  15

Gly Arg

<210> SEQ ID NO 29
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 29

Ser Asp Leu Trp Glu Met Met Met Val Ser Leu Ala Cys Gln Tyr
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: synthetic polypeptide

<400> SEQUENCE: 30

Thr Ser Pro Leu Asn Ile His Asn Gly Gln Lys Leu
1               5                   10

<210> SEQ ID NO 31
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 31

Lys Arg Arg Gln Arg Arg Arg
1               5

<210> SEQ ID NO 32
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 32

Arg Lys Lys Arg Arg Gln Arg
1               5

<210> SEQ ID NO 33
```

```
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 33

Arg Lys Lys Arg Arg Gln Arg Arg
1               5

<210> SEQ ID NO 34
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 34

Gly Arg Lys Lys Arg Arg Gln Arg Arg Arg Pro Pro Gln
1               5                   10

<210> SEQ ID NO 35
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 35

Thr Arg Gln Ala Arg Arg Asn Arg Arg Arg Trp Arg Glu Arg Gln
1               5                   10                  15

Arg

<210> SEQ ID NO 36
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 36

Thr Arg Arg Gln Arg Thr Arg Arg Ala Arg Arg Asn Arg
1               5                   10

<210> SEQ ID NO 37
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 37

Thr Arg Arg Asn Lys Arg Asn Arg Ile Gln Glu Gln Leu Asn Arg Lys
1               5                   10                  15

<210> SEQ ID NO 38
<211> LENGTH: 18
<212> TYPE: PRT
<213> ORGANISM: Artificial Sequence
<220> FEATURE:
<223> OTHER INFORMATION: synthetic polypeptide

<400> SEQUENCE: 38

Thr Ala Lys Thr Arg Tyr Lys Ala Glu Glu Ala Glu Leu Ile Ala Glu
1               5                   10                  15

Arg Arg
```

```
<210> SEQ ID NO 39
<211> LENGTH: 22
<212> TYPE: PRT
<213> ORGANISM: Artificial Sequence
<220> FEATURE:
<223> OTHER INFORMATION: synthetic polypeptide

<400> SEQUENCE: 39

Met Asp Ala Gln Thr Arg Arg Arg Glu Arg Arg Ala Glu Lys Gln Ala
 1               5                  10                  15

Gln Trp Lys Ala Ala Asn
            20

<210> SEQ ID NO 40
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 40

Arg Arg Arg Arg Asn Arg Thr Arg Arg Asn Arg Arg Arg Val Arg
 1               5                  10                  15

<210> SEQ ID NO 41
<211> LENGTH: 19
<212> TYPE: PRT
<213> ORGANISM: Artificial Sequence
<220> FEATURE:
<223> OTHER INFORMATION: synthetic polypeptide

<400> SEQUENCE: 41

Lys Met Thr Arg Ala Gln Arg Arg Ala Ala Ala Arg Arg Asn Arg Trp
 1               5                  10                  15

Thr Ala Arg

<210> SEQ ID NO 42
<211> LENGTH: 13
<212> TYPE: PRT
<213> ORGANISM: Artificial Sequence
<220> FEATURE:
<223> OTHER INFORMATION: synthetic polypeptide

<400> SEQUENCE: 42

Thr Arg Arg Gln Arg Thr Arg Arg Ala Arg Arg Asn Arg
 1               5                  10

<210> SEQ ID NO 43
<211> LENGTH: 17
<212> TYPE: PRT
<213> ORGANISM: Artificial Sequence
<220> FEATURE:
<223> OTHER INFORMATION: synthetic polypeptide

<400> SEQUENCE: 43

Thr Arg Gln Ala Arg Arg Asn Arg Arg Arg Arg Trp Arg Glu Arg Gln
 1               5                  10                  15

Arg

<210> SEQ ID NO 44
<211> LENGTH: 13
<212> TYPE: PRT
<213> ORGANISM: Artificial Sequence
<220> FEATURE:
<223> OTHER INFORMATION: synthetic polypeptide
```

```
<400> SEQUENCE: 44

Gly Arg Lys Lys Arg Arg Gln Arg Arg Pro Pro Gln
 1               5                  10

<210> SEQ ID NO 45
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 45

Arg Arg Arg Gln Arg Arg Lys Lys Arg
 1               5

<210> SEQ ID NO 46
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 46

Ala Gly Arg Lys Lys Arg Arg Gln Arg Arg Arg
 1               5                  10

<210> SEQ ID NO 47
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 47

Tyr Ala Arg Lys Ala Arg Arg Gln Ala Arg Arg
 1               5                  10

<210> SEQ ID NO 48
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 48

Tyr Ala Arg Ala Ala Ala Arg Gln Ala Arg Ala
 1               5                  10

<210> SEQ ID NO 49
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 49

Tyr Ala Arg Ala Ala Arg Arg Ala Ala Arg Arg
 1               5                  10

<210> SEQ ID NO 50
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 50
```

```
Tyr Ala Arg Ala Ala Arg Arg Ala Ala Arg Ala
1               5                   10
```

<210> SEQ ID NO 51
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 51

```
Tyr Ala Arg Arg Arg Arg Arg Arg Arg Arg
1               5                   10
```

<210> SEQ ID NO 52
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 52

```
Tyr Ala Ala Ala Arg Arg Arg Arg Arg Arg
1               5                   10
```

<210> SEQ ID NO 53
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 53

```
Lys Lys Arg Pro Lys Pro Gly
1               5
```

<210> SEQ ID NO 54
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 54

```
Lys Arg Pro Ala Ala Thr Lys Lys Ala Gly Gln Ala Lys Lys Leu
1               5                   10                  15
```

<210> SEQ ID NO 55
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 55

```
Pro Lys Lys Lys Arg Lys Val
1               5
```